US006449562B1

United States Patent
Chandler et al.

(10) Patent No.: US 6,449,562 B1
(45) Date of Patent: *Sep. 10, 2002

(54) MULTIPLEXED ANALYSIS OF CLINICAL SPECIMENS APPARATUS AND METHOD

(75) Inventors: Van S. Chandler, Austin; Jerrold R. Fulton, Cedar Hill; Mark B. Chandler, Austin, all of TX (US)

(73) Assignee: Luminex Corporation, Austin, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 141 days.

(21) Appl. No.: 09/000,286

(22) PCT Filed: Oct. 10, 1996

(86) PCT No.: PCT/US96/16198

§ 371 (c)(1),
(2), (4) Date: Aug. 18, 1998

(87) PCT Pub. No.: WO97/14028

PCT Pub. Date: Apr. 17, 1997

(51) Int. Cl.$^7$ .................. G01N 33/48; G01N 33/50; C12Q 1/68; G06F 17/30
(52) U.S. Cl. .................. 702/19; 702/20; 435/6; 707/1; 707/104
(58) Field of Search .................. 702/19, 20; 435/6; 707/104, 1

(56) References Cited

U.S. PATENT DOCUMENTS

| | | | |
|---|---|---|---|
| 3,952,091 A | 4/1976 | Grunberg et al. | 424/1.5 |
| 3,959,650 A | 5/1976 | Lukens, Jr. | 250/303 |
| 3,985,867 A | 10/1976 | Redshaw | 424/1.5 |
| 4,010,250 A | 3/1977 | Parikh et al. | 424/1 |
| 4,018,884 A | 4/1977 | Cleeland, Jr. et al. | 424/7 |
| 4,028,056 A | 6/1977 | Snyder et al. | 23/230 B |
| 4,088,746 A | 5/1978 | Blakemore et al. | 424/1 |
| 4,090,850 A | 5/1978 | Chen et al. | 23/259 |
| 4,108,972 A | 8/1978 | Drever | 424/1 |
| 4,108,974 A | 8/1978 | Wegfahrt et al. | 424/1 |
| 4,113,433 A | 9/1978 | Khare | 23/230.6 |
| 4,115,535 A | 9/1978 | Giaever | 424/1 |
| 4,115,536 A | 9/1978 | Rothman et al. | 424/1 |
| 4,166,102 A | 8/1979 | Johnson | 424/1 |
| 4,166,105 A | 8/1979 | Hirschfeld | 424/8 |
| 4,169,137 A | 9/1979 | Hirschfeld et al. | 424/8 |
| 4,177,253 A | 12/1979 | Davies et al. | 424/1 |
| 4,182,750 A | 1/1980 | Sullivan et al. | 424/1 |
| 4,184,849 A | 1/1980 | Cambiaso et al. | 23/230 B |
| 4,201,763 A | 5/1980 | Monthony et al. | 424/1 |
| 4,217,339 A | 8/1980 | Bohn et al. | 424/12 |
| 4,219,335 A | 8/1980 | Ebersole | 23/230 B |
| 4,225,783 A | 9/1980 | Palin et al. | 250/302 |
| 4,231,750 A | 11/1980 | Dowben et al. | 23/230 B |

(List continued on next page.)

FOREIGN PATENT DOCUMENTS

| | | | |
|---|---|---|---|
| CA | 1248873 | 1/1989 | 167/37 |
| EP | 0200113 A2 | 4/1986 | |
| EP | 0382433 A2 | 2/1990 | |
| EP | 0633462 A2 | 6/1994 | |
| JP | 329190 | 2/1989 | 435/6 |
| WO | WO 87/06621 | 11/1987 | |
| WO | WO 89/11101 | 11/1989 | |
| WO | WO 92/17853 | 10/1992 | |
| WO | WO 93/02360 | 2/1993 | |
| WO | WO 97/14028 | 8/1997 | |
| WO | WO 99/36564 | 5/1999 | |

OTHER PUBLICATIONS

Zilmer et al, "Flow cytometric analysis using digital signal processing", Cytometry 20:102–117, Jun. 1995.*

Hubl et al, "Precision and accuracy of monocyte counting", Am. J. Clin. Pathol. 103(2):167–170, Feb. 1995.*

Bottema, et al., "PCR Amplification of Specific Alleles: Rapid Detection of Known Mutations and Polymorphisms," Mutation Research, 288,93–102 (1993).

Cantarero, et al., "The Adsorptive Characteristics of Proteins for Polystyrene and Their significance in Solid–Phase Immunoassays," Analytical Biochemistry, 105, 375–382 (1980).

Colvin, et al., "The Covalent Binging of Enzymes and Immunoglobulins to Hydrophilic Microspheres" in Microspheres: Medical and Biological Applications, 1–013, CRC, Boca Raton, FL, 1988.

Fisher, "The Use or Multiple Measurements in Taxonomic Problems," Annals of Eugenics, 7, 179–188 (1936).

Fulwyler, et al., "Flow Microsphere Immunoassay for the Quantitative and Simultaneous Detection of Multiple Soluble Analytes," Methods in Cell Biology, 33, 613–629 (1990).

Goss, et al., "Major Histocompatibility Complex–specific Prolongation of Murine Skin and Cardia Allograft Survival after In Vivo Depletion of Vβ$^+$ T Cells," The Journal of Experimental Medicine, 177, 35–44 (1993).

(List continued on next page.)

*Primary Examiner*—Jeffrey Fredman
(74) *Attorney, Agent, or Firm*—Gilberto M. Villacorta; Pepper Hamilton LLP

(57) ABSTRACT

A method for the multiplexed diagnostic and genetic analysis of enzymes, DNA fragments, antibodies, and other biomolecules comprises the steps of constructing an appropriately labeled beadset, exposing the beadset to a clinical sample, and analyzing the combined sample/beadset by flow cytometry is disclosed. Flow cytometric measurements are used to classify, in real-time, beads within an exposed beadset and textual explanations, based on the accumulated data obtained during real-time analysis, are generated for the user. The inventive technology enables the simultaneous, and automated, detection and interpretation of multiple biomolecules or DNA sequences in real-time while also reducing the cost of performing diagnostic and genetic assays.

13 Claims, 65 Drawing Sheets

U.S. PATENT DOCUMENTS

| | | | | |
|---|---|---|---|---|
| 4,238,565 A | 12/1980 | Hornby et al. | | 435/7 |
| 4,244,940 A | 1/1981 | Jeong et al. | | 424/1 |
| 4,254,096 A | 3/1981 | Monthony et al. | | 424/8 |
| 4,259,313 A | 3/1981 | Frank et al. | | 424/8 |
| 4,278,653 A | 7/1981 | Harris et al. | | 424/1 |
| 4,279,992 A | 7/1981 | Boguslaski et al. | | 435/7 |
| 4,283,382 A | 8/1981 | Frank et al. | | 424/8 |
| 4,302,536 A | 11/1981 | Longenecker | | 435/7 |
| 4,317,810 A | 3/1982 | Halbert et al. | | 424/12 |
| 4,340,564 A | 7/1982 | Harte et al. | | 422/56 |
| 4,341,957 A | 7/1982 | Wieder | | 250/461.2 |
| 4,342,739 A | 8/1982 | Kakimi et al. | | 424/1 |
| 4,075,462 A | 2/1985 | Rowe | | 235/92 |
| 4,499,052 A | 2/1985 | Fulwyler | | 422/52 |
| 4,661,913 A | 4/1987 | Wu et al. | | 364/500 |
| 4,665,020 A | 5/1987 | Saunders | | 435/7 |
| 4,673,288 A | 6/1987 | Thomas et al. | | 356/72 |
| 4,676,640 A | 6/1987 | Briggs | | 356/317 |
| 4,710,021 A | 12/1987 | von Behrens | | 356/72 |
| 4,713,348 A | 12/1987 | Ullman | | 436/501 |
| 4,714,682 A | 12/1987 | Schwartz | | 436/10 |
| 4,767,205 A | 8/1988 | Schwartz et al. | | 356/71 |
| 4,778,593 A | 10/1988 | Yamashita et al. | | 209/3.1 |
| 4,778,768 A | 10/1988 | Heinegard et al. | | 435/5 |
| 4,806,463 A | 2/1989 | Goodchild et al. | | 435/5 |
| 4,857,451 A | 8/1989 | Schwartz | | 435/7 |
| 4,859,582 A | 8/1989 | Stryer et al. | | 435/5 |
| 4,868,104 A | 9/1989 | Kurn et al. | | 435/6 |
| 4,884,886 A | 12/1989 | Salzman et al. | | 356/367 |
| 4,887,721 A | 12/1989 | Martin et al. | | 209/579 |
| 4,904,583 A | 2/1990 | Mapes et al. | | 435/7 |
| 4,905,169 A | 2/1990 | Buican et al. | | 364/525 |
| 4,918,004 A | 4/1990 | Schwartz | | 435/7 |
| 4,987,539 A | 1/1991 | Moore et al. | | 364/413.08 |
| 5,028,545 A | 7/1991 | Soini | | 436/501 |
| 5,055,556 A | 10/1991 | Stryer et al. | | 530/370 |
| 5,073,497 A | 12/1991 | Schwartz et al. | | 436/8 |
| 5,093,234 A | 3/1992 | Schwartz | | 435/7.21 |
| 5,104,791 A | 4/1992 | Abbott et al. | | 435/6 |
| 5,107,422 A | 4/1992 | Kamentsky et al. | | 364/413.08 |
| 5,127,730 A | 7/1992 | Brelje et al. | | 356/318 |
| 5,149,661 A | 9/1992 | Gjerde et al. | | 436/178 |
| 5,150,313 A | 9/1992 | van den Engh et al. | | 364/569 |
| 5,156,810 A | 10/1992 | Ribi | | 422/82.01 |
| 5,199,576 A | 4/1993 | Corio et al. | | 209/564 |
| 5,204,884 A | 4/1993 | Leary et al. | | 377/10 |
| 5,219,763 A | 6/1993 | Van Hoegaerden | | 436/523 |
| 5,224,058 A | 6/1993 | Mickaels et al. | | 364/554 |
| 5,567,627 A | 11/1993 | Lehnen | | 536/518 |
| 5,273,881 A | 12/1993 | Sena et al. | | 425/6 |
| 5,281,517 A | 1/1994 | Bacus et al. | | 435/6 |
| 5,286,452 A | 2/1994 | Hansen | | 422/73 |
| 5,290,707 A | 3/1994 | Wood | | 436/523 |
| 5,314,802 A | 5/1994 | Kidwell | | 435/7.1 |
| 5,319,079 A | 6/1994 | Reddy et al. | | 536/25.32 |
| 5,326,692 A | 7/1994 | Brinkley et al. | | 435/6 |
| 5,367,474 A | 11/1994 | Auer et al. | | 364/555 |
| 5,380,663 A | 1/1995 | Schwartz et al. | | 436/10 |
| 5,385,822 A | 1/1995 | Melnicoff et al. | | 435/5 |
| 5,393,673 A | 2/1995 | Gjerde | | 436/171 |
| 5,646,001 A | 2/1995 | Terstappen et al. | | 435/7.21 |
| 5,401,847 A | 3/1995 | Glazer et al. | | 546/107 |
| 5,403,711 A | 4/1995 | Walder et al. | | 435/6 |
| 5,405,784 A | 4/1995 | Van Hoegaerden | | 436/523 |
| 5,408,307 A | 4/1995 | Yamamoto et al. | | 356/73 |
| 5,413,907 A | 5/1995 | Worton et al. | | 435/6 |
| 5,413,914 A | 5/1995 | Franzusoff | | 435/23 |
| 558,524 A | 6/1995 | Lindmo | | 435/6 |
| 5,723,218 A | 6/1995 | Haugland et al. | | 428/402 |
| 5,429,923 A | 7/1995 | Seidman et al. | | 435/6 |
| 5,524,227 A * | 6/1996 | Cuthbertson et al. | | 395/412 |
| 5,692,220 A * | 11/1997 | Diamond et al. | | 395/924 |
| 5,739,000 A * | 4/1998 | Bierre et al. | | 435/7.24 |
| 5,853,984 A | 12/1998 | Davis et al. | | 435/6 |
| 5,930,154 A * | 7/1999 | Thalhammer-Reyero | | 364/578 |
| 6,057,107 A | 5/2000 | Fulton | | 435/6 |

OTHER PUBLICATIONS

Horan, et al., "Fluid Phase Particle Fluorescence Analysis: Rheumatoid Factor Specificity Evaluated by Laser Flow Cytophotometry" in Immunoassays in the Clinical Laboratory, 185–198 (Liss 1979).

Illum, et al., "Attachment of Monoclonal Antibodies to Microspheres," methods in Enzymology, 112, 67–84 (1985).

Lindmo, et al., , "Immunometric Assay by Flow Cytometry Using Mixtures of Two Particle Types of Different Affinity," Journal of Immunological Methods, 126, 183–189 (1990).

McHugh, "Flow Microsphere Immunoassay for the Quantitative and Simultaneous Detection of Multiple Soluble Analytes," in Methods in Cell Biology, 42, Part B, 575–595 (Academic Press 1994).

McHugh, et al., "Microsphere–Based Fluorescence Immunoassays Using Flow Cytometry Instrumentation," in Clinical Flow Cytometry Ed. K.D. Bauer, et al., Williams and Williams, Baltimore, MD 1993, 535–544.

McHugh, "Flow Cytometry and the Application of Microsphere–Based Fluorescence Immunoassays," Immunochemica, 5, 1–6, (1991).

Saiki, et al., "Genetic Analysis of Amplified DNA with Immobilized Sequence–Specific Oligonucleotide Probes," Proceedings of the national Academy of Sciences of the United States of America, 86, 6230–6234 (1989).

Vener, et al., "A Novel Approach to Nonradioactive Hybridization Assay of Nucleic Acids Using Stained Latex Particles," Analytical Biochemistry, 198, 308–311 (1991).

Vlieger, et al., "Quantitation of Polymerase Chain Reaction Products by Hybridization–Based Assays with Fluorescent, Colorimetric, or Chemiluminescent Detection," Analytical Biochemistry, 205, 1–7 (1992).

Wilson, et al., "A New Microsphere–Based Immunofluorescence Assay Using Flow Cytometry," Journal of Immunological Methods, 107, 225–230 (1988).

(A molecular study of the delta–F508 mutation and genetic analysis of a sample of cystic fibrosis patients., Estudio molecular de la mutacion delta–F508 y analisis genetico de una muestra de pacientes con fibrosis quistica., Orozco L; Lezana JL; Chavez M; Valdez H; Moreno M; Carnevale A, Bol Med Hosp Infant Mex 1993 Jul; 50 (7):457–62.

A novel method for detecting point mutations or polymorphisms and its application to population screening for carriers of phenylketonuria., 32 REFS, Sommer SS; Cassidy JD; Sobell JL; Bottema CD, Mayo Clin Proc 1989 Nov; 64 (11) 1361–72.

A novel RNA helicase gene tightly linked to the Triplo–lethal locus of Drosophila., Dorer DR; Christensen AC; Johnson DH, Nucleic Acids Res Sep. 25, 1990; 18 (18).

An exon–skipping mutation in the btk gene of a patient with X–linked agammaglobulinemia and isolated growth hormone deficiency., Duriez B; Ducluesnoy P; Dastot F; Bougneres P; Amselem S; Goossens M, FEBS Lett Jun. 13, 1994; 346 (2–3): 165–70.

Analysis of the first polar body: preconception genetic diagnosis., Verlinsky Y; Ginsberg N; Lifchez A; Valle J; Moise J; Strom CM, Hum Reprod Oct. 1990; 5 (7): 826–9.

Asymmetric PCR–based strategy for genetic analysis of the p53 tumor suppressor gene in cell lines and tumor tissues., Bartek J; Iggo R; Vojtesek B; Lane DP, Neoplasme 1991; 38 (1): 93–9.

Best's vitelliform dystrophy (VMD2) maps between D11S903 and PYGM: no evidence for locus heterogeneity., Weber BH; Walker D; Muller B; Mar L, Genomics Mar. 15, 1994; 20 (2): 267–74.

Characterization of virulence genes of enteroinvasive *Escherichia coli* by TnphoA mutagenesis: identification of invx, a gene required for entry into HEp–2 cells., Hsia RC; Small PL; Bavoil PM, J Bacteriol Aug. 1993; 175 (15): 4817–23.

Cloning, sequencing, and mapping of an alpha–actinin gene from the nematode *Caenorhabditis elegans*., Barstead RJ; Kleiman L; Waterston RH, Cell Motil Cytoskeleton 1991; 20 (1): 69–78.

Congenitally defective aldosterone biosynthesis in humans: the involvement of point mutations of the P–45OC18 gene (CYP11B2) in CMO II deficient patients (published erratum appears in Biochem Biophys Res Commun May 15, 1992; 184 (3) :1529–301 ., Mitsuuchi Y; Kawamoto T; Naiki Y; Miyahara K; Toda K; Kuribayashi I; Orii T; Yasuda K; Miura K; Nakao K; et al, Biochem Biophys Res Commun Jan. 31, 1992; 182 (2): 974–9.

Cys209 Ser mutation in the platelet membrane glycoprotein Ib alpha gene is associated with Bernard–Soulier syndrome., Simsek S; Noris P; Lozano M; Pico M; Von dem Borne AE; Ribera A; Gallardo D, Br J Haematol De. 1994; 88 (4) : 839–44.

Deficiency of coagulation factor XIII A subunit caused by the dinucleotide deletion at the 51 end of exon III., Kamura T; Okamura T; Murakawa M; Tsude H; Teshima T; Shibuya T; Harada M; Niho Y, J Clin Invest Aug. 1992; 90 (2) : 315–9.

Detection of novel germ–line p53 mutations in diverse–cancer–prone families identified by selecting patients with childhood adrenocortical carcinoma., Sameshima Y; Tsunematsu Y; Watanabe S; Tsukamoto T; Kawa–ha K; Hirata Y; Mizoguchi H; Sugimura T; Terada M; Yokota J. J Natl Cancer Inst May 6 1992; 84 (9):703–7.

Diagnosis of pancreatic lesions using fine needle aspiration cytology: detection of K–ras point mutations using solid phase minisequencing., Ihalainen J; Taavitsainen M; Salmivaara T; Palotie A, J Clin Pathol Dec. 1994; 47 (12) 1082–4.

[DNA diagnosis: its induction, problem and future—with special reference to congenital goiter]., 16 REFS, Ieiri T; Ohuchi T; Oikawa S, Rinsho Byori Sep. 1994; 42 (9) : 931–7.

DNA enzyme immunoassay: a rapid and convenient calorimetric method for diagnosis of cystic fibrosis., Mazza C; Mantero G; Primi D, Mol Cell Probes Dec. 1991; 5 (6): 459–66.

Frengen et al., Dual analyte assay based on Particle types of Different Size measured by Flow Cytometry, Journal of Immunological Methods 178: 141–151 (1994).

Fulwyler, et al., "Immunoreactive Bead (IRB) Assay for the Quantitative and Simultaneous Flow Cytometric Detection of Multiple Analytes," Cytometry, Supplement 2, p. 19.

Genetic analysis of amplified DNA with immobilized secluence–specific oligonucleotide probes., Saiki RK; Walsh PS; Levenson CH; Erlich HA, Proc Natl Acad Sci U S A Aug. 1989; 86 (16): 6230–4.

Genetic analysis of a large–kindred exhibiting type I protein C deficiency and associated thrombosis., Tomczak JA; Ando RA; Sobel HG; Bovill EG; Long GL, Thromb Res May 1, 1994; 74 (3): 243–54.

Genetic analysis of familial amyloidotic polyneuropathy, an autosomal dominant disease., Sakaki Y; Sasaki H; Yoshioka K; Furuya H, Clin Chim Acta Dec. 15, 1989; 185 (3): 291–7.

Genetic analysis of Japanese pedigrees with Leber's hereditary optic neuropathy., Nakamura M, Kobe J Med Sci Dec. 1993; 39 (5–6): 171–82.

Genetic analysis of p53 and RB1 tumor–suppressor genes in blast crisis of chronic myeloid leukemia., Gaidano G; Serra A; Guerrasio A; Rege–Cambrin G; Mazza U; Saglio G, Ann Hematol Jan. 1994; 68 (1): 3–7.

Genetic analysis of the arylamine N–acetyltransferase polymorphism in breast cancer patients., Agundez JA; Ladero JM; Olivera M; Abildua R; Roman JM; Benitez J, Oncology Jan.–Feb. 1995; 52 (1): 7–11.

Genetic analysis of the cellular oncogene fos in patients with chromosome 14 encoded Alzheimer's disease., Cruts M: Backhovens H; Martin JJ; van Broeckhoven C, Neurosci Lett Jun. 6, 1994; 174 (1): 97–100.

Genetic analysis of the interethnic difference between Chinese and Cauccasians in the polymorphic metabolism of debrisoquine and codeine., Johansson I; Yue QY; Dahl ML; Heim M; Sawe J; Bertilsson L; Meyer UA; Sjoqvist F; Ingelman–Sundberg M, Eur J Clin Pharmacol 1991: 40 (6):553–6.

Genetic analysis using polymerase chain reaction–amplified DNA and immobilized oligonucleotide probes: reverse dot–blot typing., Kawasaki E; Saiki R; Erlich H, methods Enzymol 1993: 218: 369–81.

Heterozygosity for the "DN allele" (G533–greater than A) of the beta–hexosaminidase alpha subunit gene identified by direct DNA sequencing in a family with the Di variant of GM2–gangliosidosis., Whitley CB; Anderson RA; McIvor RS, Neuropediatrics Apr. 1992; 23 (2) : 96–101.

High resolution genetic analysis suggests one ancestral predisposing haplotye for the origin of the myotonic dystrophy mutation., Neville CE; Mahadevan MS; Barcelo JM; Korneluk RG, Hum Mol Genet Jan. 1994; 3 (1): 45–51.

(MELAS associated with diabetes mellitus and point mutation in mitochondrial DNA., Onishi H; Inoue K; Osaka H; Nagatomo H; Ando N; Yamada Y; Suzuki K; Hanihara T; Kawamoto S; Okuda K; et al, No To Shinkei Mar. 1992; 44 (3) : 259–64.

Molecular and genetic analysis of a compound heterozygote for dysprothrombinemia of prothrombin Tokushima and hypoprothrombinemia., Iwahana H; Yoshimoto K; Shigekiyo T; Shirakami A; Saito S; Itakura M, Am J Hum Genet Dec. 1992; 51 (6): 1386–95.

(Molecular genetic analysis of a Japanese family with Fabry disease., Ishiura M, Nippon Rinsho Sep. 1993; 51 (9): 2286–92.

Molecular genetic analysis of chromosome lip in familial tumour [see comments], Baird PN; Pritchard J; Cowell JK, Br J Cancer Jun. 1994; 69 (6): 1072–7.

Molecular genetic analysis of the von Recklinghausen neurofibromatosis (NFI) gene using polymerase chain reaction–single strand conformation polymorphism (PCR–SSCP) method., Sawada S; Honda M; Niimura M, J Dermatol May 1994; 21 (5) 294–300.

[Molecular genetic analysis of 2 Chilean cystic fibrosis patients and their families]., Analisis genetico molecular de la fibrosis quistica en dos pacientes chilenos y sus familias., Rios J; orellana 0; Riveros N, Rev Med Chil Jan. 1994; 122 (1): 13–8.

Multiple PCR analyses on trace amounts of DNA extracted from fresh and paraffin wax embedded tissues after random hexamer primer PCR amplification., Peng HZ; Isaacson PG; Diss TC; Pan LX, J Clin Pathol Jul. 1994; 47 (7) : 605–8.

Mutation of Ki–ras and N–ras oncogenes in myelodysplastic syndromes., Lyons J; Janssen JW; Bartram C; Layton M; Mufti Gi, Blood Jun. 1998; 71 (6) : 1707–12.

Mutational activation of the c–K–ras gene in human pancreatic carcinoma., 9G REFS, Shibata D; Capella G; Perucho M, Baillieres Clin Gastroenterol Mar. 1990; 4 (1): 151–69.

PCR amplification of specific alleles: rapid detection of known mutations and polymorphisms., 20 REFS, Bottema CD; Sommer SS, Mutat Res Jul. 1993; 288 (1): 93–102.

Pelizaeus–Merzbacher disease: an X–linked neurologic disorder of myelin metabolism with a novel mutation in the gene encoding proteolipid protein., Gencic S; Abuelo D; Ambler M; Hudson LD, Am J Hum Genet Sep. 1989; 45 (3) : 435–42.

Polymerase chain reaction in diagnostic pathology)., Die Polymerase–Kettenreaktion in der diagnostischen Pathologie., 15 REFS, Dietel M, Verh Dtsch Ges Pathol 1994; 78: 136–45.

Prenatal diagnosis and treatment of 21–hydroxylase deficiency., 38 REFS, Forest MG; David M; Morel Y, J Steroid Biochem Mol Biol Apr. 1993; 45 (1–3):75–82.

p53 protein detected by immunohistochemical staining is not always mutant., MacGeoch C; Barnes DM; Newton JA; Mohammed S; Hodgson SV; Ng M; Bishop DT; Spurr NK, Dis Markers Dec. 1993; 11 (5–6): 239–50.

Rapid preparation of tissue DNA from paraffin–embedded blocks and analysis by polymerase chain reaction., Chen BF; Clejan S, J Histochem Cytochem May 1993; 41 (5): 765–8.

Reliability of polymerase chain reaction (PCR) analysis of single cells for preimplantation genetic diagnosis., Strom CM; Rechitsky S; Wolf G; Verlinsky Y, J Assist Reprod Genet Feb. 1994; 11 (2): 55–62.

[RFLP–PCR technique for exclusion of carrier status of the mutated Rb gene]. Technika RFLP–PCR w wykluczeniu nosicielstwa zmutowanego genu Rb., zajaczek S; Podolski J; Lubinski J; Roslawska A; Krzystolik Z; Sagan Z, Klin Oczna Jun. 1993; 95 (6)L 216–8 Abstract only.

Ser–752—>Pro mutation in the cytoplasmic domain of integrin beta 3 subunit and defective activation of platelet integrin alpha IIb beta 3 (glycoprotein IIb–IIIa) in a variant of Glanzmann thrombasthenia., Chen YP; Djaffar I; Pidard D; Steiner B; Cieutat AM; Caen JP; Rosa TP, Proc Natl Acad Sci U S A Nov. 1, 1992; 89 (21): 10169–73.

[VNTR–PCR in diagnosis of inherited Rb gene mutation]., VNTR–PCR w diagnostyce nosicielstwa zmutowanego genu Rb., Zajaczek S; Gorski B; Debniak T; Podolski J; Lubinski J; Krystolik Z; Iwanick T; Sagan Z, Klin Oczna Aug.–Sep. 1994; 96 (8–9): 290–2 Abstract only.

Yang et al., "Detection of Hepatitis B Virus in Plasma Using Flow Cytometric Analyses of Polymerase Chain Reaction–Amplified DNA Incorporating Digonigenin–11–duTP," Blood, vol. 81(4), pp. 1083–1088.

* cited by examiner

SAMPLE BASELINE DATA ACQUISITION

| ANALYTE | $C_1$: SIDE LIGHT SCATTER | $C_2$: FORWARD LIGHT SCATTER | $C_3$: ORANGE FLUORESCENCE | $C_4$: RED FLUORESCENCE | $F_1$: GREEN FLUORESCENCE |
|---|---|---|---|---|---|
| 1 | $\mu = 560$<br>$\sigma = 5.1$ | * | $\mu = 0$ | $\mu = 0$ | $\mu = 170$<br>$\sigma = 1.3$ |
| 2 | $\mu = 579$<br>$\sigma = 5.1$ | * | $\mu = 48$<br>$\sigma = 0.69$ | $\mu = 368$<br>$\sigma = 1.92$ | $\mu = 170$<br>$\sigma = 1.3$ |
| 3 | $\mu = 519$<br>$\sigma = 4.56$ | * | $\mu = 98$<br>$\sigma = 0.99$ | $\mu = 550$<br>$\sigma = 2.35$ | $\mu = 170$<br>$\sigma = 1.3$ |
| 4 | $\mu = 519$<br>$\sigma = 4.56$ | * | $\mu = 0$ | $\mu = 527$<br>$\sigma = 2.30$ | $\mu = 170$<br>$\sigma = 1.3$ |

\* Not used in illustrative example

FIG. 5

| ASSAY NAME | SUBSET TOKEN | SUBSET NAME | $F_1$'s BASE VALUE | $F_1$'s STANDARD DEVIATION | TEST TOKEN TYPE |
| --- | --- | --- | --- | --- | --- |
| TEST_ASSAY | 46 | KRAS CODON 46 WILDTYPE | 170 | 1.3 | 0 |
| TEST_ASSAY | 21 | KRAS CODON 21 MUTANT | 170 | 1.3 | 0 |
| TEST_ASSAY | 50 | KRAS CODON 50 MUTANT | 170 | 1.3 | 0 |
| TEST_ASSAY | 5 | KRAS CODON 5 MUTANT | 170 | 1.3 | 0 |

FIG. 6

SAMPLE DISCRIMINANT FUNCTION TABLE

| ASSAY NAME | ROW ID | PARAMETER | LOW VALUE | HIGH VALUE | TRUE ROW ID | FALSE ROW ID | TRUE TOKEN | FALSE TOKEN |
|---|---|---|---|---|---|---|---|---|
| TEST_ASSAY | 0 | $C_1$ | 500 | 620 | 1 | 0 | 0 | 0 |
| TEST_ASSAY | 1 | $C_4$ | 0 | 514 | 2 | 3 | 0 | 0 |
| TEST_ASSAY | 2 | $C_4$ | 0 | 200 | 0 | 0 | 50 | 5 |
| TEST_ASSAY | 3 | $C_3$ | 0 | 98 | 0 | 0 | 46 | 21 |

FIG. 7

SAMPLE RESULTS TABLE

| ASSAY NAME | SUBSET TOKEN | COUNT | SUM | OVER COUNT | UNDER COUNT |
|---|---|---|---|---|---|
| TEST_ASSAY | 46 | 1,000 | 71,111 | * | * |
| TEST_ASSAY | 21 | 1,000 | 90,000 | * | * |
| TEST_ASSAY | 50 | 1,000 | 1,700,000 | * | * |
| TEST_ASSAY | 5 | 1,000 | 70,000 | * | * |

\* Not used in illustrative example

FIG. 10

| ASSAY NAME | SUBSET TOKEN | OUTCOME ID | TEST-TYPE TOKEN | LOW VALUE | HIGH VALUE | INTERPRETATION |
|---|---|---|---|---|---|---|
| test_assay | 5 | 1 | 1 | 10 | 667 | Identical complementary strand |
| test_assay | 5 | 2 | 1 | 668 | 970 | Similar oligo |
| test_assay | 5 | 3 | 1 | 971 | 2,000 | Not found in sample |
| test_assay | 21 | 1 | 1 | 10 | 667 | Identical complementary strand |
| test_assay | 21 | 2 | 1 | 668 | 970 | Similar oligo |
| test_assay | 21 | 3 | 1 | 971 | 2,000 | Not found in sample |
| test_assay | 50 | 1 | 1 | 10 | 667 | Identical complementary strand |
| test_assay | 50 | 2 | 1 | 668 | 970 | Similar oligo |
| test_assay | 50 | 3 | 1 | 971 | 2,000 | Not found in sample |
| test_assay | 46 | 1 | 1 | 10 | 667 | Identical complementary strand |
| test_assay | 46 | 2 | 1 | 558 | 970 | Similar oligo |
| test_assay | 46 | 3 | 1 | 971 | 2,000 | Not found in sample |

FIG. 11

Assay Definition Table

| Antigen | Microsphere identified via dye color | Antigen-Microsphere Complex | Fluorescent Antibody ($F_m$) | Subset Token |
|---|---|---|---|---|
| LH | 1 μm Crimson Beads | LH-Crimson Beads | anti-LH | 18 |
| TSH | 1 μm Dark Red Beads | TSH-Dark Red Beads | anti-TSH | 45 |
| IgA | 3 μm Clear Beads | IgA-Clear Beads | anti-Ig | 50 |

FIG. 13A

Baseline Data Table

| Bead Subset | $C_1$ mean side light scatter | $C_2$ mean orange fluorescence | $C_3$ mean red fluorescence | $F_m$ mean green fluorescence |
|---|---|---|---|---|
| LH | 38.46 | 1.71 | 30.69 | 9.15 |
| TSH | 40.37 | 0.00 | 88.62 | 5.44 |
| IgA | 167 | 0.00 | 0.00 | 7.83 |

FIG. 13B

Discriminant Function Table

| ROW ID | Parameter | Low Value | High Value | True Node | False Node | True Token | False Token |
|---|---|---|---|---|---|---|---|
| 0 | $C_3$ | 0 | 5 | 3 | 1 | 0 | 0 |
| 1 | $C_1$ | 400 | 420 | 2 | 0 | 0 | 0 |
| 2 | $C_3$ | 0 | 454 | 0 | 0 | 18 | 45 |
| 3 | $C_1$ | 600 | 580 | 0 | 0 | 50 | 0 |

FIG. 13C

Interpretation Table
$-F_m \pm 1.5 \log (\text{baseline } F_m \text{ value}) -$

| Subset Token | Outcome ID | Test-Type Token | Low Value | High Value | Interpretation |
|---|---|---|---|---|---|
| 18 | 1 | 1 | 289.35 | - | Anti-LH found. |
| 18 | 2 | 1 | - | 289.35 | Anti-LH not found. |
| 45 | 1 | 1 | 172.03 | - | Anti-TSH found. |
| 45 | 2 | 1 | - | 172.03 | Anti-TSH not found. |
| 50 | 1 | 1 | 247.61 | - | Anti-IgA found. |
| 50 | 2 | 1 | - | 247.61 | Anti-IgA not found. |

FIG. 13D

Results Table

| Sample | Antibody Present | Measured $F_m$ Subset 18 | Measured $F_m$ Subset 45 | Measured $F_m$ Subset 50 |
|---|---|---|---|---|
| 1 | Anti-IgA | 70 | 10 | 6049 |
| 2 | anti-LH | 132 | 442 | 180 |
| 3 | anti-TSH | 2124 | 108 | 182 |
| 4 | anti-IgA + anti-TSH | 2152 | 115 | 5917 |

FIG. 13E

MULTIPLEXED ANALYSIS OF CLINICAL SPECIMENS APPARATUS AND METHOD

RELATED APPLICATIONS

This patent application claims priority to U.S. patent application Ser. No. 08/540,814, filed Oct. 11, 1995, and U.S. Pat. No. 5,736,330, filed Oct. 11, 1995, and PCT application Ser. No. PCT/US/96/16198, filed Oct. 10, 1996, all of which are incorporated herein by reference, including all reference cited therein.

Microfiche appendix A contains a listing of selected Visual Basic and C programming source code in accordance with the inventive multiplexed assay method. Microfiche appendix A, comprising 1 sheet having a total of 58 frames, contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

The invention relates generally to laboratory diagnostic and genetic analysis and, more particularly, to a flow cytometric method for the simultaneous and multiplexed diagnostic and genetic analysis of clinical specimens.

Analysis of clinical specimens is important in science and medicine. A wide variety of assays to determine qualitative and/or quantitative characteristics of a specimen are known in the art. Detection of multiple analytes, or separately identifiable characteristics of one or more analytes, through single-step assay processes are presently not possible or, to the extent possible, have provided only very limited capability and have not yielded satisfactory results. Some of the reasons for these disappointing results include the extended times typically required to enable the detection and classification of multiple analytes, the inherent limitations of known reagents, the low sensitivities achievable in prior art assays which often lead to significant analytical errors and the unwieldy collection, classification, and analysis of prior art algorithms vis a vis the large amounts of data obtained and the subsequent computational requirements to analyze that data.

Clearly, it would be an improvement in the art to have adequate apparatus and methods for reliably performing real-time multiple determinations, substantially simultaneously, through a single or limited step assay process. A capability to perform simultaneous, multiple determinations in a single assay process is known as "multiplexing" and a process to implement such a capability is a "multiplexed assay."

Flow Cytometry

One well known prior art technique used in assay procedures for which a multiplexed assay capability would be particularly advantageous is flow cytometry. Flow cytometry is an optical technique that analyzes particular particles in a fluid mixture based on the particles' optical characteristics using an instrument known as a flow cytometer. Background information on flow cytometry may be found in Shapiro, "Practical Flow Cytometry," Third Ed. (Alan R. Liss, Inc. 1995); and Melamed et al., "Flow Cytometry and Sorting," Second Ed. (Wiley-Liss 1990), which are incorporated herein by reference. a Flow cytometers hydrodynamically focus a fluid suspension of particles into a thin stream so that the particles flow down the stream in substantially single file and pass through an examination zone. A focused light beam, such as a laser beam illuminates the particles as they flow through the examination zone. Optical detectors within the flow cytometer measure certain characteristics of the light as it interacts with the particles. Commonly used flow cytometers such as the Becton-Dickinson Immunocytometry Systems "FACSCAN" (San Jose, Calif.) can measure forward light scatter (generally correlated with the refractive index and size of the particle being illuminated), side light scatter (generally correlated with the particle's size), and particle fluorescence at one or more wavelengths. (Fluorescence is typically imparted by incorporating, or attaching a fluorochrome within the particle.) Flow cytometers and various techniques for their use are described in, generally, in "Practical Flow Cytometry" by Howard M. Shapiro (Alan R. Liss, Inc., 1985) and "Flow Cytometry and Sorting, Second Edition" edited by Melamed et al. (Wiley-Liss, 1990).

One skilled in the art will recognize that one type of "particle" analyzed by a flow cytometer may be man-made microspheres or beads. Microspheres or beads for use in flow cytometry are generally known in the art and may be obtained from manufacturers such as Spherotech (Libertyville, Ill.), and Molecular Probes (Eugene, Oreg.).

Although a multiplexed analysis capability theoretically would provide enormous benefits in the art of flow cytometry, very little multiplexing capability has been previously achieved. Prior multiplexed assays have obtained only a limited number of determinations. A review of some of these prior art techniques is provided by McHugh, "Flow Microsphere Immunoassay for the Quantitative and Simultaneous Detection of Multiple Soluble Analytes," in Methods in Cell Biology, 42, Part B, (Academic Press, 1994). For example, McHugh et al., "Microsphere-Based Fluorescence Immunoassays Using Flow Cytometry Instrumentation," in Clinical Flow Cytometry Ed. K. D. Bauer, et al., Williams and Williams, Baltimore, Md., 1993, 535–544, describe an assay where microspheres of different sizes are used as supports and the identification of microspheres associated with different analytes was based on distinguishing a microsphere's size. Other references in this area include Lindmo, et al., "Immunometric Assay by Flow Cytometry Using Mixtures of Two Particle Types of Different Affinity," J. Immun. Meth., 126, 183–189 (1990); McHugh, "Flow Cytometry and the Application of Microsphere-Based Fluorescence Immunoassays," Immunochemica, 5, 116 (1991); Horan et al., "Fluid Phase Particle Fluorescence Analysis: Rheumatoid Factor Specificity Evaluated by Laser Flow Cytophotometry" in Immunoassays in the Clinical Laboratory, 185–198 (Liss 1979); Wilson et al., "A New Microsphere-Based Immunofluorescence Assay Using Flow Cytometry," J. Immunological Methods, 107, 225–230 (1988); and Fulwyler et al., "Flow Microsphere Immunoassay for the Quantitative and Simultaneous Detection of Multiple Soluble Analytes," Meth. Cell Biol., 33, 613–629 (1990).

The above cited methods have been unsatisfactory as applied to provide a filly multiplexed assay capable of real-time analysis of more than a few different analytes. For example, certain of the assay methods replaced a single ELISA procedure with a flow cytometer-based assay. These methods were based on only a few characteristics of the particles under analysis and enabled simultaneous determination of only a very few analytes in the assay. Also, the analytic determinations made were hampered due to software limitations including the inability to perform real-time processing of the acquired assay data. In summary, although it has been previously hypothesized that flow cytometry may possibly be adapted to operate and provide benefit in a multiple analyte assay process, such an adaptation has not in reality been accomplished.

Analysis of Genetic Information

The availability of genetic information and association of disease with mutation(s) of critical genes has generated a rich field of clinical analysis. In particular, the use polymerase chain reaction (PCR) and its variants have facilitated genetic analysis. A major advance in this field is described in our co-pending and contemporaneously filed U.S. Application entitled "Methods and Compositions for Flow Cytometric Determination of DNA Sequences." This co-pending application describes a powerful flow cytometric assay for PCR products, which may be multiplexed in accordance with the present invention. A multiplexed flow cytometric assay for PCR reaction products would provide a significant advantage in the field of genetic analysis.

Recent advances in genetic analyses have provided a wealth of information regarding specific mutations occurring in particular genes in given disease states. Consequently, use of an individual's genetic information in diagnosis of disease is becoming increasingly prevalent. Genes responsible for disease have been cloned and characterized in a number of cases, and it has been shown that responsible genetic defects may be a gross gene alteration, a small gene alteration, or even in some cases, a point mutation. There are a number of reported examples of diseases caused by genetic mutations. Testing of gene expression by analysis of cDNA or mRNA, and testing of normal genes and alleles, as in cases of tissue typing and forensics, are becoming ,widespread. Other uses of DNA analysis, for example in paternity testing, etc., are also important and can be used in accordance with the invention.

Current techniques for genetic analysis have been greatly facilitated by the development and use of polymerase chain reaction (PCR) to amplf selected segments of DNA. The power and sensitivity of the PCR has prompted its application to a wide variety of analytical problems in which detection of DNA or RNA sequences is required.

PCR is capable of amplifying short fragments of DNA, providing short (20 bases or more) nucleotides are supplied as primers. The primers anneal to either end of a span of denatured DNA target and, upon renaturation, enzymes synthesize the intervening complementary sequences by extending the primer along the target strand. During denaturation, the temperature is raised to break apart the target and newly synthesized complementary sequence. Upon cooling, renaturation and annealing, primers bind to the target and the newly made opposite strand and now the primer is extended again creating the complement. The result is that in each cycle of heating and renaturation followed by primer extension, the amount of target sequence is doubled.

One major difficulty with adoption of PCR is the cumbersome nature of the methods of analyzing the reaction's amplified DNA products. Methods for detecting genetic abnormalities and PCR products have been described but they are cumbersome and time consuming. For example, U.S. Pat. No. 5,429,923 issued Jul. 4, 1995 to Seidman, et al., describes a method for detecting mutations in persons having, or suspected of having, hypertrophic cardiomyopathy. That method involves amplifying a DNA sequence suspected of containing the disease associated mutation, combining the amplified product with an RNA probe to produce an RNA-DNA hybrid and detecting the mutation by digesting unhybridized portions of the RNA strand by treating the hybridized product with an RNAse to detect mutations, and then measuring the size of the products of the RNAse reaction to determine whethercleavage of the RNA molecule has occurred.

Other methods used for detecting mutations in DNA sequences, including direct sequencing methods (Maxim and Gilbert, Proc. Natl. Acad. Sci. U.S.A., 74, 560–564, 1977); PCR amplification of specific alleles, PASA (Botttema and Sommer, Muta. Res., 288, 93–102, 1993); and reverse dot blot method (Kawasaki, et al., Methods in Enzymology, 218, 369-81, 1993) have been described. These techniques, while useful, are time consuming and cumbersome and for that reason are not readily adaptable to diagnostic assays for use on a large scale.

At least one use of flow cytometry for the assay of a PCR product has been reported but that assay has not been adapted to multiplexing. See Vlieget et al., "Quantitation of Polymerase Chain Reaction Products by Hybridization-Based Assays with Fluorescent Colorimetric, or Chemiluminescent Detection," Anal. Biochem., 205, 1–7 (1992). In Vlieger et al. a PCR product was labeled using primers that contained biotinylated nucleotides. Unreacted primers were first removed and the amplified portion annealed with a labeled complementary probe in solution. Beaded microspheres of avidin were then attached to the annealed complementary material. The avidin beads bearing the annealed complementary material were then processed by a flow cytometer. The procedure was limited, inter alia, in that avidin beads having only a single specificity were employed. Further, real-time analysis of the assay's data was not possible.

Data Manipulation

The large volume of data typically generated during flow cytometric multiple analyte assays, combined with the limited capabilities of prior techniques to collect, sort and analyze such data have provided significant obstacles in achieving a satisfactory multiplexed assay. The computing methods used in prior art flow cytometric analyses have generally been insufficient and unsuited for accurately and timely analyzing large volumes of data such as would be generated by multiplexed assays; particularly when more than two analytes (or properties of a single analyte) are to be simultaneously determined.

The present invention enables the simultaneous determination of multiple distinct analytes to a far greater degree than existing techniques. Further, the invention provides an improved data classification and analysis methodology that enables the meaningful analysis of highly multiplexed assays in real-time. The invention is broadly applicable to multiplexed analysis of a number of analytes in a host of bioassays in which there is currently a need in the art.

The present invention provides improved methods, instrumentation, and products for detecting multiple analytes in a fluid sample by flow cytometric analysis and for analyzing and presenting the data in real-time. An advantage of the invention is that it allows one rapidly and simultaneously to detect a wide variety of analytes of interest in a single assay step.

The invention employs a pool of bead subsets. The individual subsets are prepared so that beads within a subset are relatively homogeneous but differ in at least one distinguishing characteristic from beads in any other subset. Therefore, the subset to which a bead belongs can readily be determined after beads from different subsets are pooled.

In a preferred embodiment, the beads within each subset are uniform with respect to at least three and preferably four known classification parameter values measured with a flow cytometer: e.g., forward light scatter ($C_1$) which generally correlates with size and refractive index; side light scatter ($C_2$) which generally correlates with size; and fluorescent emission in at least one wavelength ($C_3$), and preferably in two wavelengths ($C_3$ and $C_4$), which generally results from the presence of fluorochrome(s) in or on the beads. Because beads from different subsets differ in at least one of the above listed classification parameters, and the classification parameters for each subset are known, a bead's subset identity can be verified during flow cytometric analysis of the pool in a single assay step and in real-time.

Prior to pooling subsets of beads to form a beadset, the beads within each subset can be coupled to a reactant that will specifically react with a given analyte of interest in a fluid sample to be tested. Usually, different subsets will be coupled to different reactants so as to detect different analytes. For example, subset 1 may be labeled so as to detect analyte A (AnA); subset 2 may be labeled so as to detect analyte B (AnB); etc.

At some point prior to assay, the variously labeled subsets are pooled. The pooled beads, or beadset, are then mixed with a fluid sample to test for analytes reactive with the various reactants bound to the beads. The system is designed so that reactions between the reactants on the bead surfaces and the corresponding analytes in the fluid sample will cause changes in the intensity of at least one additional fluorescent signal ($F_m$) emitted from a fluorochrome that fluoresces at a wavelength distinct from the wavelengths of classification parameters $C_3$ or $C_4$. The $F_m$ signal serves as a "measurement signal," that is, it indicates the extent to which the reactant on a given bead has undergone a reaction with its corresponding analyte. The $F_m$ signal may result from the addition to the assay mixture of fluorescently labeled "secondary" reagent that binds to the bead surface at the site where a reactant-analyte reaction has occurred.

When the mixture (pooled beads and fluid sample) is run through a flow cytometer, each bead is individually examined. The classification parameters, e.g., $C_1$, $C_2$, $C_3$, and $C_4$, are measured and used to classify each bead into the subset to which it belongs and, therefore, identify the analyte that the bead is designed to detect. The $F_m$ value of the bead is determined to indicate the concentration of analyte of interest in the fluid sample. Not only are many beads from each subset rapidly evaluated in a single run, multiple subsets are evaluated in a single run. Thus, in a single-pass and in real-time a sample is evaluated for multiple analytes. Measured $F_m$ values for all beads assayed and classified as belonging to a given subset may be averaged or otherwise manipulated statistically to give a single meaningful data point, displayed in histogram format to provide information about the distribution Of $F_m$ values within the subset, or analyzed as a function of time to provide information about the rate of a reaction involving that analyte.

In a preferred embodiment, the beads will have two or more fluorochromes incorporated within or on them so that each of the beads in a given subset will possess at least four different classification parameters, e.g., $C_1$, $C_2$, $C_3$, and $C_4$. For example, the beads may be made to contain a red fluorochrome ($C_3$), such as nile red, and bear an orange fluorochrome ($C_4$), such as Cy3 or phycoerythrin. A third fluorochrome, such as fluorescein, may be used as a source of the $C_n$ or $F_m$ signal. As those of skill in the art will recognize, additional fluorochromes may be used to generate additional $C_n$ signals. That is, given suitable fluorochromes and equipment, those of skill in the art may use multiple fluorochromes to measure a variety of $C_n$ or $F_m$ values, thus expanding the multiplexing power of the system even further.

In certain applications designed for more quantitative analysis of analyte concentrations or for kinetic studies, multiple subsets of beads may be coupled to the same reactant but at varying concentrations so as to produce subsets of beads varying in density of bound reactant rather than in the type of reactant. In such an embodiment, the reactant associated with classification parameter $C_4$, for example, may be incorporated directly into the reactive reagent that is coupled to the beads, thereby allowing $C_4$ conveniently to serve as an indicator of density of reactant on the bead surface as well as an indicator of reactant identity.

To prepare subsets varying in reactant density one may, for example, select, isolate, or prepare a starting panel of different subsets of beads, each subset differing from the other subsets in one or more of $C_1$, $C_2$, or $C_3$. Each of those subsets may be further subdivided into a number of aliquots. Beads in each aliquot may be coupled with a reactant of choice that has been fluorescently labeled with a fluorochrome associated with $C_4$ (e.g., Analyte A labeled with Cy3) under conditions such that the concentration or density of reactant bound to the beads of each aliquot will differ from that of each other aliquot in the subset. Alternatively, an entire subset may be treated with the $C_4$ fluorochrome under conditions that produce a heterogeneous distribution of $C_4$ reactant on beads within the subset. The subset may then be sorted with a cell sorter on the basis of the intensity of $C_4$ to yield further subsets that differ from one another in $C_4$ intensity.

One limitation of the alternative embodiment of using $C_4$ labeled reactant as a classification agent is that one must design the system so that the value of $C_4$ as a classification parameter is not lost. Therefore, one must take care to assure that the $C_4$ intensities of all subsets carrying reagent A differs from the $C_4$ intensities of all subsets carrying reagents B, C, and so forth. Otherwise, $C_4$ would not be useful as a parameter to discriminate reactant A from reactant B, etc.

With either embodiment, the number of subsets that can be prepared and used in practice of the invention is theoretically quite high, but in practice will depend, inter alia, on the level of homogeneity within a subset and the precision of the measurements that are obtained with a flow cytometer. The intra-subset heterogeneity for a given parameter, e.g., forward angle light scatter $C_1$, correlates inversely with the number of different subsets for that parameter that can be discriminated by flow cytometric assay. It is therefore desirable to prepare subsets so that the coefficients of variation for the value of each classification parameter ($C_1$, $C_2$, $C_3$, and $C_4$) to be used in a given analysis is minimized. Doing this will maximize the number of subsets that can be discriminated by the flow cytometer. Bead subsets may be subjected to flow cytometric sorting or other procedures at various different points in preparation or maintenance of the bead subsets to increase homogeneity within the subset. Of course, with simple assays designed to detect only a few different analytes, more heterogeneity can be allowed within a subset without compromising the reliability of the assay.

In an illustrative embodiment set forth here to explain one manner in which the invention can work in practice, the beads are used to test for a variety of antibodies in a fluid sample. A panel of bead subsets having known varying $C_1$, $C_2$, $C_3$, and $C_4$ values is first prepared or otherwise obtained. The beads within each subset are then coupled to a given antigen of interest. Each subset receives a different antigen. The subsets are then pooled to form an assay beadset and may be stored for later use and/or sold as a commercial test kit.

In the assay procedure, the beads are mixed with the fluid to be analyzed for antibodies reactive with the variety of antigens carried on the beads under conditions that will permit antigen-antibody interaction. The beads are labeled with a "secondary" reagent that binds to antibodies bound to the antigens on the beads and that also bears the measurement fluorochrome associated with parameter $F_m$ (e.g., fluorescein). A fluoresceinated antibody specific for immunoglobulin may be used for this purpose. The beads are then run through a flow cytometer, and each bead is classified by its characteristic classification parameters as belonging to subset-1, subset-2, etc. At the same time, the presence of antibodies specific for antigen A, B, etc., can be detected by measuring green fluorescence, $F_m$, of each bead. The classification parameters $C_1$, $C_2$, $C_3$, and $C_4$ allow one to determine the subset to which a bead belongs, which serves as an identifier for the antigen carried on the bead. The $F_m$ value of the bead indicates the extent to which the antibody reactive with that antigen is present in the sample.

Although assays for antibodies were used above as an illustration, those of ordinary skill in the art will recognize that the invention is not so limited in scope, but is widely applicable to detecting any of a number of analytes in a sample of interest. For example, the methods described here may be used to detect enzymes or DNA or virtually any analyte detectable by virtue of a given physical or chemical reaction. A number of suitable assay procedures for detection and quantification of enzymes and DNA (particularly as the result of a PCR process) are described in more detail below.

The present invention also provides a significant advance in the art by providing a rapid and sensitive flow cytometric assay for analysis of genetic sequences that is widely applicable to detection of RNA, differing alleles, and any of a number of genetic abnormalities. In general, the methods of the present invention employ a competitive hybridization assay using DNA coupled microspheres and fluorescent DNA probes. Probes and microsphere-linked oligonucleotides could also include RNA, PNA, and non-natural nucleotide analogs.

In practice of the invention, oligonucleotides from a region of a gene of interest, often a polymorphic allele or a region to which a disease associated mutation has been mapped, are synthesized and coupled to a microsphere (bead) by standard techniques such as by carbodiimide coupling. A fluorescent oligonucleotide, complementary to the oligonucleotide on the bead, is also synthesized. To perform a test in accordance with the invention, DNA which is to be tested is purified and either assayed unamplified, or subjected to amplification by PCR, RT-PCR, or LCR amplification using standard techniques and PCR initiation probes directed to amplify the particular region of DNA of interest. The PCR product is then incubated with the beads under conditions sufficient to allow hybridization between the amplified DNA and the oligonucleotides present on the beads. A fluorescent DNA probe that is complementary to the oligonucleotide coupled to the beads is also added under competitive hybridization conditions. Aliquots of the beads so reacted are then run through a flow cytometer and the intensity of fluorescence on each bead is measured to detect the level of fluorescence which indicates the presence or absence of given sequences in the samples.

For example, when beads labeled with an oligonucleotide probe corresponding to a non-mutated (wild-type) DNA segment are hybridized with the PCR product from an individual who has a non-mutated wild-type DNA sequence in the genetic region of interest, the PCR product will effect a significant competitive displacement of fluorescent oligonucleotide probe from the beads and, therefore, cause a measurable decrease in fluorescence of the beads, e.g., as compared to a control reaction that did not receive PCR reaction product. If, on the other hand, a PCR product from an individual having a mutation in the region of interest is incubated with the beads bearing the wild-type probe, a significantly lesser degree of displacement and resulting decrease in intensity of fluorescence on the beads will be observed because the mutated PCR product will be a less effective competitor for binding to the oligonucleotide coupled to the bead than the perfectly complementary fluorescent wild-type probe. Alternatively, the beads may be coupled to an oligonucleotide corresponding to a mutation known to be associated with a particular disease and similar principles applied. In the multiplexed analysis of nucleic acid sequences, bead subsets are prepared with all known, or possible, variants of the sequence of interest and then mixed to form a bead set. The reactivity of the test sample, e.g. PCR product, with the wild-type sequence and other variants can then be assayed simultaneously. The relative reactivity of the PCR product with subsets bearing the wild-type or variant sequences identifies the sequence of the PCR product. The matrix of information derived from this type of competitive hybridization in which the test sequence and the entire panel of probe sequences react simultaneously allows identification of the PCR product as wild-type, known mutant, or unknown mutant. The invention thus provides one with the ability to measure any of a number of genetic variations including point mutations, insertions, deletions, inversions, and alleles in a simple, exquisitely sensitive, and efficient format.

FIG. 5 shows a baseline data acquisition table for an illustrative multiple analyte assay in accordance with the invention.

FIG. 6 shows an assay definition table in accordance with the invention.

FIG. 7 shows a discriminant table for an illustrative multiple analyte assay in accordance with the invention.

FIG. 10 shows a results table for an illustrative multiple analyte assay in accordance with the invention.

FIG. 11 shows a interpretation table for an illustrative multiple analyte assay in accordance with the invention.

FIGS. 13*a* through 13*e* show an assay database in accordance with the invention for a specific experimental example.

Figure 15A:
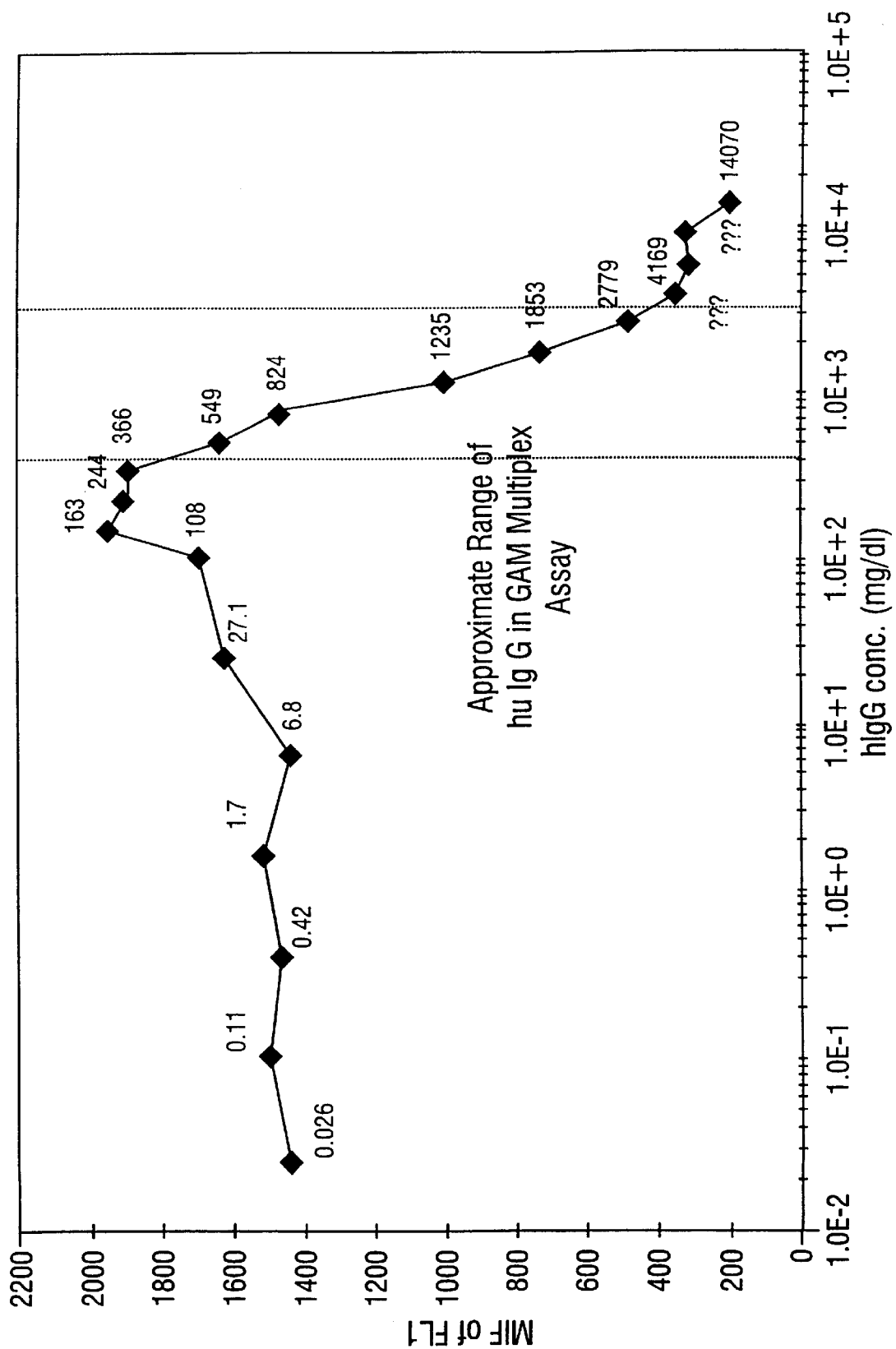
Figure 15B:
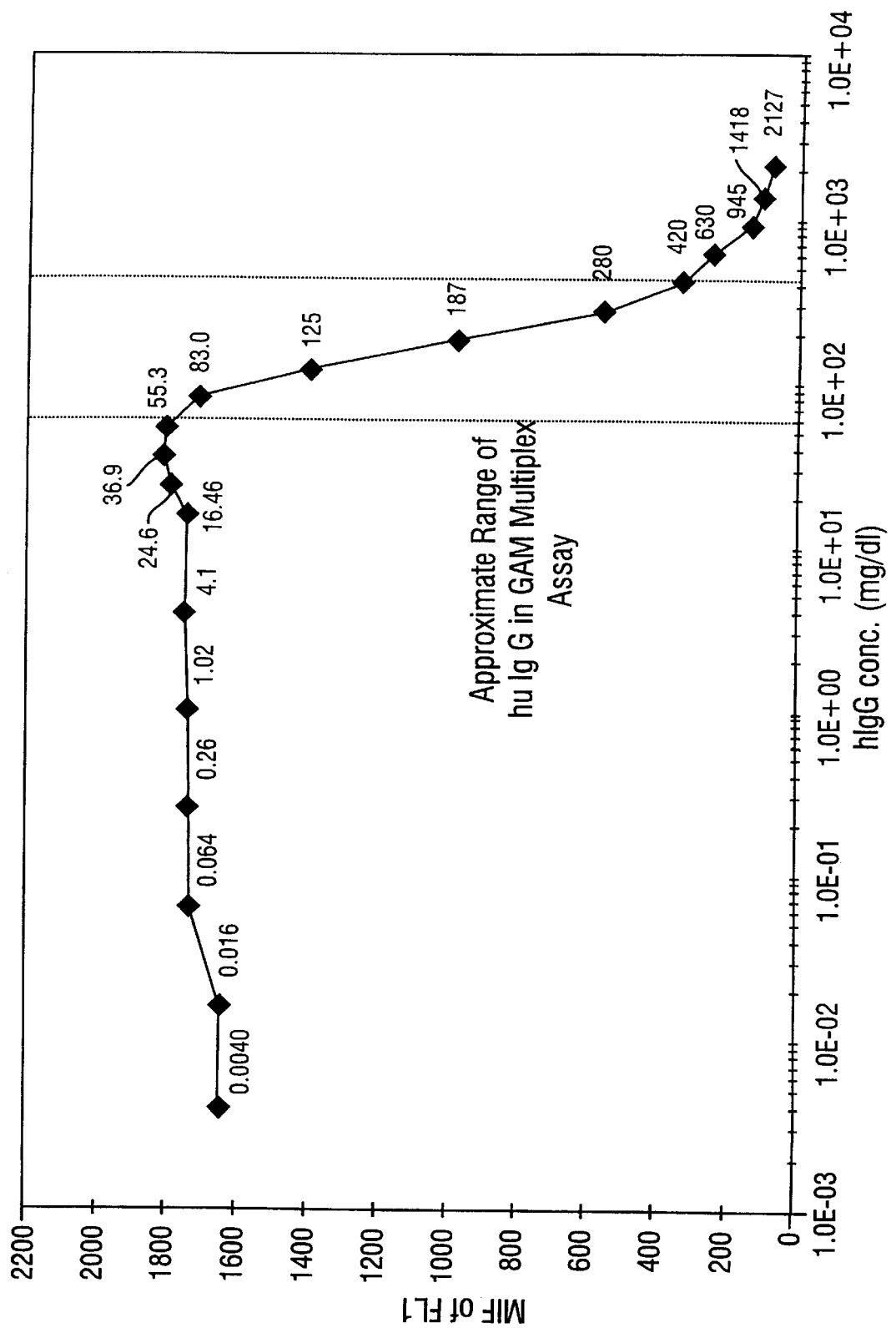

FIGS. 15*a*, 15*b*, and 15*c* show individual inhibition assays for IgG, IgA, and IgM antibodies.

Figure 16A:
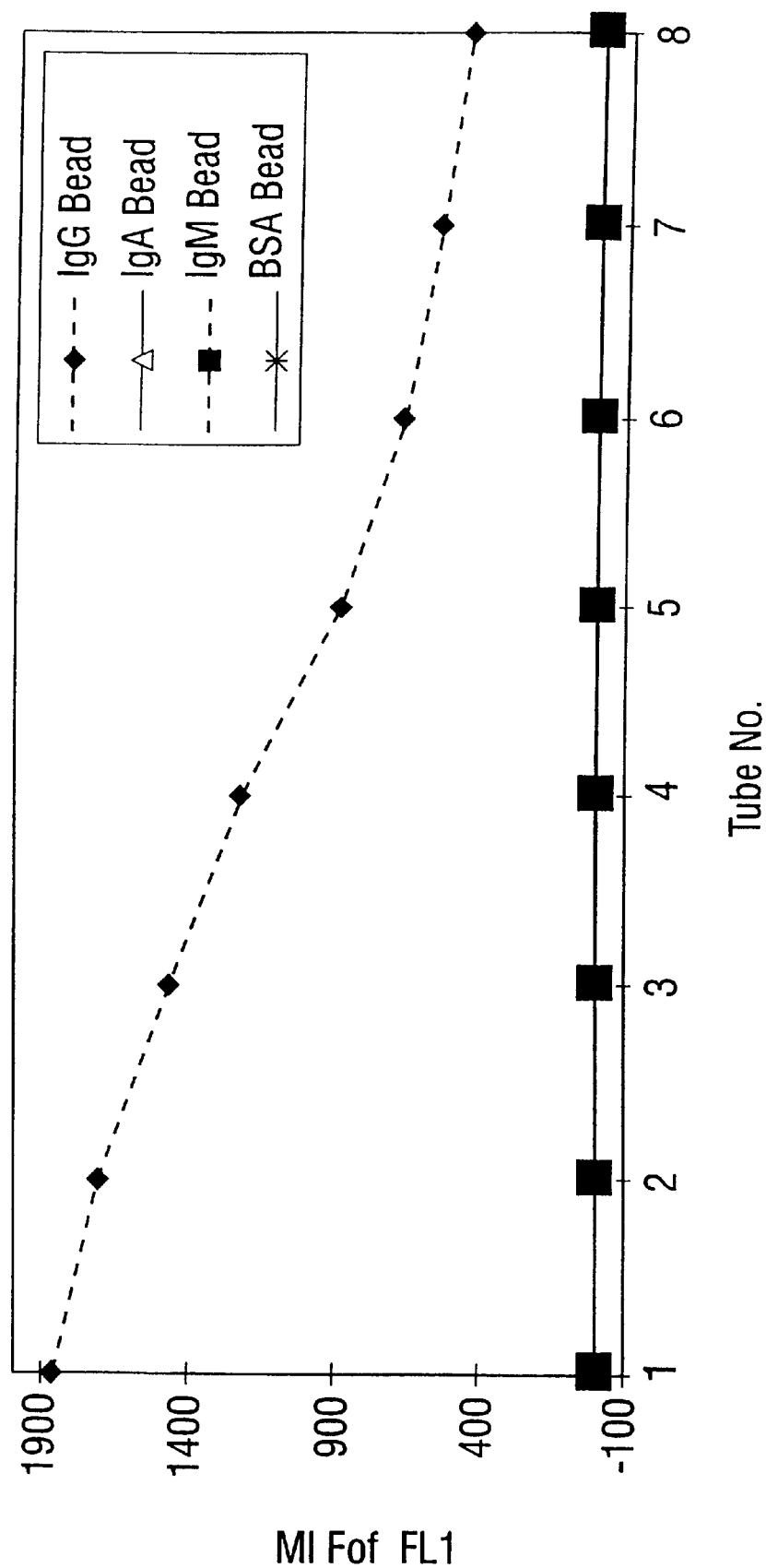
Figure 16B:
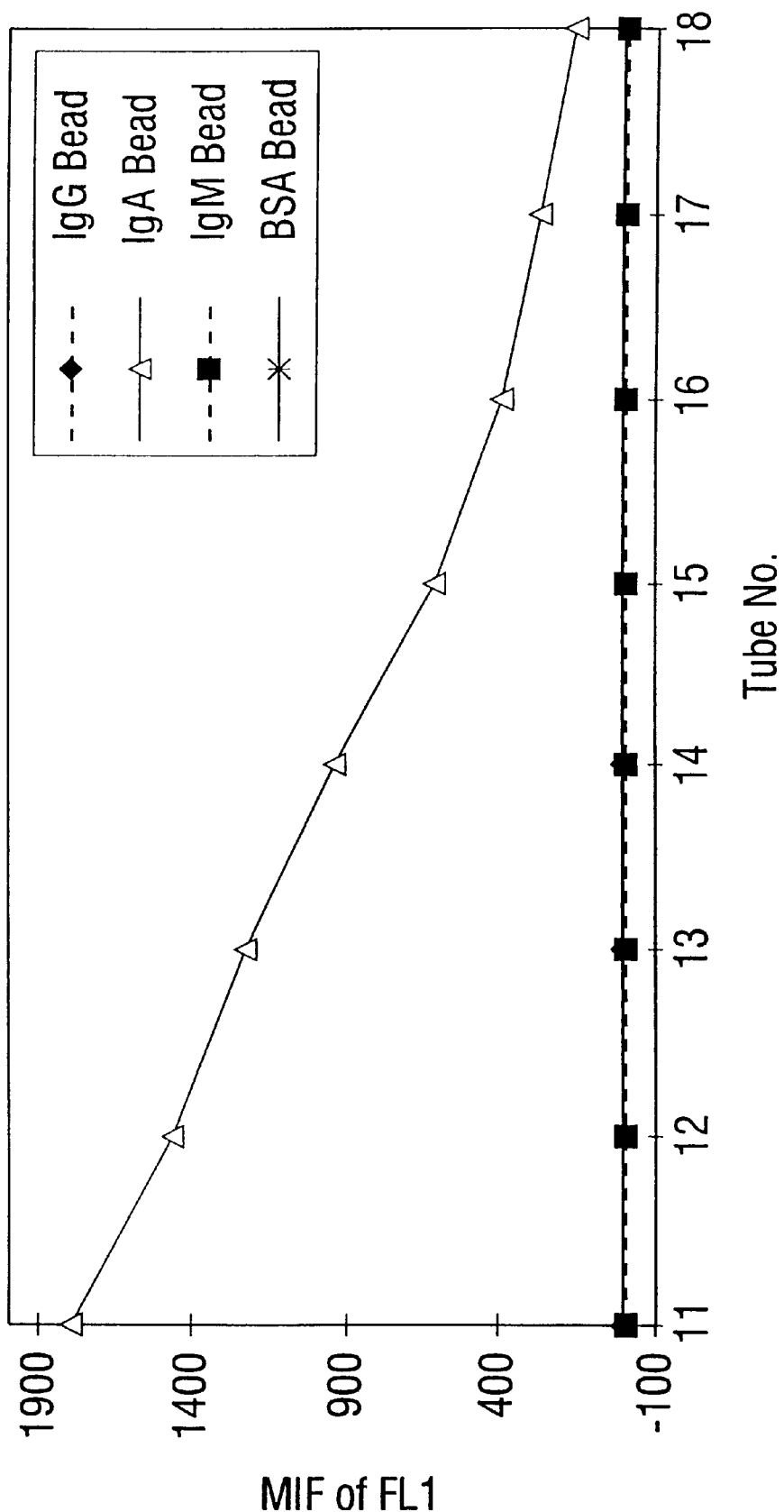
Figure 16C:
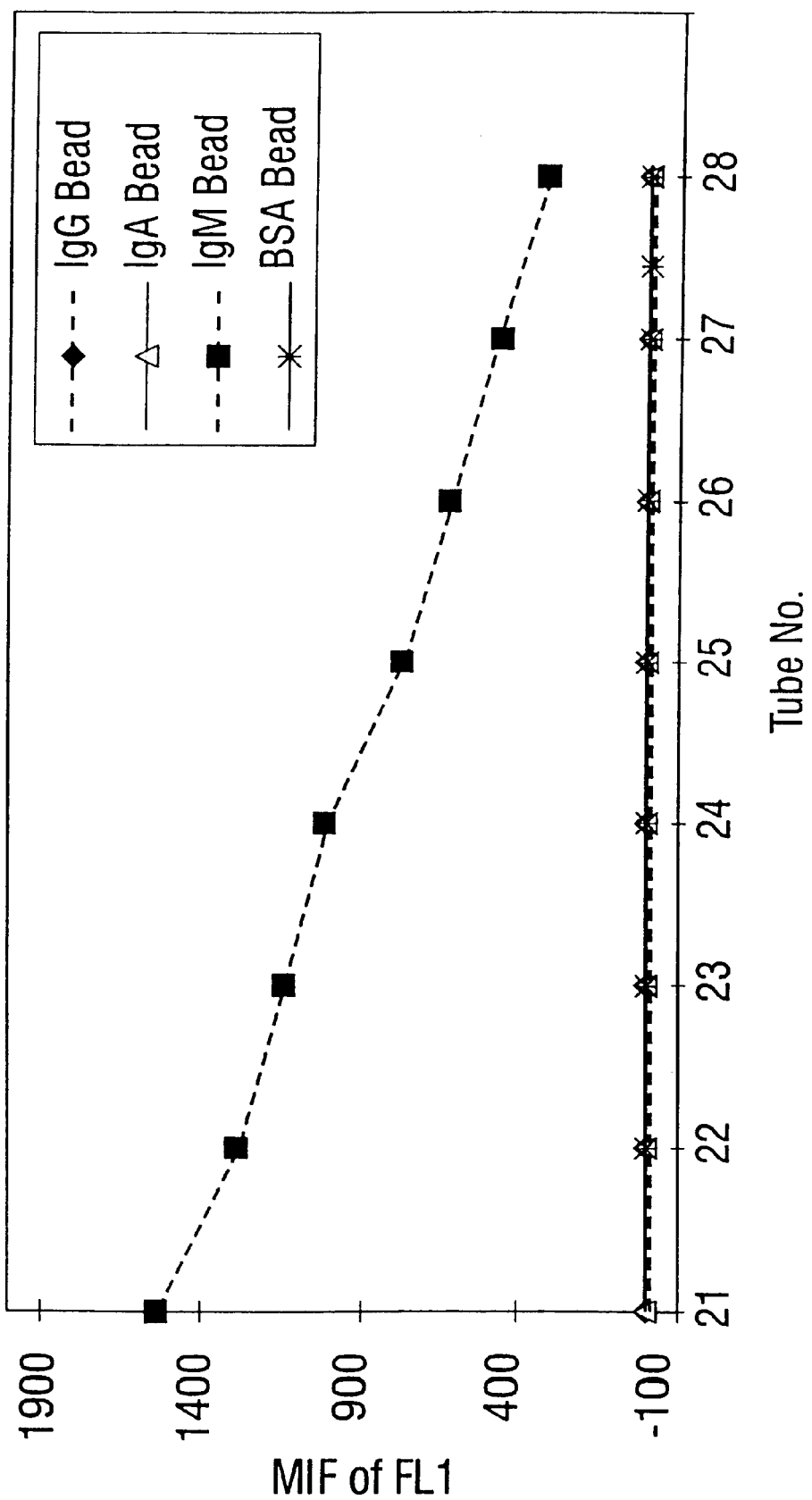

FIGS. 16*a*, 16*b*, and 16*c* show cross reactivity determinations between IgG, IgA, and IgM assay components.

Figure 17:
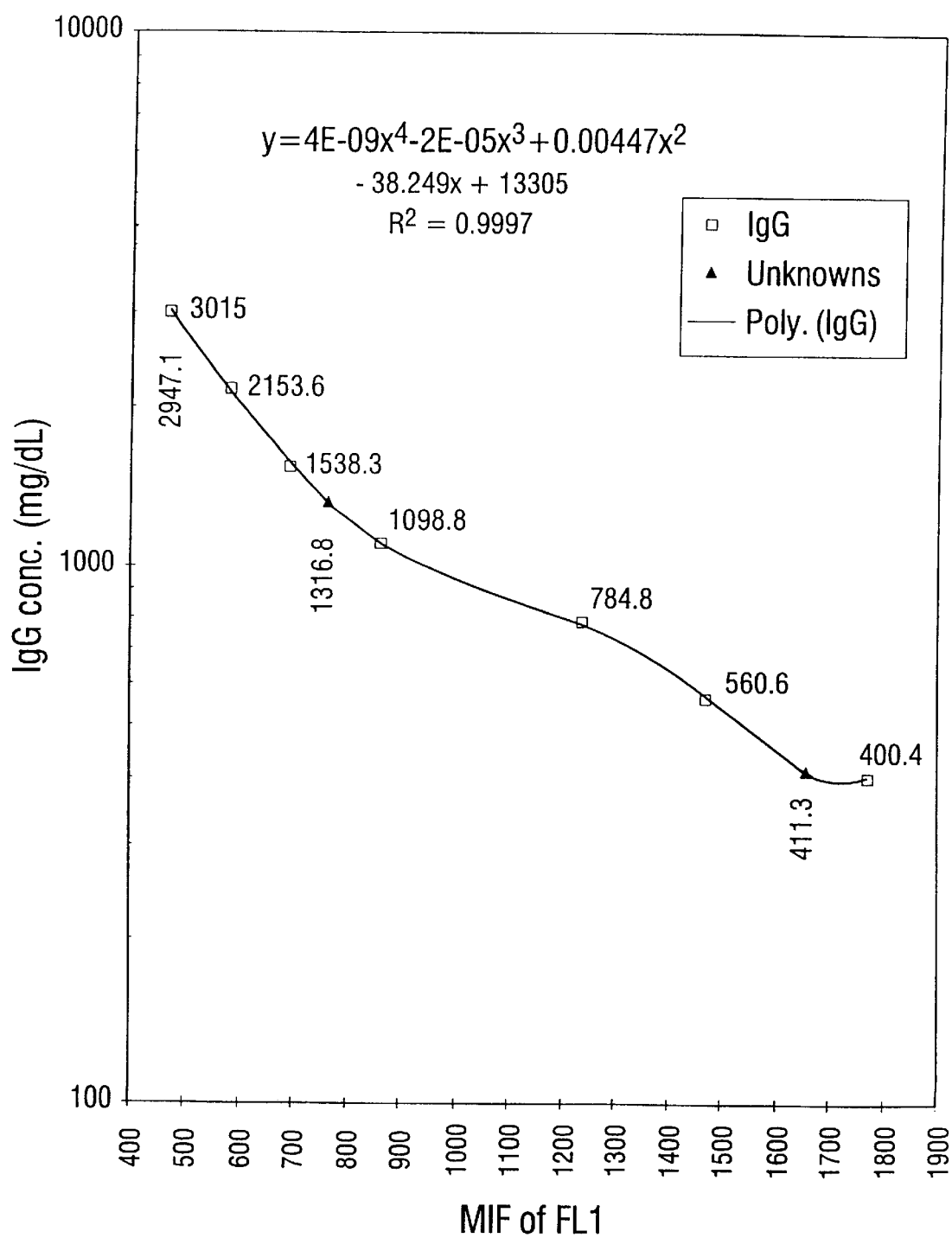

FIG. 17 shows the determination of human IgG concentrations by flow cytometry.

Figure 18:
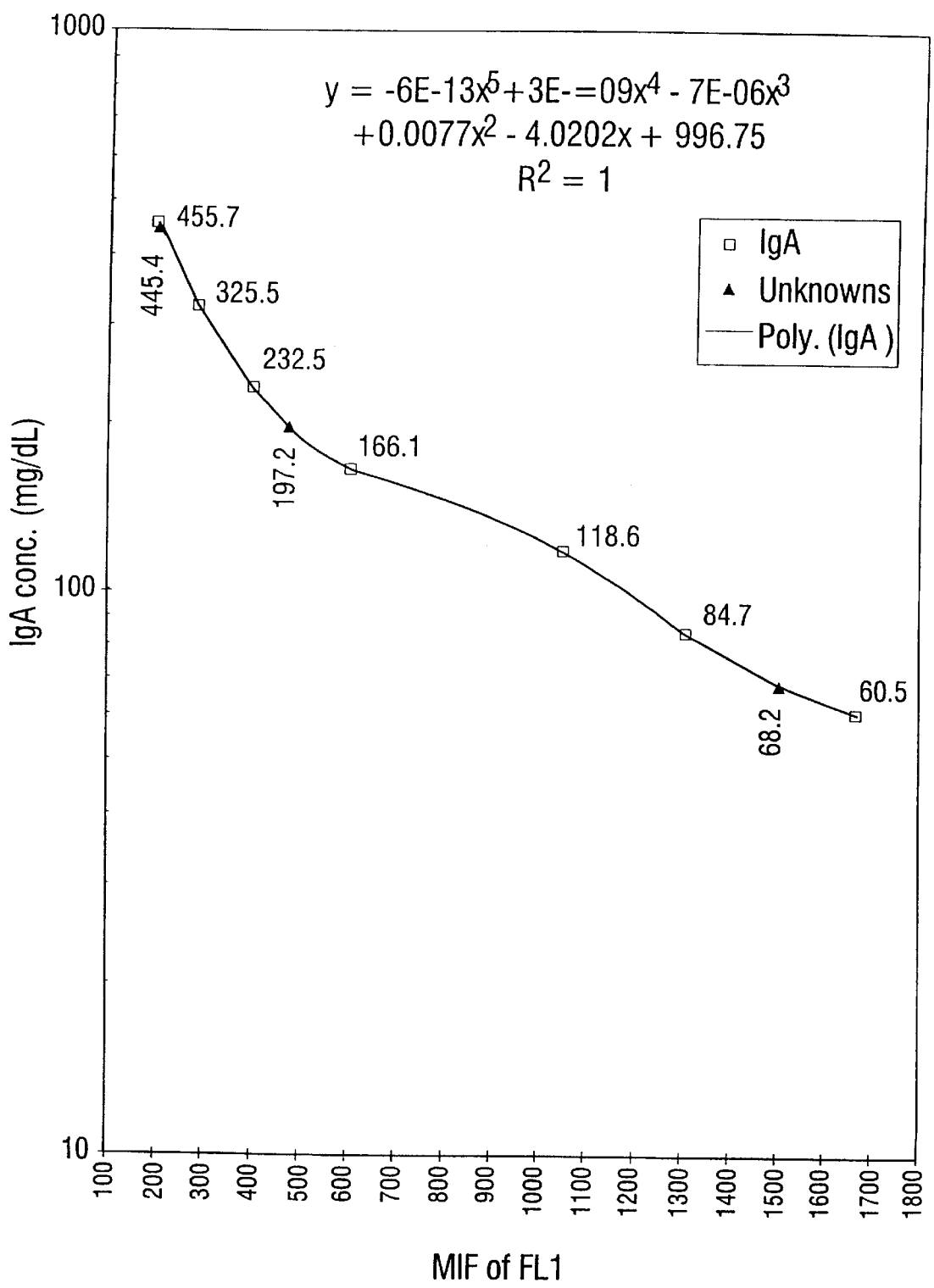

FIG. 18 shows the determination of human IgA concentrations by flow cytometry.

Figure 19:
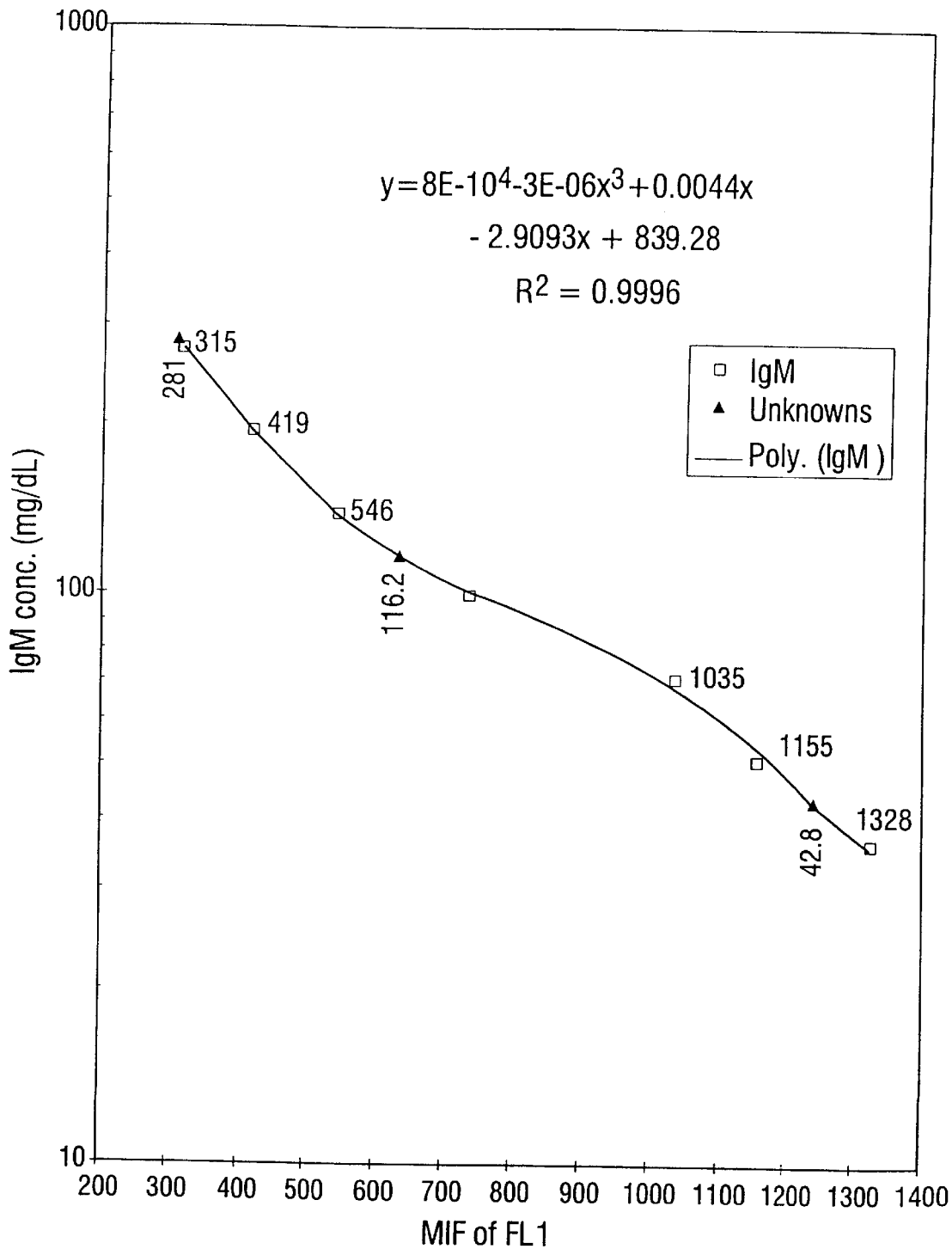

FIG. 19 shows the determination of human IgM concentrations by flow cytometry.

Figure 20:
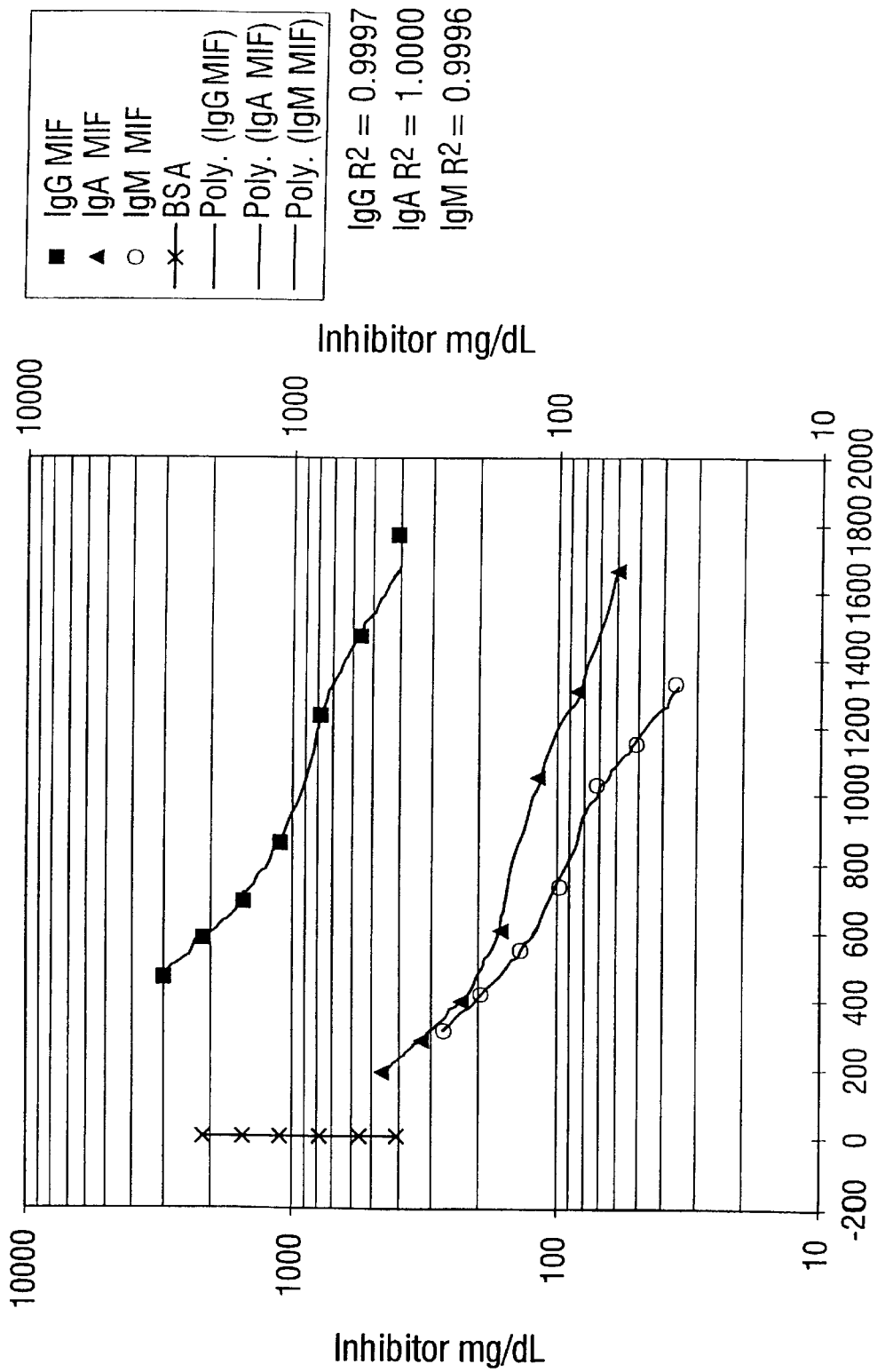

FIG. 20 shows the simultaneous determination of human IgG, IgA, and IgM concentrations by flow cytometry.

Figure 21:
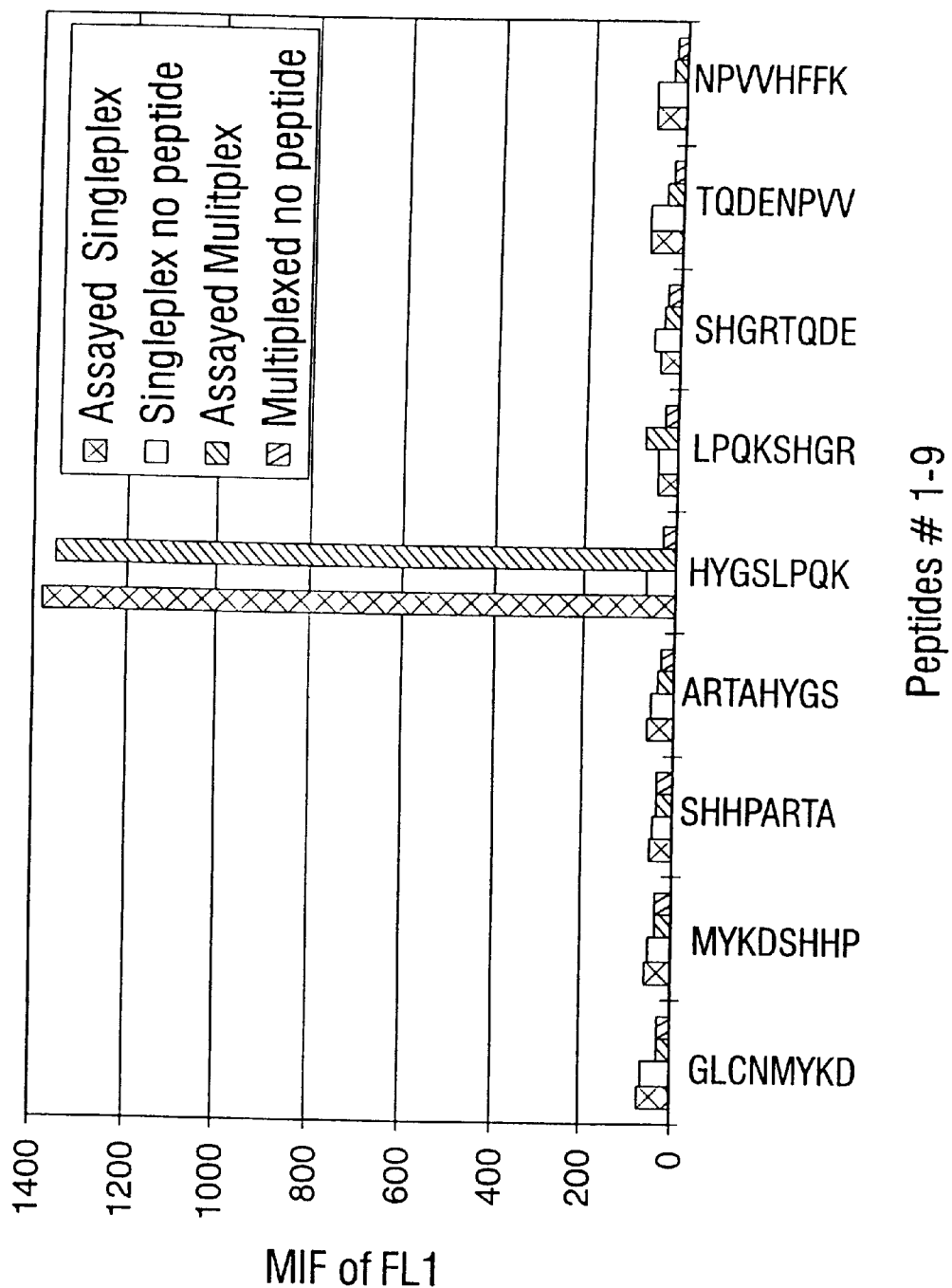

FIG. 21 shows the specificity of monoclonal antibody MAB384 binding towards bead immobilized epitope sequences.

Figure 22:
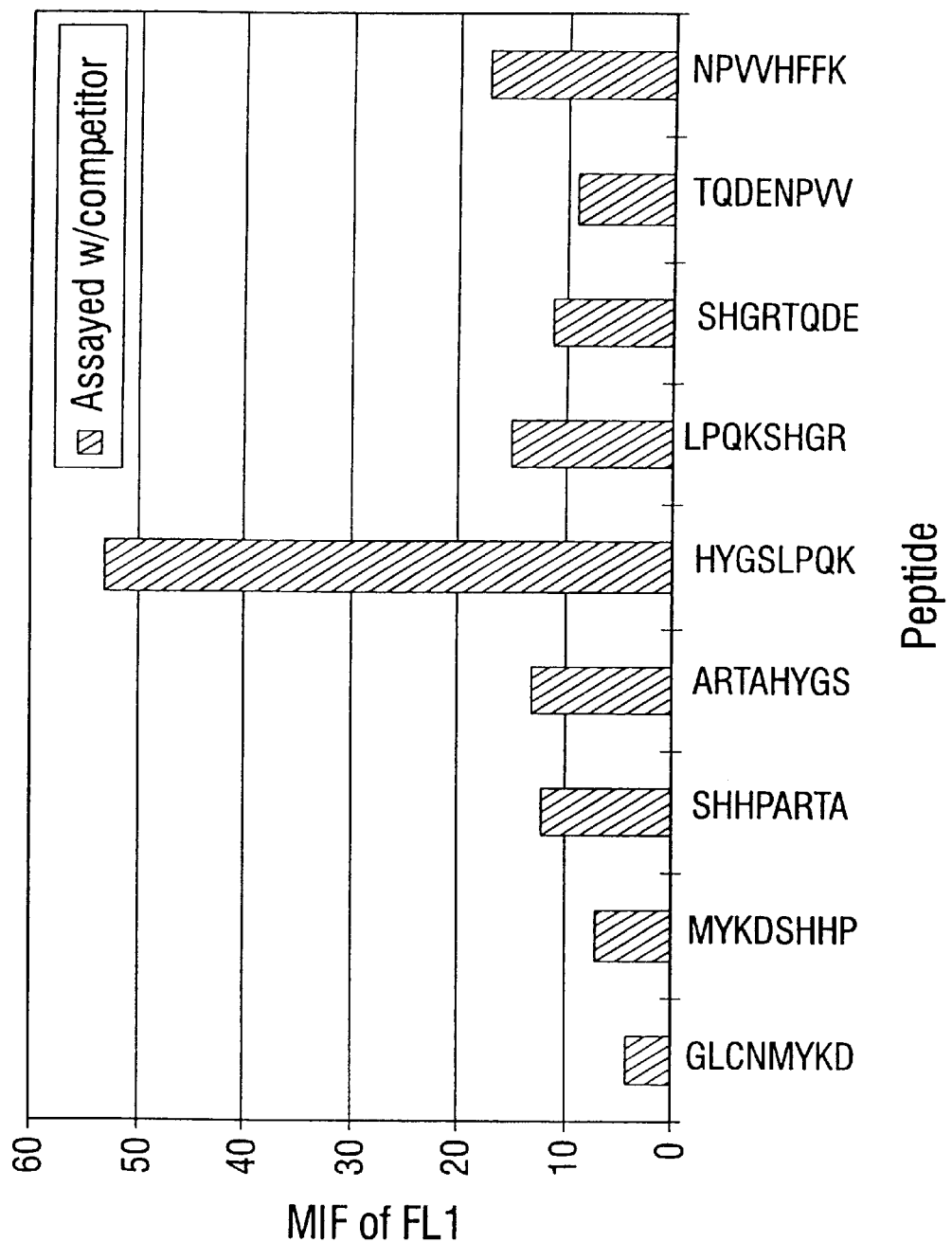

FIG. 22 shows the specificity of monoclonal antibody MAB384 binding in the presence of soluble epitope containing peptide.

Figure 23:
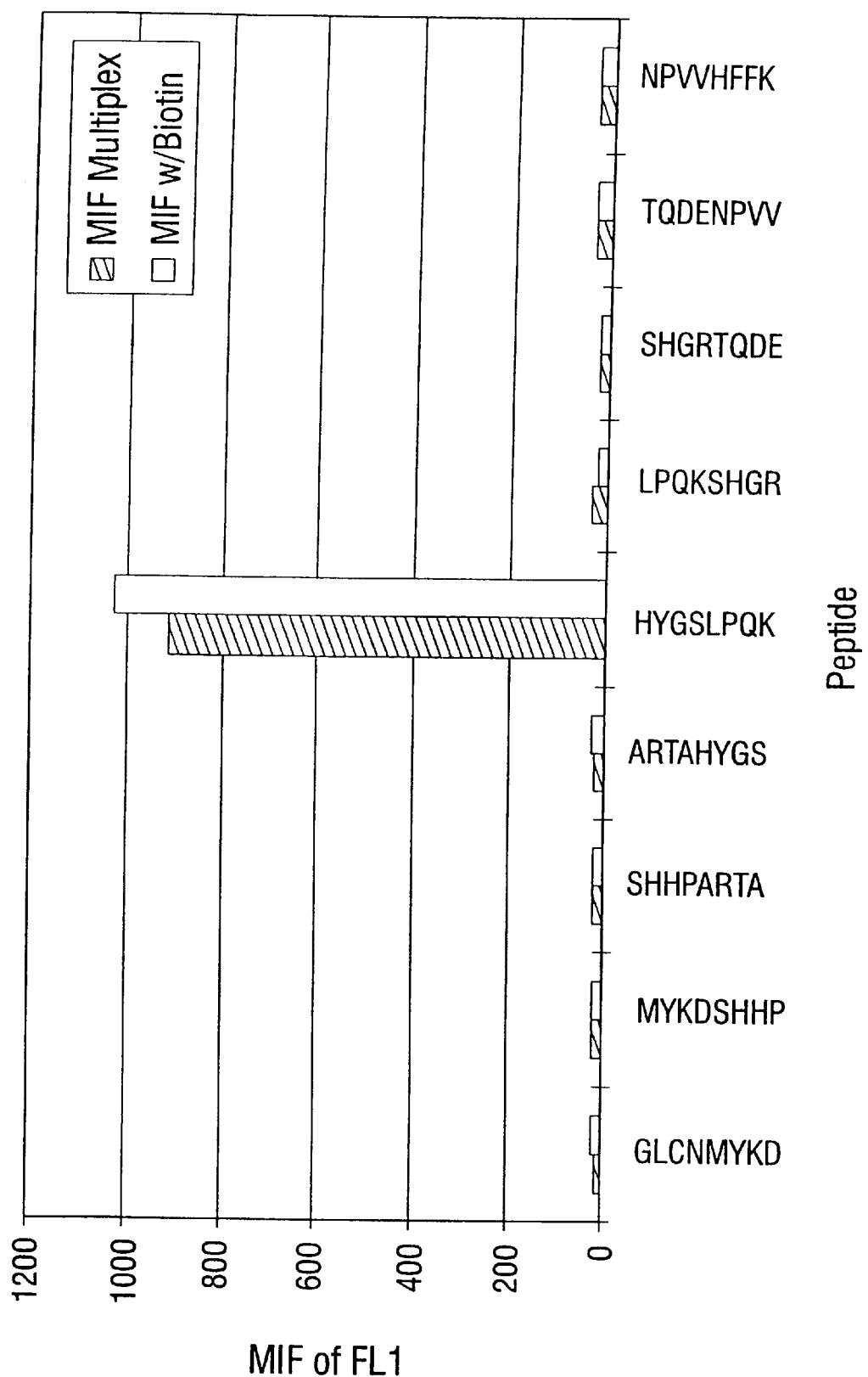

FIG. 23 shows the specificity of monoclonal antibody MAB384 binding in the presence of soluble biotin.

Figure 24:
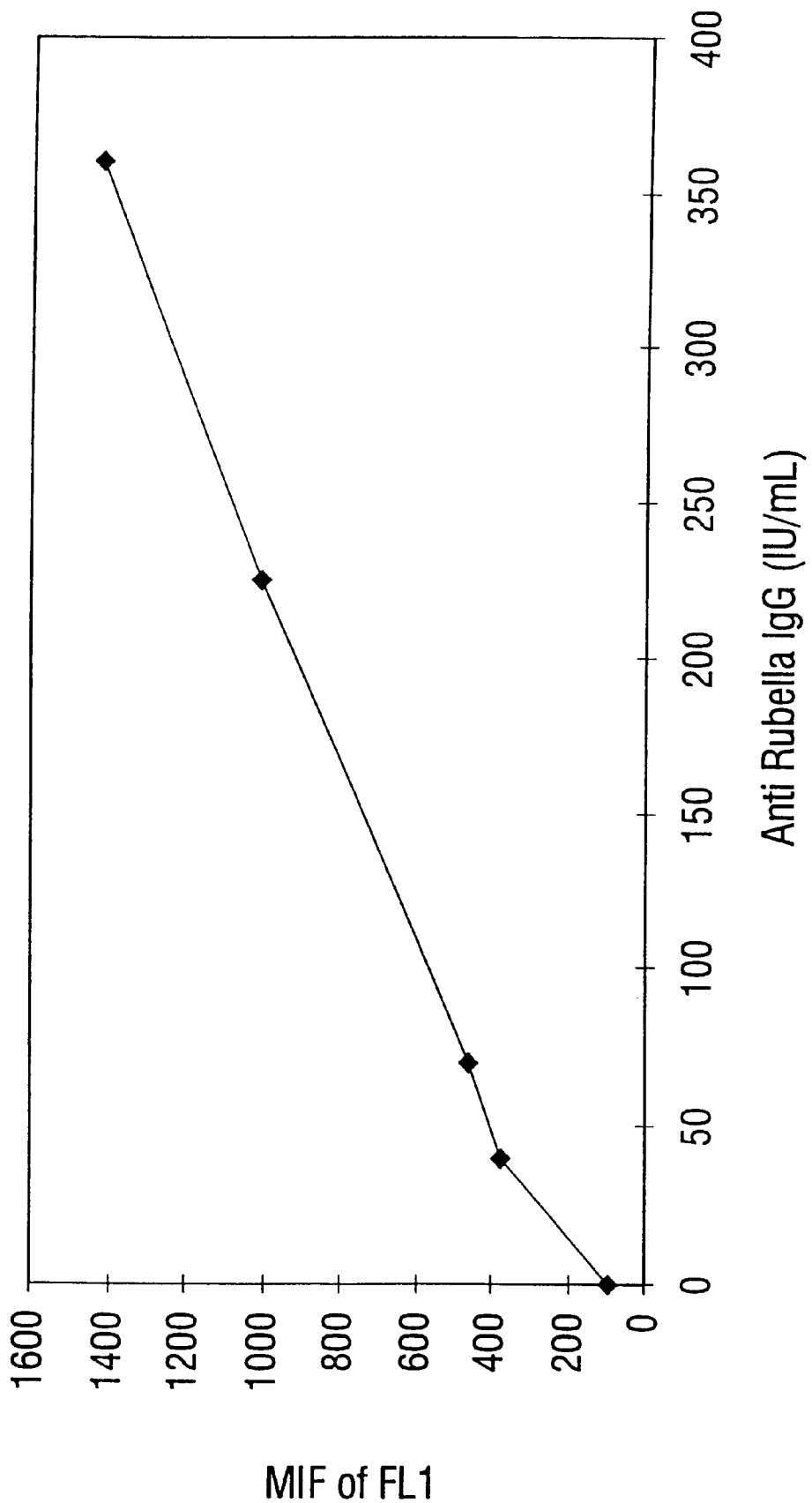

FIG. 24 shows the detection of anti-Rubella IgG antibodies by a sandwich assay between rubella coated beads and a fluorescent goat anti-human IgG antibody.

Figure 25:
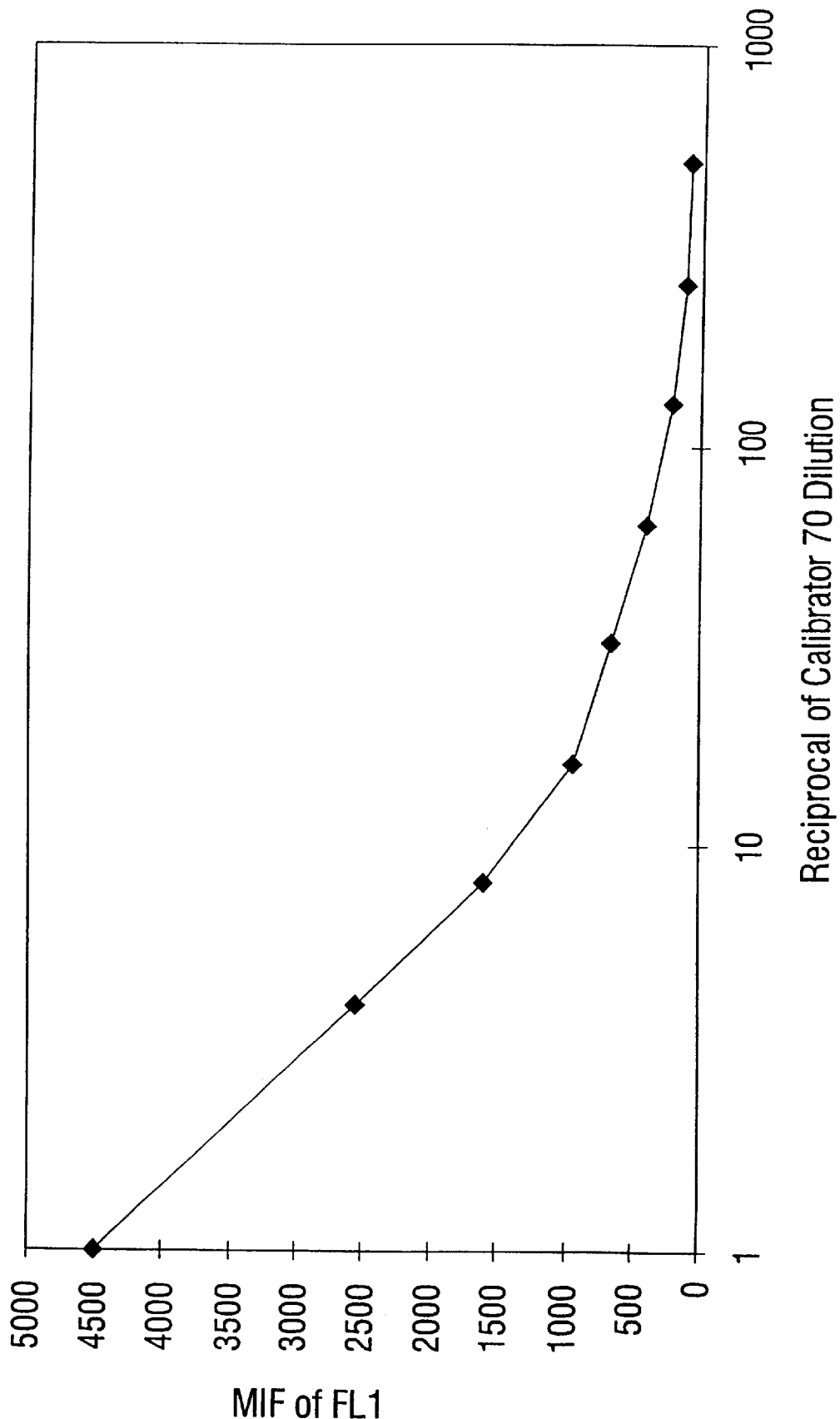

FIG. 25 shows a calibration assay using serial dilutions of anti-Rubella IgG antibodies in a sandwich assay between rubella coated beads and a fluorescent goat anti-human IgG antibody.

Figure 26A:
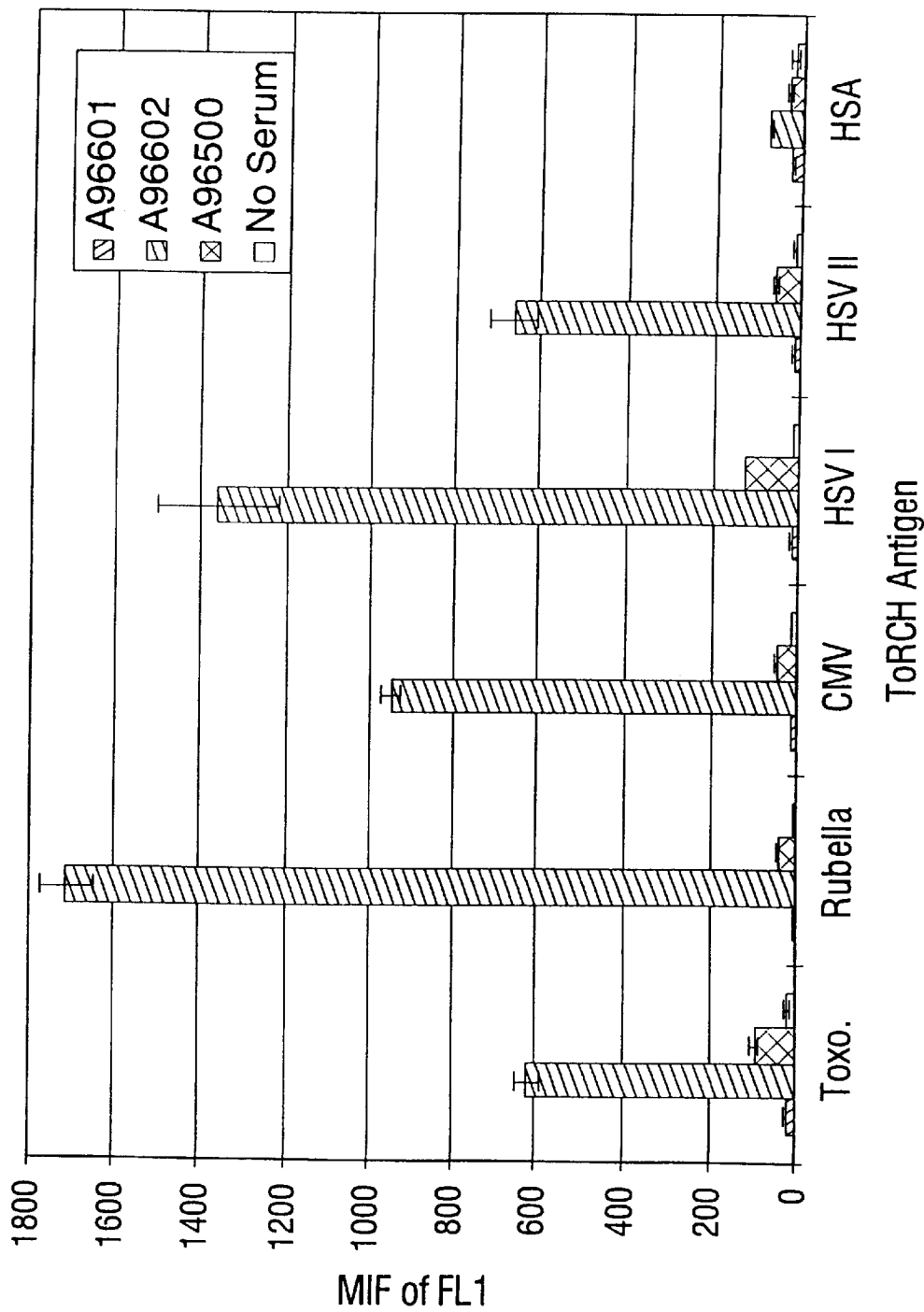
Figure 26B:
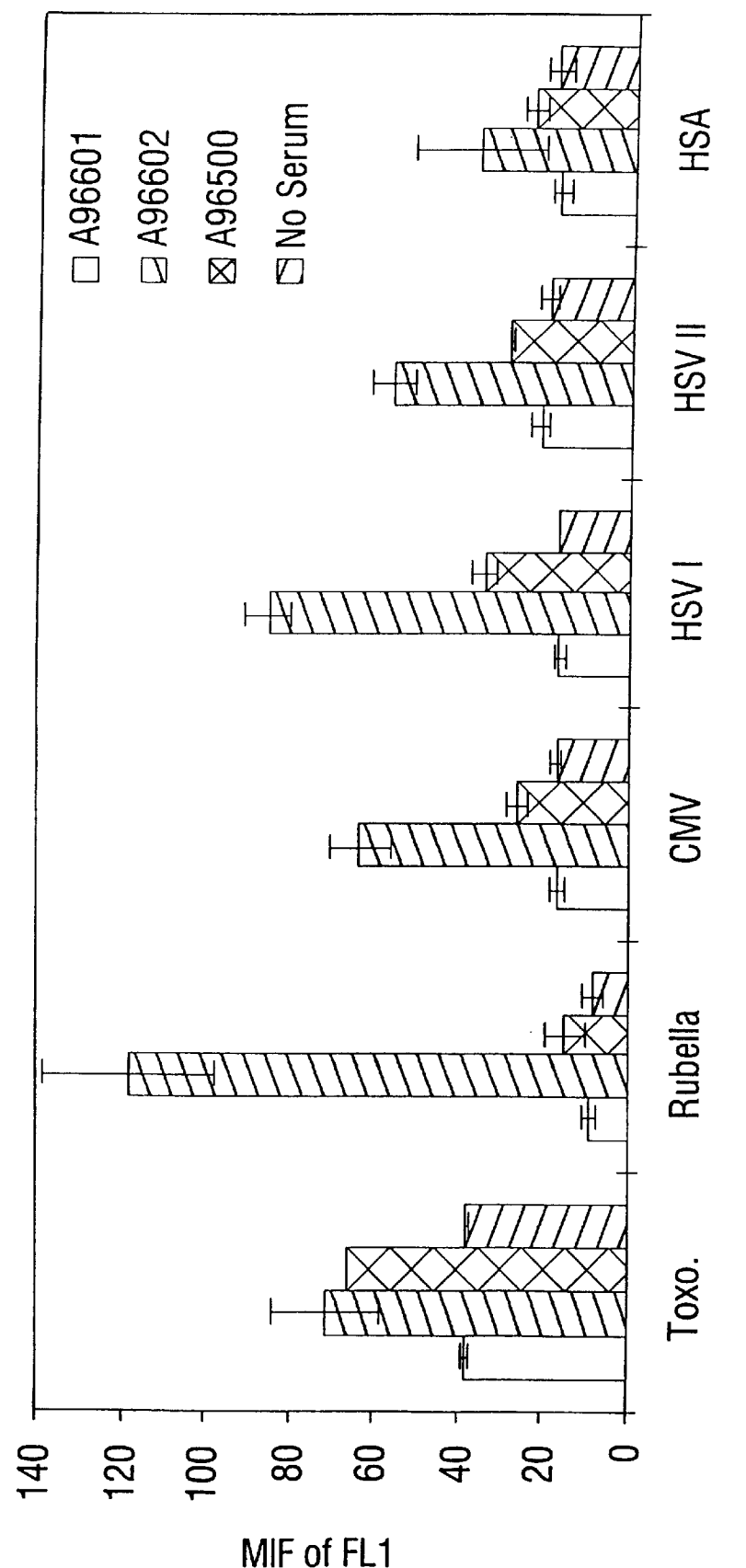

FIGS. 26a and 26b show the simultaneous assay for six anti-ToRCH IgG, and simultaneous assay for the six anti-ToRCH IgM antibodies.

Figure 27:

FIG. 27 shows the determination of IgG anti-grass allergen activities for six dogs.

Figure 28:
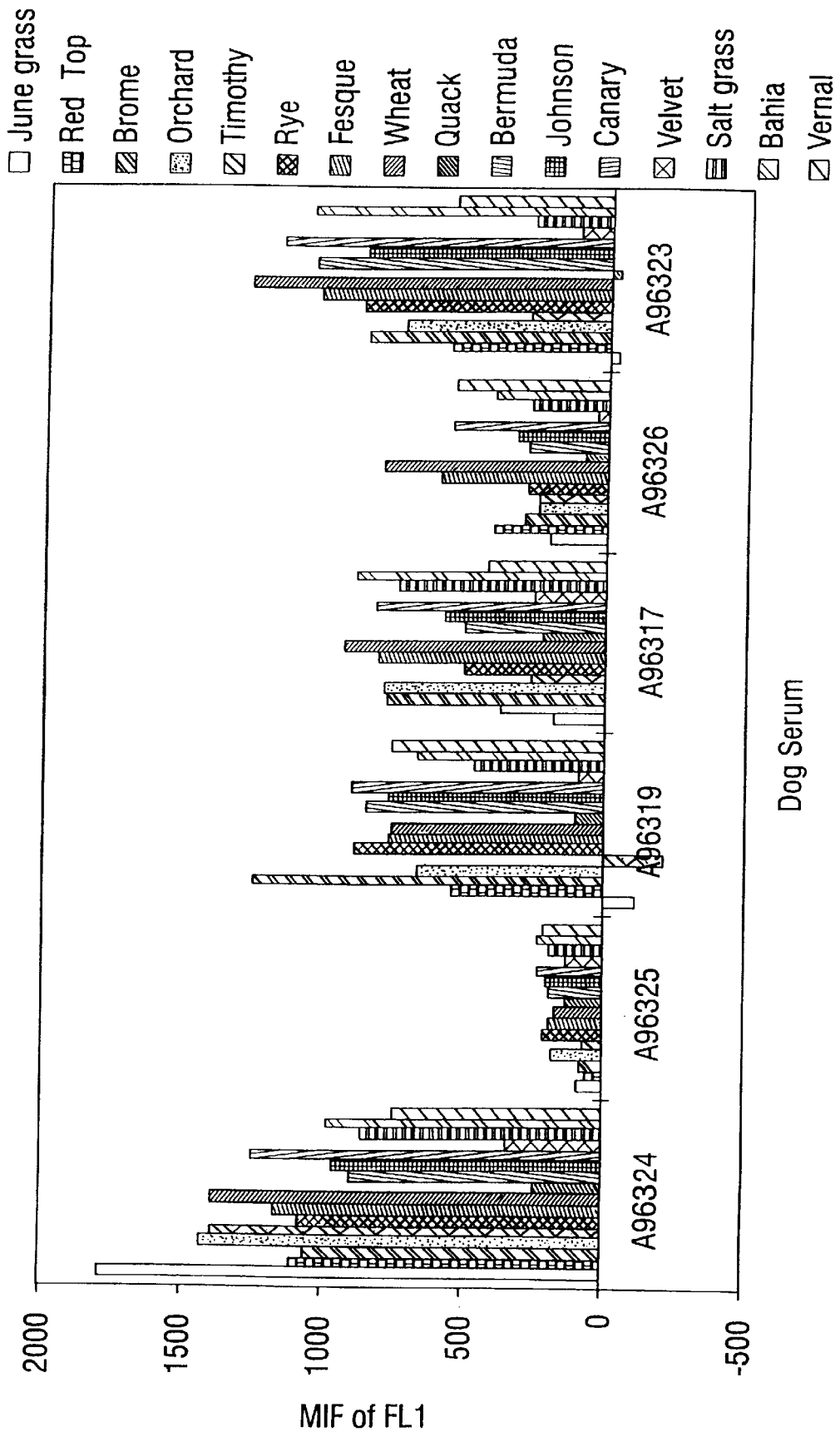

FIG. 28 shows the determination of IgE anti-grass allergen activities for six dogs.

Figure 29:
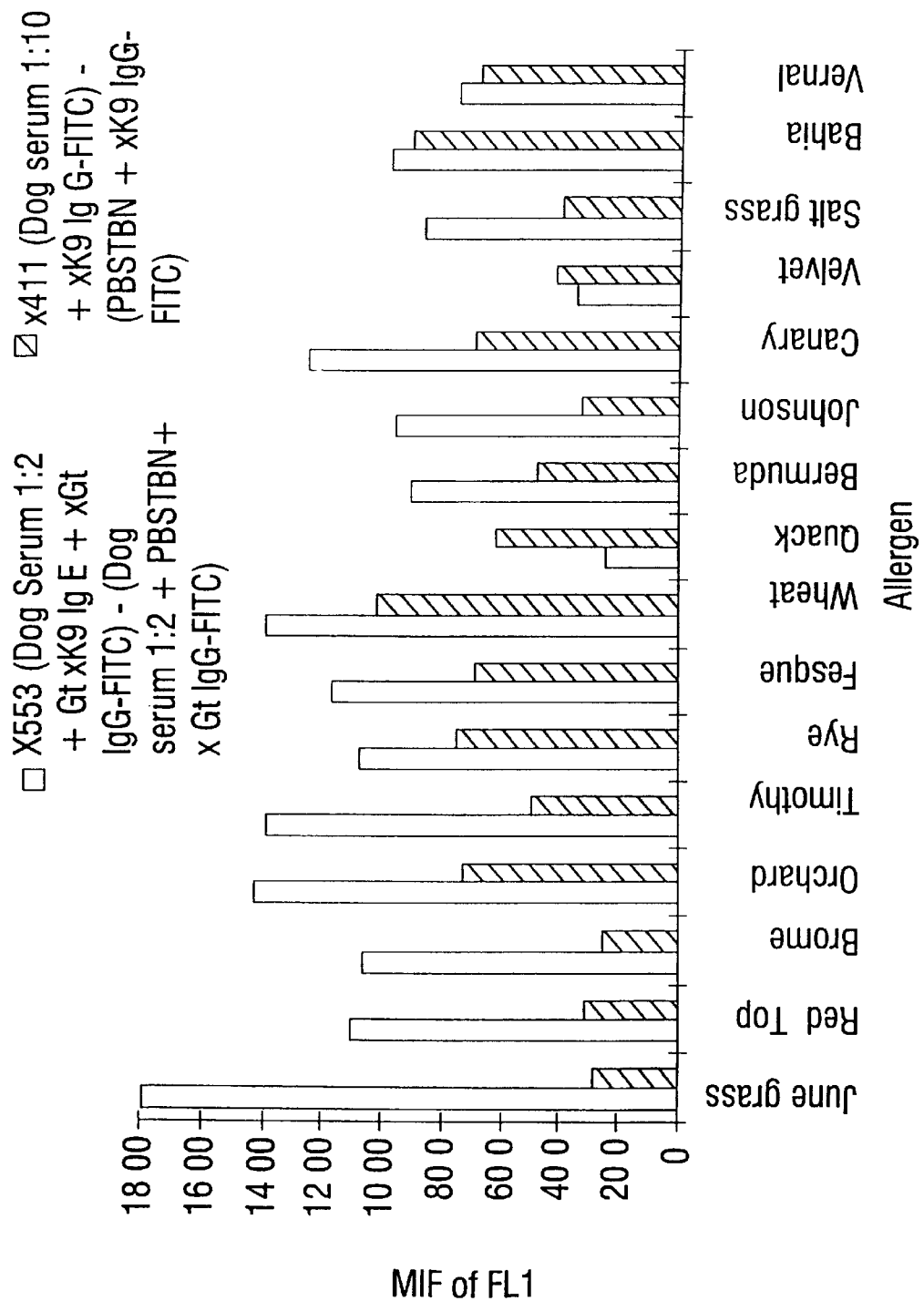
Figure 30:
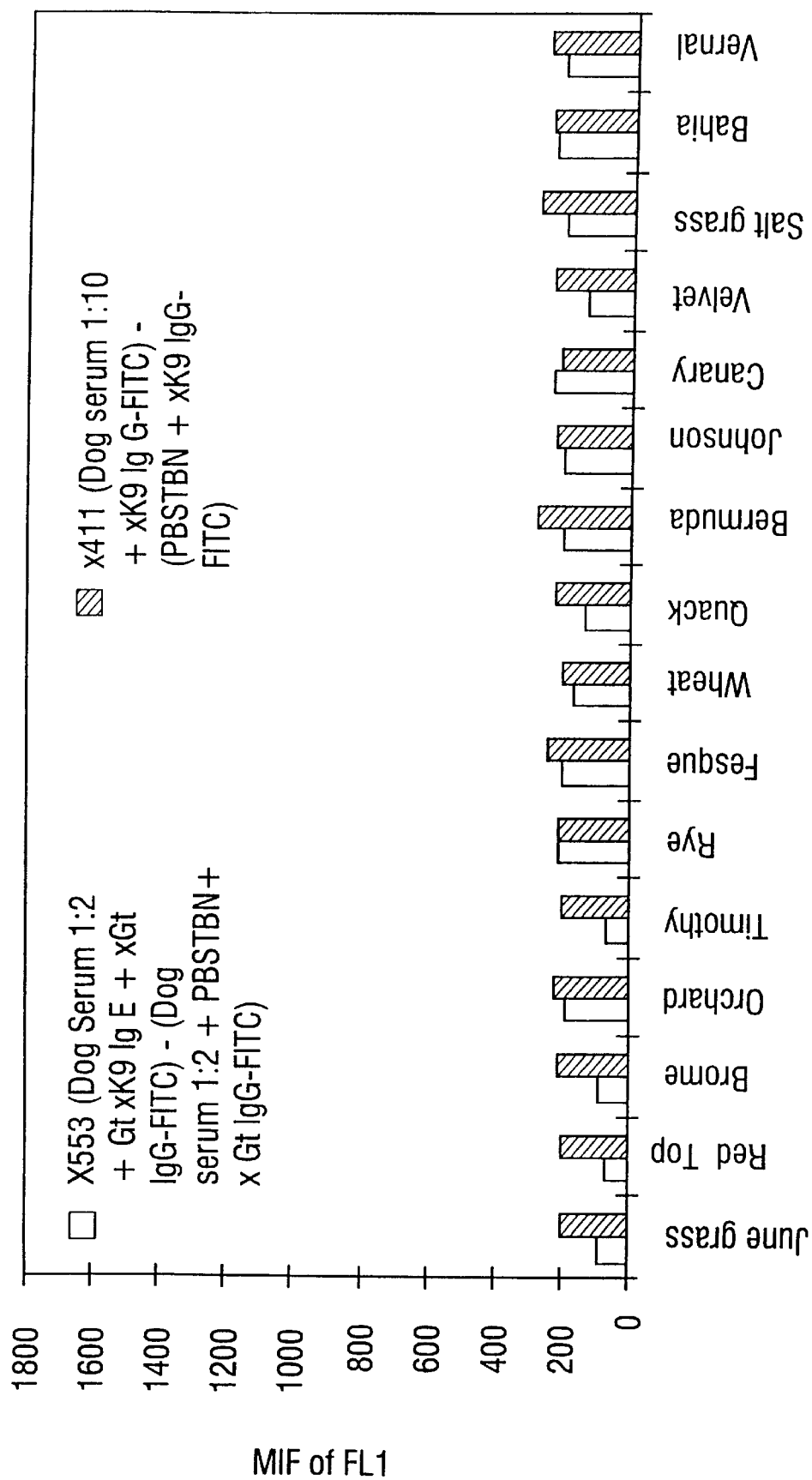
Figure 31:
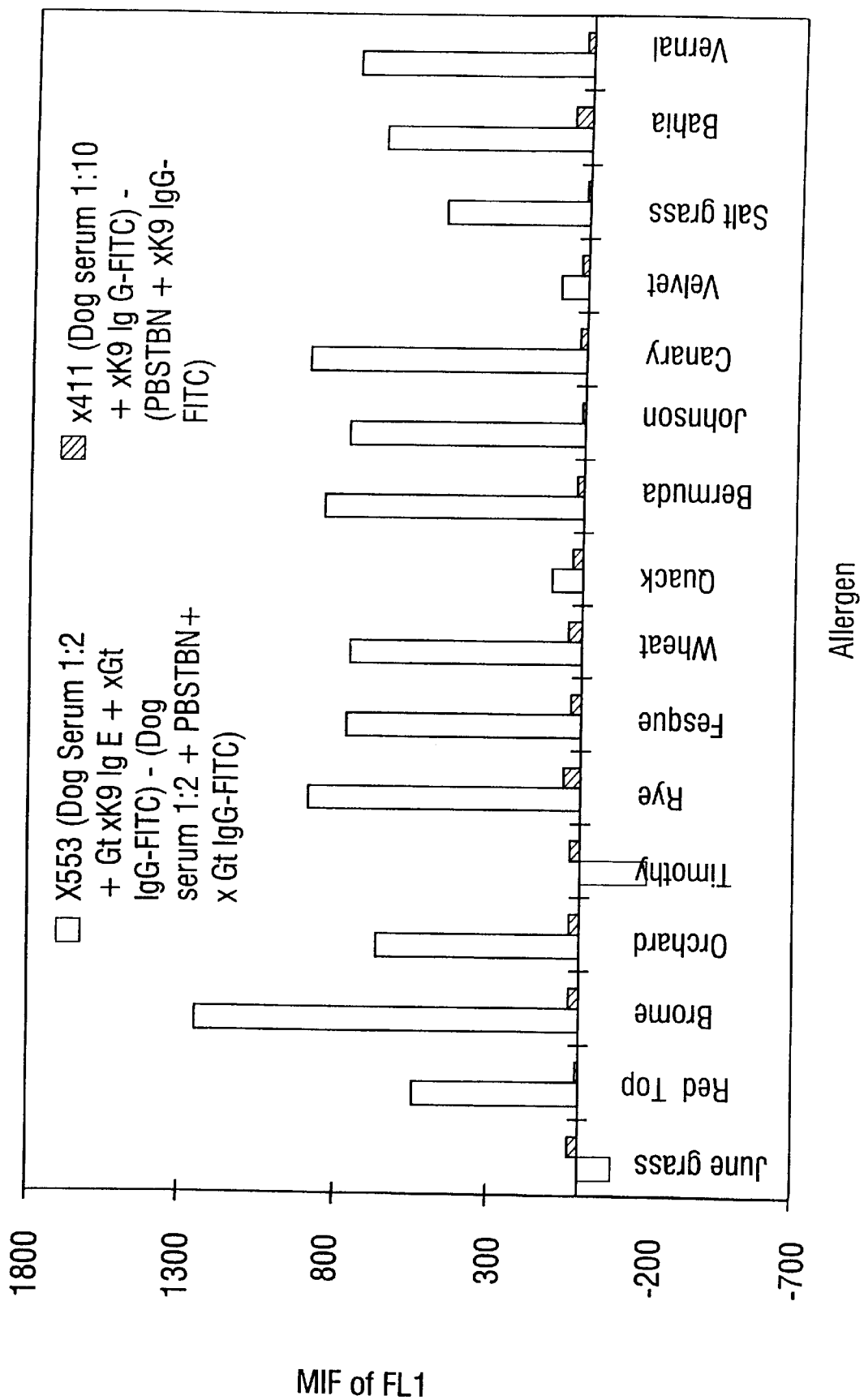
Figure 32:
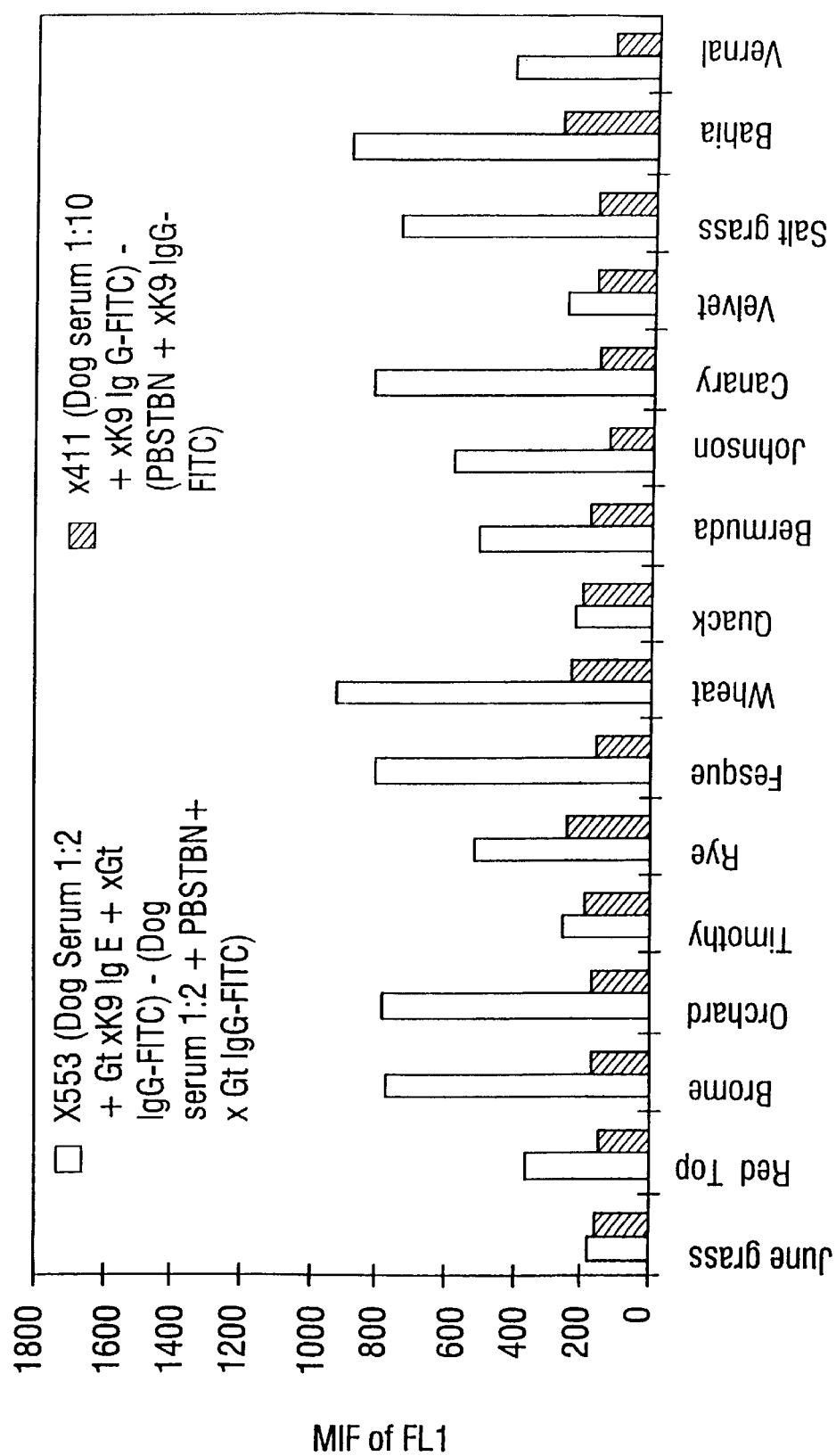
Figure 33:
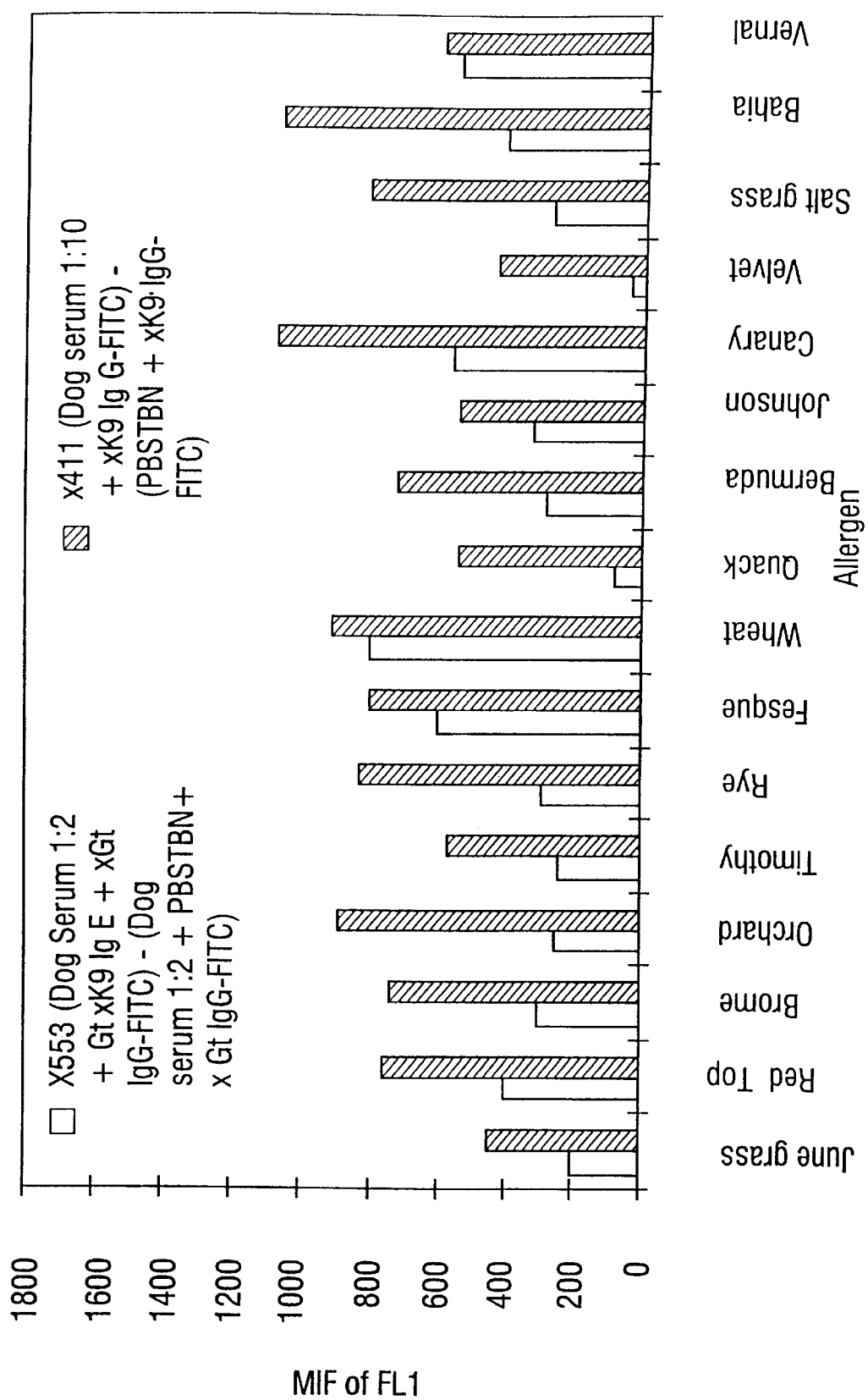
Figure 34:
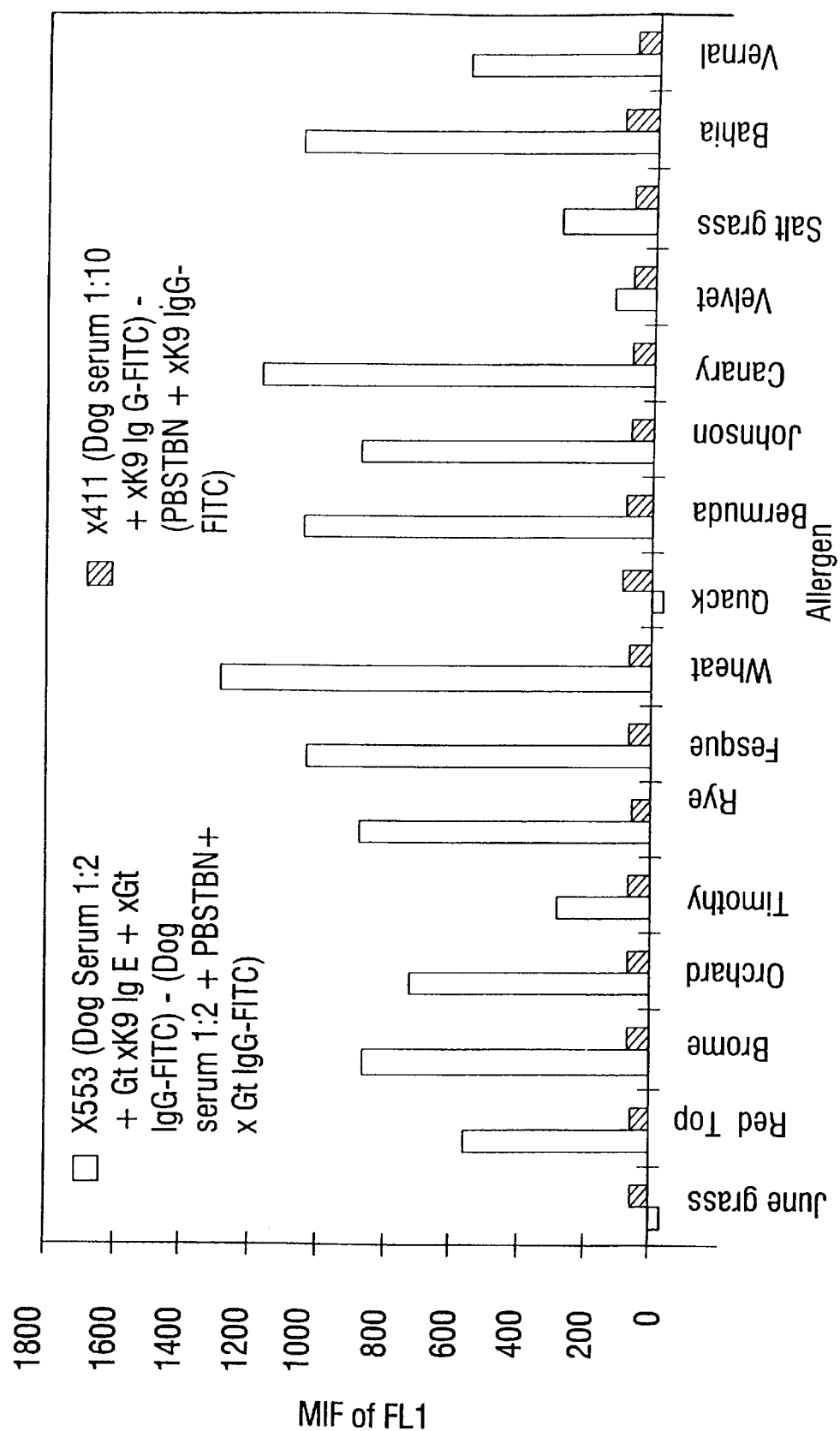
Figure 35:
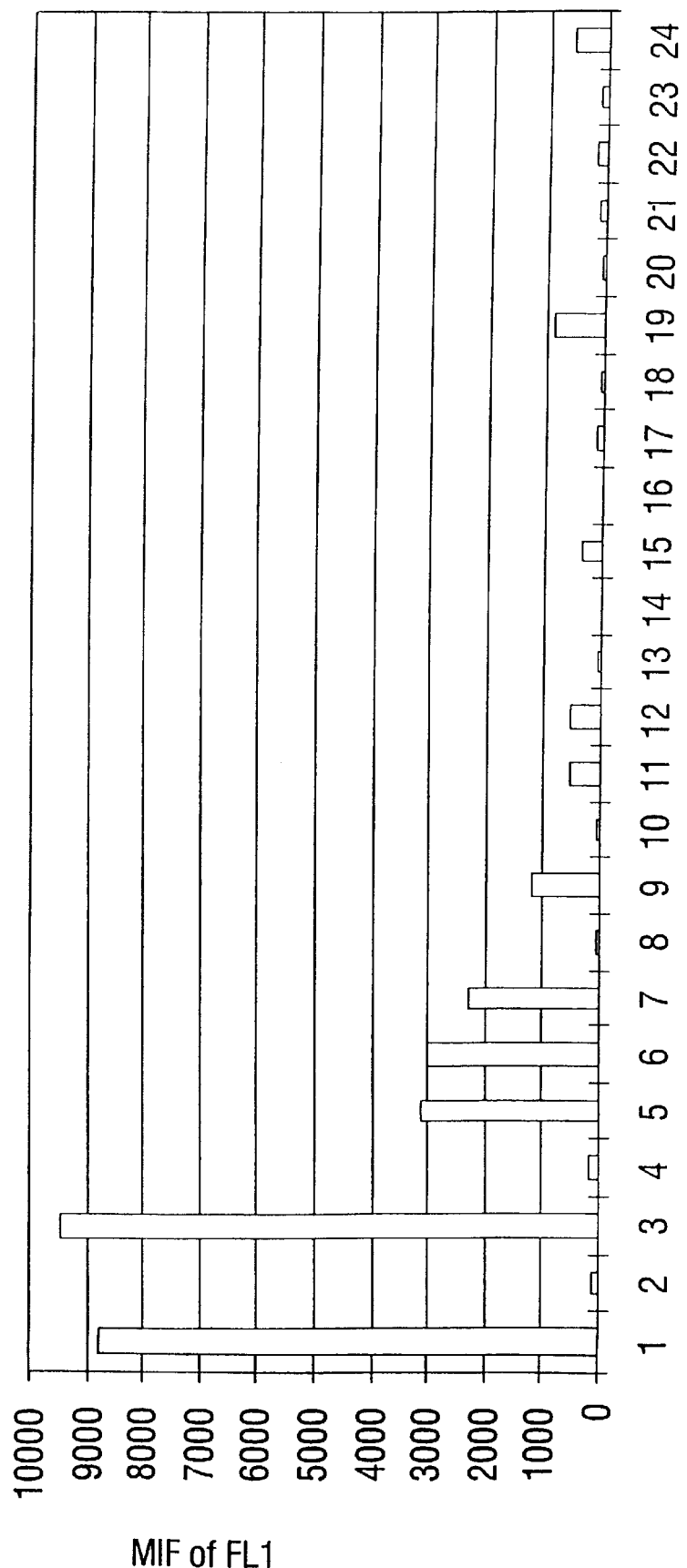

FIG. 29 shows the multiple analyte IgG and IgE screening of dog serum A96324 for sixteen grass allergens FIG. 30 shows the multiple analyte IgG and IgE screening of dog serum A96325 for sixteen grass allergens FIG. 31 shows the multiple analyte IgG and IgE screening of dog serum A96319 for sixteen grass allergens FIG. 32 shows the multiple analyte IgG and IgE screening of dog serum A96317 for sixteen grass allergens FIG. 33 shows the multiple analyte IgG and IgE screening of dog serum A96326 for sixteen grass allergens FIG. 34 shows the multiple analyte IgG and IgE screening of dog serum A96323 for sixteen grass allergens FIG. 35 shows an antibody pair analysis for use with a human chorionic gonadotropin capture assay.

Figure 36:
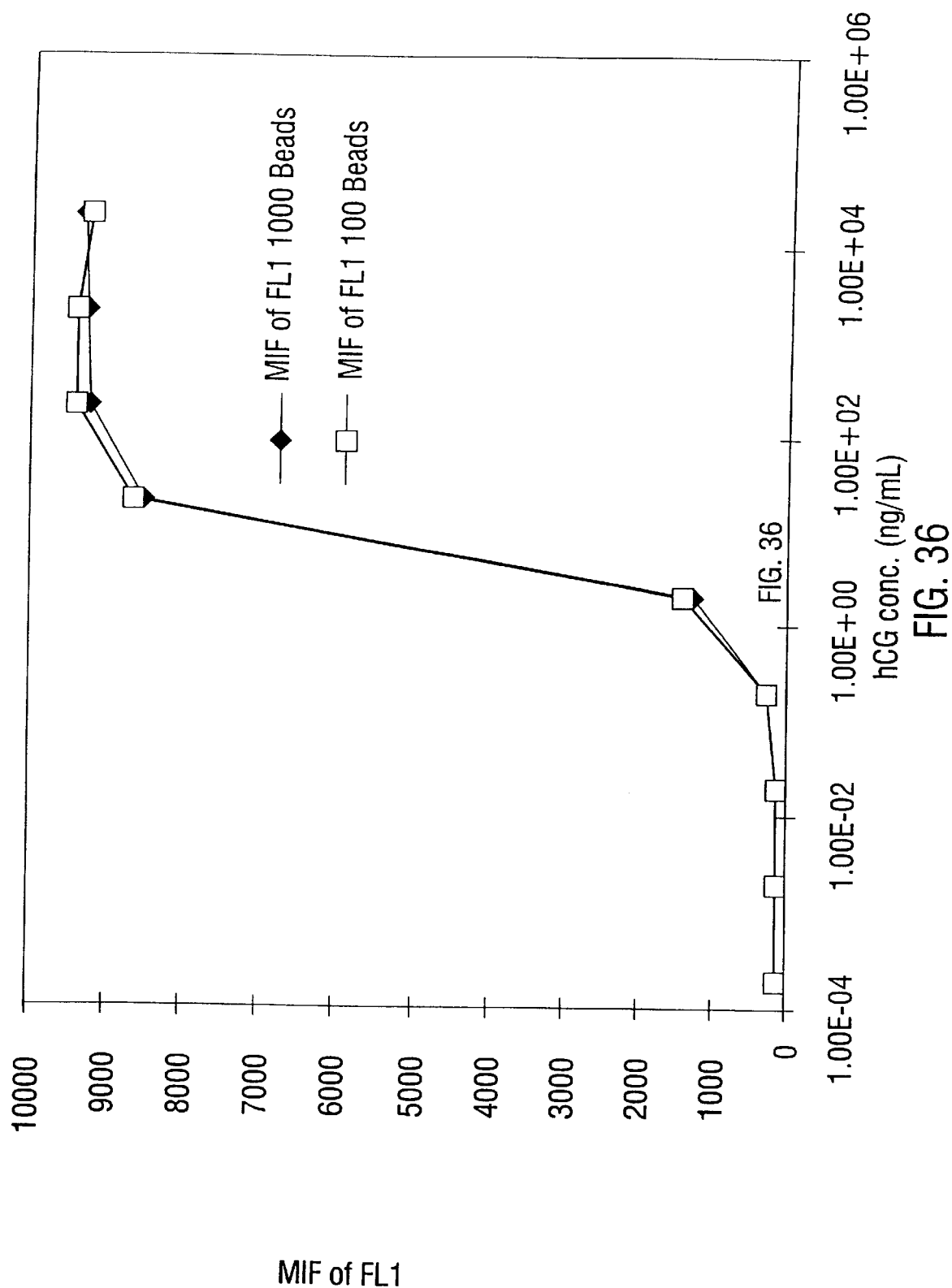

FIG. 36 shows the use of bead linked antibody MAB602 with fluorescently labeled antibody AB633 in a human chorionic gonadotropin capture assay.

Figure 37A:
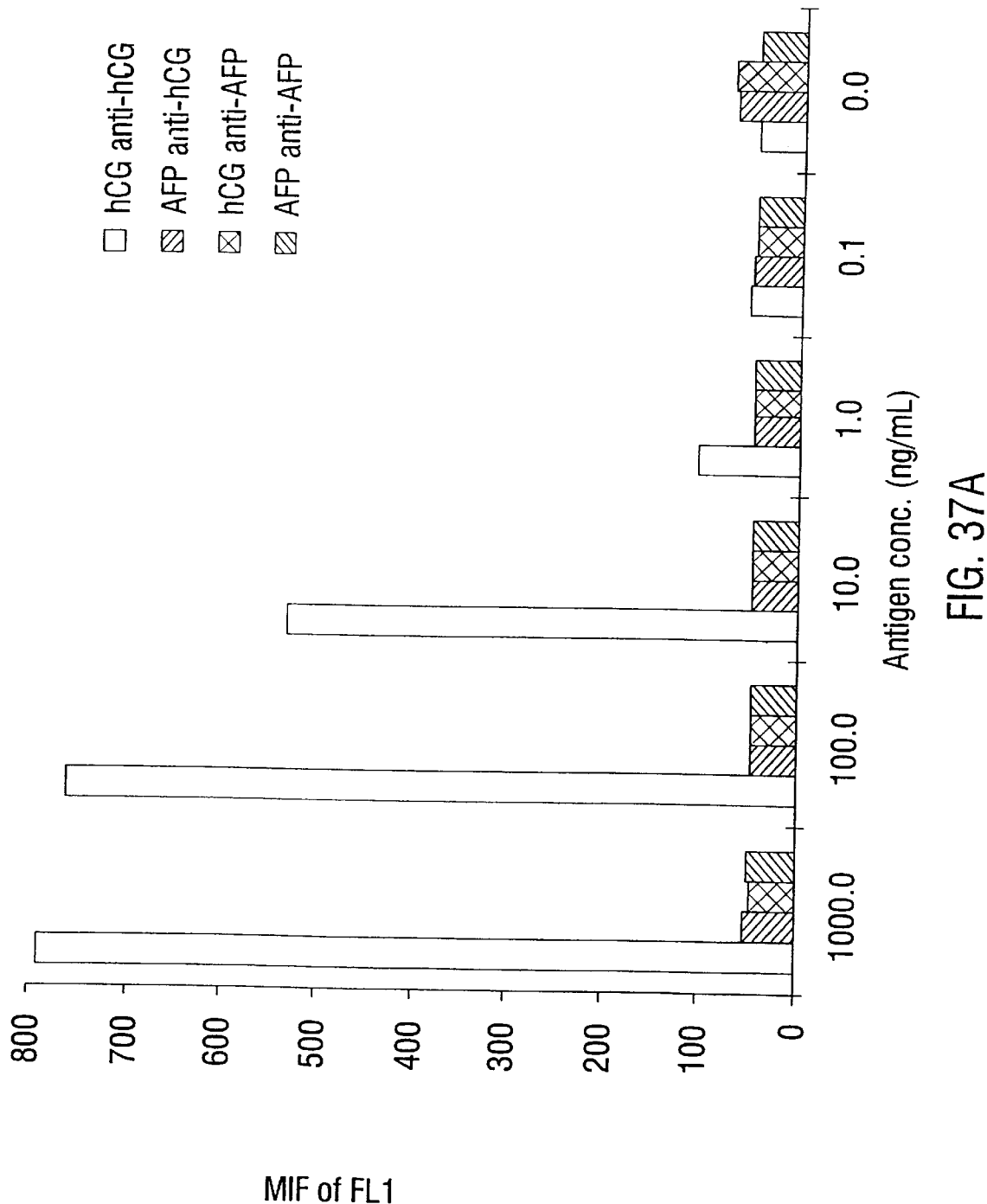
Figure 37B:
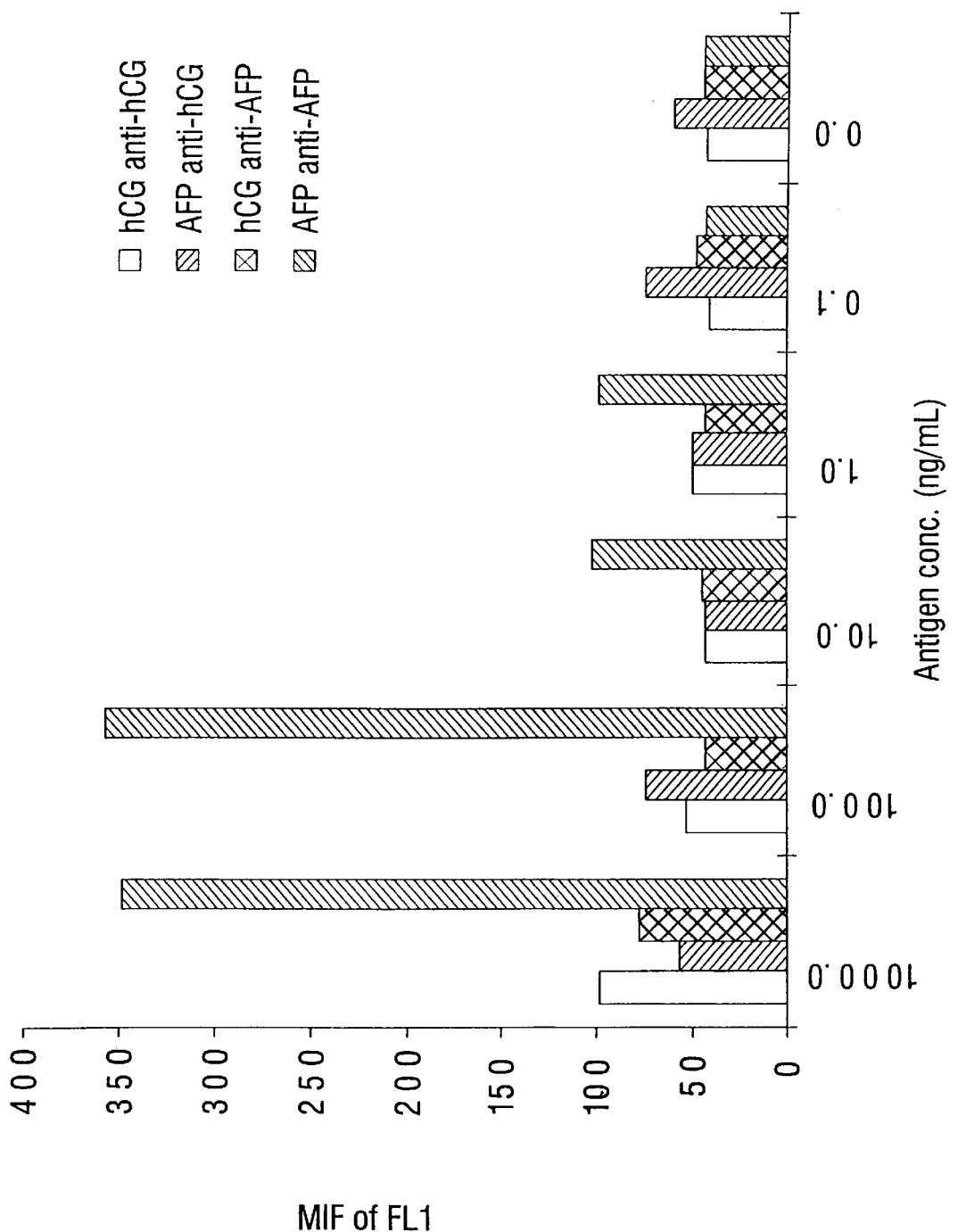

FIGS. 37a and 37b show cross reactivity analyses between components of an anti-hCG capture system and an anti-AFP capture system.

Figure 38A:
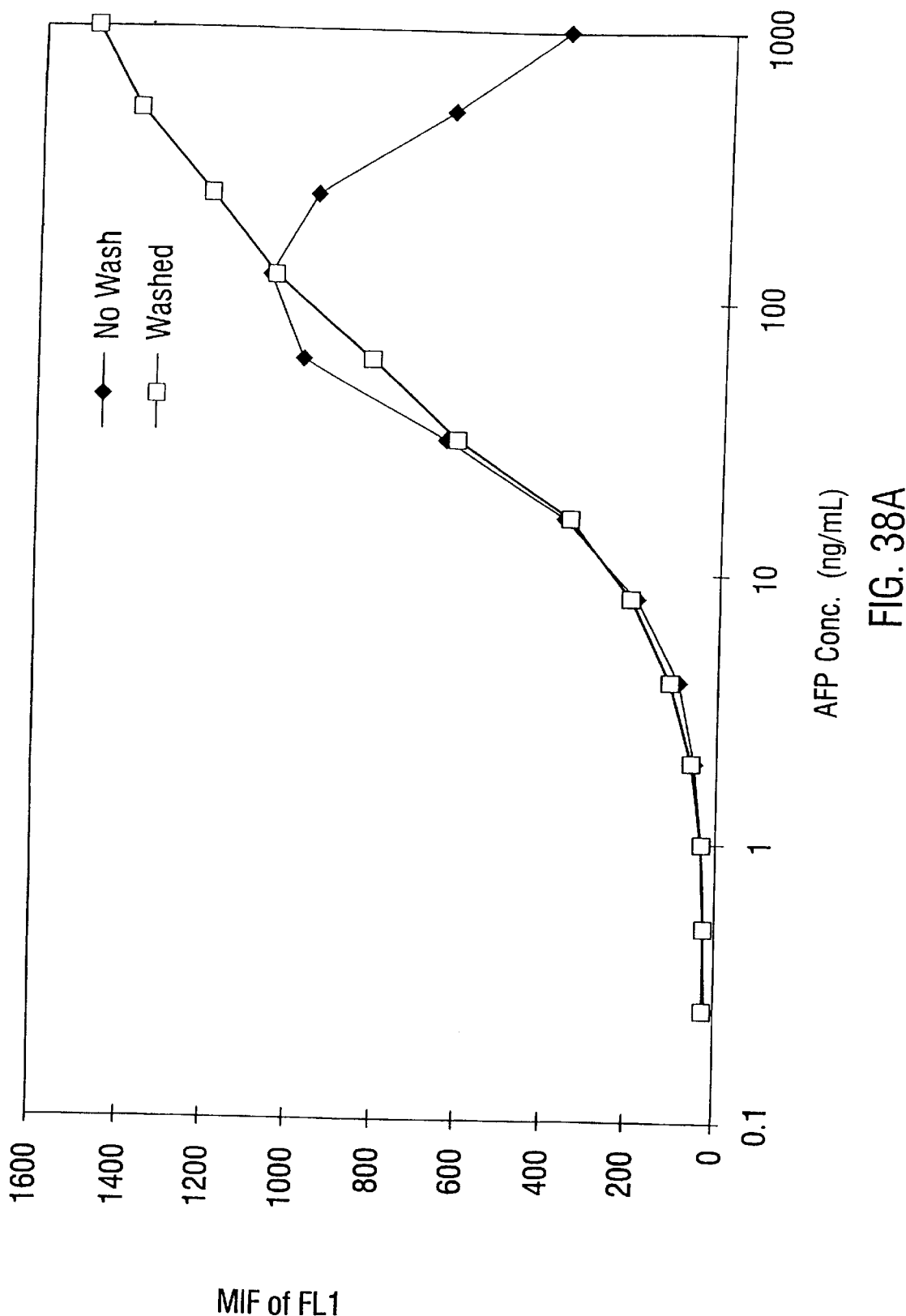
Figure 38B:
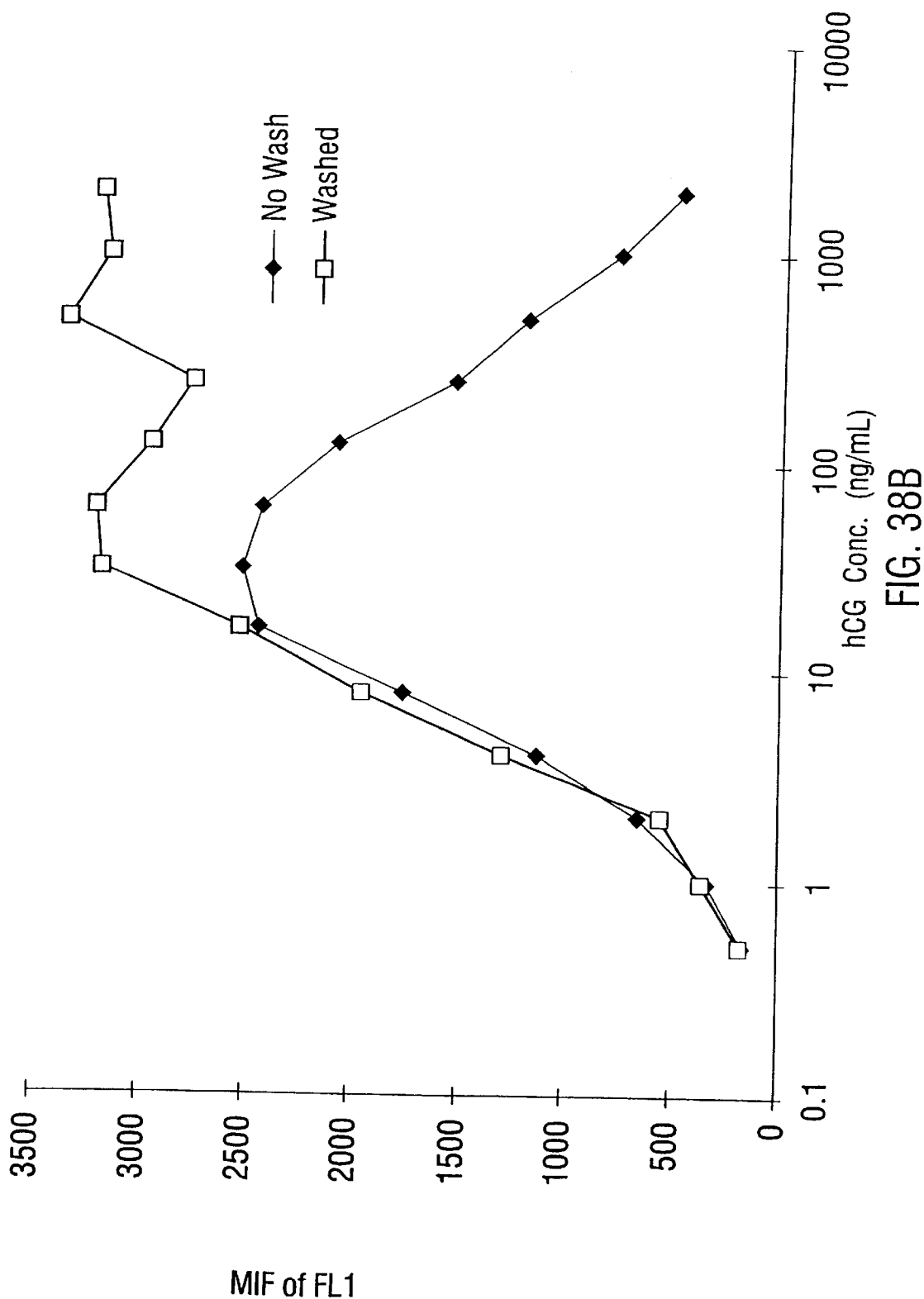

FIGS. 38a and 38b compare the effects of eliminating wash steps in hCG and AFP capture system assays.

Figure 39A:
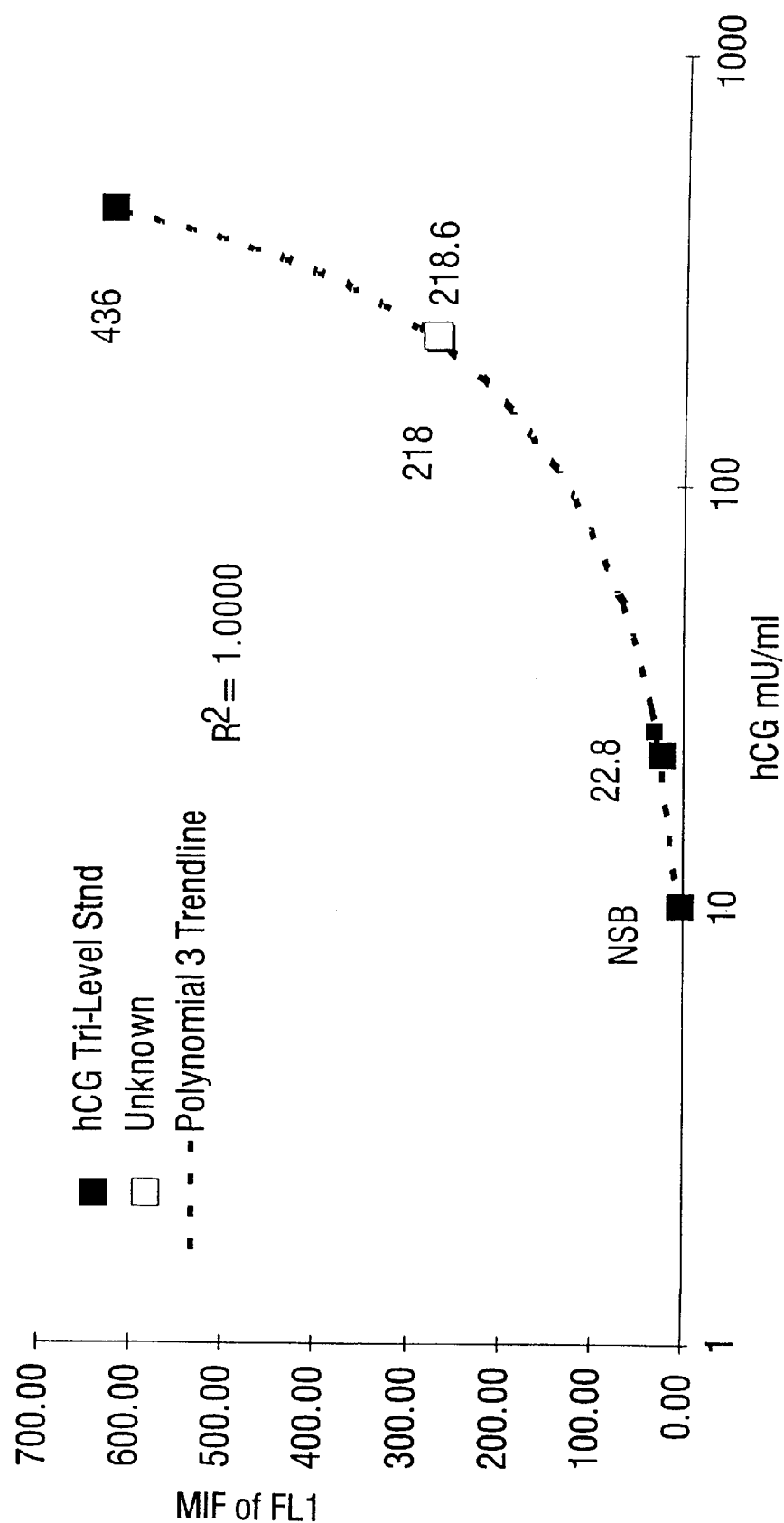
Figure 39B:
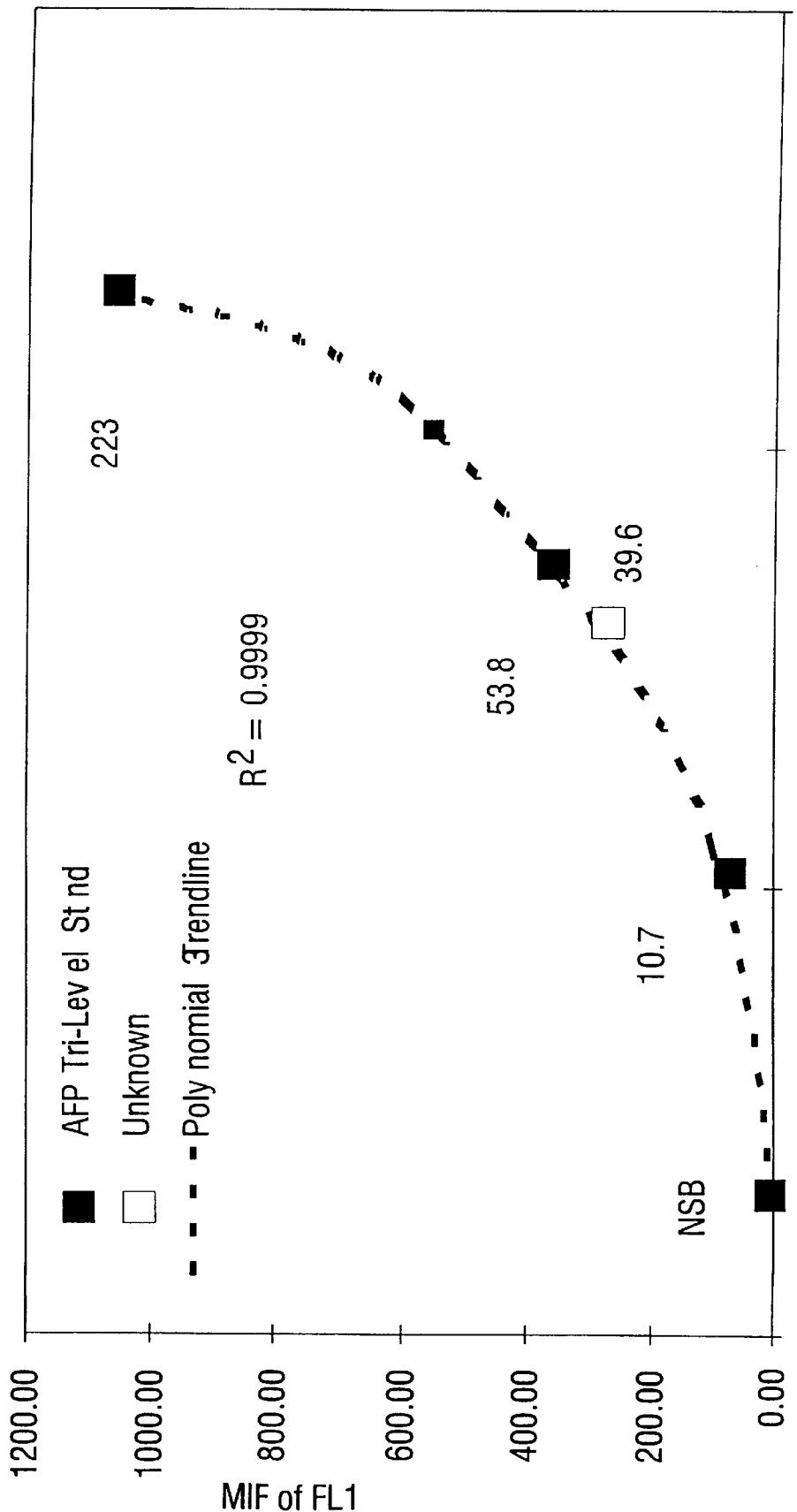

FIGS. 39a and 39b show the determination of hCG and AFP concentrations in samples and standards using a homogeneous capture assay format.

Figure 40:
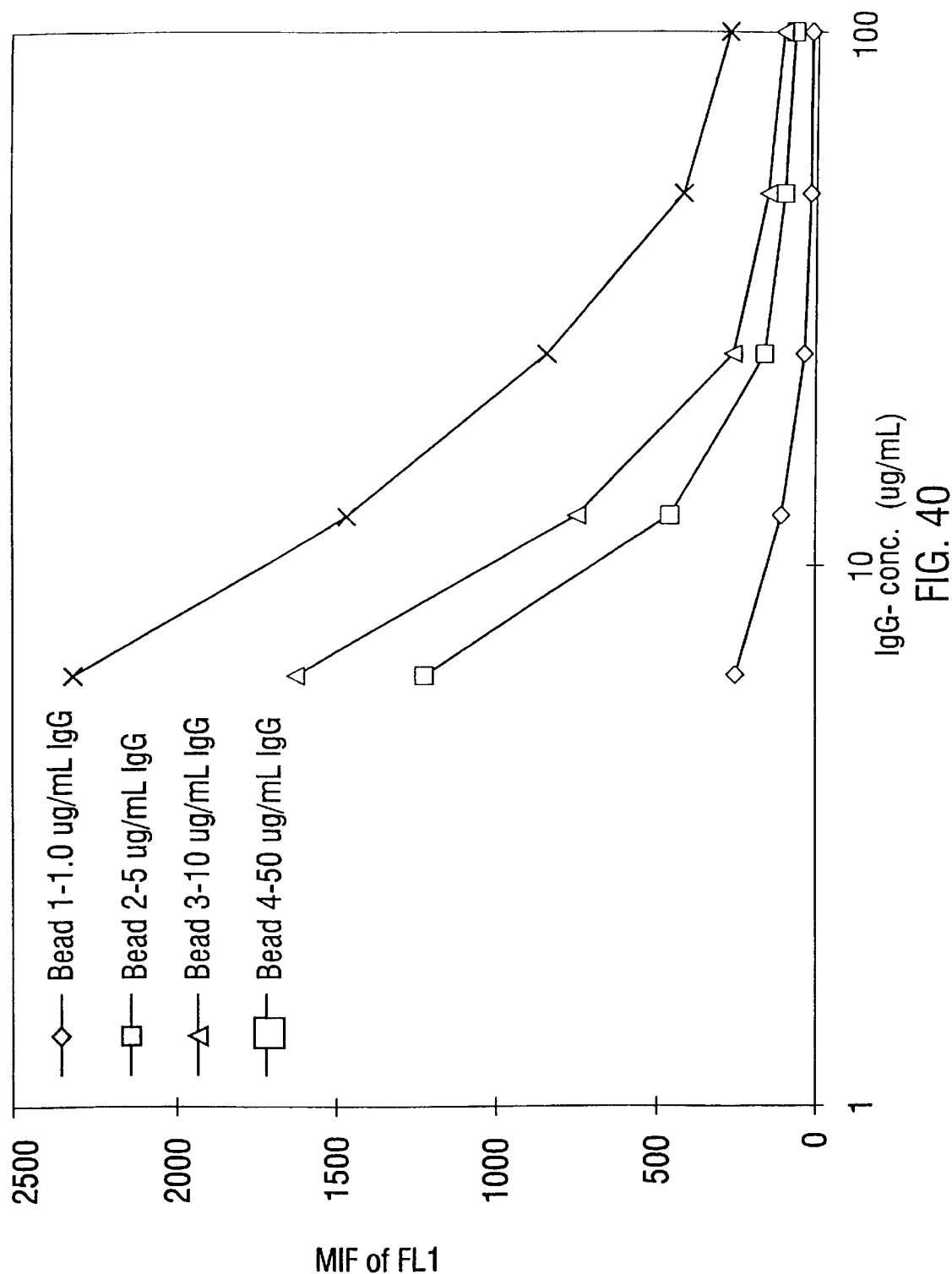

FIG. 40 shows the inhibition of Anti-IgG binding to bead based IgG by soluble IgG antibodies. Inhibition was determined at five concentrations of soluble IgG, and four IgG loading levels on the beads.

Figure 41:
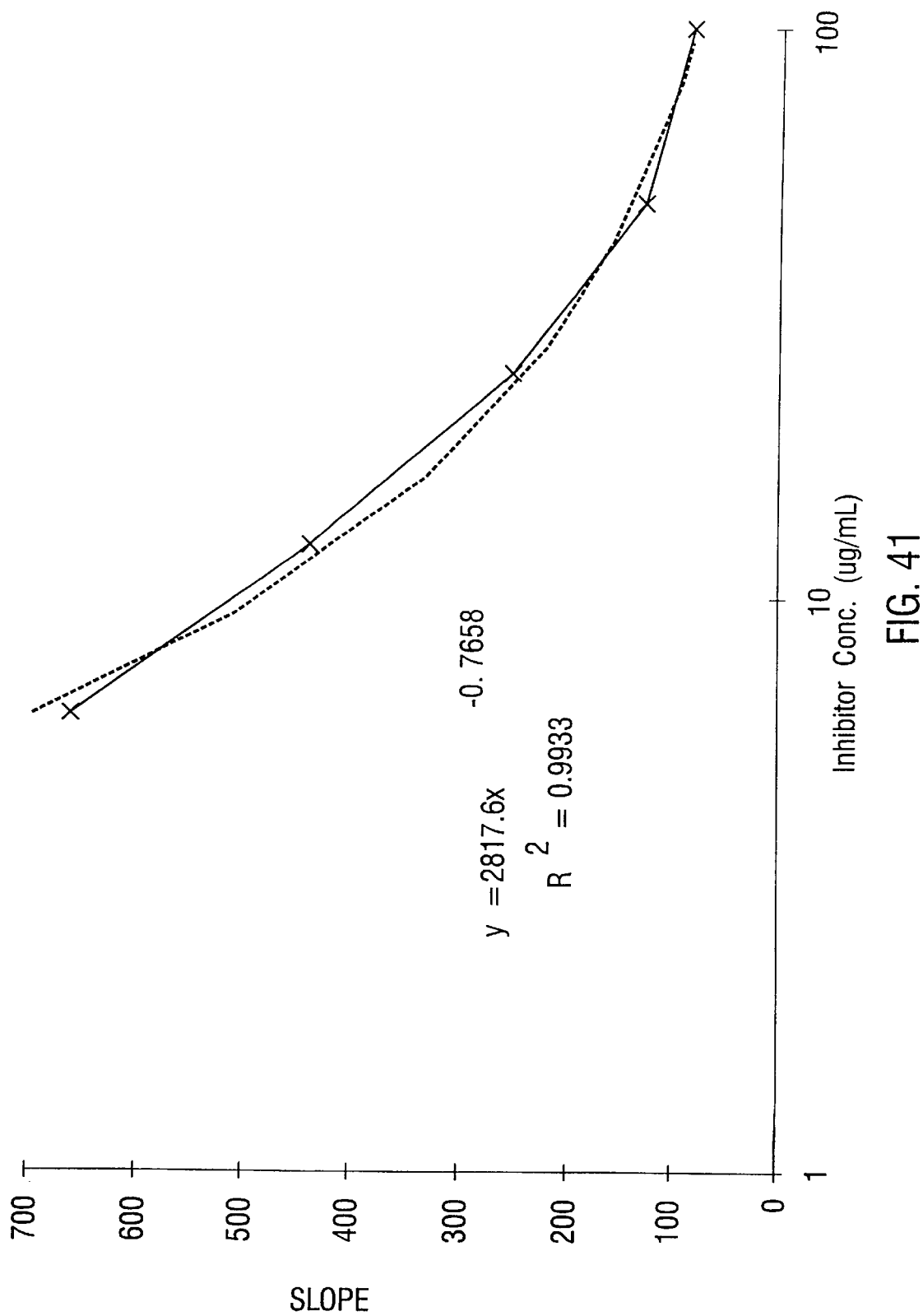

FIG. 41 shows the slope of the inhibition pattern across the four loading levels of IgG on the beads plotted against the soluble IgG concentration.

Figure 42:
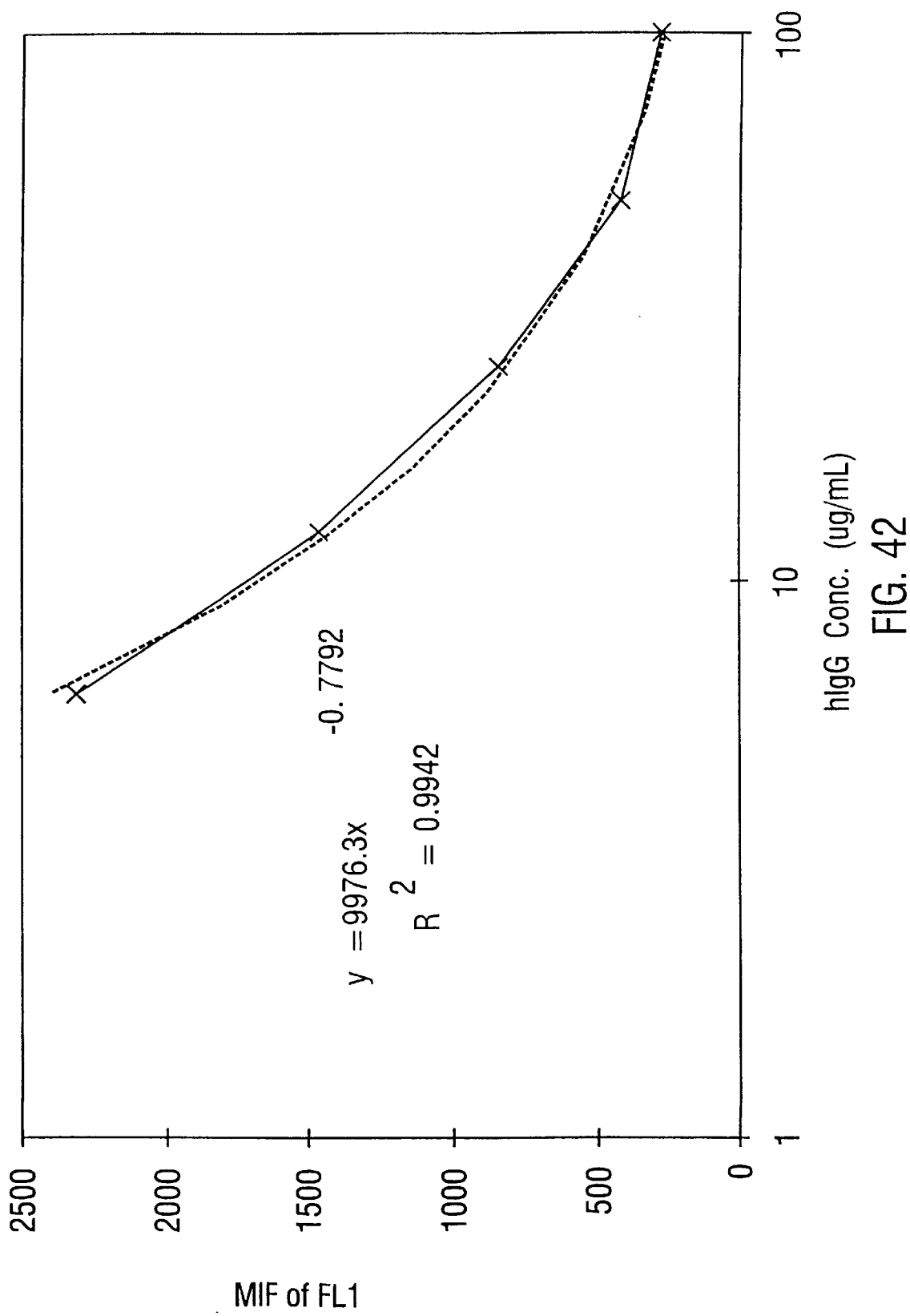

FIG. 42 shows a five point standard curve derived from inhibition data of the 50 µg/mL IgG bead set.

Figure 43A:
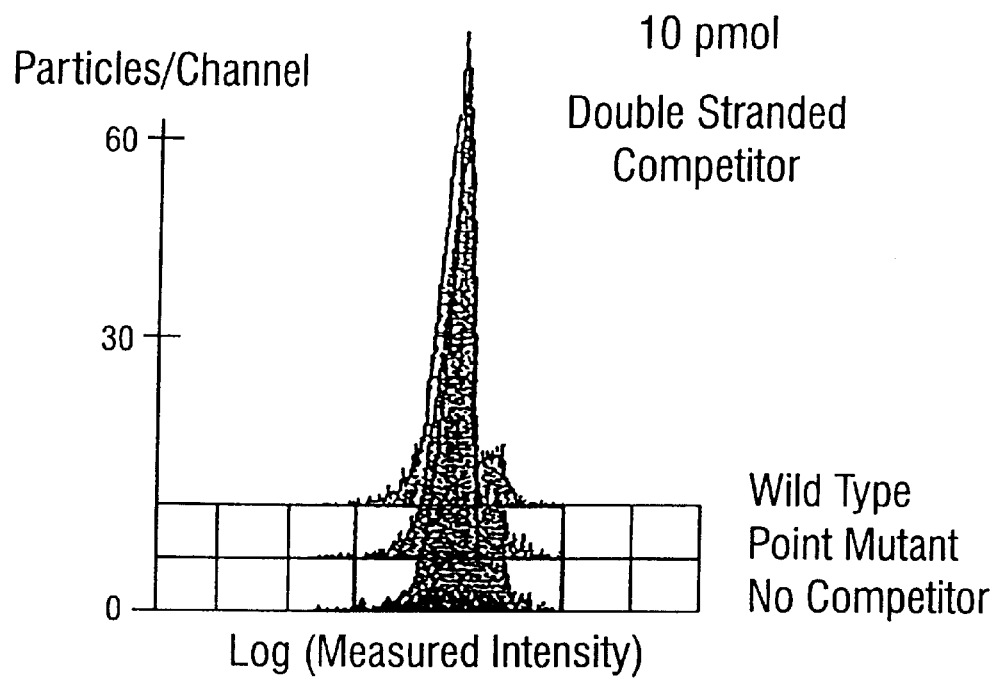
Figure 43B:
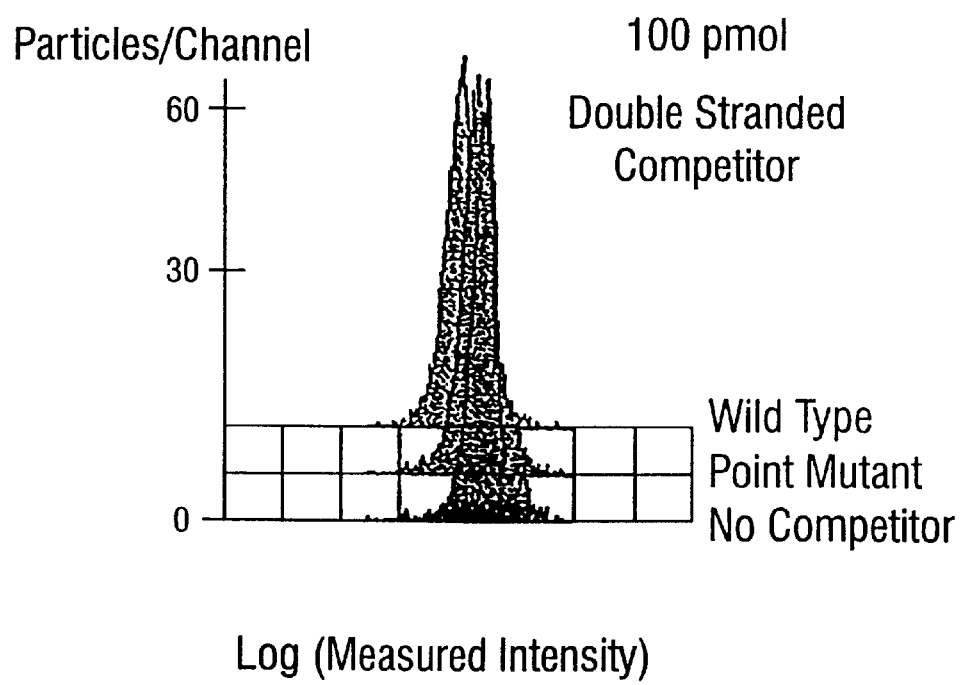
Figure 43C:
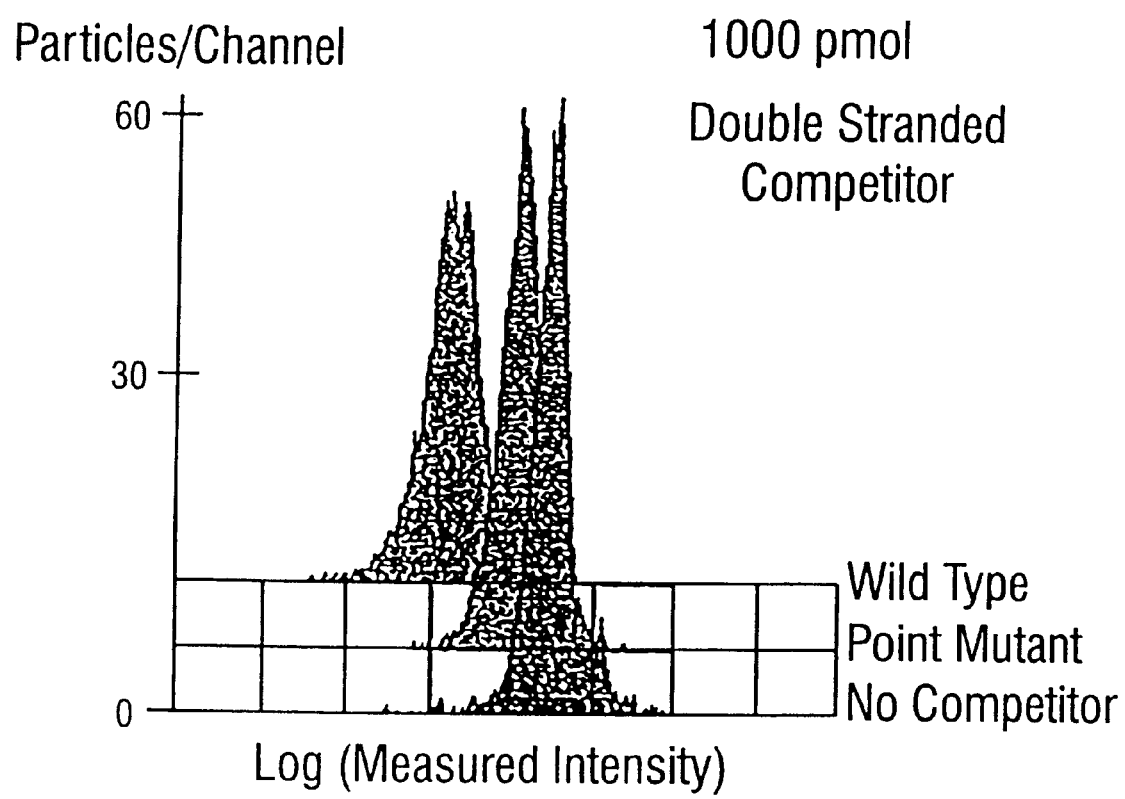

FIGS. 43a through 43c show DNA detection using a double stranded competitor and a wild-type "B" oligonucleotide probe.

Figure 44A:
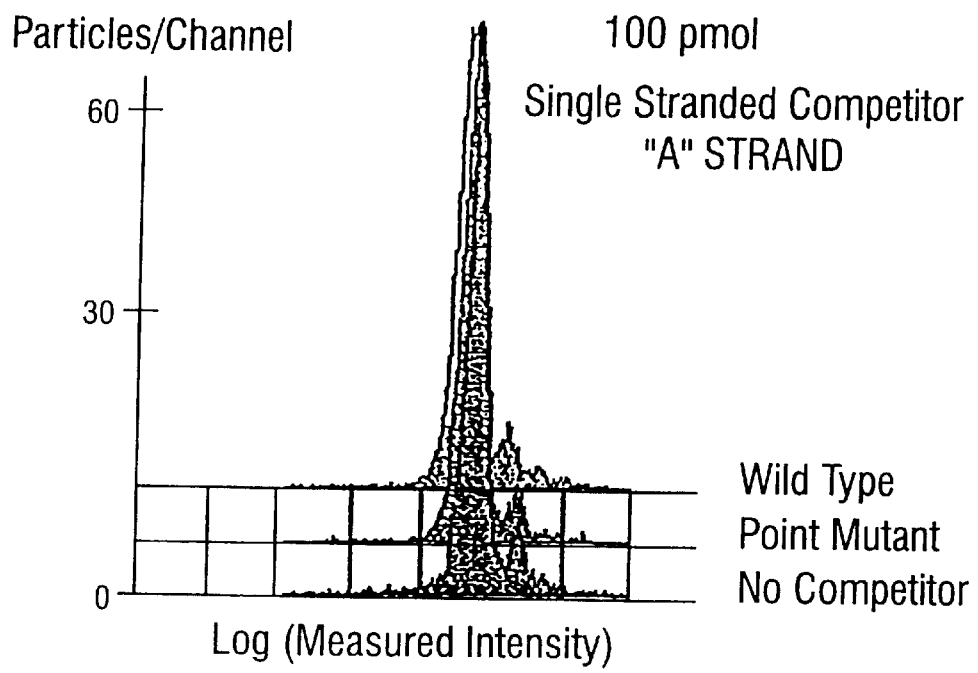
Figure 44B:
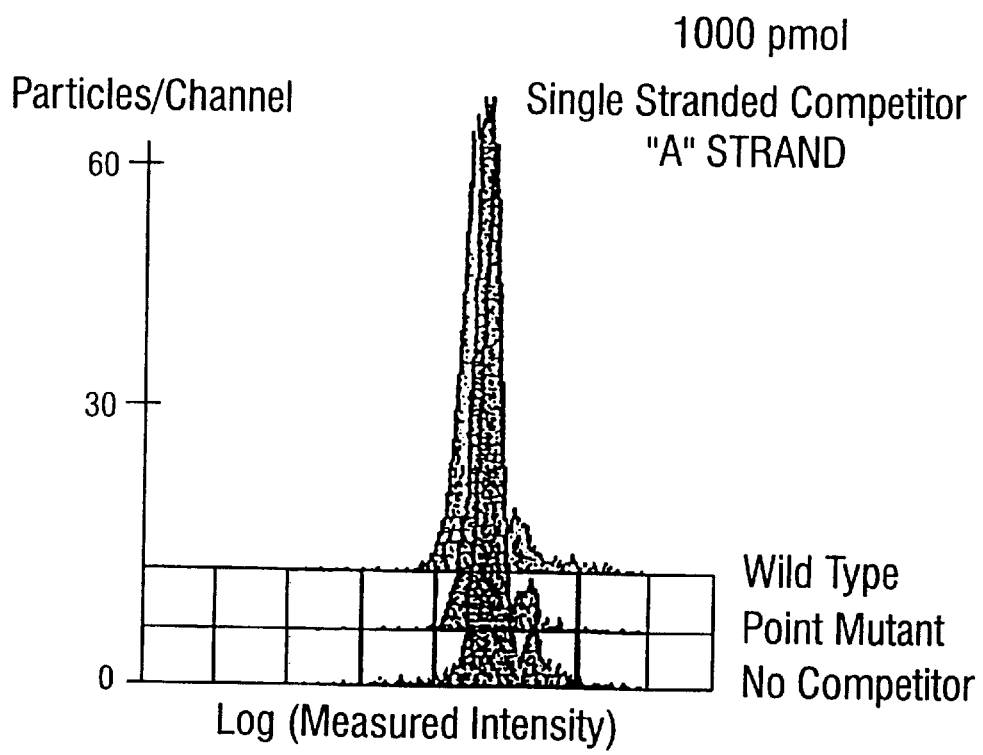

FIGS. 44a and 44b show DNA detection using a single stranded competitor and a wild-type "B" oligonucleotide probe.

Figure 45:
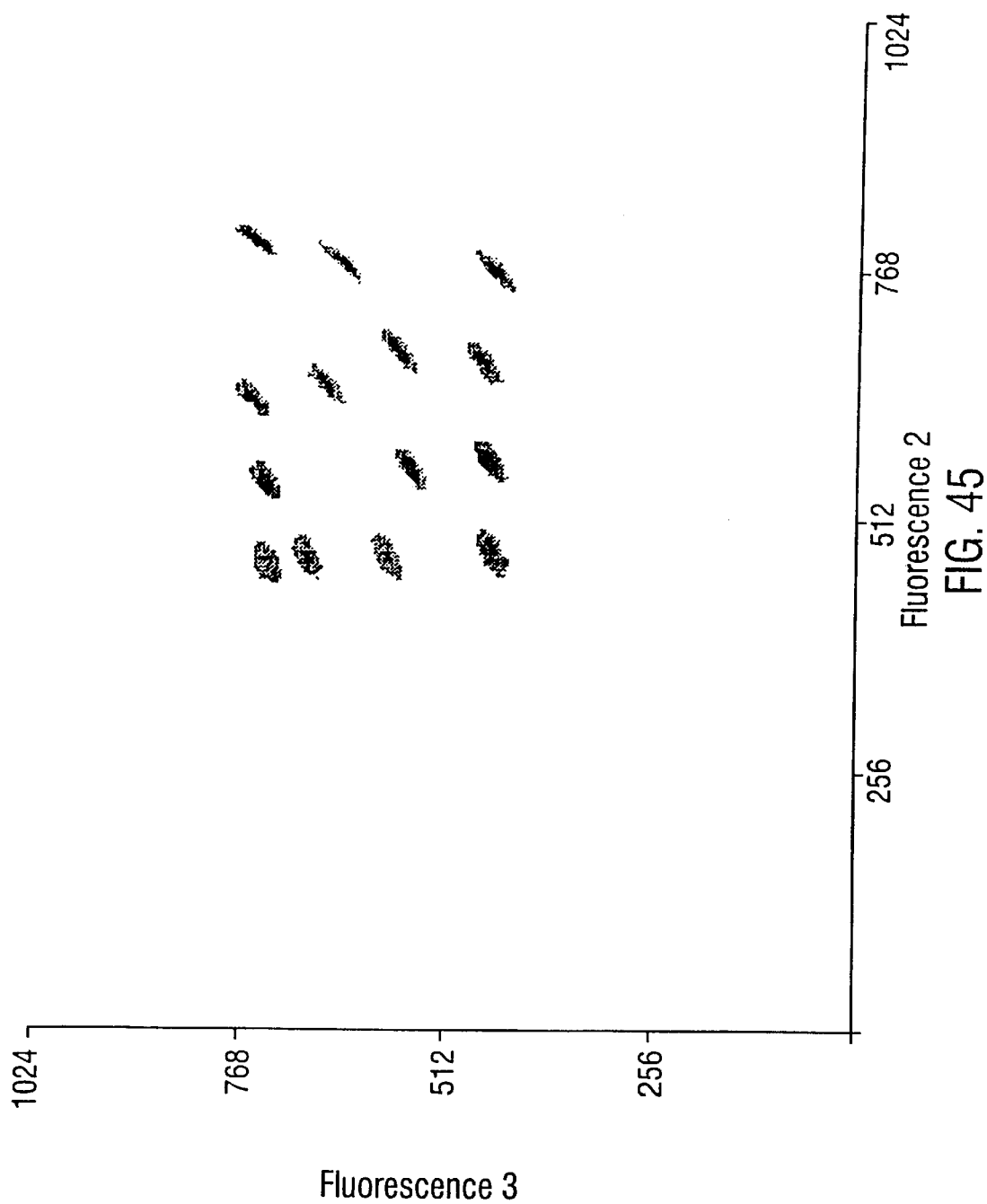

FIG. 45 shows the differentiation by orange and red fluorescence of fourteen bead sets.

Figure 46:
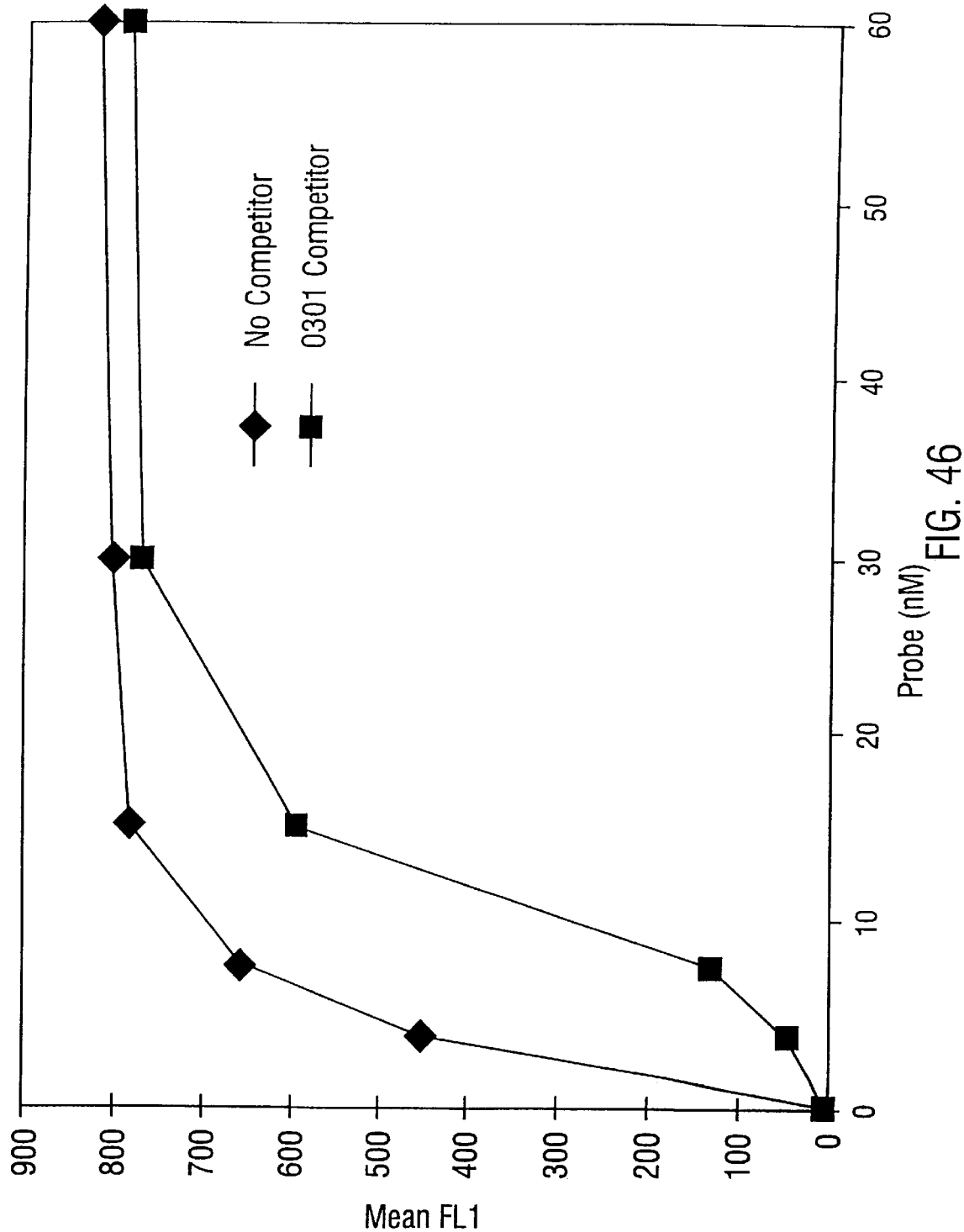

FIG. 46 shows a titration of a fluorescent oligonucleotide in the presence or absence of an inhibitor. Beads bearing complementary oligonucleotides were used in a capture assay.

Figure 47:
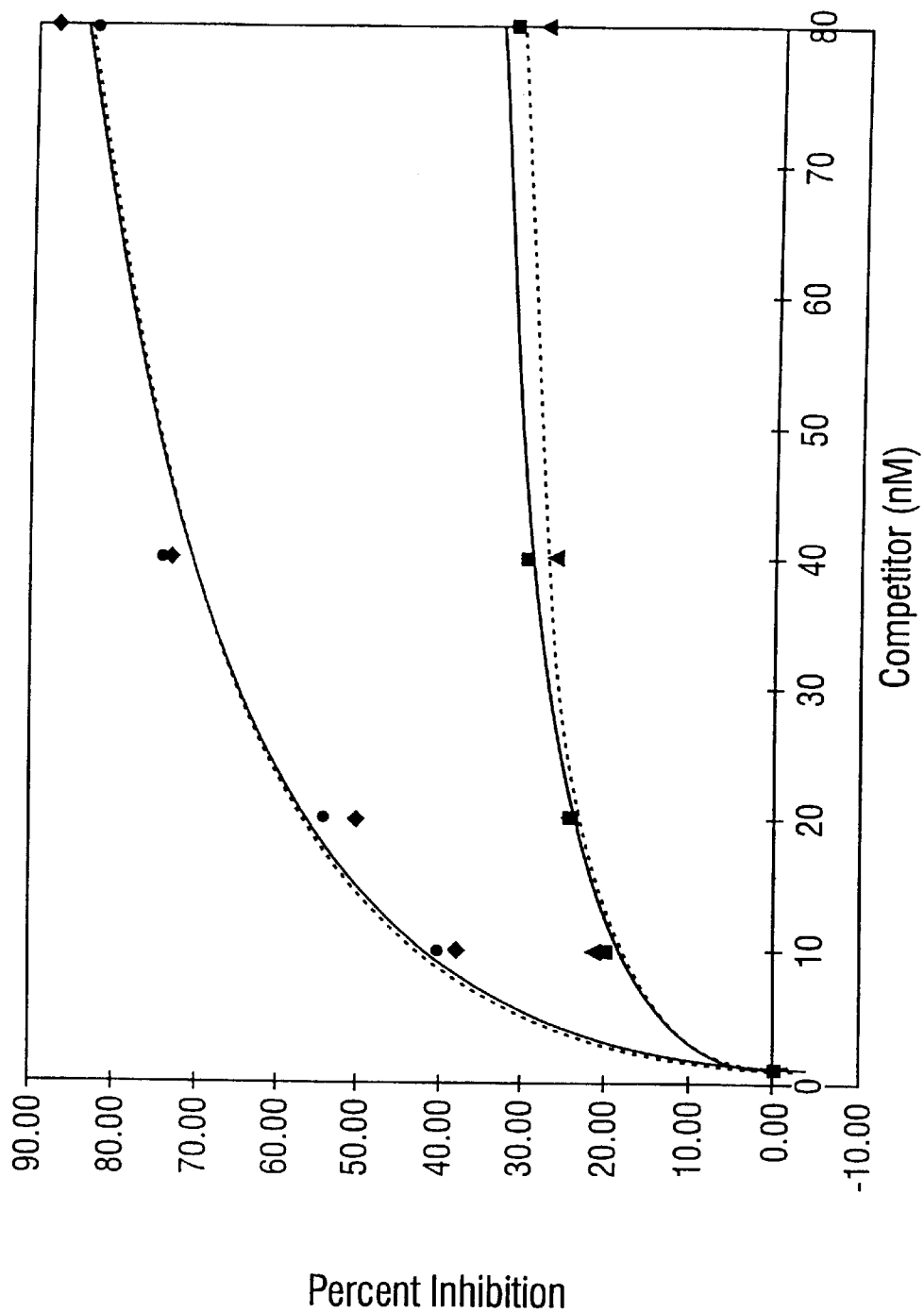

FIG. 47 shows the inhibition of binding between a fluorescent oligonucleotide and its complementary oligonucleotide bound to a bead. Varying concentrations of complementary and point mutant competitors were used in the determination.

Figure 48:
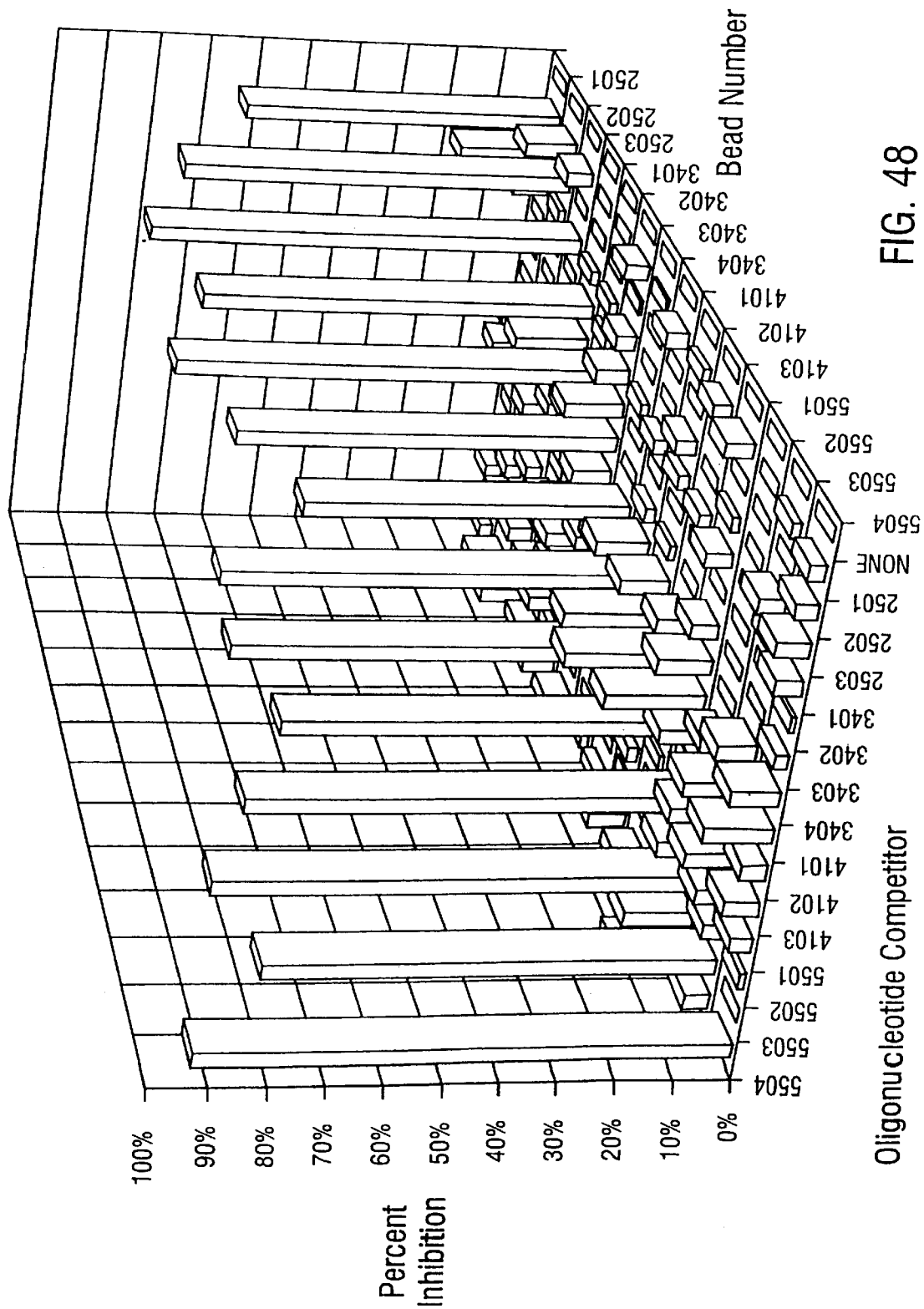
Figure 49A:
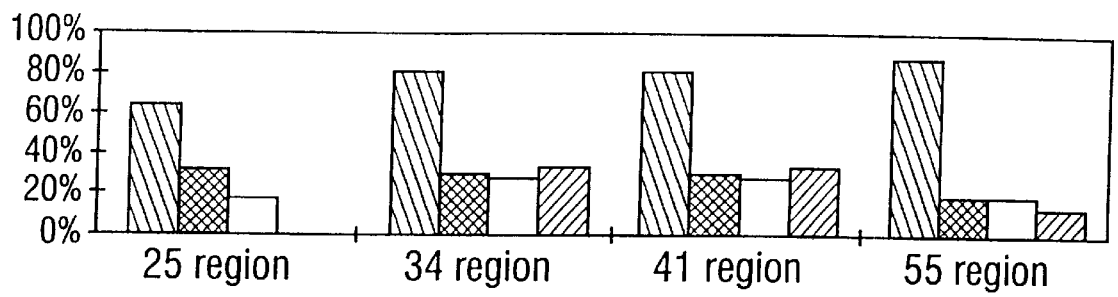
Figure 49B:
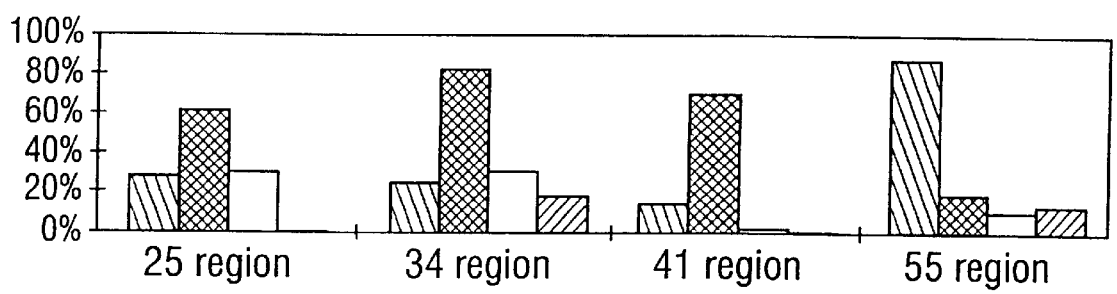
Figure 49C:
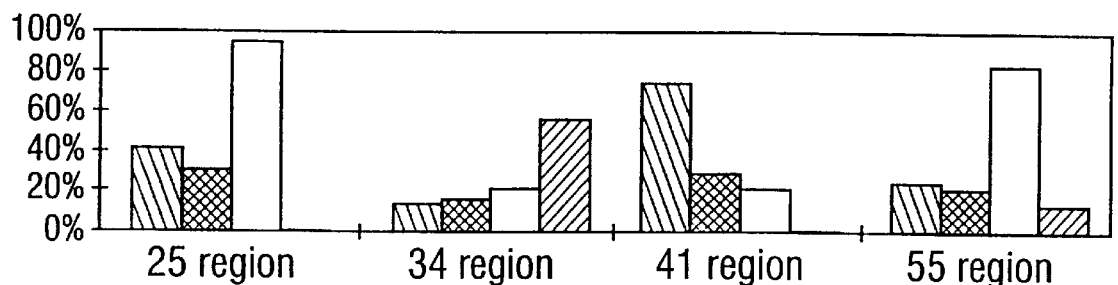
Figure 49D:
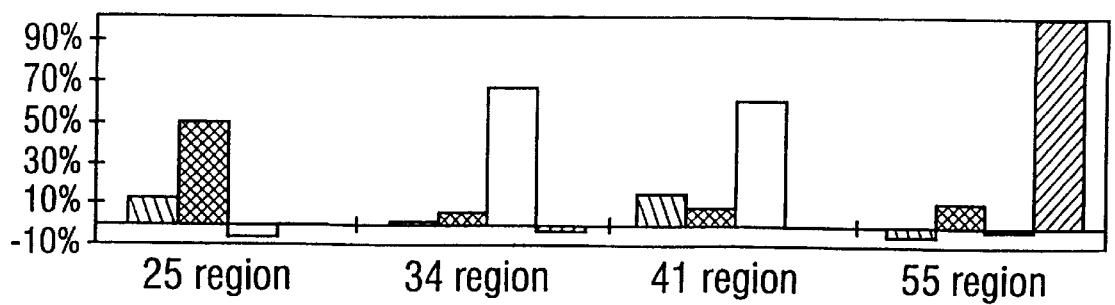
Figure 50A:
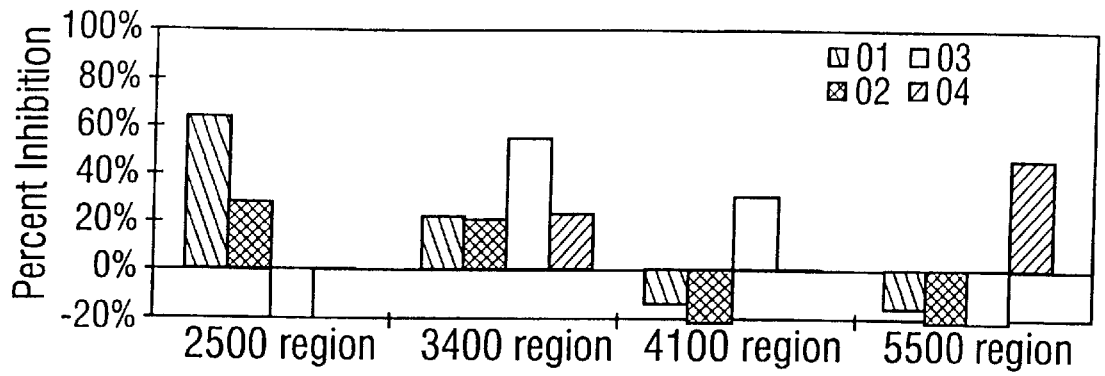
Figure 50B:
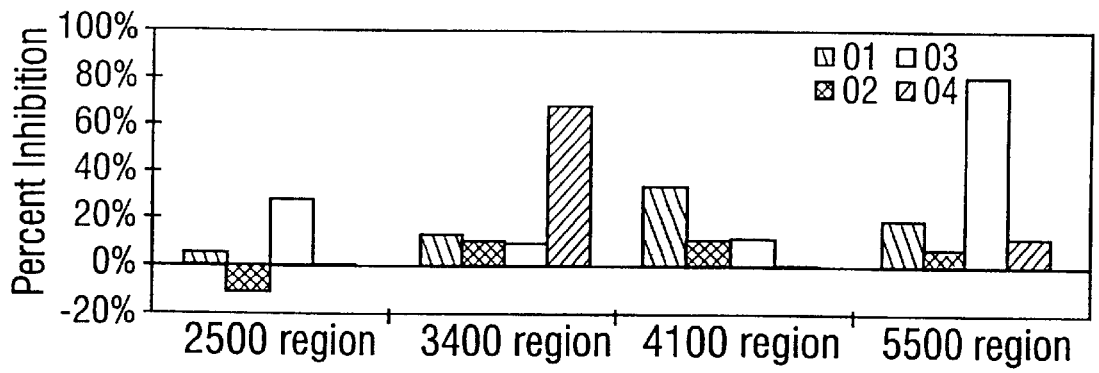
Figure 50C:
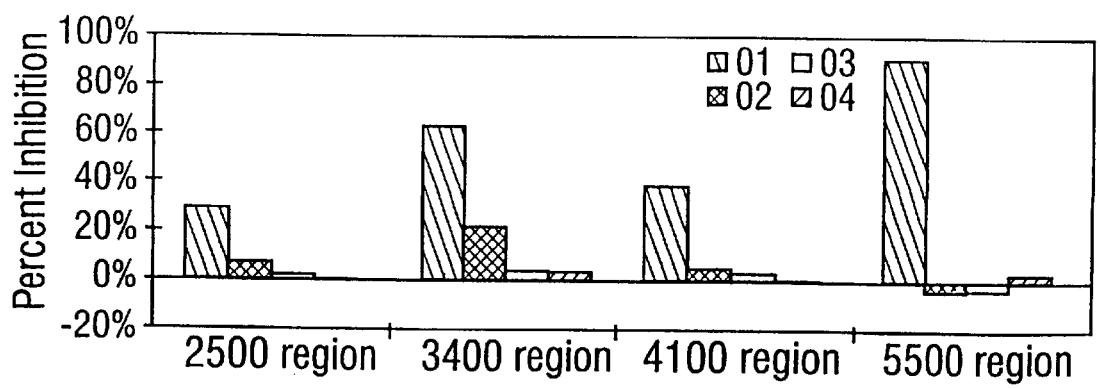
Figure 50D:
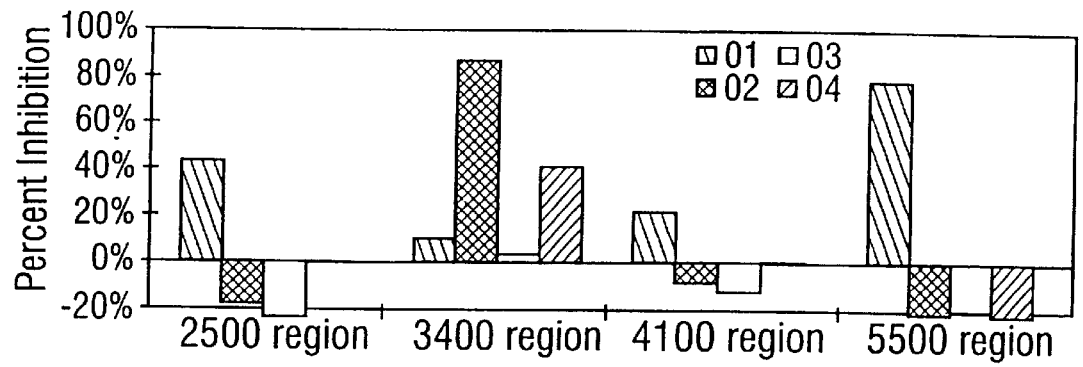
Figure 50E:
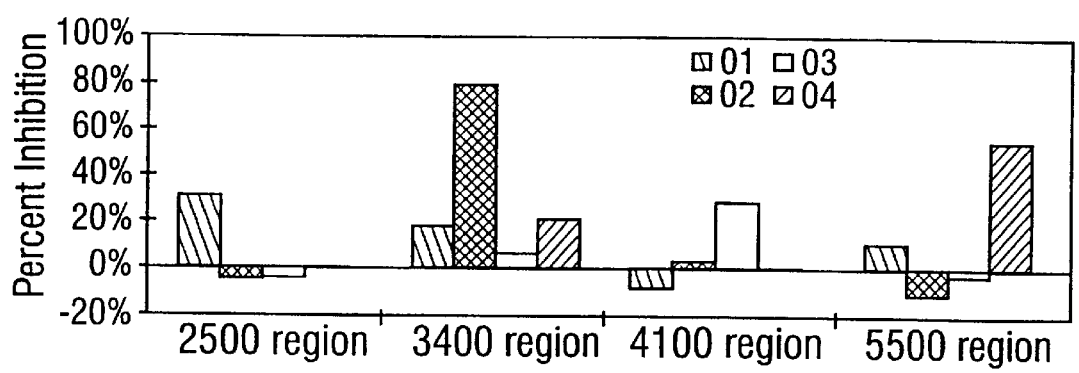

FIG. 48 shows the efficacy of inhibitors across fourteen DNA sequence binding sets.

FIG. 49 shows the typing of four simulated alleles of DQA1.

FIG. 50 shows the typing of five known, homozygous DQA1 alleles.

FIGS. 51a through 51f show the results of an exemplary multiplexed assay according to the invention.

According to the present invention, assay components and methods for the measurement of enzymes, DNA fragments, antibodies, and other biomolecules are provided. The inventive technology improves the speed and sensitivity of flow cytometric analysis while reducing the cost of performing diagnostic and genetic assays. Further, and of tremendous significance, a multiplexed assay in accordance with the invention enables the simultaneous automated assay of multiple (at least an order of magnitude greater than available in the prior techniques) biomolecules or DNA sequences in real-time.

As those of ordinary skill in the art will recognize, the invention has an enormous number of applications in diagnostic assay techniques. Beadsets may be prepared, for example, so as to detect or screen for any of a number of sample characteristics, pathological conditions, or reactants in fluids. Beadsets may be designed, for example, to detect antigens or antibodies associated with any of a number of infectious agents including (without limitation, bacteria, viruses, fungi, mycoplasma, rickettsia, chlamydia, and protozoa), to assay for autoantibodies associated with autoimmune disease, to assay for agents of sexually transmitted disease, or to assay for analytes associated with pulmonary disorders, gastrointestinal disorders, cardiovascular disorders, and the like. Similarly, the beadset may be designed to detect any of a number of substances of abuse, environmental substances, or substances of veterinary importance. An advantage of the invention is that it allows one to assemble a panel of tests that may be run on an individual suspected of having a syndrome to simultaneously detect a causative agent for the syndrome.

Suitable panels may include, for example, a tumor marker panel including antigens such as prostate-specific antigen (PSA), carcinoembryonic antigen (CEA), and other suitable tumor markers; a regional allergy panel including pollen and allergens tested for by allergists of a particular region and comprising allergens known to occur in that region; a pregnancy panel comprising tests for human chorionic gonadotropin, hepatitis B surface antigen, rubella virus, alpha fetoprotein, 3' estradiol, and other substances of interest, in a pregnant individual; a hormone panel comprising tests for T4, TSH, and other hormones of interests; an autoimmune disease panel comprising tests for rheumatoid factors and antinuclear antibodies and other markers associated with autoimmune disease; a blood borne virus panel and a therapeutic drug panel comprising tests for Cyclosporin, Digoxin, and other therapeutic drugs of interest.

Bead Technology

An important feature of the flow cytometric technology and techniques described here is the fabrication and use of particles (e.g., microspheres or beads that make up a beadset). It is through the use of appropriately labeled homogeneous bead subsets, combined to produce a pooled beadset, that the instant multiplexed assay method is practiced. Beads suitable for use as a starting material in accordance with the invention are generally known in the art and may be obtained from manufacturers such as Spherotech (Libertyville, Ill.) and Molecular Probes (Eugene, Oreg.). Once a homogeneous subset of beads is obtained, the beads are labeled with an appropriate reactant such as a biomolecule, DNA sequence, and/or other reactant. Known methods to incorporate such labels include polymerization, dissolving, and attachment.

A Method for the Multiplexed Assay of Clinical Samples

Development of a multiplexed assay for use in accordance with the invention can be divided into three phases: (1) preprocessing, (2) real-time analysis, and (3) interpretation. During the preprocessing phase, baseline data is collected independently, via flow cytometric techniques, for each of an assay's bead subsets. Baseline data is used to generate a set of functions that can classify any individual bead as belonging to one of the assay's subsets or to a rejection class. During the analysis phase, flow cytometric measurements are used to classify, in real-time, each bead within an exposed beadset according to the aforementioned functions.

Additionally, measurements relating to each subset's analyte are accumulated. During the interpretation phase the assay's real-time numerical results are associated with textual explanations and these textual explanations are displayed to a user.

The inventive method allows the detection of a plurality of analytes simultaneously during a single flow cytometric processing step. Benefits of the inventive multiplex assay method include increased speed and reduced cost to analyze a clinical sample.

System Hardware

Figure 1:
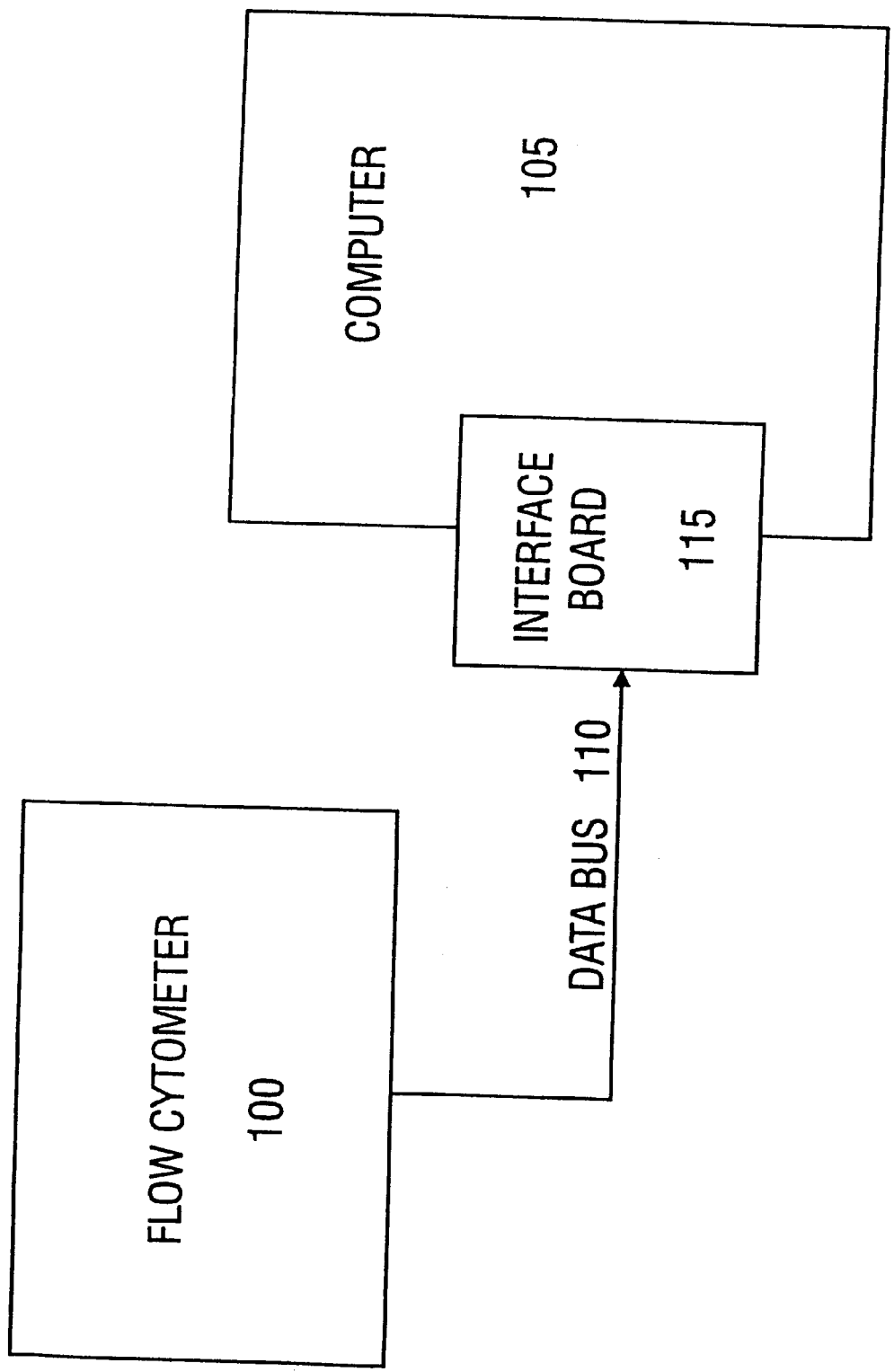
FIG. 1 is a block diagram of an illustrative hardware system for performing a multiplex assay method in accordance with the invention.

FIG. 1 shows, in block diagram form, a system for implementing the inventive multiplexed assay method. Flow cytometer 100 output consists of a series of electrical signals indicative of one or more specified measured characteristics on each bead processed. These measurement signals are transmitted to computer 105 via data bus 110 and interface board 115. During the preprocessing phase, the signals are used by the computer to generate an assay database. During the real-time analysis phase, the signals are processed by the computer (using the assay database) in accordance with the inventive method to produce a multiplexed/simultaneous assay of a clinical sample.

Flow cytometer 100 operates in a conventional manner. That is, beads are processed by illuminating them, essentially one at a time, with a laser beam. Measurements of the scattered laser light are obtained for each illuminated bead by a plurality of optical detectors. In addition, if a bead contains at least one appropriate fluorescing compound it will fluoresce when illuminated. A plurality of optical detectors within the flow cytometer measure fluorescence at a plurality of wavelengths. Typical measured bead characteristics include, but are not limited to, forward light scatter, side light scatter, red fluorescence, green fluorescence, and orange fluorescence. One of ordinary skill in the use of flow cytometric techniques will recognize that the use of green fluorescent markers or labels can cause cross-channel interference between optical detectors designed to detect green and orange wavelengths (e.g., approximately 530 nanometers and approximately 585 nanometers respectively). A training set of beads, in combination with standard data manipulation, can correct for this cross-channel interference by providing the physical measurements required for mathematical correction of the fluorescence measurements.

One of ordinary skill will further recognize that many alternative flow cytometer setups are possible. For instance, additional color sensitive detectors could be used to measure the presence of other fluorescence wavelengths. Further, two or more laser beams can be used in combination to illuminate beads as they flow through the cytometer to allow excitation of fluorochromes at different wavelengths.

Computer 105 can be a conventional computer such as a personal computer or engineering workstation. In one embodiment, the computer is a personal computer having an Intel "486" processor, running Microsoft Corporation's "WINDOWS" operating system, and a number of ISA expansion slots.

Interface board 115 is designed to plug into one of the computer's 100 ISA (Industry Standard Architecture) expansion slots. While the design of an interface board is, in general, different for each specific type of flow cytometer 100, its primary functions include (1) receiving and parsing measurement data signals generated by the flow cytometer's detectors, (2) receiving control parameter status information from the flow cytometer, and (3) sending control parameter commands to the flow cytometer. The precise manner in which these functions are carried out are dependent upon the type (make and model) of the flow cytometer used. In one embodiment, employing a Becton-Dickinson "FACSCAN" flow cytometer (San Jose, Calif.), the interface board uses control signals generated by the flow cytometer to distinguish measurement data and flow cytometer parameter and control signals. Measured data include forward light scatter, side light scatter, red fluorescence, green fluorescence, and orange fluorescence.

Parameter and control signals include flow cytometer amplifier gain adjustments and status information.

While the design of an interface board 115 for use with the inventive assay method would be a routine task for one skilled in the art of diagnostic medical equipment design having the benefit of this disclosure, an important aspect for any interface board is its ability to accommodate the transmission data rate generated by whatever flow cytometer is used. For example, the "FACSCAN" flow cytometer can transmit a 16-bit (2 byte) word every 4 a microseconds resulting in burst data rates of 500,000 bytes per second. Microfiche appendix A provides a detailed source code embodiment of the inventive assay method for use with the "FACSCAN" flow cytometer.

Data bus 115 provides a physical communication link between the flow cytometer 100 and the interface board 110. Its physical and electrical characteristics (e.g., data width and bandwidth) are dependent upon the capabilities of the flow cytometer. It is noted that the data bus need not be a totally digital bus. If the flow cytometer does not include analog-to-digital conversion of measured bead characteristics (e.g., light scatter and fluorescence signals), then the data bus must communicate these analog signals to the interface board It is then necessary that digital conversion of these signals be provided by either the interface board, or another peripheral device before the data is transmitted to the computer 105.

System Software

Figure 2:
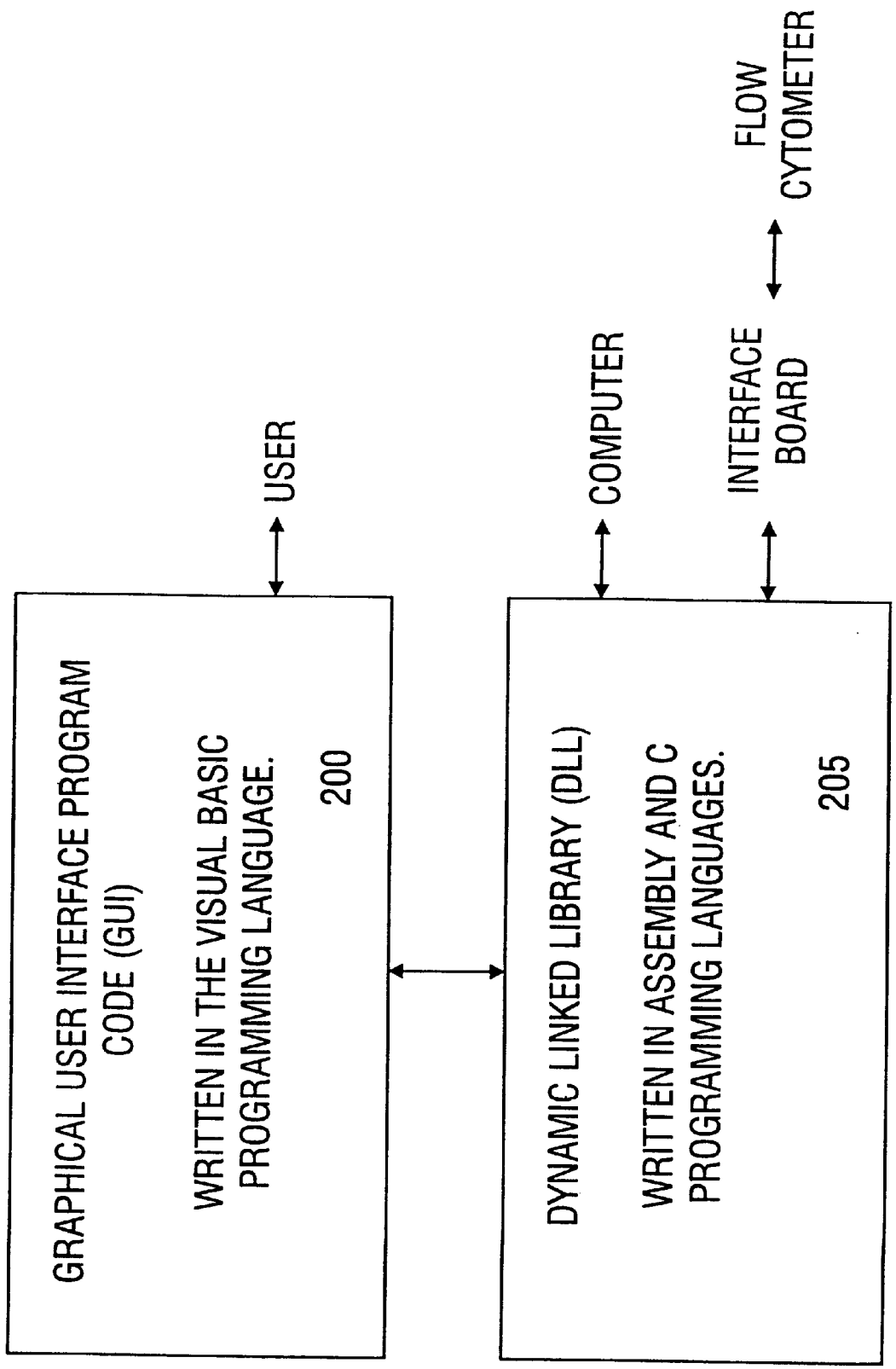
FIG. 2 is a block diagram of an illustrative software system for performing a multiplex assay method in accordance with the invention.

As shown in FIG. 2, the software architecture for the inventive assay method can be divided into two parts. A graphical user interface (GUI) 200 provides the means by which a user (1) receives assay results and (2) interacts with the flow cytometer. A dynamically linked library (DLL) 205 provides the means through which the inventive real-time assay is performed and includes routines necessary to (1) interact with interface board 115 and (2) send and receive information to the flow cytometer 100.

An important aspect of the inventive assay method is that it performs a simultaneous analysis for multiple analytes in real-time. One of ordinary skill in the art of computer software development will realize that real-time processing can impose severe time constraints on the operational program code, i.e., the DLL 205. For example, the "FACS-CAN" flow cytometr can process, or measure, approximately 2,000 beads per second, where each bead is associated with eight 16-bit data values. Thus, to process flow cytometer data in real-time from a "FACSCAN," the DLL should be able to accept, and process, at a consistent data rate of at least 32,000 bytes per second. The need to accommodate this data rate, while also having sufficient time to perform real-time analysis based on the data, will generally necessitate that some of the DLL code be written in assembly language.

In a current embodiment, the GUI 200 is implemented in the visual basic programming language and the DLL 205 is implemented in C and assembly language programming. Microfiche appendix A contains source code listings for one embodiment of the GUI and DLL.

Preprocessing

Figure 3:
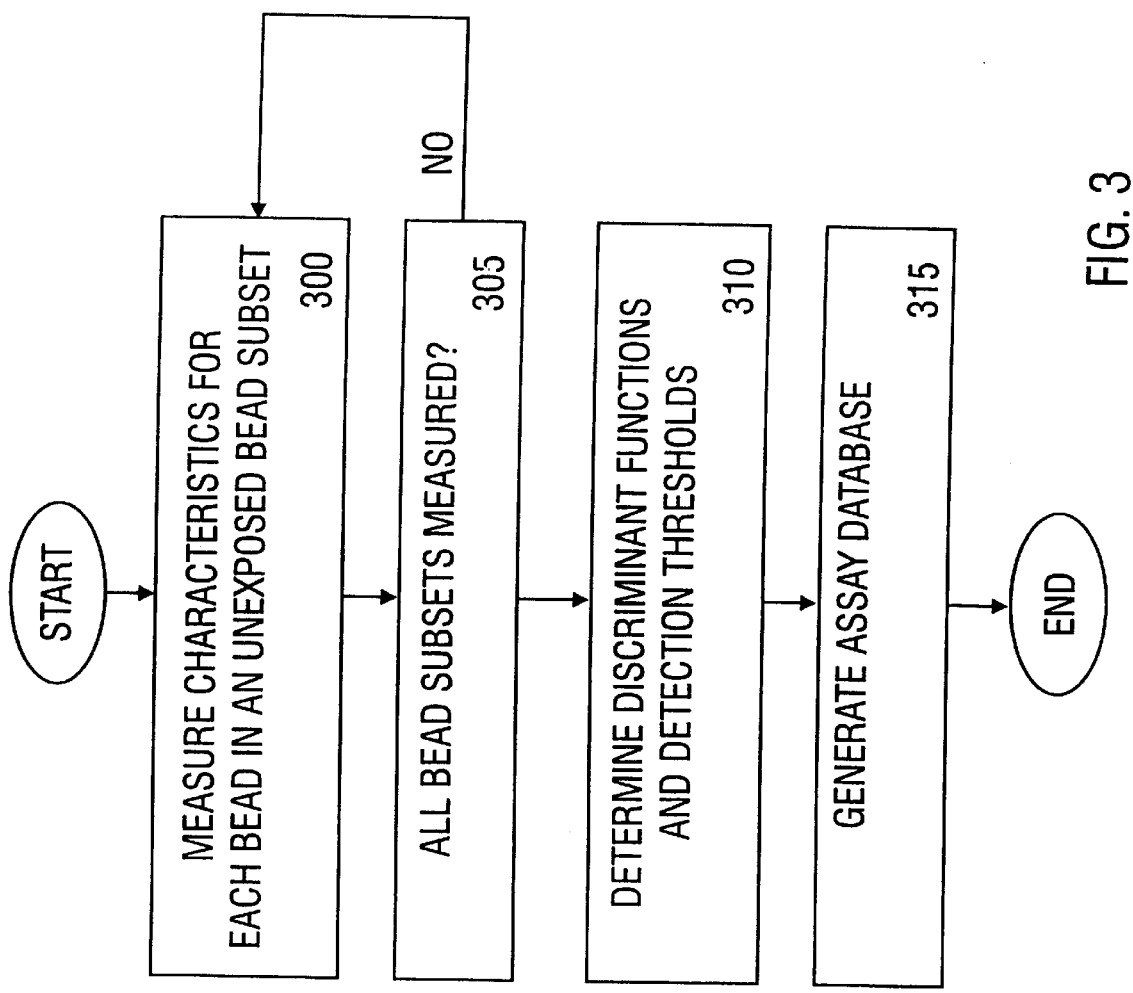
FIG. 3 is a flow-chart for a preprocessing phase in accordance with the inventive multiplexed assay method.

A function of the preprocessing phase is to generate an assay database for use during the real-time analysis of an exposed beadset (clinical sample). Thus, preprocessing is performed prior to combining separately labeled bead subsets to form assay beadsets. Assay definition, discriminant function definition, and interpretation tables are created at the time an assay beadset is created. FIG. 3 shows, in flow chart form, the steps taken during the preprocessing phase.

A bead subset is characterized by (1) the analyte it is designed to identify, (2) one or more classification parameters $C_1 \ldots C_n$, and (3) one or more measurement parameters $F_{m1}$–$F_{mx}$. During the preprocessing phase the classification parameters are used to generate a set of functions, referred to as discriminant functions, that can classify a bead as belonging to one of the assay's subsets or a rejection class. Measurement parameters are used during the real-time analysis phase to determine if a specified analyte is present in the clinical sample being analyzed.

The precise number of individual beads contained in any given subset is relatively unimportant, the only significant criterion being that a sufficient number are used so that a good statistical characterization of the subset's parameters can be achieved during the real-time analysis phase. In a current embodiment, each bead subset contains an equal number of beads. One of ordinary skill in the field will recognize that the precise number of beads within any given bead subset can vary depending upon many factors including, but not limited to, the number of analytes an assay beadset is designed to detect, the uniformity of the labeled beads (with respect to each of the measured parameters $C_1 \ldots C_n, F_{m1} \ldots F_{mx}$), and the penalty of misclassifying (e.g., making a type 1 or type 2 classification error) a bead during analysis.

During preprocessing, each bead in an unexposed subset is measured by a flow cytometer 100 and the resulting data values accumulated for later use 300. For example, if the flow cytometer measures n classification parameters and x measurement parameters, i.e., generates (n+x) values for each bead, data for each of the subset's (n+x) parameters are updated based on each bead's measurements. This data collection step is repeated independently for each subset in the assay's beadset 305. The collection of such data for each of an assay's subsets constitutes an assay's baseline data.

After an assay's baseline data has been collected, a set of discriminant functions are determined 310. During real-time analysis, the discriminant functions are used to classify a bead into one of the assay's bead subsets or a rejection class based solely on the measured classification parameters, $C_1 \ldots C_n$. This step, in principle and practice, is a problem of multi-dimensional classification or cluster analysis. Many prior art techniques and commercial software programs exist to perform this task.

Beads are generally manufactured in large quantities referred to as batches. Each bead in a batch is of nearly identical size and has substantially the same dye absorption capacity. In light of this manufacturing process, bead subsets can be created using precise dilutions of chosen dyes and, because of their nearly identical size, all classification parameters will exhibit essentially equal variances. By correcting for scaling of the photo-multipliers within a flow cytometer, a linear classification rule can be generated. Further, since there are equal quantities of beads in each subset, the prior probabilities will be equal. This allows use of Fisher's linear discriminant technique to calculate the discriminant functions which define classification boundaries. See, Fisher, "The Use of Multiple Measurements in Taxonomic Problems," Annals of Eugenics, 7, 179–188 (1936). For instance, linear hierarchical discriminant functions may be chosen which are equidistant, in a Euclidean sense, between the centers or centroids of any two of an assay's bead subsets. Notwithstanding the present example, other types of discriminant functions, such as quadratic functions and those discriminating on more than two classification parameters at once, are also possible.

In addition to the discriminant functions, a set of threshold values are chosen which are used during the real-time analysis phase to detect the presence of a target analyte. For example, assume measurement parameter $F_{m1}$ is used to detect analyte-A. During preprocessing, the baseline or unexposed value for $F_{m1}$ is measured and accumulated for that subset's beads. Analyte-A's threshold could then, for example, be set to $F_{m1}$'s baseline mean value plus one standard deviation of $F_{m1}$'s baseline value. One of ordinary skill will recognize that the precise function or value selected for a threshold depends upon the parameter being measured (e.g., its distribution) and the cost of making a classification error (e.g., a type 1 or a type 2 ,error). It is routine that such values be based on an empirical review of the baseline data. Thee important criterion is that the threshold reliably distinguish between the presence and absence of the target analyte in an exposed assay beadset.

After baseline data for each of an assay's bead subsets are collected and discriminant functions and analyte threshold values are established, an assay database is generated 315.

Assay Database

Figure 4:
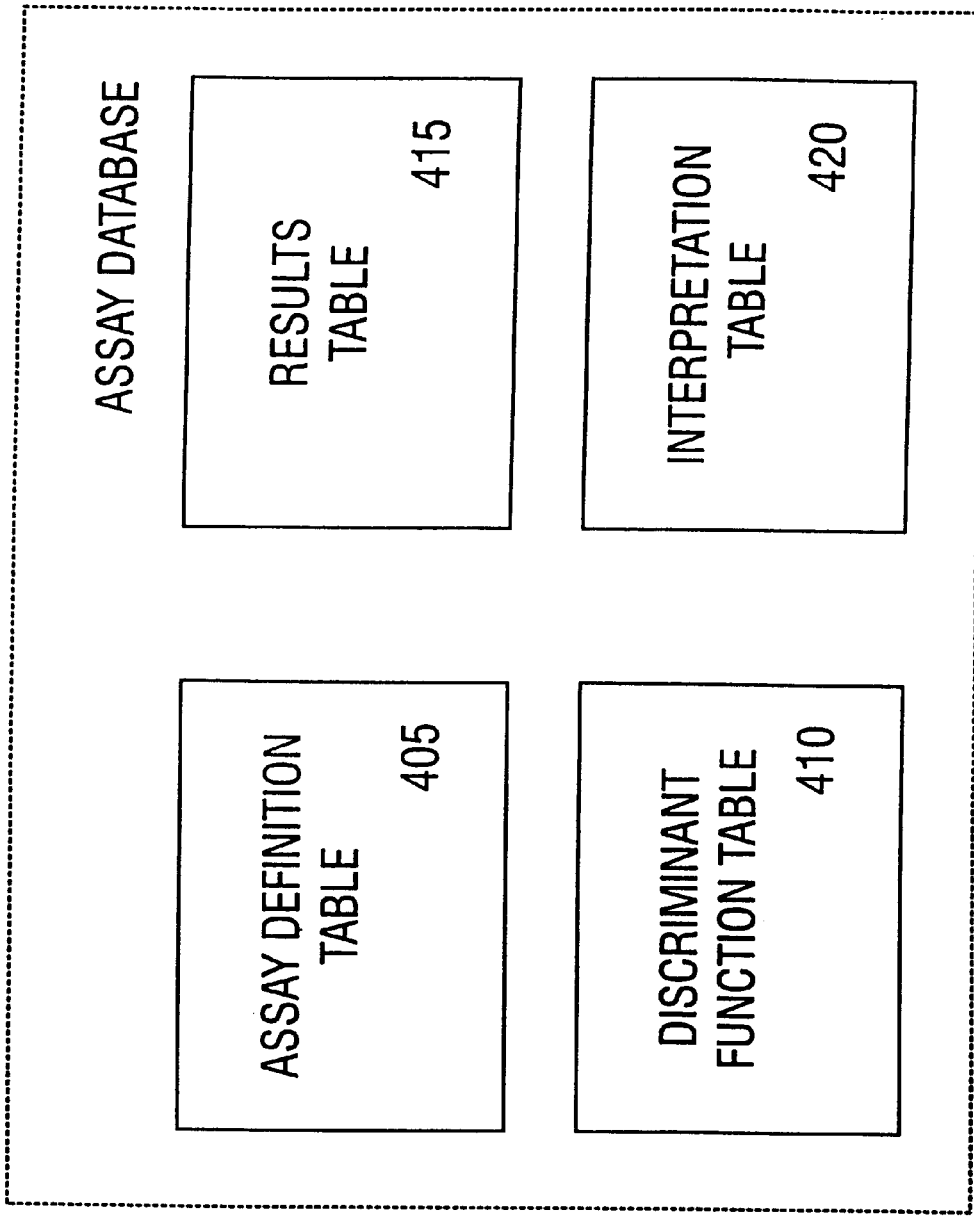
FIG. 4 shows an assay database in accordance with the invention.

As shown in FIG. 4, an assay database 400 consists of an assay definition table 405, a discriminant function table 410, a results table 415, and an interpretation table 420. See FIG. 4.

The assay definition table 405 defines an assay which, as described above, comprises two or more bead subsets each of which is designed to detect a specified analyte. Each row in the assay definition table describes a bead subset and contains the following entries: (1) assay name, (2) subset name, (3) subset token, (4) baseline values for each of the subsets measurement parameters $F_{m1}$–$F_{mx}$, and (5) test-type token. The subset name entry is a text string identifying the subset by, for example, the type of analyte it is labeled to detect. The subset token is a unique subset identifier. The measurement parameter baseline entries are used during the interpretation phase to associate a numerical result (collected during the real-time analysis of a clinical sample) with a textual output string. Finally, the test-type token identifies; which one of a possible plurality of interpretation tests to perform on the collected (real-time) data during the interpretation phase.

The discriminant function table 410 is used to systematically set forth an assay's set of discriminant functions. Each row in the discriminant function table implements a single discriminant function and includes entries for (1) the assay's name, (2) a unique row identifier, (3) one or more classification parameters upon which to evaluate, (4) high and low discriminant values for each of the listed classification parameters, and (5) evaluation tokens which are assigned as a result of evaluating the discriminant function.

The results table 415 is used to store, or accumulate, data on an assay's beadset during the real-time analysis phase of the inventive method and is discussed further in Section 6.2(d).

The interpretation table 420 provides a means to associate text messages with each enumerated assay result and is discussed further in Section 6.2(e).

PREPROCESSING EXAMPLE

Consider an assay beadset designed to simultaneously detect four analytes: analyte-A, analyte-B, analyte-C, and analyte-D. Thus, the assay's beadset is comprised of four bead subsets, each labeled for a different analyte. Suppose further that the assay beadset is to be processed by a Becton-Dickinson Immunocytometry Systems "FACS-CAN" flow cytometer. For each bead processed, the "FAC-SCAN" measures forward light scatter, side light scatter, red fluorescence, orange fluorescence, and green fluorescence. Let classification parameter $C_1$ be forward light scatter, classification parameter $C_2$ be side light scatter, classification parameter $C_3$ be red fluorescence, classification parameter $C_4$ be orange fluorescence, and measurement parameter $F_{m1}$ be green fluorescence. (This notation implies; that each bead in a subset is labeled with a green fluorophore bearing, for example, an antibody or dye specifically targeted to that subset's analyte.)

After preparing each of the four subsets and before they are combined to form the assay beadset, they are processed by the flow cytometer and their measured data are accumulated: values for each of the parameters $C_1$, $C_2$, $C_3$, $C_4$, and $F_m$. are recorded for each bead. Each bead subset is similarly processed. Completion of this task constitutes completion of baseline data acquisition.

Using baseline data, the assay's beads are clustered in the four-dimensional parameter space defined by $C_1$, $C_2$, $C_3$, and $C_4$. The result of this cluster analysis is that each subset is characterized by a mean ($\mu$) and standard deviation ($\sigma$) for each of its four classification parameters. See FIG. 5. As previously noted, the precise number of individual beads contained in any given bead subset can be calculated by those of ordinary skill in the art. This calculation is required to obtain good statistical characterization of the subset's parameters—e.g., small, or relatively fixed, coefficient of variations for each parameter.

As shown in FIG. 6, the assay definition table 405 is comprised of general information relevant to the overall diagnostic function of the assay. For instance, in a genotyping assay, each of the assay's subset's may be assigned a token used for identification: e.g., token 46 represents the bead subset labeled to detect a wildtype coding sequence for a specified gene; subset tokens 21, 50, and 5 represent subsets labeled to detect various mutant type coding sequences for a specified gene(s). Additionally, measurement parameter $Fm_j$'s baseline (in this example the mean) and standard deviation values are listed. Finally, a test-type token is listed. In the current embodiment a test-type token of '0' means an OVER/UNDER interpretation test is to be performed and a test-type token of '1' means a SHIFT interpretation test is to be performed. See Section 6.2(f) for further discussion of these issues.

Discriminate functions are generated by viewing the assay's baseline data graphically in three dimensions and creating planes to separate the different subset clusters. These "planes" are created by applying Fischer's Linear Discriminant to the n-dimensional classification parameter space. A populated discriminate function table based on the baseline data of FIG. 5. is shown in FIG. 7.

The discriminant function table provides a systematic means of evaluating a series of classification values ($C_1$, $C_2$, $C_3$, $C_4$) in order to classify a bead. In general bead classification proceeds by entering the discriminant function table at row 0, performing a test on a specified parameter (e.g., $C_1$, $C_2$, $C_3$, or $C_4$) and then, depending upon the result, either classifying the bead or proceeding to another test which involves evaluating a different row in the table. For example, suppose bead A has the following measured classification parameter values: $C_1=V_1$, $C_2=V_2$, $C_3=V_3$, and $C_4=V_4$. Classification of bead A via the discriminant function table of FIG. 7 begins as follows (the pseudo-code below would demonstrate to those skilled in the art of programming the logic involved in the classification process):

1. Enter table at row 0 with measured values for $C_1$, $C_2$, $C_3$, and $C_4$.
2. If (LOW VALUE=500)$\leq$(PARAMETER=$C_1$=$V_1$)$\leq$ (HIGH VALUE=620) then (result=TRUE), else (result=FALSE).
3. If (result=TRUE) and (TRUE ROW ID$\neq$# 0), then re-enter table at TRUE ROW ID, else
4. If (result=TRUE) and (TRUE ROW ID=0), then (class=TRUE TOKEN).
5. If (result=FALSE) and (FALSE ROW ID$\neq$0), then re-enter table at (row=FALSE ROW ID), else
6. If (result=FALSE) and (FALSE ROW ID=0), then (class=FALSE TOKEN).
7. If (TRUE TOKEN or FALSE TOKEN)=0, then (class=reject class).

Figure 8:
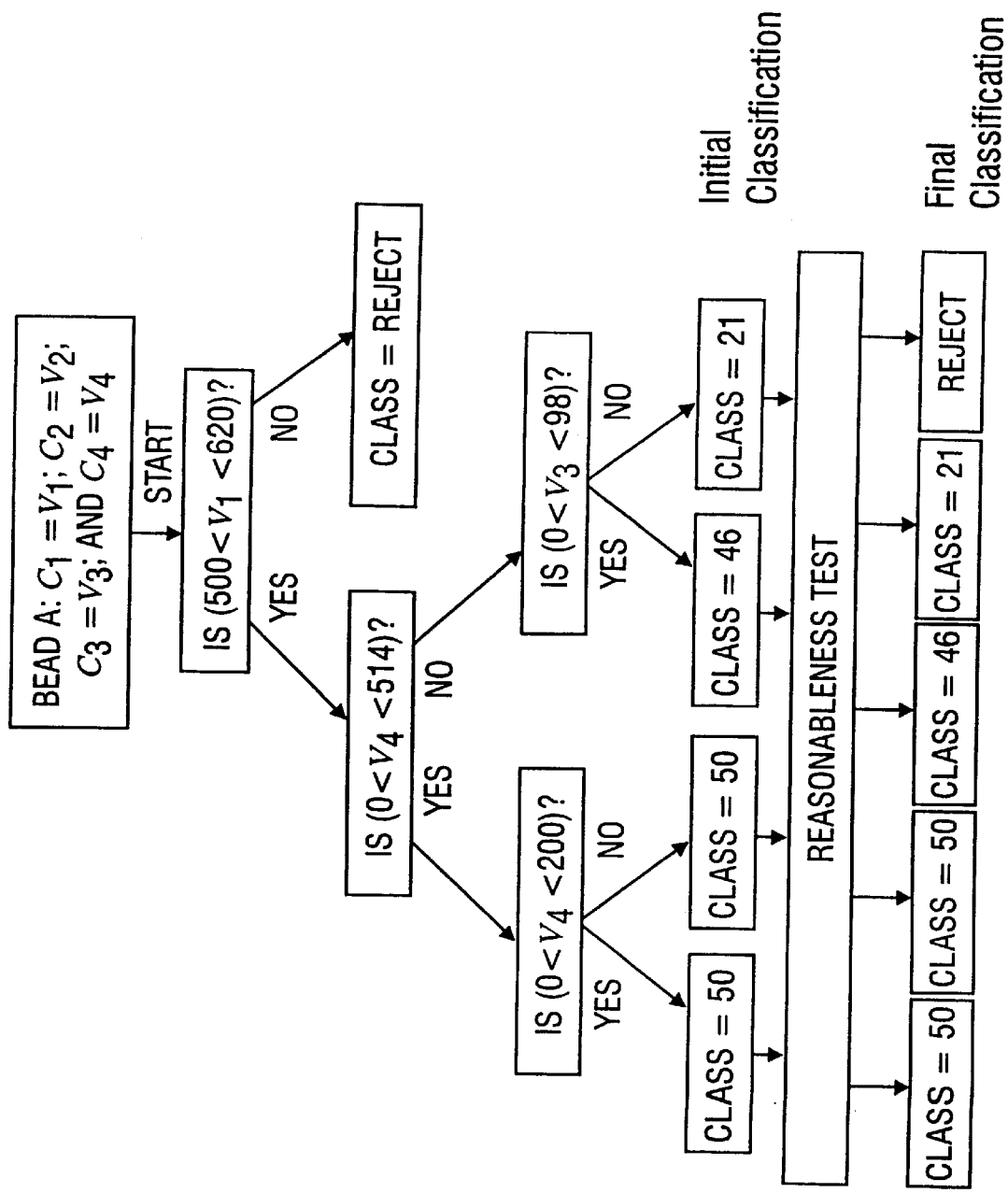
FIG. 8 shows a decision tree view of the illustrative discriminant function table of FIG. 7.

One of ordinary skill will recognize from the above discussion that a discriminant function table embodies a (classification) decision tree. FIG. 8 shows this relationship for the discriminant function table of FIG. 7 explicitly. A discussion of the discriminant function table as it relates to the real-time processing of an exposed assay beadset is provided in Section 6.2(d). Once a beadset is preprocessed, the data may be employed in real-time analysis of many assays using that set. One of ordinary skill in the art will also recognize that instead of a decision tree, a bitmap or look up table could be used to classify the bead sets.

Real-Time Analysis

Once a collection of bead subsets have been characterized as described above and combined to form an assay beadset, the beadset may be exposed to a test sample. That is, they may be used to analyze a clinical sample. After exposure the beadset is ready for real-time analysis. The real-time. analysis phase is initiated by installing the exposed beads into a, conventional flow cytometer for processing.

As described above, for each bead processed a flow cytometer 100 generates electrical signals indicative of a plurality of measured parameters, $C_1 \ldots C_n$, $F_{m1} \ldots F_{mx}$. These values are transmitted to computer 105 via data bus 110 and interface board 115. Values for a bead's classification parameters $C_1 \ldots C_n$ are used to evaluate the assay's discriminant functions, as encoded in a discriminant function table 410, the result of which is an initial classification of the bead into one of the assay's bead subsets or a reject class.

After this initial classification, a bead's measured classification parameter values $C_1 \ldots C_n$ can be checked against their ($C_1 \ldots C_n$) baseline values to determine if it is "reasonable" to classify the bead as belonging to the initially identified class. In a current embodiment, this reasonableness test is implemented by computing the distance between the measured classification parameter values and the mean values obtained during preprocessing. If tae measured values for $C_1 \ldots C_n$ for a particular bead are sufficiently distant from the identified subsets baseline values, the bead is assigned to a reject class. Use of this technique allows for the rejection of beads that were initially misclassified and improves the overall reliability of the analysis.

To ensure proper classification, a preferred embodiment's pooled beadset will include a bead subset which has no bound reactants (e.g., a placebo bead subset) in a known ratio to the beadset's other subsets.

It is noted that when a beadset is comprised of beads manufactured in a single batch, the above described reasonableness test can be incorporated into the linear discriminant functions by creating reject space between all subsets. However, when a beadset is comprised of beads from more than one batch a Euclidean (or similar) distance measure is needed to validate the classification result.

Figure 9:
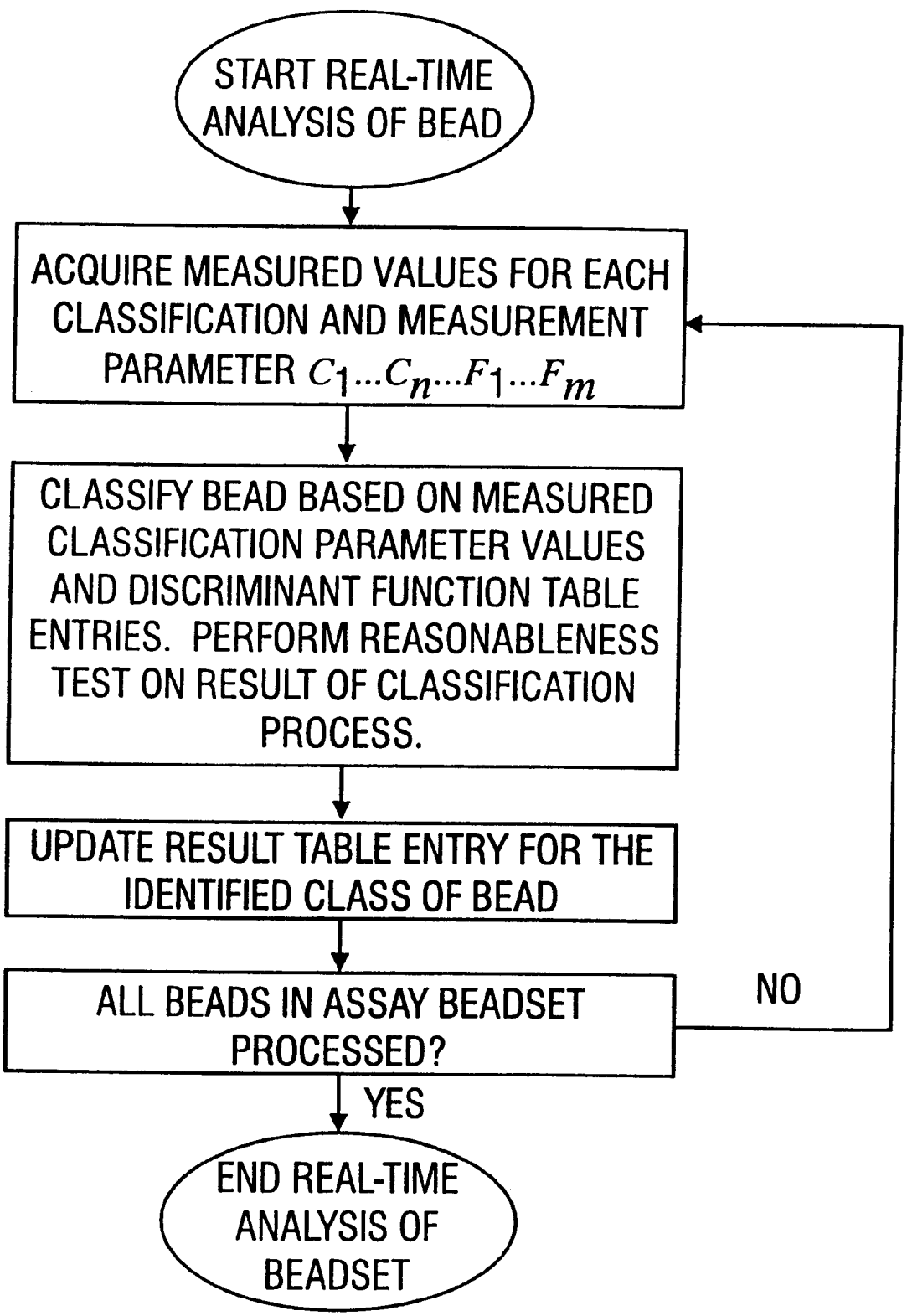
FIG. 9 is a flow-chart for a real-time analysis phase of a multiple analyte assay in accordance with the invention.

Once a bead is assigned its final classification, the assay's results table 415 is updated to reflect the newly classified bead's measurement parameter values $F_{m1} \ldots F_{mx}$. This data acquisition, classification, and update process is repeated for each bead in the assay beadset in real-time. FIG. 9 shows, in block diagram form, the general steps performed during the real-time analysis phase of a method in accordance with the invention In one embodiment the following data are accumulated in the results table for each class (subset) of bead in the assay: (1) total count of the number of beads detected in the specified class, (2) a running sum for each measurement parameter $F_{m1}$–$F_{mx}$, (3) for each measurement parameter the total count of the number of beads in the class whose measurement value is less than the parameter's baseline value, and (4) for each measurement parameter the total count of the number of beads in the class whose measurement value is more than the parameter's baseline value.

REAL-TIME ANALYSIS EXAMPLE

In the illustrative embodiment introduced in Section 6.2 (c), the assay beadset is designed to simultaneously detect four analytes using four classification parameters (Cl represents forward light scatter, $C_2$ represents side light scatter, $C_3$ represents red fluorescence, and (4 represents orange fluorescence) and one measurement parameter ($F_{m1}$ representing green fluorescence). After exposing the beadset to a suitable biological sample, it is placed into a flow cytometer 100 which processes each bead (e.g., measures parameters $C_1$, $C_2$, $C_3$, $C_4$, and $F_{m1}$) and transmits to computer 105 signals indicative of these measurements via data bus 110 and interface board 115.

For each bead processed by the flow cytometer, values for $C_1$, $C_2$, $C_3$, and $C_4$ are evaluated in accordance with the discriminant function table shown in FIG. 7 to initially classify the bead as belonging to a particular subset, for example, in a genetic analysis intended to detect mutations in the Kras oncogene, the classification could proceed as follows: (1) class 46, Kras CODON 46 WILDTYPE, (2) class 21, Kras CODON 21 MUTANT, (3) class 50, Kras 5CODON 50 MUTANT, (4) class 5, Kras CODON 5 MUTANT, or (5) a reject class. (See FIG. 8 for a decision tree representation of the discriminate function table of FIG. 7.) If the bead is initially classified as belonging to any class except the reject class, a reasonableness test is performed on the bead's classification parameter values, $C_1$–$C_n$. For example, if the bead received an initial classification of class 50 and its $C_1$ value is more than two standard deviations away from its mean, the bead is given a final classification of reject. Otherwise the bead's final classification is the same as its initial classification—50.

If the bead's final classification is other than reject, its $F_{m1}$, value is used to update the assay's results table in the following manner (see FIG. 10):

1. Identifying, based on the bead's classification token (i.e., subset token 46, 21, 50, or 5), the row in the results table which is to be updated.
2. Incrementing the identified row's COUNT value. The COUNT value reflects the total number of beads of the specified class that have been identified during the analysis.
3. Adding the bead's $F_{m1}$ value to the value contained in the rows SUM column. The SUM value reflects a running sum of the identified classes measurement values.
4. If the bead's $F_{m1}$ value is greater than $F^{m1}$'s base value (determined during the preprocessing phase, see FIG. 6), then incrementing the row's OVER COUNT value. The OVER COUNT value reflects the total number of beads of the specified class that have been processed whose $F_{m1}$ values are above that of baseline.
5. If the bead's $F_{m1}$ value is less than $F_{m1}$'s base value (as determined during the preprocessing phase, see FIG. 6), then incrementing the row's UNDER COUNT value. The UNDER COUNT value reflects the total number of beads of the specified class that have been processed whose $F_{m1}$ values are below that of baseline.

In a preferred embodiment, data (i.e., count, and measured $F_{m1}$ values) for each bead classified as a reject can also be collected.

Interpretation

Following the real-time classification and accumulation of results as described above, the user may select to see a text based presentation or interpretation of the assay's numerical results.

During the interpretation phase the assay's real-time numerical results are associated with textual explanations. These textual explanations can be displayed to the user.

It is the function of the interpretation table 420 to associate textual descriptions of an assay's possible outcomes with an actual assay's numerical results. Each row in the interpretation table provides the necessary information to make a single interpretation and typically includes entries for (1) the assay's name, (2) a subset token identifying the class or subset on which the interpretation is based, (3) an outcome identifier for the identified subset, (4) a test-type token, (5) high and low discriminant values for each measurement parameter utilized in the identified test, and (6) a text string describing the row's result.

The test-type token identifies which one of a possible plurality of interpretation tests to perform on the collected (real-time) data during the interpretation phase. In a current embodiment the test-type token is either '0' or '1'. A value of '0' indicates an OVER/UNDER interpretation test is to be performed. A value of '1' indicates a SHIFT interpretation test is to be performed. These tests are defined in the following manner:

$$\text{OVER/UNDER Test Value} = \frac{\text{OVER COUNT}}{\text{UNDER COUNT}}, \text{ and}$$

$$\text{SHIFT Test Value} = \frac{\text{SUM/COUNT}}{\text{Baseline } F_m \text{ Value}},$$

where the variables OVER COUNT, UNDER COUNT, SUM, COUNT, and baseline $F_m$ are described above in Section 6.2(d).

The OVER/UNDER test is generally used for qualitative measurements where the level of reactivity of beads is an indication of the condition or concentration of a biomolecule present: in the sample. The shift test is used where the result sought is a determination of the a. minimally detectable level of a particular biomolecule. One of ordinary skill will recognize that many other tests could be performed. Examples include ranking, stratification, ratio of means to a standard, or to each other, etc.

In general an interpretation table 420 may associate any number of, entries or interpretations (e.g., rows within the table) with a single assay class or bead subset. For instance, bead subset Y could have a single measurement parameter ($F_{m1}$) associated with it and this measurement parameter could indicate, depending upon its value, that one or more interpretations are appropriate.

Note, the contents of the interpretation table 420 are generated during the preprocessing phase. This implies that the target assay be understood and that the various assay results be considered prior to construction of multiplexed assays.

INTERPRETATION EXAMPLE

Consider again the assay beadset, introduced above, designed to simultaneously detect four analytes. FIG. 11 shows a sample interpretation table for this assay. Interpretation of the assay's real-time numerical results is initiated by, for example, the user selecting "interpret results" via the inventive method's graphical user interface.

Figure 12:
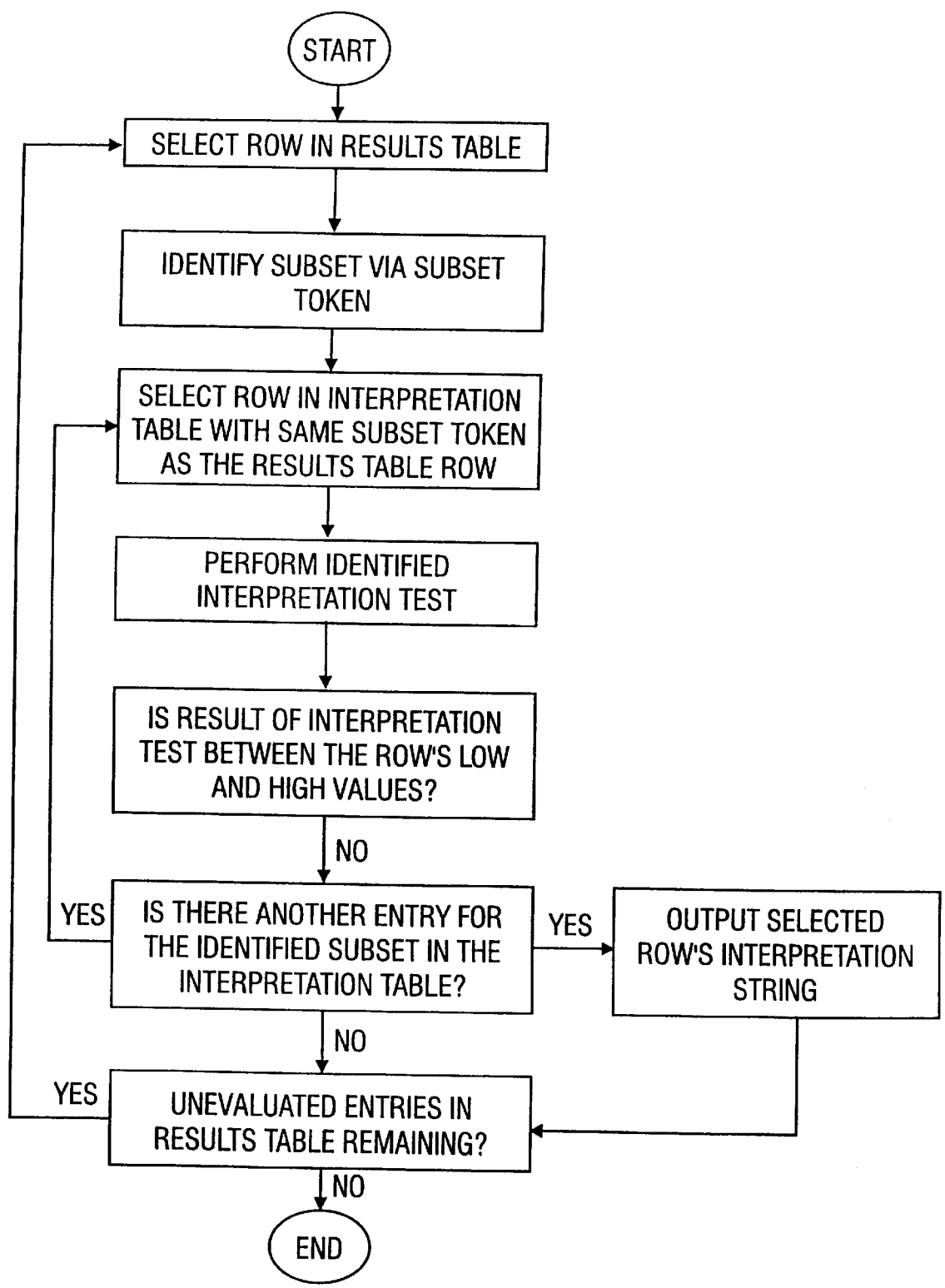
FIG. 12 is a flow-chart for an interpretation phase of a multiple analyte assay in accordance with the invention

As described above, each bead subset (class) within an assay has an entry or row in the results table, FIG. 10. The general procedure for interpreting an assay's real-time numerical results is shown in flow-chart form in FIG. 12. In general, each row of the results table is so matched against every row in the interpretation table with the same subset token. If the result of performing the specified test is between the identified row's low and high values, then the associated textual message is displayed to the user. When all rows in the interpretation table for a single results table row have been checked, the next results table row is evaluated. This process is repeated until the every row in the interpretation table has been compared to the appropriate results table entry.

As a specific example, consider the interpretation of subset 50's (KRAS CODON 50 MUTANT, see FIG. 6) results table entry. The subset's token, 50, is used to identify three .rows in the interpretation table (having outcome IDs of 1, 2, and 3) that contain information regarding evaluation of the mutant analyte For the first identified row, the test-type token indicates a SHIFT type interpretation test is to be performed. Performing this test as defined above, yields:

$$\text{SHIFT Test Value} = \frac{\text{SUM/COUNT}}{\text{Baseline } F_m \text{ Value}} = \frac{1,700,000/1,000}{170} = 10$$

Next, the computed SHIFT test value is compared against each interval in the identified rows of the interpretation table. For the row having OUTCOME ID equal to 1, since (LOW VALUE=10)≦SHIFT Test Value=10 ≦(HIGH VALUE=667) is true, that row's INTERPRETATION entry—"identical complementary strand"—is displayed to the user. This process is repeated for subset 50's remaining two rows in the interpretation table. Further, this process is repeated for each row in the results table.

The result of the interpretation phase is a series of textual messages that describe the results of the assay. Conclusion of the interpretation phase marks the end of the assay.

Operational Considerations

Assay definition, discriminant function definition, and interpretation tables are created at the time an assay beadset is created. Baseline classification data is collected only once for a given assay. That is, once an assay is defined and its baseline data is obtained, any number of beadsets can be manufactured to perform the analysis. To allow this "sharing" of baseline data the assay beadset may contain a center or calibration bead subset.

As would be known to those of ordinary skill in the field, a calibration beadset can be used to adjust any given flow cytometer to a standard. Calibration beadsets are typically processed separately from an assay. Further, calibration is generally performed daily. The purpose of calibration is to adjust the sensitivity of a flow cytometer's photomultipliers to accommodate day to day and machine to machine differences.

Unlike prior art calibration techniques which are performed manually, the processing of a calibration beadset and the adjustment of flow cytometer operational parameters (e.g., photomultiplier voltages) is performed under software control automatically. Seel microfiche appendix A for embodiment details.

Antibody Detection

Assays for antibody are widely used in medicine and clinical analysis for an wide variety of purposes, from detection of infections to determination of autoantibody. The following example illustrates use of the inventive method in an antibody assay and assumes the use of a flow cytometer capable of providing at least five measurements for each bead processed: forward light scatter as classification parameter $C_1$, side light scatter as classification parameter $C_2$, red fluorescence as classification parameter $C_3$, orange fluorescence as classification parameter $C_4$, and green fluorescence as measurement parameter $F_m$.

In one method a number of bead subsets, e.g., subsets 1 through 10 (identified as sS1–sS10), are prepared, for example, by using a cell sorter to sort a heterogeneous population 1o collect a homogeneous subset or alternatively, by preparing the beads using tightly controlled specifications to ensure production of a homogeneous subset. Each subset is distinguishable by its characteristic pattern of classification parameters $C_1$, $C_2$, $C_3$, and $C_4$. The beads in each subset are then labeled with a different antigen such as AgA, AgB, etc. so as to create a collection of labeled subsets as follows: sS1-AgA, sS2-AgB, sS3-AgC, sS4-AgD, sS5-AgE, sS6-AgF, sS7-AgG, sS8-AgH, sS9-AgI, and sS 1 O-AgJ.

Antigens AgA through AgJ may be attached to the beads by any of a number of conventional procedures such as by chemical or physical absorption as described by Colvin el s al., "The Covalent Binding of Enzymes and Immunoglobulins to Hydrophilic Microspheres" in Microspheres: Medical and Biological Applications, 1–13, CRC, Boca Raton, Fla., 1988; Cantarero et al., "The Adsorptive Characteristics of Proteins for Polystyrene and Their Significance in Solid-Phase Immunoassays," Anal. Biochem., 105, 375–382 (1980); and Illum et al., "Attachment of Monoclonal Antibodies to Microspheres," Methods in Enzymol., 112, 67–84 (1985).

After attachment of antigen to the beads' surface, aliquots from each subset are mixed to create a pooled or assay beadset, containing known amounts of beads within each subset. Preferably, the pooled set is prepared with equal volumes of beads from each subset, so that the set contains about the same number of beads from each subset.

The assay beadset may then be incubated with a fluid sample of interest, such as serum or plasma, to test for the presence of antibodies in the fluid that are reactive with antigens on the beads. Such incubation will generally be performed under conditions of temperature, pH, ionic concentrations, and the like that facilitate specific reaction of antibodies in the fluid sample with antigen on the bead surface. After a period for binding of antibody, the beads in the mixture are centrifuged, washed and incubated (again under controlled conditions) for another period of time with a "secondary" antibody such as, for example, fluorescein labeled goat anti human immunoglobulin. The secondary antibody will bind to and fluorescently label antibodies bound to antigen on the beads. Again after washing (or without washing), the beads are processed by the flow cytometer and the four classification parameters forward light scatter, side light scatter, red fluorescence, and orange fluorescence are measured and used to identify the subset to which each bead in the assay beadset belongs. A simultaneous measurement of green fluorescence (measurement parameter) for each bead allows one to determine whether the bead has antibody bound to it. Because the subset to which a bead belongs is correlated with the presence of a particular antigen, e.g., sS1-AgA, one may readily determine the specificity of the antibody bound to a bead as a function of the subset to which it belongs.

EXPERIMENTAL EXAMPLE

Three different antigen-antibody pairs were used in a multiplex experiment demonstrating the ability to detect the presence or absence of several antibodies in a single sample. Antigens were coupled to latex microspheres via carbodiimide coupling, and the corresponding antibodies were fluorescently labeled with fluorescein isothiocyanate (green fluorescence—$F_m$). Each antigen was coupled to a unique microsphere. Baseline data for the fluorescent antibodies and antigen-microsphere complexes used in this experiment are shown in FIG. 13a. Baseline data for the three bead subsets of FIG. 13a are given in FIG. 13b.

Figure 14:
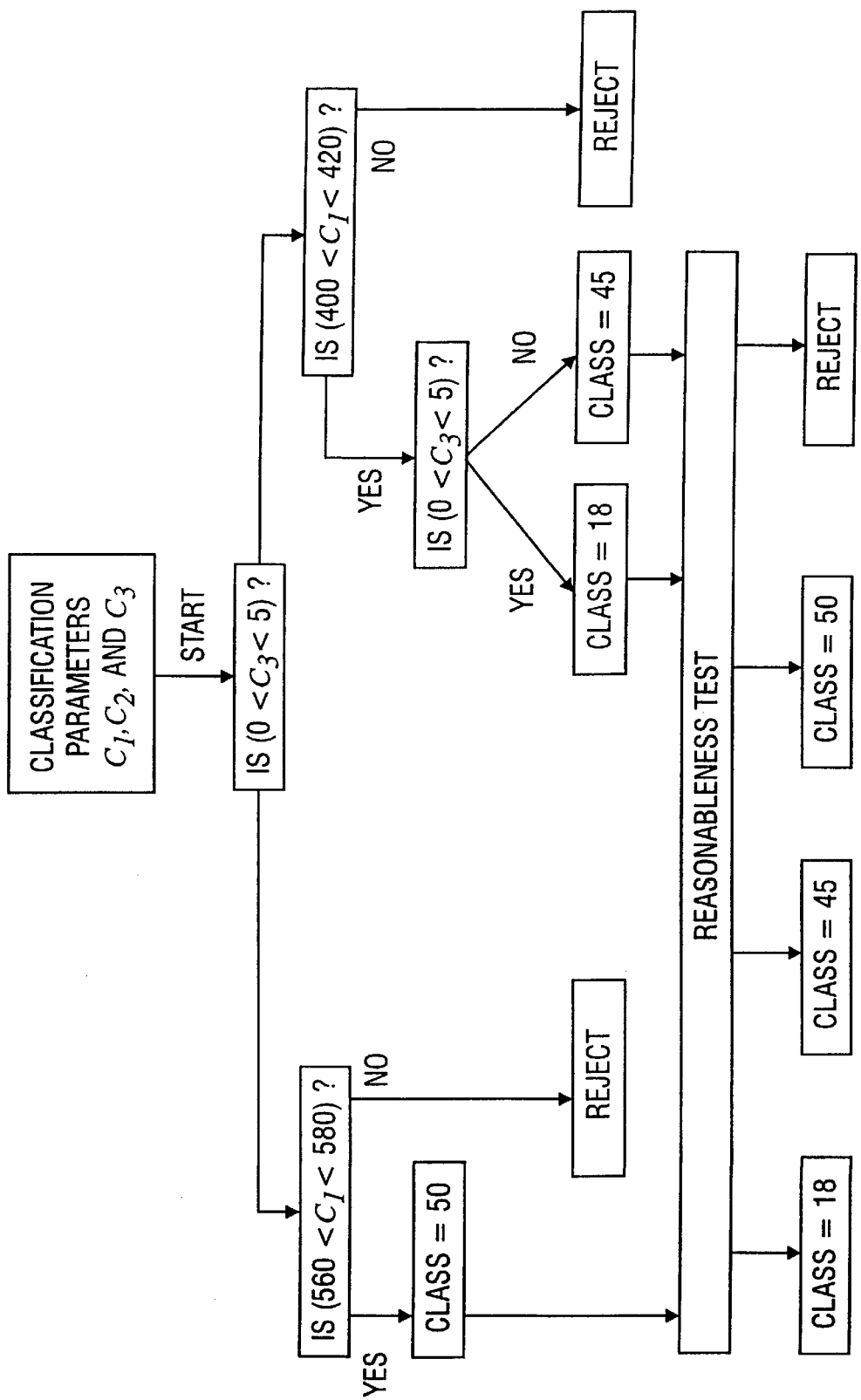
FIG. 14 shows a decision tree view for an illustrative (experimental example) discriminant table.

The absence of fluorescence ($C_2$ and $C_3$) immediately discriminates the clear beads (subset 50) from beads in the other two subsets. Subsets 45 and 50 were further discriminated by side light scatter ($C_1$) and red fluorescence ($C_3$). Linear discriminant functions based on these observations and created as described in Section 6.2(c); are shown in FIG. 13c. Accepting only clear beads with side light scatter ($C_1$) within ±0.25 standard deviations of the mean, doublets (two beads stuck together) were eliminated from the analyses. The remaining beads were classified by red fluorescence ($C_3$) at a midpoint of 59.6. A decision tree based on the discriminant function table (FIG. 13c) is shown in FIG. 14.

In this experiment, each of four samples (e.g., blood serum from four patients) contained all three antigen-microsphere complexes and either 1 or 2 different fluorescent antibodies in PBS buffer. After addition of the antibodies, the reactions were incubated at room temperature for 45 minutes, and then analyzed on the "FACSCAN" using side light scatter ($C_1$), orange fluorescence ($C_2$), and red fluorescence ($C_3$) as classification parameters. Green fluorescence was used as the measurement parameter ($F_m$); an increase in green fluorescence by 30-fold indicates a specific interaction between an antigen and its corresponding fluorescinated antibody. In other words, if a subset's mean measured $F_m$ value is greater than 30-fold times that subset's baseline $F_m$ value, then the target analyte is determined to be present. These "interpretive" observations are embodied in the interpretation table shown in FIG. 13d.

Once the assay database was built, it was tested by running 5,000 beads from each bead subset individually through the system. After rejecting 23.8% of the beads as doublets, the remaining crimson beads (subset 18) were classified with 99.88% accuracy. Dark red beads (subset 45) were classified with 99.96% accuracy with 22.9% rejected as doublets. Clear beads (subset 50) were classified with 100% accuracy with 9.4% of the beads rejected as doublets.

The three bead subsets were pooled to form an assay beadset and divided into 4 sample tubes and processed by the system shown in FIG. 1. The contents of each sample and the mean measured fluorescence ($F_m$) for each bead subset are listed in FIG. 13e. The inventive method correctly identified the antibody or antibodies present in each sample.

An Experimental Refinement

In an alternative embodiment using a $C_4$ (e.g., orange fluorescence) labeled reactant as a classification parameter, a variety (for example five) of protein antigens are employed. Bead subsets are first generated based on differences in one or more of $C_1$, $C_2$, and $C_3$. Next, a selected antigen labeled with Cy3NHS (an orange fluorophore) is bound to the beads in each subset. To minimize the measured orange fluorescence coefficient of variation for each bead subset, the beads are sorted with a high speed cell sorter so that only a narrow range of antigen (orange fluorophore) is found on each bead within a subset. Care should be taken to select or prepare the beadset so that different $C_4$ values are measured/obtained for each of the (e.g., five) different antigens used. In other words, the measured intensity of $C_4$ for AgA should differ from the measured intensity of $C_4$ from AgB, etc. To ensure that uniformity is achieved, saturation binding with fluoresceinated monoclonal antibody is tested—each bead ought to have restricted ranges of both orange and green fluorescence. While the construction of beadsets by this method is more laborious, the increase in measurement precision may be useful and will allow the sampling of fewer beads to arrive at a suitable determination of antibody concentration.

The assays previously mentioned measure any antibody with specificity for antigen upon an appropriately labeled bead. The antigen can be quite simple or rather complex and thus, the inventive methods can measure a highly restricted antibody or a broad array of antibodies. For example, a hexapeptide just large enough to bind to a monoclonal antibody can be employed as antigen or a large protein with many epitopes can be used. One of ordinary skill will recognize that the level of antibody eventually found associated with the bead ($F_{m1}$) is a function of the number of epitopes per bead, the concentration of epitopes, the amount of antibody and the affinity of the antibody and the valence of the antibody-antigen interaction.

Displacement Assays

Assays for many substances in a clinical laboratory are based on the interference with specific ligand-ligate or antigen-antibody interactions. In these assays, one member of the ligand-ligate pair is labeled with the $F_m$ fluorophore and one member is immobilized on the beads. Soluble, unlabeled material (analyte),which may be ligand or ligate, is added to the reaction mixture to competitively inhibit interaction of the labeled component with the immobilized component. It is usually not important which member of the pair is labeled and which is immobilized; however, in certain assays, functional advantages may dictate the orientation of the assay.

In an exemplary assay of this type, each bead subset is modified with an antigen. The antigen-coated beads are then reacted with an $F_m$ labeled antibody specific for the antigen on the bead surface. Subsequent addition of a test fluid containing soluble analyte (inhibitor) will displace the $F_m$ labeled antibody from the beads in direct proportion to the concentration of the soluble analyte. A standard curve of known analyte concentrations is used to provide accurate quantification of analyte in the test sample.

One of ordinary skill will recognize that the time necessary to achieve equilibrium may be quite lengthy due to the kinetics and association constant of the interaction. To lessen the time required for the assay, the fluid containing the beadset may be subjected to dissociating conditions such as a change in pH, ionic strength or temperature, after mixture of the beadset with the sample to be tested Alternatively, the $F_m$ labeled component may be added to the beadset after addition of the test sample. In either case, it is not necessary for equilibrium to be achieved to determine analyte concentration if the kinetics and linearity of the assays have been established.

ADDITIONAL EXPERIMENTAL EXAMPLES

The following series of experimental examples illustrates how the above referenced techniques can be used in practice in effective diagnostic assays. In one embodiment for example, a competitive inhibition analysis is used to quantitate levels of selected analytes, here IgG, IgA, and IgM. A second experimental refinement demonstrates the utility of multiplexed assays in epitope mapping of a monoclonal antibody. In one embodiment, that approach involved the use of antibody detection technology using a fluoresceinated monoclonal antibody in combinatorial epitope screening (e.g. of peptide libraries) to map a particular epitope to which a monoclonal antibody of interest bound, together with a displacement (competitive inhibition) aspect to demonstrate the specificity of the assay. Also described is a ToRCH assay for screening of human serum for antibodies to a number of infectious agents known to pose special hazards to pregnant women. Allergy screening is exemplified by detection of serum IgE against a panel of grass antigens. Yet an additional experimental example reflects the ability of the multiplexed assay in pregnancy testing, e.g. in testing for hormones or other analytes commonly elevated during pregnancy. Each of these examples is set forth below.
Simultaneous competitive inhibition assay of human immunoglobuling G, A and M levels in serum.

This example illustrates the determination of multiple analyte levels in a liquid sample simultaneously using competitive inhibition analysis. The use of a competitive inhibition assay to accurately determine analyte levels in liquid solutions is a commonly used format for many analyte assays. The uniqueness of this assay is the simultaneous determination of three distinct serum proteins at the same time in the same tube from one serum sample.

Imnmunoglobulins G, A and M are three distinct serum proteins whose levels are determined by a number of genetic and environmental factors in human serum. As changes to these levels may indicate the presence of disease, clinicians often request assay determinations of IgG, A and M using conventional techniques. The most common technique is nephelometry that depends upon the absorption of light by precipitates formed between these immunoglobulins and antibodies made in animals to the human immunoglobulins. As these immunoglobulins are present in human serum at fairly high levels, this type of assay is sufficient. Nephelometry however suffers from a number of limitations including the need for large quantities of reagents, long reaction times for precipitation to equilibrate and an inability to perform more than one reaction per tube or sample.

Three competitive inhibition assays are described, one for human IgG, one for human IgM and one for human IgA using three Differentially Fluorescent Microspheres (DYM). Each assay consists of a DFM coated with the immunoglobulin of choice and a polyclonal, goat anti-human Ig labeled with a green fluorescent molecule (Bodipy). In the absence of inhibitor, the Bodipy-antibody causes the immunoglobulin (Ig) coated microsphere to emit green fluorescence (Fm). In the presence of inhibitor (soluble Ig), the green signal is reduced. Each assay is balanced to reflect a sensitivity range near the physiological level of the Ig in question at a 1:500 dilution of human serum. Once balanced, the three assays were combined into a multiple analyte format and assayed simultaneously using flow cytometry.
Antibody Labeling:

Goat anti-human IgG, goat anti-human IgA, and goat anti-human IgNI antibodies (Cappel Division, Organon Teknika, Durham, N.C.) were labeled with Bodipy FL-CASE (Molecular Probes, Inc., Eugene, Oreg.) using methods described by the manufacturer of the Bodipy succinymidyl ester. The resulting Bodipy labeled antibodies were stored in PBS containing 1 mg/mL BSA as stabilizer.
Antigen Conjugation to Microspheres:

Four DFM (5.5 $\mu$M carboxylate, Bangs Laboratories, Inc. (Carmel, Ind.), dyed by Emerald Diagnostics, Inc. (Eugene, Oreg.)) were conjugated separately to human IgG, human IgA, human IgM (Cappel Division, Organon Teknika, Durham, N.C.) and BSA with a two-step EDC coupling method (Pierce Chemicals, Rockford, Ill.) using sulfo-NHS to stabilize the amino-reactive intermediate. 100 $\mu$L of each bead type (4.2×107 microspheres) was activated for 20 minutes in a total volume of 500 $\mu$L containing 500 $\mu$g of EDC and Sulfo-NHS in 50 mM sodium phosphate buffer, pH 7.0. The microspheres were washed twice with 500 $\mu$L PBS, pH 7.4 using centrifugation at 13,400×g for 30 seconds to harvest the microspheres. Activated, washed beads were suspended in 250 $\mu$L of a 0.05 mg/mL solution of protein in PBS, pH 7.4. After 1 hour, the microspheres were blocked by addition of 250 $\mu$L of 1.0 mg/mL BSA, 0.02% Tween, 0.2 M glycine, in PBS, pH 7.4 and incubated for an additional 30 minutes. Protein coated microspheres were washed twice with 500 PL 0.02% Tween 20, 1 mg/mL BSA in PBS, pH 7.4 (PBSTB). and stored in PBSTB at approximately 3,000,000 microspheres/mL. Microsphere concentrations were determined using a hemacytometer.
Determination of Appopriate Ranges of Quantitation for each Ig Assay:

The normal range of human Ig levels in serum as reported in Clinical Chemistry: Principles and Technics, 2nd Edition, Edited by R. J. Henry, D. C. Cannon and J. W. Winkleman are 569–2210 mg/dL for IgG, 51–425 mg/dL for IgA and 18–279 mg/dL for IgM. Each inhibition assay was designed to be sensitive to inhibition across these ranges.
Single Analyte Assay:

10 μL of dilutions of a serum calibrator with known Ig levels (Kamiya Biomedical, Thousand Oaks, Calif.) was first mixed with 10 μL of Ig loaded microspheres containing 7,500 beads. Next, 10 μL of the Bodipy-labeled Goat Anti-Ig was added and the mixture incubated at ambient temperature for 30 minutes. The mixture was diluted to 300 μL in PBSTB and assayed by flow cytometry. For IgG, the Bodipy-labeled goat anti-hIgg was used at 30 μg/mL. For IgA, the Bodipy-labeled goat anti-hIgA was used at 8 μg/mL. For IgM, the Bodipy-labeled goat anti-hIgM was used at 2.5 μg/mL. Cross reactivity assay: Equivalent amounts of each of the four protein loaded microspheres were mixed to produce a bead mixture. 10 μL of the bead mixture (7,500 microspheres) was mixed with 10 μL of diluted serum calibrators of known Ig level The assay was initiated by addition of 10 μL of one of the Bodipy-labeled antibodies "spiked" with a small quantity of soluble Ig antigen to alleviate the "hook effect". The mixtures were incubated for 30 minutes, diluted to 300 μL in PBSTB and assayed by flow cytometry. As before for the single analyte assay, the Bodipy-labeled goat anti-hIgG was used at 30 μ/mL. For IgA, the Bodipy-labeled goat anti-hIgA was used at 8 μg/mL. For IgM, the Bodipy-labeled goat anti-hIgM was used at 2.5 μg/mL. The quantities of antigen "spikes" were 1.6 μg/mL for IgG, 0.6 μg/mL for IgA and 0.4 μg/mL for IgM.

Multiple Analyte Assay:

Equivalent amounts of each of the four protein loaded microspheres were mixed to produce a bead mixture. 10 μL of the bead mixture (7,500 microspheres) was mixed with 10 μL of diluted serum calibrators of known Ig level as well as three other calibrator sera of known Ig level to serve for this purpose as unknowns. The assay was initiated by addition of 10 μL of a mixture of the three Bodipy-labeled antibodies "spiked" with a small quantity of the three soluble Ig antigen to alleviate the "hook effect". The mixtures were incubated for 30 minutes, diluted to 300 μL in PBSTB and assayed by flow cytometry. As before, the Bodipy-labeled goat anti-hIgg was used at 30 μg/mL. For IgA, the Bodipy-labeled goat anti-hIgA was used at 8 μg/mL. For IgM, the Bodipy-labeled goat anti-hIgM was used at 2.5 μg/mL. The quantities of antigen "spikes" were 1.6 μg/mL for IgG, 0.6 μg/mL for IgA and 0.4 μg/mL for IgM.

Results

IgG Single Analyte Assay:

Results of the single analyte inhibition analysis for IgG level is shown in Table 1 and FIG. 15A. This assay was designed to be most sensitive to inhibition in the anticipated range of IgG in human serum at a 1:500 dilution. In FIG. 15A, the area of the inhibition curve between the dotted lines, left and right, cover the range of sensitivity. In this case, the inhibitor was known amounts of human IgG from a serum calibrator diluted into human serum containing no IgG, IgA or IgM. Dilutions of the calibrator were then diluted 1:500 in PBSTB and included as inhibitor in the assay. The Bodipy-labeled anti-higg was used, at 30 μg/mL in PBSTB. 7,500 microspheres were used in this experiment and 250 were counted by flow cytometry. Note that as the amount of soluble IgG increased, the degree of inhibition as monitored by the MIF of $F_m$ increased proportionally until saturation of the system was achieved. On the other end of the inhibition curve note that the lower levels of soluble inhibitor caused an elevation in the MIF of $F_m$ as compared with the negative control (human serum with no Ig). This "hook effect" is common in immunoassay and can be adjusted up or down the inhibition curve by adjusting both the amount of antibody and antigen in the soluble portion of the assay. The "hook effect" was most prominent in the IgG assay due to the higher concentrations of both antigen and antibody per microsphere. This was necessary as IgG is found in serum at higher concentrations than IgA or IgM.

IgA Single Analyte Assay:

Results of single analyte inhibition analysis for IgA level is shown in Table 1 and FIG. 15B. This assay was designed to be most sensitive to inhibition in the anticipated range of IgA in human serum at a 1:500 dilution. In FIG. 15B, the area of the inhibition curve between the dotted lines, left and right, cover the range of sensitivity. In this case, the inhibitor was known amounts of human IgA from a serum calibrator diluted into human serum containing no IgG, IgA or IgM. Dilutions of the calibrator were then diluted 1:500 in PBSTB and included as inhibitor in the assay. The Bodipy-labeled anti-hIgA was used at 8 μg/mL in PBSTB. 7,500 microspheres were used in this experiment and 250 were counted by flow cytometry. Note that as the amount of soluble IgA increased, the degree of inhibition as monitored by the MIF of $F_m$ increased proportionally until saturation of the system was achieved. On the other end of the inhibition curve note that the lower levels of soluble inhibitor cause a slight elevation in the MIF of $F_m$ as compared with the negative control (human serum with no Ig). The "hook effect" was much less pronounced for both IgA and IgM due to their lower concentrations in serum.

IgM Single Analyte Assay:

Results of single analyte inhibition analysis for IgM level is shown in Table 1 and FIG. 15C. This assay was designed to be most sensitive to inhibition in the anticipated range of IgM in human serum at a 1:500 dilution. In FIG. 15C, the area of the inhibition curve between the dotted lines, left and right, cover the range of sensitivity. In this case, the inhibitor was known amounts of human IgM from a serum calibrator diluted into human serum containing no IgG, IgA or IgM. Dilutions of the calibrator were then diluted 1:500 in PBSTB to be included as inhibitor in the assay. The Bodipy-labeled anti-hIgM was used at 2.5 μg/mL in PBSTB. 7,500 microspheres were used in this experiment and 250 were counted by flow cytometry. Note that as the amount of soluble IgM increased, the degree of inhibition as monitored by the MIF of $F_m$ increased proportionally until saturation of the system was achieved. On the other end of the inhibition curve note that the lower levels of soluble inhibitor cause a slight elevation in the MIF of $F_m$ as compared with the negative control (PBS with no added IgM). The "hook effect" is much less pronounced for both IgA and IgM due to their lower concentrations in serum.

Cross Reactivity Analysis:

To determine the cross-reactivity of the various assay components, a multiple analyte assay was performed using only one of the three Bodipy-labeled, antibodies. Equivalent numbers of the IgG, IgA, IgM and BSA beads were mixed to make a dAM mixed bead set. To 10 μL of the bead set (7,500 microspheres) was added 10 μL of dilutions of the calibrator containing IgG, IgA and IgM. The multiple analyte assay was then performed using only one of the Bodipy-labeled anti-IgG, IgA or IgM preparations rather than a mixture. Table 2 and FIGS. 16A, 16B, and 16C show the results of these assays. Results indicated that Anti-IgG-Bodipy only reacted with DFM-IgG Bodipy and not the IgA or IgM beads. No cross-reactivity with IgA or IgM was noted and the assay was validated for further multiple analyte analysis. Also added to this analysis was the antigen "spike". By adding a small amount of soluble antigen to the probe antibody solution the "hook effect" can be minimized. Note in the IgG cross-reactivity experiment that the MIF of $F_m$ for negative control is higher than the lowest concentration of inhibitor. By spiking the experiment with 1.6 μg/mL IgG the hook effect has, no effect at the lower end of inhibitor range leading to a more accurate assay over the entire dynamic range.

GAM Simultaneous Analysis:

Equivalent numbers of the IgG, IgA, IgM and BSA beads were mixed to make a GAM mixed bead set. To 10 μL of the bead set (7,500 microspheres) was added 10 μL of dilutions of the calibrator containing IgG, IgA and IgM. Also included were several additional calibrators that served as unknowns for the demonstrative purpose of this assay. The multiple analyte assay was then initiated by adding 10 μL of a mixture of the Bodipy-labeled anti-IgG, IgA and IgM plus the soluble Ig "spikes". After a 30 minute, room temperature incubation the reaction mixture was diluted to 300 μL and 1000 microspheres counted by flow cytometry. Tables 3–5 and FIGS. 17–19 show the results of these assays. For each of the inhibition curves produced, a polynomial trendline was used as a non-linear regression analysis. The fit of this trendline to the data was demonstrated by the R correlation factor (1.0 is a perfect fit). The factors of the polynomial formula were used to predict the quantity of inhibitor in each dilution of calibrator and "unknown" serum. The differences between the predicted inhibitor quantities and actual amounts were also included in Tables 3–5. Results indicate that this multiple analyte inhibition assay can determine the level of these 3 serum proteins with an error of less than 10%. Coefficients of variation (CV) between the triplicate data points indicated that the assay was highly precise (no CV greater, than 6%). Limits of quantitation for each assay were 400–3000 mg/dL for IgG, 60–455 mg/dL for IgA, and 36–272 mg/dL for IgM. FIG. 20 shows the results of the three assays graphically represented on the same graph as all three assays were performed at the same time in the same tube.

A multiple analyte, competitive inhibition assay for human serum IgG, IgA, and IgM levels has been developed. This assay, that allows the simultaneous assay of these three protein levels in serum diluted 1:500, demonstrated excellent sensitivity, precision and accuracy.

TABLE 1

Single analyte inhibition assays

| Tube # | IgG mg/dL | MIF of Fm | IgA mg/dL | MIF of Fm | IgM mg/dL | MIF of Fm |
|---|---|---|---|---|---|---|
| 1 | 0 | 1445 | 0 | 1654 | 0 | 1765 |
| 2 | 0.026 | 1500 | 0.0040 | 1645 | 0.0024 | 1794 |
| 3 | 0.11 | 1460 | 0.016 | 1729 | 0.010 | 1929 |
| 4 | 0.42 | 1512 | 0.064 | 1734 | 0.038 | 1921 |
| 5 | 1.7 | 1426 | 0.26 | 1733 | 0.15 | 1815 |
| 6 | 6.8 | 1619 | 1.02 | 1747 | 0.61 | 1829 |
| 7 | 27.1 | 1684 | 4.1 | 1746 | 2.4 | 1833 |
| 8 | 108 | 1943 | 16.4 | 1788 | 9.8 | 1807 |
| 9 | 163 | 1898 | 24.6 | 1813 | 14.7 | 1792 |
| 10 | 244 | 1885 | 36.9 | 1806 | 22.0 | 1723 |
| 11 | 366 | 1624 | 55.3 | 1703 | 33.0 | 1704 |
| 12 | 549 | 1456 | 83.0 | 1391 | 49.6 | 1446 |
| 13 | 824 | 998 | 125 | 971 | 74.3 | 1267 |
| 14 | 1235 | 722 | 187 | 558 | 112 | 879 |
| 15 | 1853 | 473 | 280 | 336 | 167 | 591 |
| 16 | 2779 | 350 | 420 | 240 | 251 | 360 |
| 17 | 4169 | 313 | 630 | 140 | 376 | 269 |
| 18 | 6253 | 316 | 945 | 103 | 564 | 242 |
| 19 | 9380 | 196 | 1418 | 75 | 847 | 136 |
| 20 | 14070 | 165 | 2127 | 54 | 1270 | 102 |

TABLE 2

Cross-reactivity analysis in multiple analyte assay

| Tube | hu IgG mg/dL | Bead 1-MIF HuIgG | huIgA mg/dL | Bead 2-MIF HuIgA | huIgM mg/dL | Bead 3-MIF HuIgM | Bead 4-MIF BSA |
|---|---|---|---|---|---|---|---|
| 1) GAM Beads reacted with anti-IgG -Bodipy @ 30 μg/mL + Ag spikes. | | | | | | | |
| 1 | 0 | 1868 | 0 | 4 | 0 | 6 | 5 |
| 2 | 400 | 1702 | 60.5 | 4 | 36.1 | 7 | 5 |
| 3 | 561 | 1463 | 84.7 | 4 | 50.6 | 5 | 5 |
| 4 | 785 | 1218 | 119 | 3 | 70.8 | 4 | 5 |
| 5 | 1099 | 880 | 166 | 3 | 99.2 | 3 | 5 |
| 6 | 1538 | 674 | 233 | 3 | 139 | 3 | 5 |
| 7 | 2154 | 549 | 326 | 2 | 194 | 3 | 5 |
| 8 | 3015 | 450 | 456 | 2 | 272 | 2 | 5 |
| 2) GAM Beads reacted with anti-IgA -Bodipy @ 8 μg/mL + Ag spikes. | | | | | | | |
| 11 | 0 | 3 | 0 | 1800 | 0 | 2 | 3 |
| 12 | 400 | 2 | 60.5 | 1455 | 36.1 | 2 | 3 |
| 13 | 561 | 8 | 84.7 | 1225 | 50.6 | 1 | 3 |
| 14 | 785 | 3 | 119 | 930 | 70.8 | 1 | 3 |
| 15 | 1099 | 2 | 166 | 605 | 99.2 | 1 | 3 |
| 16 | 1538 | 2 | 233 | 392 | 139 | 1 | 3 |
| 17 | 2154 | 2 | 326 | 278 | 194 | 1 | 3 |
| 18 | 3015 | 2 | 456 | 163 | 272 | 1 | 3 |
| 3) GAM Beads reacted with anti-IgM -Bodipy @ 2.5 μg/mL + Ag spikes. | | | | | | | |
| 21 | 0 | 3 | 0 | 6 | 0 | 1536 | 2 |
| 22 | 400 | 3 | 60.5 | 9 | 36.1 | 1284 | 2 |
| 23 | 561 | 3 | 84.7 | 2 | 50.6 | 1135 | 2 |
| 24 | 785 | 3 | 119 | 2 | 70.8 | 1011 | 2 |
| 25 | 1099 | 2 | 166 | 2 | 99.2 | 776 | 2 |
| 26 | 1538 | 2 | 233 | 1 | 139 | 620 | 2 |
| 27 | 2154 | 2 | 326 | 2 | 194 | 463 | 2 |
| 28 | 3015 | 2 | 456 | 1 | 272 | 330 | 2 |

TABLE 3

Multiple analyte IgG inhibition data

| Tube # | hIgG mg/dL | MIF of Fm | Average MIF | MIF CV | Calculated mg/dL | % Difference |
|---|---|---|---|---|---|---|
| 1 | | 1917 | | | | |
| 2 | 0 | 1943 | 1926 | 0.6% | na | na |
| 3 | | 1918 | | | | |
| 4 | | 1811 | | | | |
| 5 | 400.4 | 1737 | 1772 | 1.7% | 399.3 | 0.3% |
| 6 | | 1767 | | | | |
| 7 | | 1408 | | | | |
| 8 | 560.6 | 1529 | 1471 | 3.4% | 566.9 | −1.1% |
| 9 | | 1476 | | | | |
| 10 | | 1250 | | | | |
| 11 | 784.8 | 1163 | 1236 | 4.4% | 775.3 | 1.2% |
| 12 | | 1295 | | | | |
| 13 | | 852 | | | | |
| 14 | 1099 | 867 | 862 | 0.8% | 1102.5 | −0.3% |
| 15 | | 868 | | | | |
| 16 | | 661 | | | | |
| 17 | 1538 | 726 | 691 | 3.9% | 1556.1 | −1.2% |
| 18 | | 687 | | | | |
| 19 | | 575 | | | | |
| 20 | 2154 | 575 | 580 | 1.1% | 2126.3 | 1.3% |
| 21 | | 589 | | | | |
| 22 | | 461 | | | | |
| 23 | 3015 | 466 | 468 | 1.5% | 3025.1 | −0.3% |
| 24 | | 478 | | | | |
| | | "UNKNOWNS" | | | | |
| 25 | | 1691 | | | | |
| 26 | 446 | 1657 | 1657 | 1.7% | 411.3 | 7.8% |
| 27 | | 1624 | | | | |
| 28 | | 749 | | | | |
| 29 | 1243 | 737 | 763 | 3.8% | 1316.8 | −5.9% |
| 30 | | 804 | | | | |

TABLE 3-continued

Multiple analyte IgG inhibition data

| Tube # | hIgG mg/dL | MIF of Fm | Average MIF | MIF CV | Calculated mg/dL | % Difference |
|---|---|---|---|---|---|---|
| 31 |  | 464 |  |  |  |  |
| 32 | 3045 | 486 | 476 | 1.9% | 2947.1 | 3.2% |
| 33 |  | 479 |  |  |  |  |

TABLE 4

Multiple analyte IgA inhibition data

| Tube # | hIgA mg/dL | MIF of Fm | Average MIF | MIF CV | Calculated mg/dL | % Difference |
|---|---|---|---|---|---|---|
| 1 |  | 1954 |  |  |  |  |
| 2 | 0 | 1941 | 1952 | 0.4% | na | na |
| 3 |  | 1960 |  |  |  |  |
| 4 |  | 1661 |  |  |  |  |
| 5 | 60.5 | 1664 | 1665 | 0.2% | 60.5 | 0.0% |
| 6 |  | 1669 |  |  |  |  |
| 7 |  | 1222 |  |  |  |  |
| 8 | 84.7 | 1391 | 1307 | 5.3% | 84.7 | 0.0% |
| 9 |  | 1308 |  |  |  |  |
| 10 |  | 1055 |  |  |  |  |
| 11 | 118.6 | 974 | 1051 | 5.9% | 118.6 | 0.0% |
| 12 |  | 1125 |  |  |  |  |
| 13 |  | 615 |  |  |  |  |
| 14 | 166.1 | 595 | 606 | 1.4% | 166.1 | 0.0% |
| 15 |  | 607 |  |  |  |  |
| 16 |  | 376 |  |  |  |  |
| 17 | 232.5 | 426 | 400 | 5.1% | 232.6 | 0.0% |
| 18 |  | 399 |  |  |  |  |
| 19 |  | 283 |  |  |  |  |
| 20 | 325.5 | 280 | 287 | 2.9% | 325.4 | 0.0% |
| 21 |  | 299 |  |  |  |  |
| 22 |  | 193 |  |  |  |  |
| 23 | 455.7 | 198 | 195 | 1.2% | 455.7 | 0.0% |
| 24 |  | 193 |  |  |  |  |
| "UNKNOWNS" | | | | | | |
| 25 |  | 1569 |  |  |  |  |
| 26 | 65 | 1483 | 1504 | 3.1% | 68.2 | -4.9% |
| 27 |  | 1460 |  |  |  |  |
| 28 |  | 455 |  |  |  |  |
| 29 | 187 | 457 | 477 | 6.1% | 197.2 | -5.5% |
| 30 |  | 518 |  |  |  |  |
| 31 |  | 187 |  |  |  |  |
| 32 | 454 | 199 | 201 | 5.9% | 445.4 | 1.9% |
| 33 |  | 216 |  |  |  |  |

TABLE 5

Multiple analyte IgM inhibition data

| Tube # | hIgM mg/dL | MIF of Fm | Average MIF | MIF CV | Calculated mg/dL | % Difference |
|---|---|---|---|---|---|---|
| 1 |  | 1566 |  |  |  |  |
| 2 | 0 | 1615 | 1605 | 1.8% | na | na |
| 3 |  | 1635 |  |  |  |  |
| 4 |  | 1345 |  |  |  |  |
| 5 | 36.1 | 1312 | 1328 | 1.0% | 35.7 | 1.2% |
| 6 |  | 1328 |  |  |  |  |
| 7 |  | 1133 |  |  |  |  |
| 8 | 50.6 | 1182 | 1155 | 1.8% | 52.9 | -4.6% |
| 9 |  | 1151 |  |  |  |  |
| 10 |  | 1038 |  |  |  |  |
| 11 | 70.8 | 994 | 1035 | 3.2% | 68.1 | 3.9% |
| 12 |  | 1074 |  |  |  |  |
| 13 |  | 728 |  |  |  |  |
| 14 | 99.2 | 733 | 735 | 0.9% | 100.7 | -1.5% |
| 15 |  | 744 |  |  |  |  |
| 16 |  | 514 |  |  |  |  |
| 17 | 138.8 | 585 | 546 | 5.4% | 138.3 | 0.4% |
| 18 |  | 539 |  |  |  |  |
| 19 |  | 424 |  |  |  |  |
| 20 | 194.4 | 414 | 419 | 1.0% | 194.0 | 0.2% |
| 21 |  | 418 |  |  |  |  |
| 22 |  | 298 |  |  |  |  |
| 23 | 272.1 | 339 | 315 | 5.6% | 272.4 | -0.1% |
| 24 |  | 307 |  |  |  |  |
| "UNKNOWNS" | | | | | | |
| 25 |  | 1266 |  |  |  |  |
| 26 | 40 | 1248 | 1241 | 1.9% | 42.8 | -7.0% |
| 27 |  | 1209 |  |  |  |  |
| 28 |  | 608 |  |  |  |  |
| 29 | 113 | 621 | 635 | 4.7% | 116.2 | -2.8% |
| 30 |  | 677 |  |  |  |  |
| 31 |  | 289 |  |  |  |  |
| 32 | 268 | 315 | 306 | 3.9% | 281.0 | -4.9% |
| 33 |  | 313 |  |  |  |  |

Epitope Mapping of a Monoclonal Antibody using Flow Cytometry.

This example demonstrates the screening of combinatorial chemistry products for a biologically active molecule. The generation of random chemical products for empirical discovery of biologically significant molecules is a method that holds great promise for progress in numerous disciplines of science including biology, pharmacology and medicine One general problem with the technique is the screening of large numbers of unique molecules for a specific activity. Screening methods are required that provide high throughput levels of screening with adequate specificity and sensitivity for detection of the biological event in question.

An experiment was designed to demonstrate the screening of peptides for the epitope of a monoclonal antibody A monoclonal antibody (MAB 384) was chosen that was produced using the spleen cells of a mouse hyperimmunized with a defined peptide (amino acid 67–74) from the amino acid sequence of human myelin basic protein (MBP). Using the amino acid sequence of this region of MBP, nine overlapping octapeptides were synthesized that covered the predicted epitope. To the carboxyl terminal end of each peptide, glycine-lysine-biotin residues were added. Nine Differentially Fluorescent Microspheres (DFM) were each coated with avidin and one unique peptide of the set was linked through the avidin-biotin interaction to one unique member of the bead set. This resulted in a set of microspheres that contained nine members each carrying a unique peptide either flanking or representing the monoclonal antibody's epitope. The bead carrying the epitope peptide was detected using the MAB 384 antibody labeled with a green fluorescent tag in a multiple analyte analysis. The detection was shown to be specific for the peptide in question by competitive inhibition and was not affected by high levels of free biotin.

Antibody Labeling:

MAB 384 (Chemicon International, Inc., Temecula, Calif.) was labeled with Bodipy FL-X (Molecular Probes, Inc., Eugene, Oreg.) using methods described by the manufacturer of the Bodipy succinymidyl ester. Absorbance at 280 nm and 504 rn revealed that the resulting Bodipy-labeled antibody had a Bodipy to protein ratio of 3.31 and was stored in PBS containing 1 mg/mL BSA as stabilizer.

Avidin Conjugation to Microspheres:

Nine distinctly dyed DFM (5.5 IM, Bangs Laboratories, Inc. (Carmel, Ind.), dyed by Emerald Diagnostics, Inc. (Eugene, Oreg.)) were conjugated separately to Neutravidin (deglycosylated avidin) with a two-step EDC coupling method (Pierce Chemicals, Rockford, Ill.) using sulfo-NHS to stabilize the amino-reactive intermediate. 20 μL (8.4 million microspheres) of each bead type was activated for 20 minutes in a total volume of 100 μL containing 500 μg of EDC and Sulfo-NHS in 50 MM sodium phosphate buffer, pH 7.0. The microspheres were washed twice with 100 μL PBS, pH 7.4 using centrifugation at 13,400×g for 30 seconds to harvest the microspheres. Activated, washed beads were suspended in 50 μL of a 0.25 mg/mL solution of Neutravidin in PBS, pH 7.4. After 2 hours, the microspheres were blocked by addition of 50 μL of 0.2 M glycine, 0.02% Tween 20 in PBS, pH 7.4 and incubated for an additional 30 minutes. Protein coated microspheres were washed twice with 100 μL 0.02% Tween 20, 1 mg/mL BSA in PBS, pH 7.4 (PBSTB) and stored in PBSTB at approximately 3,000,000 microspheres/mL as determined by hemocytometer count.

Pentide Attachment to Microspheres:

Each of the nine DFM conjugated to Neutravidin were treated separately with one of the nine biotinylated peptides. 10 μL of biotinylated peptides at 100–200 μg/mL was mixed with 10 μL of microspheres and reacted for 5 minutes followed by 2×100 μL washes in PBSTB. The peptide loaded microspheres were suspended in 20 μL of PBSTB.

Single Analyte Assay:

10 μL of each of the peptide loaded microspheres was reacted with 10 μL of the Bodipy-labeled MAB 384 at 15.5 μg/mL in PBSTB for 1 hour, diluted to 300 μL in PBSTB and assayed using flow cytometry. Negative controls included the microspheres without peptide and with the Bodipy MAB 384.

Multiple Analyte Assay:

10 μL of each of the 9 peptide loaded microspheres was mixed to produce a bead set. 10 μL of the set was reacted with 10 μL of the Bodipy-labeled MAB 384 at 15.5 μg/mL in PBSTB for 1 hour, diluted to 300 μL in PBSTB and assayed using flow cytometry. Negative controls included the microsphere set without peptide and treated with the Bodipy MAB 384.

Competitive Inhibition with Soluble Peptide:

10 μL of each of the 9 peptide loaded microspheres was mixed to produce a bead set. 10 μL of the Bodipy-labeled MAB 384 at 15.5 μg/mL in PBSTB was reacted with 10 μL of soluble peptide containing the epitope sequence HYGSLPQK (SEQ ID NO. 1) at 10 μg/mL and incubated for 1 hr. The microsphere set was then treated with peptide absorbed Bodipy-labeled MAB 384 at 15.5 μg/mL for 1 hour, diluted to 300 μL in PBSTB and assayed using flow cytometry.

Examination of the Effects of Free Biotin:

10 μL of each of the 9 peptide loaded microspheres was mixed to produce a bead set. 10 μL of the mixture was reacted with 10 μL of 10 μg/mL free biotin and incubated for 1 hr. The microsphere set was then treated with Bodipy-labeled MAB 384 at 15.5 μg/mL for 1 hour, diluted to 300 ;L in PBSTB and assayed using flow cytometry.

Results

Description of Peptides to be Screened:

The amino acid sequence upstream and downstream from the epitope of monoclonal antibody MAB 384 (amino acid 67–74, YGSLPQ, SEQ ID NO. 2) was determined using the published amino acid sequence (Roth, H. J., et al., J. Neurosci. Res. 17, 321–328, 1990). The table below shows the amino acid sequence of the nine overlapping peptides produced for the screening assay. Note that to the carboxy-terminal end of all peptides was added a glycine (G)-lysine (K)biotin.

```
1 GLCNMYKDGK-biotin
2     MYKDSHHPGK-biotin
3         SHHPARTAGK-biotin
4             ARTAHYGSGK-biotin
5                 HYGSLPQKGK-biotin
6                     LPQKSHGRGK-biotin
7                         SHGRTQDEGK-biotin
8                             TQDENPVVGK-biotin
9                                 NPVVHFFKGK-biotin
```

Single vs. Multiple Analyte Analysis:

Each of the nine DFM coated with Neutravidin was reacted for 5 minutes with one of the nine biotinylated peptides diluted to 250 ng/mL in PBS. For single analyte analysis, each separate microsphere was reacted with Bodipy-labeled MAB 384 at 15.5 μg/mL for 60 minutes and the mixture assayed using flow cytometry. The Mean Intensity of Fluorescence (MIF) of the green fluorescence channel ($F_m$) is shown for each peptide-bead as the darker set of bars in FIG. 21. The darkest bars represents single analyte analysis of each bead in the absence of peptide as a negative control.

For multiple analyte analysis, the nine bead-peptides were mixed and then reacted with Bodipy-MAB 384 at 15.5 μg/mL. After 60 minutes, the mixture was assayed using flow cytometry and results (MIF of $F_m$) are also shown in FIG. 21. Both assays minus added peptide are shown as a negative control. Results indicated that peptide #5 contained the epitope for MAB 384. Peptides #4 and #6 although containing 3 of the epitope's amino acids showed little reactivity. The multiple and single analyte assays provided identical results. Numerical data is shown in Table 6.

Competitive Inhibition using Soluble Epitope Peptide:

To further demonstrate the specificity of the assay, soluble peptide containing the epitope (#5) was used to inhibit the reaction shown in FIG. 21. A 10 μL aliquot of the Bodipy-labeled MAB 384 was mixed with an equal volume of the epitope containing peptide (HYGSLPQK) at 10 μg/mL. After 1 hour the mixture was reacted with 10 μL of the bead mixture for 1 hour and assayed by flow cytometry. Results shown in FIG. 22 reveal that the reaction was significantly inhibited to a MIF of $F_m$ of 53. Numerical data for the inhibition assay is shown in Table 7.

Effects of Free Biotin:

The high avidity of the biotin-avidin interaction makes it unlikely that the various peptides could be released or exchanged from microsphere to microsphere, To demonstrate that such a release or exchange does not occur under strenuous conditions the following experiment was performed. A 10 μL aliquot of free biotin at 10 μg/mL (40 μM) was incubated with 10 μL of the bead-peptide mixture for 1 hour and then the microspheres reacted with the MAD 384 Bodipy at 15.5 μg/mL for 1 hour and assayed by flow cytometry. Results shown in FIG. 23 indicate that the free biotin at 10 μg/mL did not displace significant amounts of the biotinylated epitope peptide. Numerical data for the inhibition assay is shown in Table 8.

This epitope mapping example demonstrates the useful application of the instant invention to the area of combinatorial screening. The peptide carrying the epitope for the mouse monoclonal antibody screened in this example was clearly identified in a set of nine peptides. The identification was further shown to be specific by competitive inhibition with soluble epitope peptide. In addition, the stability of the avidin-biotin interaction for use with flow cytometry was demonstrated in an excess of free biotin.

TABLE 6

MIF of Fm

| Bead | Peptide plus GL-Biotin | Assayed Single | Single no peptide | Assayed Multiple | Multiple no peptide |
|---|---|---|---|---|---|
| 70/50 | GLCNMYKD | 72 | 66 | 28 | 28 |
| 60/70 | MYKDSHHP | 57 | 48 | 36 | 36 |
| 40/70 | SHHPARTA | 47 | 43 | 36 | 34 |
| 40/50 | ARTAHYGS | 57 | 47 | 35 | 27 |
| 70/70 | HYGSLPQK | 1381 | 66 | 1348 | 25 |
| 40/40 | LPQKSHGR | 43 | 44 | 67 | 25 |
| 40/60 | SHGRTQDE | 42 | 54 | 35 | 26 |
| 70/60 | TQDENPVV | 73 | 70 | 32 | 23 |
| 70/40 | NPVVHFFK | 60 | 60 | 29 | 21 |

TABLE 7

| Peptide plus GL-Biotin | Assayed w/free Biotin |
|---|---|
| GLCNMYKD | 4 |
| MYKDSHHP | 7 |
| SHHPARTA | 12 |
| ARTAHYGS | 13 |
| HYGSLPQK | 53 |
| LPQKSHGR | 15 |
| SHGRTQDE | 11 |
| TQDENPVV | 9 |
| NPVVHFFK | 17 |

TABLE 8

| Bead | Peptide plus GL-Biotin | MIF Multiple | MIF w/Biotin |
|---|---|---|---|
| 70/50 | GLCNMYKD | 13 | 17 |
| 60/70 | MYKDSHHP | 17 | 19 |
| 40/70 | SHHPARTA | 20 | 22 |
| 40/50 | ARTAHYGS | 20 | 26 |
| 70/70 | HYGSLPQK | 915 | 1023 |
| 40/40 | LPQKSHGR | 32 | 20 |
| 40/60 | SHGRTQDE | 19 | 23 |
| 70/60 | TQDENPVV | 31 | 34 |
| 70/40 | NPVVHFFK | 31 | 36 |

Multiple Analyte Simultaneous ToRCH Assay for Seroconversion.

This example demonstrates the utility of this invention in the screening of human serum for antibodies to infectious disease agents. Screening of serum for antibodies to certain infectious disease agents is often the only method available to determine if a patient has been, or is infected with the agent in question For example, a common method of diagnosing HIV infection is by detection of HIV specific antibodies in the serum. This phenomenon known as seroconversion is commonly employed for diagnosis of several important pathogenic infections. One of the most commonly employed assay panels of this type is the ToRCH panel. ToRCH assays detect both serum IgG and serum IgM responses to *Toxoplasma gondii*, Rubella virus, Cytomegalovirus, and Herpes Simplex Virus Types 1 and 2. The importance of this assay especially to the pregnant woman has been well documented as any one of these infectious agents is capable of crossing the placental barrier and entering the immunologically naive fetus. These infectious agents can cause severe damage to the fetus and must be avoided. Currently, all ToRCH panel assays for antibodies specific to each of these pathogens is performed separately in a unique assay tube or microtiter well. This invention provides for a multiple analyte format that allows assay for either IgG or IgM antibodies specific for each of the five pathogens at the same time in the same tube with the same sample.

A ToRCH assay using flow cytometry has been developed by coupling purified antigens of *T. gondii*, Rubella, CMV and HSV Type 1 and Type 2 to five Differentially Fluorescent Microspheres (DFM). The specificity of the assay has been demonstrated by treating this bead set with human serum calibrators certified to be either positive or negative for all five agents. After this treatment, the bead set was treated with either Goat anti-human IgG-Bodipy or Goat anti-human IgM-Bodipy used to develop the assay. In addition, a third calibrator with known levels of reactivity to each agent was assayed and the results reported.

Antibody Labeling:

Goat anti-human IgG and goat anti-human IgM (Cappel Division, Organon Teknika, Durham, N.C.) were labeled with Bodipy FL-CASE (Molecular Probes, Inc., Eugene, Oreg.) using methods described by the manufacturer of the Bodipy succinymidyl ester. Bodipy-labeled antibodies were stored in PBS containing 1 mg/mL BSA as stabilizer.

Antigen Coniugation to Microspheres:

Five DFM (5.5 μM carboxylate, Bangs Laboratories, Inc., Carmel, Ind., dyed by Emerald Diagnostics, Inc., Eugene, Oreg.) were conjugated separately to the five ToRCH antigens (Viral Antigens, Inc.) with a two-step EDC coupling method (Pierce Chemicals, Rockford, Ill.) using sulfo-NHS to stabilize the amino-reactive intermediate. All antigens were dialyzed into PBS to remove any reactive amino groups such as sodium azide or glycine. The *T. gondii* preparation (Chemicon, Inc., Temecula, Calif.) was sonicated for 2 minutes in PBS, 10 mM EDTA to lyse the tachyzoites. 20 μL (8.4 million microspheres) of each bead type was activated for 20 minutes in a total volume of 100 μL containing 500 μg of EDC and Sulfo-NHS in 50 mM sodium phosphate buffer, pH 7.0. Microspheres were washed twice with 200 μL PBS, pH 7.4 using centrifugation at 13,400×g for 30 seconds to harvest the microspheres. Activated and washed beads were suspended in 100 μL of antigen at 0.05 to 0.15 mg/mL in PBS, pH 7.4. After 2 hours, the microspheres were blocked by addition of 100 μL of 0.2 M glycine, 0.02% Tween 20 in PBS, pH 7.4 and incubated for an additional 30 minutes. Antigen coated microspheres were washed twice with 200 μL 0.02% Tween 20, 1 mg/mL BSA in PBS, pH 7.4 (PBSTB). and stored in PBSTB at approximately 3,000,000 microspheres/mL as determined by hemacytometer count.

Rubella Assay:

Rubella antigen loaded microspheres were used to examine several parameters of the assay in a single analyte format prior to the performance of multiple analyte assays. 10 μL (30,000 microspheres) of Rubella antigen coated beads were reacted with 10 μL of a 1:10 dilution of four different Rubella calibrator sera (Consolidated Technologies, Inc., Oak Brook, Ill.) and the mixture incubated for 1 hour. These sera were defined using a standard assay for the anti-Rubella IgG activity by the manufacturer of the calibrators. The units were defined as International Units/ mL or IU/nmL. Beads were washed in PBSTB by centrifugation at 13,400×g for 30 seconds and suspended in 40 μL of a 10 μg/mL solution of Bodipy-labeled anti-human IgG. This mixture was incubated for 1 hour, diluted to 300 μL in PBSTB and assayed using flow cytometry. Negative controls included the microspheres with no serum treated with the Bodipy-labeled antibodies. In addition one calibrator serum containing 70 IU/mL of anti-ARubella IgG activity was titrated in a single analyte assay. Multiple analyte assay for IgG and lpM activities: Equivalent amounts of each of the 5 antigen loaded microspheres was mixed to produce a ToRCH bead mixture. 10 μL (30,000 microspheres) of the mixture was reacted with 10 μL of a 1:400 dilution of ToRCH control or calibrator sera and incubated for 1 hour. The positive and negative ToRCH control sera did not have defined units of activity. The ToRCH calibrator, however, did have defined levels of anti-ToRCH IgG activities as defined by INX and DiaMedix diagnostic instruments. These values were provided by the manufacturer for the lot of calibrator purchased. Beads were washed in PBSTB by centrifugation at 13,400×g for 30 seconds and suspended in 20 μL of a 40 μg/mL solution of Bodipy-labeled anti-human IgG or IgM. This mixture was incubated for 1 hour, diluted to 300 μL in PBSTB and assayed using flow cytometry. Negative controls included the microspheres with no serum treatment and the microspheres treated with the ToRCH negative control serum. Both negative controls were developed with the Bodipy-labeled antibodies.

Results
Rubella Assay:

Rubella coated DFM were reacted with 4 human serum calibrators containing known levels of IgG antibodies specific for Rubella virions defined by International units (IU/mL). The beads were washed and developed with goat anti-human Ige-Bodipy. Results are shown in Table 9 and FIG. 24. Increasing units of anti-Rubella activity were reflected in the Mean Intensity of Fluorescence (MIF) of $F_m$ (green channel). Luminex Units (LU) were defined as the MIF of Fay for each data point minus the MIF of $F_m$ for the negative control (no serum) multiplied by 0.1, and are included in Table 9.

Rubella calibrator titration: The human serum calibrator containing 70 IU/mL of anti-Rubella IgG was serially diluted in PBSTB3 and assayed with the Rubella coated microspheres and Bodipy-labeled anti-human IgG. Results shown in Table 10 and FIG. 25 show that, as expected, the IgG antibodies specific for Rubella were titrated with dilution.

Multiple analyte ToRCH analysis for serum IgG and IgM:

Each of the five distinct DFM coated with ToRCH antigens plus one DFM coated with human serum albumin (Miles, Inc., West Haven, CT) were mixed in equal volumes and 10 μL (30,000 microspheres) of the mixture is reacted for 1 hour with triplicate, 20 μL aliquots of a 1:400 dilution of the ToRCH controls as well as the Low ToRCH calibrator. The calibrator from Blackhawk Systems, Inc. contained known levels of each pathogen specific antibody as measured on other diagnostic machines. After washing, one set of triplicates was developed with Bodipy-labeled anti-human IgG and another set with Bodipy-1abeled anti-human IgM. Numerical results are shown in Tables 11 and 12. Results are presented graphically in FIGS. 26A and 26B. Included in the figures are standard deviation bars for the triplicate measurements. For both IgG and IgM measurements, the ToRCH negative control serum (A96601, tubes #1-3) produced MIF of $F_m$ similar to the negative control with no serum (tubes #10-12). The ToRCH positive control serum (A96602, tubes #4-6) demonstrated significant IgG activity to all five pathogens. Conversely, the positive control serum had only slight IgM based reactivity to the five pathogens. The known levels of anti-ToRCH IgG reactivities for the ToRCH Calibrator (A96500, tubes #7-9) were compared to the Luminex units of each IgG activity as determined by the multiple analyte analysis. Luminex units were defined by subtracting the negative control serum average MIF of $F_m$ from the average MIF of $F_m$ for each antigen and multiplying by 0.1. The levels of the ToRCH calibrator were defined by the manufacturer as a factor of activity for each antigen above the limit of detection for that antigen on a specific diagnostic machine. These results are listed in Table 13.

A demonstrative ToRCH assay has been developed to simultaneously assay for serum IgG or IgM specific for the five ToRCH pathogens in a single tube. Results of the assay indicate that it is specific for each pathogen and is as sensitive as currently available instrument based assays. The multiple analyte format provides a uniquely powerful technology for rapid and less expensive serum testing for seroconversion to ToRCH pathogens as well as other infectious agents diagnosed in this manner.

TABLE 9

Anti-Rubella calibration curve

| Calibrator IU/mL | MIF of Fm | LU/mL |
| --- | --- | --- |
| 360 | 1419 | 133 |
| 225 | 1004 | 91 |
| 70 | 458 | 37 |
| 40 | 376 | 28 |
| 0 | 92 | 0 |

TABLE 10

Anti-Rubella calibrator titration

70 IU/mL Calibrator

| Reciprocal of Dilution | MIF of Fm |
| --- | --- |
| 1 | 4510 |
| 4 | 2554 |
| 8 | 1597 |
| 16 | 954 |
| 32 | 652 |
| 64 | 392 |
| 128 | 209 |
| 256 | 121 |
| 512 | 99 |
| 0 | 59 |

TABLE 11

IgG ToRCH assay

| Tube # | Calibrator (1:400) | Toxo. | Rubella | CMV | HSV I | HSV II | HSA |
| --- | --- | --- | --- | --- | --- | --- | --- |
| | | \multicolumn{6}{c}{MIF of Fm in Triplicate} | | | | | |
| 1 | A96601 | 21 | 9 | 12 | 16 | 17 | 22 |
| 2 | A96601 | 22 | 8 | 10 | 17 | 15 | 26 |
| 3 | A96601 | 25 | 9 | 11 | 14 | 17 | 22 |
| 4 | A96602 | 647 | 1786 | 956 | 1223 | 664 | 78 |
| 5 | A96602 | 590 | 1677 | 967 | 1511 | 719 | 81 |
| 6 | A96602 | 620 | 1670 | 922 | 1348 | 611 | 72 |
| 7 | A96500 | 103 | 38 | 50 | 128 | 64 | 27 |
| 8 | A96500 | 95 | 43 | 48 | 127 | 58 | 43 |
| 9 | A96500 | 87 | 41 | 49 | 127 | 56 | 29 |
| 10 | No Serum | 21 | 7 | 15 | 18 | 13 | 22 |
| 11 | No Serum | 23 | 8 | 11 | 15 | 19 | 19 |
| 12 | No Serum | 21 | 5 | 12 | 12 | 16 | 23 |

TABLE 11-continued

IgG ToRCH assay

| Tube # | Calibrator (1:400) | Toxo. | Rubella | CMV | HSV I | HSV II | HSA |
|---|---|---|---|---|---|---|---|
| | | Average MIF of Fm | | | | | |
| | A96601 | 23 | 9 | 11 | 16 | 16 | 23 |
| | A96602 | 619 | 1711 | 948 | 1361 | 665 | 77 |
| | A96500 | 95 | 41 | 49 | 127 | 59 | 33 |
| | No Serum | 22 | 7 | 13 | 15 | 16 | 21 |

TABLE 12

IgM ToRCH assay

| Tube # | Calibrator (1:400) | Toxo. | Rubella | CMV | HSV I | HSV II | HSA |
|---|---|---|---|---|---|---|---|
| | | MIF of Fm in Triplicate | | | | | |
| 1 | A96601 | 40 | 10 | 17 | 17 | 21 | 16 |
| 2 | A96601 | 36 | 9 | 15 | 15 | 20 | 17 |
| 3 | A96601 | 39 | 9 | 19 | 18 | 23 | 20 |
| 4 | A96602 | 68 | 109 | 53 | 80 | 52 | 27 |
| 5 | A96602 | 69 | 112 | 56 | 84 | 52 | 23 |
| 6 | A96602 | 77 | 133 | 81 | 91 | 64 | 60 |
| 7 | A96500 | 66 | 15 | 27 | 34 | 26 | 20 |
| 8 | A96500 | 67 | 15 | 23 | 37 | 29 | 22 |
| 9 | A96500 | 66 | 15 | 28 | 31 | 31 | 29 |
| 10 | No Serum | 40 | 9 | 18 | 17 | 21 | 21 |
| 11 | No Serum | 36 | 8 | 20 | 17 | 19 | 16 |
| 12 | No Serum | 38 | 8 | 14 | 17 | 19 | 18 |
| | | Average MIF of Fm | | | | | |
| | A96601 | 38 | 9 | 17 | 17 | 21 | 18 |
| | A96602 | 71 | 118 | 63 | 85 | 56 | 37 |
| | A96500 | 66 | 15 | 26 | 34 | 29 | 24 |
| | No Serum | 38 | 8 | 17 | 17 | 20 | 18 |

TABLE 13

Comparison of known levels of anti-ToRCH IgG for the ToRCH calibrator from Blackhawk BioSystems with Luminex Units

| | T. gondii | Rubella | CMV | HSV 1 | HSV 2 |
|---|---|---|---|---|---|
| Diagnostic Machine used | INX | INX | INX | Diamedix | DiaMedix |
| Factor above Limit of Detection | 1.7 x | 2.7 x | 1.7 x | 2.5 x | 1.1 x |
| Units of Activity | 11.3 IU/mL | 26.9 IU/mL | 24.5 IU/mL | 50 EU/mL | 22 EU/mL |
| Luminex Units/mL | 7.2 LU/mL | 3.2 LU/mL | 3.8 LU/mL | 11.1 LU/mL | 4.3 LU/mL |

Simultaneous Assay of Dog Sera for Allergic IgE and Allergen-Specific IgG

This example demonstrates the screening of serum for IgE antibodies specific for allergens. Screening of serum for IgE antibodies specific to allergens is a viable option for allergy testing as compared with skin sensitivity testing. The instant invention provides for a format that can assay for either IgG or IgE responses to numerous allergens at the same time in the same tube with the same sample and is therefore a uniquely powerful method of screening.

An allergy assay has been developed including 16 grass allergens in a multiple analyte, simultaneous format. A panel of 16 grass allergens were attached to 16 Differentially Fluorescent Microspheres (DFM) with one grass allergen being coated onto one unique member of the bead set. The allergen bead set was treated with diluted dog serum for 1 hour and treated with a solution of either Goat anti-Dog IgE or goat anti-dog IgG-FITC for an additional hour. For the IgE assay, beads were washed clear of this antibody and the bead set treated with an affinity purified rabbit anti-goat IgG-FITC antibody as probe.

Results demonstrate a uniquely powerful method of serum screening for allergies that provides a true multiple analyte format, as well as sensitivity and specificity.

Allergen Conjugation to Microspheres: Sixteen DFM (5.5 µM carboxylate) were conjugated separately to 16 soluble grass allergens (provided by Dr. Bill Mandy, BioMedical Services, Austin, Tex.) with a two-step EDC coupling method (Pierce Chemicals, Rockford, Ill.) using sulfo-NHS to stabilize the amino-reactive intermediate. All grass allergens were diluted 1:100 into PBS, pH 7.4. 20 µL (8.4 million microspheres) of each bead type was activated for 20 minutes in a total volume of 100 µL containing 500 µg of EDC and Sulfo-NHS in 50 mM sodium phosphate buffer, pH 7.0. Microspheres were washed twice with 100 µL PBS, pH 7.4 using centrifugation at 13,400×g for 30 seconds to harvest the microspheres. Activated, washed beads were suspended in 50 µL of diluted allergen. After 2 hours, the microspheres were blocked by addition of 50 µL of 0.2 M glycine, 0.02% Tween 20 in PBS, pH 7.4 and incubated for an additional 30 minutes. Protein coated microspheres were washed twice with 100 µL 0.02% Tween 20, 1 mg/mL BSA in PBS, pH 7.4 (PBSTB). and stored in PBSTB at approximately 3,000,000 microspheres/mL as determined by hemacytometer count.

Multiplexed K-9 Grass Allergen IgE Assay:

Equivalent amounts of each of the 16 grass allergen loaded microspheres was mixed to produce a bead mixture. 20 µL (60,000 microspheres) of the mixture was reacted with 60 µL of a 1:3 dilution of dog serum in PBSTB and the mixture incubated for 1 hour. Beads were washed in 200 µL PBSTB by centrifugation at 13,400×g for 30 seconds and suspended in 40 µL of a 50 µg/mL solution of anti-dog IgE (provided by Dr. Bill Mandy, BioMedical Services, Austin, Tex.). After incubation for 1 hour, beads were washed in 200 µL PBSTB by centrifugation at 13,400×g for 30 seconds. Beads were then treated with 40 µL of rabbit anti-goat IgG-FITC (Sigma, St. Louis, Mo.) at 20 µg/mL. After one hour the bead mixture was diluted to 300 µL in PBSTB and assayed using flow cytometry. Negative controls included the microspheres with dog serum, without the goat anti-dog IgE and with the rabbit anti-goat IgG-FITC. A negative control of the bead set with no dog serum was also included. Allergen specific dog IgE was determined by subtraction of the mean intensity of fluorescence (MIF) of the green channel ($F_m$) for the negative controls for each grass allergen from the MIF of $F_m$ for the tubes including the goat anti-dog IgE.

Simultaneous K-9 Grass Allergen IgG Assay:

Equivalent amounts of each of the 16 grass allergen loaded microspheres was mixed to produce a bead mixture. 20 µL (8.4 million microspheres) of the mixture was reacted with 20 µL of a 1:10 dilution of dog serum in PBSTB and the mixture incubated for 1 hour. Beads were washed in 200 µL PBSTB by centrifugation at 13,400×g for 30 seconds and suspended in 25 µL of a 50 µg/mL solution of goat anti-dog IgG-FITC. After one hour the bead mixture was diluted to 300 µL in PBSTB and assayed using flow cytometry. Negative controls included the microspheres with no dog serum and with the goat anti-dog IgG-FITC. Allergen specific dog IgG was determined by subtraction of the mean intensity of fluorescence (MIF) of the green channel ($F_m$) for the negative control for each grass allergen from the MIF of $F_m$ for the tubes including dog serum.

Results
Multiple Analyte Dog Anti-Grass Allergen IgG Assay:

Grass allergen coated DFM were reacted with 6 dog sera provided by BioMedical Services, Austin, Tex. that had been characterized by ELISA for anti-grass allergen IgE. The IgG response to these grass allergens was not measured by BioMedical Services. The beads were washed and developed with goat anti-dog IgG-FITC.

Results are shown in FIG. 27. The MIF of $F_m$ in the absence of dog serum was subtracted from the MIF of $F_m$ for each bead with each dog serum. Two dogs, A96324 and A96326 demonstrated relatively high IgG reactivity to most of the grass allergens. Two dogs, A96325 and A963 17 demonstrated relatively medium IgG reactivity to most of the grass allergens. Two dogs, A96319 and A96323 demonstrated relatively low IgG reactivity to most of the grass allergens.

Multiple Analyte Dog Anti-Grass Allergen IgE Assay:

Grass allergen coated DFM were reacted with 6 dog sera provided by BioMedical Services, Austin, Tex. that had been characterized by ELISA for anti-grass allergen IgE. The beads were washed and treated with goat anti-dog IgE for 1 hour. The assay was developed with rabbit anti-goat IgG-FITC. Results are shown in FIG. 28. The MIF of $F_m$ in the absence of dog serum was subtracted from the MIF of Fen for each bead with each dog serum. Two dogs, A96325 and A96326 demonstrated relatively low reactivity to most of the grass allergens with the exception of Wheat grass and several others for A96326. These results agree with the ELISA results provided by BioMedical Services. A96325 was negative for 11 grass allergens (only ones tested) and A96326 was negative for the same 11 grass allergens except for a "Borderline" result in ELISA against a mixture of Wheat and Quack grass (due to the non-multiplexed format of ELISA assays, allergens are often mixed to increase the throughput levels). The other four dog sera demonstrated medium to high IgE responses to several of the grass allergens. Although agreement between ELISA and flow cytometry assay results was not absolute, the two assays followed the same trends. Dogs with IgE reactivity to grass allergens were detected by both assays.

Comparison of Multiple Analyte IgG and IgE Results:

The IgG and IgE anti-grass allergen response to each of the 16 allergens was compared by graphing. FIGS. 29–34 demonstrate that there was no correlation between IgG and IgE response to grass allergens in the six dogs. Some dogs were low responders for both IgE and IgG, some were reactive with both immunoglobulin subclasses, and some demonstrated IgE reactivity in a low background of IgG specific for the grass allergens. Examination of the IgG reactivity in a serum could identify those sera in which the IgE reactivity could be masked by the high IgG reactivity.

A demonstrative assay for serum lgG or IgE activity to 16 grass allergens has been developed that allows simultaneous assay of all 16 allergens at the same time in the same tube using the same sample. Results with 6 dog sera suggested that IgE anti-grass allergen activity as determined by ELISA was in general agreement with results provided using flow cytometry. In addition, the ease of determination for IgG anti-grass allergen activity in the six dogs was demonstrated.

A Simultaneous Immunometric Assay For Human Chorionic Gonadotropin and Alpha-Fetoprotein This example illustrates the determination of multiple analyte levels in a liquid sample simultaneously by immunometric or capture-sandwich assay. The use of capture-sandwich assays to accurately determine analyte levels in liquid solutions is a commonly used format for many analyte assays. The technique is especially useful for those analytes present in low quantities as the first step serves to capture and thus concentrate the analyte. The uniqueness of this assay is the multiple analyte format allowing the simultaneous determination of two distinct serum proteins at the same time in the same tube from the same serum sample.

Human chorionic gonadotropin (hCG), a gonadotropic hormone secreted by the placenta, is the primary hormonal marker utilized for pregnancy testing. hCG is elevated both in urine and serum during pregnancy. Alpha fetoprotein (AFP) is the fetal cell equivalent to human serum albumin. AFP is elevated in pregnancy and in certain types of malignancies. Many clinical fertility or pregnancy test panels include immunometric assays for these two serum proteins. Immunometric or capture-sandwich assays for hCG and AFP were developed separately and then combined in a multiple analyte format.

The hCG assay was developed by examining several antibody pairs for their ability to capture and quantitate hCG levels in solution. First, a monoclonal antibody was coupled through carbodiimide linkage to a carboxylate substituted Differentially Fluorescent Microsphere (DFM). Next, a polyclonal, affinity purified antibody was Bodipy-labeled and used to probe DFM captured hormone. Once this assay was adjusted to include physiological sensitive ranges, the process was repeated for AFP. Cross-reactivity of the two assays was examined to demonstrate that the two assays would not interfere. The assays were then performed simultaneously. Commercially available serum calibrators were used to demonstrate that both assays were sensitive in clinically relevant ranges and an unknown was include to demonstrate how the two assays work simultaneously.

Antibody Labeling:

The two affinity purified polyclonal anti-hCG (AB633) and anti-AFP (M20077) antibodies (Chemicon, Inc., Temecula, Calif. and Medix Division, Genzyme, San Carlos, Calif.) were labeled with Bodipy FL-CASE (Molecular Probes, Inc., Eugene, Oreg.) using methods described by the manufacturer of the Bodipy succinymidyl ester. The resulting Bodipy-labeled antibodies were stored in PBS containing 1 mg/mL BSA as stabilizer. Antibody conjugation to microspheres: Monoclonal anti-hCG (MAB602) and anti-AFP (S10473) capture antibodies were conjugated to microspheres with a two-step EDC coupling method (Pierce Chemicals, Rockford, Ill.) using sulfo-NHS to stabilize the amino-reactive intermediate. 20 $\mu$L (8.4 million microspheres) of each DFM was activated for 20 minutes in a total volume of 100 $\mu$L containing 500 $\mu$g of EDC and Sulfo-NHS in 50 mM sodium phosphate buffer, pH 7.0. Microspheres were washed twice with 200 $\mu$L PBS, pH 7.4 using centrifigation at 13,400×g for 30 seconds to harvest the microspheres. Washed, activated beads were suspended in 50 $\mu$L of a 0.05 mg/mL solution of antibody in PBS, pH 7.4. After 2 hours, microspheres were blocked by addition of 50 $\mu$L of 0.5 mg/niL BSA, 0.02% Tween 20 in PBS, pH 7.4 and incubated for an additional 30 minutes. Protein coated microspheres were washed twice with 200 $\mu$L 0.02% Tween 20, 1 mg/mL BSA in PBS, pH 7.4 (PBSTB) and stored in PBSTB at approximately 3,000,000 microspheres/mL. Microsphere concentrations were determined using a hemacytometer.

Antibody Pairs Analysis of Hormone Capture Assay:

Capture assay antibody pairs were screened by coupling potential capture antibodies to microspheres and assaying them using all potential combinations of capture antibody-bead/ Bodipy-labeled probe antibody. Assays were performed using 10 µL of capture antibody microspheres (approximately 30,000) plus 20 µL of antigen solution at 10 µg/mL in PBSTB for a 1 hour incubation. Beads were washed in PBSTB by centrifugation at 13,400×g for 30 seconds and suspended in 20 µL of a 25 µg/mL solution of Bodipy-labeled probe antibody. This mixture was incubated for 1 hour, diluted to 300 µL in PBSTB and assayed using flow cytometry.

Antigen Titration Assay:

Once an antibody pair was chosen for use, the pair was analyzed for sensitivity and limit of detection by titration of antigen. Assays were performed using 10 µL of capture antibody microspheres plus 20 µL of antigen dilutions in PBSTB for a 1 hour incubation. Beads were washed in 200 µL PBSTB by centrifugation at 13,400×g for 30 seconds and suspended in 20 µL of a 25 µg/lmL solution of Bodipy-labeled probe antibody. This mixture was incubated for 1 hour, diluted to 300 µL in PBSTB and assayed using flow cytometry.

Cross-Reactivity Analysis:

To examine the possibility of cross-reactivity, 10 µL of MAB 602 anti-hCG capture beads (5,000 microspheres) were treated with 20 µL dilutions of hCG or AFP. After 1 hour the beads were washed in 200 µL PBSTB by centrifugation at 13,400×g for 30 seconds and suspended in 20 µL of either Bodipy-labeled anti-hCG or Bodipy-labeled anti-AFP at 25 µg/mL. Conversely, 10 µL of S-10473 anti-AFP capture beads (5,000 microspheres) were treated with 20 µL dilutions of hCG or AFP. After 1 hour, beads were washed in 200 µL PBSTB by centrifugation at 13,400×g for 30 seconds and suspended in 20 µL of either Bodipy-labeled anti-hCG or Bodipy-labeled anti-AFP at 25 µg/mL. Mixtures were incubated for 1 hour, diluted to 300 µL in PBSTB and assayed using flow cytometry. Washed vs. no-wash assay format: An AFP/hCG capture antibody bead mixture was made by mixing equal amounts of the two bead types. In duplicate, 10 µL of this bead mixture (10,000 microspheres) was mixed with 20 µL dilutions of AFP/hCG and incubated for 1 hour. One set of beads were washed in PBSTB by centrifugation at 13,400×g for 30 seconds and suspended in 20 µL of a mixture of Bodipy-labeled anti-hCG and anti-AFP both at 25 µg/mL. This mixture was incubated for 1 hour, diluted to 300 µL in PBSTB and assayed using flow cytometry. The second set of beads were treated directly with 20 µL of a mixture of Bodipy-labeled anti-hCG and anti-AFP both at 25 µg/mL. This mixture representing a homogenous (no-wash) assay was also incubated for 1 hour, diluted to 300 µL in PBSTB and assayed using flow cytometry.

Multiple Analyte Assay:

Once the AFP and hCG antibody pairs were shown not to cross-react and were adjusted to provide clinically relevant ranges of sensitivity in a homogenous assay, the assays were performed simultaneously using commercially available serum calibrators as the source of AFP and hCG antigens. Equivalent amounts of each of the two capture antibody loaded microspheres was mixed to produce an AFP/hCG capture mixture. In triplicate, 10 µL of this bead mixture (5,000 of each microsphere) was mixed with 20 µL of three serum calibrators (high, medium and low) containing known levels of AFP and hCG and incubated for 1 hour. Mixtures were treated directly with 20 µL of a blend of Bodipy-labeled anti-hCG and anti-AFP both at 25 µg/mL. Mixtures were incubated for 1 hour, diluted to 300 µL in PBSTB and assayed by flow cytometry.

Results

Antibody Pair Analysis for hCG Capture Assay:

For hCG antibody pair analysis, five capture antibody/microspheres were prepared and the identical five antibodies were Bodipy-labeled to serve as probes. Three of the antibodies were specific for the alpha sub-unit of hCG and two for the beta sub-unit. The three anti-alpha sub-unit antibody/microspheres were assayed for utility with the two Bodipy-labeled anti-beta hCG antibodies. Conversely, the two anti-beta sub-unit antibody/microspheres were assayed for utility with the three Bodipy-labeled anti-alpha hCG antibodies. Results of this screen are shown in Table 14 and FIG. 35. The 12 combinations of antibodies are shown with (odd numbers) and without (even numbers) hCG at 20 µg/mL. It is apparent that the first two antibody pairs, #1 and #3 demonstrated the highest mean intensity of fluorescence (MIF) of the $F_m$ (green channel). Further examination of these two pairs led to the decision to chose the #3 pair of MAB 602 for capture antibody and AB633-Bodipy as probe antibody for the hCG capture/sandwich assay.

Antigen Titration:

The MAB 602/AB633 anti-hCG capture system was assayed by hCG titration to determine if the level of sensitivity required for clinical assay was achievable. A limit of detection of at least 1 ng hCG/mL was the target as this was the level of hCG in the low serum calibrator to be used later in this project. The results of this antigen titration is shown in Table 15 and FIG. 36. The limit of detection was between 20 and 200 µg/mL. This revealed that the MAB602/AB3633 anti-hCG antibody pair was sufficiently sensitive for hCG analysis. Included in this analysis was MIF of $F_m$ measurements from counting of 100 or IQ00 microspheres. Results were similar. A similar analysis of antibody pairs and antigen titration for AFP identified an AFP pair that could be further developed.

Cross-Reactivity Assay:

The MAB 602/AB633 anti-hCG capture system and S-10473/M20077 is anti-AFP capture system were examined for cross reactivity by assaying each capture bead with each antigen and Bodipy-labeled antibody. Results are shown in Table 16 and FIGS. 37A and 37B. No significant cross-reactivity between the hCG and AFP capture systems was detected.

No-wash vs. Washed Assay Format:

The hCG and AFP assays were performed simultaneously and examined for the limit of quantitation or dynamic range in both a washed format and no wash or homogenous format. Result of these antigen titrations are shown in Table 17 and FIGS. 38A and 38B. Results indicated that the homogenous format provided sufficient dynamic range for the purposes of clinical relevance.

Multiple Analyte hbCGAFP assay:

The two assays were performed simultaneously using serum calibrators of known hCG and AFP levels to generate a standard curve. For each standard curve one serum of unknown hCG and AFP level was included to demonstrate how the assay would determine the level of hCG and AFP in the serum.

The Randox Tri-level calibrators consisted of three serum samples with high, medium and low levels of hCG and AFP documented in mU or U/mL for hCG and AFP respectively. These calibrators are used in at least 12 different diagnostic instruments including those of Abbott (Abbott Park, Ill.), bioMerieux (St. Louis, Mo.), Ciba Corning (Medfield, Mass.), Diagnostics Products (Los Angeles, Calif.), Kodak (Rochester, N.Y.), Syva (San Jose, Calif.), Tosoh (Atlanta, Ga.) and Wallac (Gaithersburg, Md.). Literature with the Randox Tri-Level control listed the units of each known analyte as defined by each diagnostic machine. We calculated the average of the hCG mU/nL and AFP U/mL for the three calibrators. In the case of the hCG, the low and medium calibrators contained 22.8 and 26.4 mU/nL which were extremely close considering the distance to the high calibrator (436 mU/mL). For this reason, we included a 1:2 dilution of the high range calibrator into hCG/AFP certified negative serum to produce a fourth level serum calibrator termed Level 3D. Calibrator 3D was only used in construction of the hCG standard curve so each of the assays was effectively defined by three point calibration.

Table 18 shows the results of this multiple analyte assay. The assay was performed in triplicate and the average MIF of $F_m$ computed for graphing. Coefficients of variation (CV) for the triplicates were consistently less than 10% are shown. Also included in the table are the number of microspheres correctly identified by the flow cytometry out of the 400 counted per tube. Of the 400 beads counted the expected ratio of MAB 602 containing 60140 beads to S-10473 containing 40/60 beads was 1:1. Therefore of the 200 beads expected, this was the number of beads correctly identified and used to compute the MIF of $F_m$ for that data point.

FIGS. 39A and 39B graphically represent the data of Table 18. For both hCG and AFP a plot of the MIF vs. the log of antigen concentration produced a line that was best fit using a third level polynomial equation. The fit for the hCG curve provided an $R^1$ of 1.0 and for AFP an $R^2$ of 0.9999 was achieved. Using the polynomial equation, the concentration of the unknowns was computed. Results of these analyses are seen in Table 18. The unknown serum contained 218.55±6.56 mU/mL of hCG and 39.59±1.19 U/mL of AFP.

A demonstrative immunometric assay for hCG and AFP in serum has been developed. Assays were first developed as single analyte or single bead assays, and optimized with regards to sensitivity, limit of quantitation and cross-reactivity. The assays were then combined to quantitatively determine multiple analyte levels in a liquid solution in the same tube from the same sample at the same time. Results, using commercially available calibrator sera, has proven that this invention is effective for this type of quantitative assay.

TABLE 14

| Sample | Description | hCG Conc. (µg/mL) | MIF of Fm |
|---|---|---|---|
| 1 | A1-Beads + B1 Ab-BD with hCG | 20.0 | 8790 |
| 2 | A1-Beads + B1 Ab-BD with no hCG | 0.0 | 108 |
| 3 | A2-Beads + B1 Ab-BD with hCG | 20.0 | 9441 |
| 4 | A2-Beads + B1 Ab-BD with no hCG | 0.0 | 163 |
| 5 | A3-Beads + B1 Ab-BD with hCG | 20.0 | 3150 |
| 6 | A3-Beads + B1 Ab-BD with no hCG | 0.0 | 2984 |
| 7 | A1-Beads + B2 Ab-BD with hCG | 20.0 | 2287 |
| 8 | A1-Beads + B2 Ab-BD with no hCG | 0.0 | 37 |
| 9 | A2-Beads + B2 Ab-BD with hCG | 20.0 | 1232 |
| 10 | A2-Beads + B2 Ab-BD with no hCG | 0.0 | 42 |
| 11 | A3-Beads + B2 Ab-BD with hCG | 20.0 | 566 |
| 12 | A3-Beads + B2 Ab-BD with no hCG | 0.0 | 560 |
| 13 | B1-Beads + A1 Ab-BD with hCG | 20.0 | 70 |
| 14 | B1-Beads + A1 Ab-BD with no hCG | 0.0 | 23 |
| 15 | B2-Beads + A1 Ab-BD with hCG | 20.0 | 346 |
| 16 | B2-Beads + A1 Ab-BD with no hCG | 0.0 | 20 |
| 17 | B1-Beads + A2 Ab-BD with hCG | 20.0 | 107 |
| 18 | B1-Beads + A2 Ab-BD with no hCG | 0.0 | 33 |
| 19 | B2-Beads + A2 Ab-BD with hCG | 20.0 | 886 |
| 20 | B2-Beads + A2 Ab-BD with no hCG | 0.0 | 56 |
| 21 | B1-Beads + A3 Ab-BD with hCG | 20.0 | 105 |
| 22 | B1-Beads + A3 Ab-BD with no hCG | 0.0 | 196 |
| 23 | B2-Beads + A3 Ab-BD with hCG | 20.0 | 143 |
| 24 | B2-Beads + A3 Ab-BD with no hCG | 0.0 | 609 |

TABLE 15

| Sample | hCG Conc. (ng/mL) | MIF of Fm (1000 Beads) | MIF of Fm (1000 Beads) |
|---|---|---|---|
| 1 | 20000 | 9337 | 9222 |
| 2 | 2000 | 9286 | 9392 |
| 3 | 200 | 9233 | 9400 |
| 4 | 20 | 8497 | 8664 |
| 5 | 2 | 1286 | 1382 |
| 6 | 0.2 | 258 | 254 |
| 7 | 0.02 | 120 | 147 |
| 8 | 0.002 | 122 | 121 |
| 9 | 0.0002 | 122 | 149 |
| 10 | 0 | 128 | 111 |

TABLE 16A

| MAB602 BEADS- | | Anti-hCG | | |
|---|---|---|---|---|
| Samp. | Antigen ng/mL | hCG anti-hCG | AFP anti-hCG | hCG anti-AFP | AFP anti-AFP |
| 1 | 1000.0 | 792 | 53 | 47 | 52 |
| 2 | 100.0 | 761 | 47 | 48 | 48 |
| 3 | 10.0 | 530 | 47 | 47 | 48 |
| 4 | 1.0 | 104 | 47 | 48 | 48 |
| 5 | 0.1 | 55 | 52 | 49 | 48 |
| 6 | 0.0 | 48 | 71 | 72 | 48 |

TABLE 16B

| M20077 BEADS- | | Anti-AFP | | |
|---|---|---|---|---|
| Samp. | Antigen ng/mL | hCG anti-hCG | AFP anti-hCG | hCG anti-AFP | AFP anti-AFP |
| 1 | 1000.0 | 99 | 57 | 78 | 348 |
| 2 | 100.0 | 54 | 75 | 44 | 356 |
| 3 | 10.0 | 44 | 44 | 45 | 103 |
| 4 | 1.0 | 51 | 50 | 44 | 98 |
| 5 | 0.1 | 42 | 75 | 49 | 44 |
| 6 | 0.0 | 43 | 61 | 45 | 45 |

TABLE 17

| | AFP | | | hCG | | |
|---|---|---|---|---|---|---|
| Sample No. | AFP ng/mL | No Wash | Washed | hCG ng/mL | No Wash | Washed |
| 1 | 1000 | 379 | 1481 | 2000 | 491 | 3194 |
| 2 | 500 | 643 | 1376 | 1000 | 770 | 3158 |
| 3 | 250 | 956 | 1205 | 500 | 1198 | 3342 |
| 4 | 125 | 1063 | 1052 | 250 | 1521 | 2755 |
| 5 | 62 | 980 | 814 | 125 | 2068 | 2949 |
| 6 | 31 | 639 | 612 | 62 | 2417 | 3200 |
| 7 | 16 | 359 | 347 | 31 | 2514 | 3183 |
| 8 | 8 | 190 | 205 | 16 | 2440 | 2528 |
| 9 | 4 | 94 | 108 | 8 | 1761 | 1955 |
| 10 | 2 | 51 | 59 | 4 | 1122 | 1300 |
| 11 | 1 | 33 | 35 | 2 | 650 | 547 |
| 12 | 0.5 | 24 | 25 | 1 | 330 | 359 |
| 13 | 0.25 | 17 | 24 | 0.5 | 166 | 175 |
| 14 | 0 | 15 | 13 | 0 | 15 | 18 |

TABLE 18

| | | | hCG capture system | | | | AFP capture system | | | |
|---|---|---|---|---|---|---|---|---|---|---|
| Tube No. | Descript. | hCG mU/mL | AFP U/mL | MIF of FL1 | MIF AVG | MIF CV % | Beads IDed | MIF of FL1 | MIF AVG | MIF CV % | Beads IDed |
| 1 | Level 1 | | | 23 | | | 114 | 74 | | | 98 |
| 2 | Level 1 | 22.8 | 10.7 | 27 | 25.67 | 7% | 130 | 83 | 78.00 | 5% | 80 |
| 3 | Level 1 | | | 27 | | | 140 | 77 | | | 72 |
| 4 | Level 2 | | | 32 | | | 93 | 351 | | | 58 |
| 5 | Level 2 | 26.4 | 53.8 | 34 | 31.67 | 6% | 85 | 365 | 362.67 | 2% | 61 |
| 6 | Level 2 | | | 29 | | | 94 | 372 | | | 65 |
| 7 | Level 3D | | | 268 | | | 92 | 535 | | | 56 |
| 8 | Level 3D | 218 | 111.5 | 276 | 271.67 | 1% | 101 | 562 | 552.00 | 2% | 69 |
| 9 | Level 3D | | | 271 | | | 96 | 559 | | | 61 |
| 10 | Level 3 | | | 631 | | | 106 | 1109 | | | 46 |
| 11 | Level 3 | 436 | 223 | 601 | 624.00 | 3% | 99 | 994 | 1061.00 | 5% | 38 |
| 12 | Level 3 | | | 640 | | | 97 | 1080 | | | 40 |
| 13 | Negative | | | 8 | | | 99 | 11 | | | 104 |
| 14 | Negative | 10 | 2 | 7 | 7.33 | 6% | 111 | 13 | 12.33 | 8% | 106 |
| 15 | Negative | | | 7 | | | 119 | 13 | | | 95 |
| 16 | Unknown | | | 270 | | | 140 | 268 | | | 67 |
| 17 | Unknown | 218.55 | 39.59 | 264 | 272.33 | 3% | 141 | 274 | 276.00 | 3% | 81 |
| 18 | Unknown | | | 283 | | | 113 | 286 | | | 84 |

Multiplexed Beadset Standard Curve Using an Inhibition Assay

This example provides a demonstration of the measurement of ligand-ligate reactions using a multiplexed beadset standard curve. Commonly for ligand-ligate reactions quantitation, known amounts of the ligand or ligate are introduced to the reaction leading to the production of a standard curve. Values for unknown samples are compared to the standard curve and quantified. The true multiple assay capability of this invention allows for an additional type of standard to be utilized A multiplexed beadset standard curve for measuring analyte concentration is created by using several Differentially Fluorescent Microspheres (DFM) coated with either 1) different amounts of ligand (antigen), or 2) different amounts of ligate (antibody), or 3) different ligates possessing different avidities for the ligand (different monoclonal antibodies). We have demonstrated an example of the first type of multiple analyte standard curve by developing a competitive inhibition assay for human IgG.

Four DFM were coated with human IgG at four different concentrations. When probed with goat anti-human IgG-Bodipy the Mean Intensity of Fluorescence (MIF) of $F_m$ (green channel) for each bead subset was different. The MIF of $F_m$ correlated with the amount of hIgG used to coat the beads in each subset. If soluble hIgG was mixed with the reaction in a competitive manner the MIF of $F_m$ was reduced for each bead as less of the probe antibody was bound to the beads. In a normal standard curve, the signal (MIF of $F_m$) is plotted against the concentration of the inhibitor. For the multiplexed beadset standard curve, the slope of the MIF of $F_m$ across the beads within a subset is plotted against the concentration of inhibitor. Comparison of the two types of standard curves revealed them to be of equivalent value for prediction of an unknown amount of inhibitor.

Human IgG Conjugation to Microspheres:

Four DFM (5.5 $F_m$ carboxylate, Bangs Laboratories, Inc., Cannel, Ind., dyed by Emerald Diagnostics, Inc., Eugene, Oreg.) were conjugated separately to 4 different concentrations of hIgG (Cappel Division, Organon Teknika, Durham, N.C.) with a two-step EDC coupling method (Pierce Chemicals, Rockford, Ill.) using sulfo-NHS to stabilize the amino-reactive intermediate. 20 $\mu$L (8.4 million microspheres) of each bead type was activated for 20 minutes in a total volume of 100 $\mu$L containing 500 g of EDC and Sulfo-NHS in 50 mM sodium phosphate buffer, pH 7.0. The microspheres were washed twice with 200 $\mu$L PBS, pH 7.4 using centrifugation at 13,400 x g for 30 seconds to harvest the microspheres.

Activated, washed beads were suspended in 50 $\mu$L of hIgG at 50, 10, 5, and 1 $\mu$g/mL in PBS, pH 7.4. After 2 hours, the microspheres were blocked by addition of 50 $\mu$L of 0.2 M glycine, 0.02% Tween 20 in PBS, pH 7.4 and incubated for an additional 30 minutes. Protein coated microspheres were washed twice with 200 $\mu$L 0.02% Tween 20, 1 mg/mL BSA in PBS, pH 7.4 (PBSTB). and stored in PBSTB at approximately 3,000,000 microspheres/mL as determined by hemacytometer count.

Antibody Labeling:

Goat anti-human IgG (Cappel Division, Organon Teknika, Durham, N.C.) was labeled with Bodipy FL-CASE (Molecular Probes, Inc., Eugene, Oreg.) using methods described by the manufacturer of the Bodipy succinymidyl ester. The resulting Bodipy-labeled antibody was stored in PBS containing 1 mg/mL BSA as stabilizer.

Multiplexed Beadset Standard Curve:

Equivalent amounts of each of the 4 differentially loaded IgG microspheres was mixed to produce a bead mixture. 10 $\mu$L of the goat anti-hIgG-Bodipy at 25 $\mu$g/mL in PBSTB was mixed with 10 $\mu$L of a dilution of hIgG in PBSTB. Immediately 10 $\mu$L (30,000 microspheres) of the bead mixture was added and the mixture incubated at room temperature for 30 minutes. Beads were diluted to 300 $\mu$L in PBSTB and assayed using flow cytometry. A negative control included the microspheres with the goat anti-hIgG-Bodipy with no inhibitor (hIgG). Each bead subset was assigned the value of a consecutive integer (i.e. the bead subset coupled with the lowest concentration of IgG was given a value of 1, the next highest concentration was given a value of 2, etcetera) and those numbers plotted against the MIF of each bead subset at each concentration of inhibitor tested. The slopes (designated here as inter-bead subset slopes) were computed using linear regression analysis. The inter-subset slopes were then plotted against the concentration of inhibitor using a logarithmic scale for the concentration of inhibitor. Results were plotted as the slope of the MIF of F. across the bead set against the log of hIgG concentration. Curve fitting was performed using a power function trendline and the $R^2$ correlation was reported. For a perfect fit, $R^2$=1.0.

Common Standard Curve:

Using the data from the assay described above, a common standard curve was constructed to compare results with the multiple analyte standard curve. Data from the DFM coated at 50 µg/lmL hIgG was utilized to produce a five-point standard curve by plotting the MIF of $F_m$ against the log of hIgG concentration. Curve fitting was performed using a power function trendline and the $R^2$ correlation was reported.

Results

Multiplexed Beadset Standard Curve for a Competitive Inhibition Assay:

Four differentially loaded IgG microspheres were utilized in a multiple beadset competitive inhibition assay for hIgG at five different concentrations of soluble inhibitor (hIgG). Results of the assay are shown in Table 19. The inhibition pattern on each bead is plotted in FIG. 40. The inter-bead subset slopes are plotted against the log concentration of inhibitor in FIG. 41. A Power Trendline in Excel was used to produce the $R^2$ of 0.9933.

Common Standard Curve Using One Bead of the Multiple Analyte Assay:

Data from the 50 µg/mL hIgG bead was utilized to produce a five-point standard curve by plotting the MIF of $F_m$ against the log of hIgG concentration. Results are shown in FIG. 42. Curve fitting was performed using a Power function trendline and $R^2$=0.9942.

A novel type of standard curve for ligand-ligate measurement was demonstrated. Results suggested that the multiplexed beadset standard curve was of similar utility as the common multi-point standard curve in quantitation of unknown samples. Advantages of the multiplexed beadset standard curve include the inclusion of the standard curve microspheres in each point of a multiplexed beadset assay, and the extension of an assay's dynamic range. This may be achieved by increasing the concentration range of ligand or ligate on the microspheres or by increasing the range of avidities for ligand on a series of microspheres.

TABLE 19

| Samp | Inhibitor Conc (82 g/mL) | Bead 1 1.0 µg/ mL IgG | Bead 2 5 µg/ mL IgG | Bead 3 10 µg/ mL IgG | Bead 4 50 µg/ mL IgG | SLOPE |
|---|---|---|---|---|---|---|
| 1 | 100 | 14 | 77 | 108 | 288 | 85.3 |
| 2 | 50 | 21 | 100 | 162 | 428 | 128.3 |
| 3 | 25 | 40 | 166 | 267 | 844 | 251.3 |
| 4 | 12.5 | 110 | 463 | 747 | 1467 | 435.5 |
| 5 | 6.25 | 257 | 1226 | 1629 | 2316 | 658 |
| 6 | 0 | 134 | 793 | 1432 | 2217 | 688.8 |

Nucleic Acid Measurement

The power and sensitivity of PCR has prompted its application to a wide variety of analytical problems in which detection of DNA or RNA sequences is required. One major difficulty with the PCR technique is the cumbersome nature of the methods of measuring the reacttion's products—amplified DNA.

A major advance in this area is here. That advance employs a flow cytometric bead-based hybridization assay which permits the extremely rapid and accurate detection of genetic sequences of interest. In a preferred embodiment of that invention, a bead to which a nucleic acid segment of interest has been coupled is provided. A PCR product of interest (or any other DNA or cDNA segment) is detected by virtue of its ability to competitively inhibit hybridization between the nucleic acid segment on the bead and a complementary fluorescent nucleic acid probe. The method is so sensitive and precise as to allow the detection of single point mutations in the PCR product or nucleic acid of interest. Although that method in itself provides a pivotal advance in the art of analyzing PCR reaction products, the further discovery of methods of multiplexing such an analysis, compounds the method's power and versatility to allow. simultaneously analysis of a number of nucleic acid products or a number of sequences within a single product in a single sample.

The multiplexed DNA analysis method described here can be applied to detect any PCR product or other DNA of interest for specific polymorphisms or mutations or for levels of expression, e.g. mRNA. With the multiplexed techniques provided by the instant invention, individuals can be screened for the presence of histocompatibility alleles associated with susceptibility to diseases, mutations associated with genetic diseases, autoimmune diseases, or mutations of oncogenes associated with neoplasia or risk of neoplasia. The analysis of DNA sequences occurs generally as follows:

1. A beadset containing subsets of beads coupled to nucleic acid sequences of interest is prepared by coupling a unique synthetic or purified DNA sequence to the beads within each subset.
2. Fluorescent probes complementary to the DNA coupled to each bead subset are prepared.

Methods known in the art, e.g., as described in U.S. Pat. No. 5,403,711, issued April 4, 1995 and incorporated herein by reference, or other methods may be used to fluorescently is label the DNA. Since each probe will bind optimally only to its complementary DNA-containing subset, under the conditions of the assay, the fluorescent probes may be added to the subsets before or after the subsets are pooled, and before or after addition of the DNA test sample(s) of interest.

3. Tissue, fluid or other material to be analyzed is obtained, and DNA is purified and/or amplified with PCR as necessary to generate the DNA products to be tested.
4. The DNA samples of interest are then mixed with the pooled beadset under suitable conditions to allow competitive hybridization between the fluorescent probes and the DNA of interest.
5. The beadset is then analyzed by flow cytometry to determine the reactivity of each bead subset with the DNA sample(s). If the test sample contains a DNA sequence complementary to the DNA of a given bead subset then that subset will exhibit a decreased $F_m$ value relative to the $F_m$ value of beads to which a control DNA has been added. A computer executed method in accordance with the current invention can determine the subset from which each bead is derived, and therefore, the identity of the DNA sequence on the bead and any change in $F_m$.

Detection of Foreign DNA

The methods of the present invention find wide utility in the detection of foreign DNA's in, for example, diagnostic assays. Although the DNA segment to be analyzed can be any DNA sequence, in accordance with this embodiment the selected segment will be a DNA segment of a pathogenic organism such as, but not limited to, bacterial, viral, fungal, mycoplasmal, rickettsial, chlamydial, or protozoal pathogens. The procedure has particular value in detecting infection by pathogens that are latent in the host, found in small amounts, do not induce inflammatory or immune responses, or are difficult or cumbersome to cultivate in the laboratory. The multiplexed DNA detection method of the present invention is likely to find particular utility as a diagnostic assay for analysis of a sample from a patient having clinical symptoms known to be caused by a variety of organisms using a beadset designed to detect DNAs from the variety of organisms known to cause such symptoms to determine which of such organisms is responsible for the symptoms. DNA would be extracted from tissue, fluid or other sources and analyzed as described above.

Analysis of Genetic Polymorphisms

The invention may also be used to measure a variety of genetic polymorphisms in a target DNA of interest. For example, there are several genes in the MHC and many are polymorphic. There are at least two applications in which determination of the alleles at each position of the MHC is of critical importance. The first is the determination of haplotype for transplantation, and the second is determination of haplotype as indicator of susceptibility to disease. See Gross et al., "The Major Histocompatibility Complex-Specific Prolongation of Murine Skin and Cardiac Allograft Survival After In Vivo Depletion of V$\beta^+$ T Cells," J. Exp. Med., 177, 35-44 (1993). The MHC complex contains two kinds of polymorphic molecules, Class I genes, HLA A, B and D which have 41, 61 and 18 known alleles and Class 10 genes, HLA-DR1,3,4,5 HLA-DQA1 and BI HLA-DP, DPA1, DPB1, also with many alleles. Each human can have up to 6 co-dominant Class I genes and 12 co-dominant Class 10 genes.

In the case of transplantation, the closer the match between the donor and recipient the greater the chance of transplant acceptance. A multiplexed assay in accordance with the invention may be employed to perform tissue typing quickly and accurately to identify suitable matches for transplantation.

In the situation of disease association, it has been found that individuals bearing certain alleles are more prone to some diseases than the remainder of the population. The frequency of alleles of the MHC genes is not equal, and sets of alleles are frequently found (linkage disequilibrium) so that the identification of the exact set of alleles associated with many diseases is feasible. As one example, insulin-dependent diabetes mellitus (IDDM) is associated with certain HLA-DQ alleles. The number of alleles of DQ in the population is modest and genetic typing by PCR amplification and hybridization with allele specific probes has been shown to be practical. See Saiki et al., "Genetic Analysis of Amplified DNA with Immobilized Sequence-Specific Oligonucleotide Probes," Proc. Natl. Acad. Sci. U.S.A., 86, 6230–6234 (1989).

For an assay of MHC in accordance with the invention, DNA is obtained from blood or other extractable source, and amplified with primers specific for the MHC genes under analysis, for example, HLA-DQA. For a full genotyping of the MHC, several samples of DNA would be amplified with different sets of primers to accommodate the large number of loci and the high degree of polymorphism. The PCR products are then screened for specific alleles using beadsets and fluorescent probes as described above.

Mutation Analysis of Selected Genes:

Screening Procedures There are several methodologies for determining and comparing DNA sequences in order to detect mutations which are associated with disease or neoplasia. When adapted to a bead-based, multiplexed format in accordance with the current invention, hybridization analysis allows for the rapid screening of multiple genetic loci for multiple wild type and mutant sequences.

In a preferred embodiment of the invention, a given genetic locus, or multiple loci, can be simultaneously screened for the presence of wild type or mutant sequences. In the same analysis, multiple known mutations can be distinguished from each other and from the wild type sequence and uncharacterized mutations. In addition, the homozygosity or heterozygosity of known sequences can be determined.

A general approach for detecting a DNA mutation in accordance with this aspect of the invention is as follows. In a first step, a suitable probe for detecting a mutation of interest is selected. In an illustrative embodiment, selected oligonucleotides, representing wild-type and mutant sequences, from a region of a gene known to contain a mutation are prepared. Such oligonucleotides are coupled to microspheres by techniques known in the art, (e.g., carbodiimide coupling, or other means) to produce individual aliquots of beads having known oligonucleotides coupled thereto. The oligonucleotides must be a sufficient length to allow specific hybridization in the assay, e.g., generally between about 10 and 50 nucleotides, more preferably between about 20 and 30 nucleotides in length. In a preferred embodiment, a saturating amount of the oligonucleotide is bound to the bead. Fluorescent oligonucleotides, complementary to all or part of the sequences attached to each bead, are also prepared.

Next, PCR primers are selected to amplify that region of the test DNA corresponding to the selected probe, which are then used to amplify the particular region of DNA in the sample that contains the sequence corresponding to the oligonucleotide coupled to the beads. Either double stranded or single stranded PCR techniques may be used. If double stranded product is produced, the amplified PCR product is made single stranded by heating to a sufficient temperature to and for a sufficient time to denature the DNA (e.g., for about 1 to about 5 minutes at about 90–95° C. in 2.3×SSC hybridization buffer). The mixture is cooled, and the beads are added and incubated with the PCR product under conditions suitable to allow hybridization to occur between the oligonucleotide on the beads and the PCR product (e.g., at room temperature for about 10 minutes). The fluorescent DNA probe may then be added and the entire mixture incubated under hybridization conditions suitable to allow competitive hybridization to occur (e.g., 5 minutes at 65° C., then cooling to room temperature over a period of several hours in 2.3×SSC buffer). As those of skill in the art will recognize, the concentrations of the PCR product and fluorescent probe to be used may vary and may be adjusted to optimize the reaction.

In general, the concentrations of PCR product and fluorescent probe to be used are adjusted so as to optimize the detectable loss of fluorescence resulting from competitive inhibition without sacrificing the ability of the assay to discriminate between perfect complementarity and one or more nucleotide mismatches. In an exemplary assay, the concentration of PCR product complementary to the oligonucleotide bound to the beads may be on the order of 1 to 10 times the molar concentration of fluorescent probe used. The fluorescent probe should preferably be added in an amount sufficient to achieve slightly less than saturation of the complementary oligonucleotide on the beads in order to obtain maximum sensitivity for competitive inhibition.

In a multiplexed assay employing the above principles, beadsets are separately prepared, pooled, and the bead-based hybridization analysis performed. In order to screen a given locus for mutations, beadset subsets are prepared such that subset 1 is coupled to a DNA segment identical to the wild type sequence, subset 2 is coupled to a DNA segment identical to a known mutation 1 (which may represent a single or multiple point mutations, deletions or insertions), subset 3 is coupled to a DNA segment identical to a second known mutation 2, and so on. The subsets are then mixed to create a pooled beadset.

When a nucleic acid sample is analyzed with such a beadset, only the bead subsets containing sequences identical to the test sample will show a large decrease in fluorescence ($F_m$). Bead subsets containing unrelated or greatly disparate sequences will show little or no decrease in fluorescence ($F_m$) and bead subsets containing very closely related sequences, such as point mutants, will show an intermediate decrease in fluorescence ($F_m$). Thus, a large decrease in the Fm of only subset 1 would indicate homozygous wild-type; a large decrease in the $F_m$ of both subset 1 and subset 2 would indicate heterozygous wild-type/mutant 1 and so on. If the test sample is less inhibitory than the perfectly complementary sequence for any of the known sequences represented by the subsets then a new uncharacterized mutation is indicated. The test sample could then be sequenced to characterize the new mutation, and this sequence information used to construct a new subset for the beadset to detect the newly discovered mutation The present invention has wide-spread advantages for detection of any of a number of nucleic acid sequences of interest in the genomic DNA of an individual or organism and has the advantages of being both rapid and extremely accurate in effecting the detection of such mutations.

The invention will find wide applicability in diagnosis of a number of genetically associated disorders as well as in other applications where identification of genetic mutations may be important. Exemplary diseases include without limitation, diseases such as cystic fibrosis, generalized myotonia and myotonia congenita, hyperkalemic periodic paralysis, hereditary ovalocytosis, hereditary spherocytosis and glucose malabsorption; which are associated with mutations in the genes encoding ion transporters; multiple endocrine neoplasia, which is associated with mutations in the MEN2a, b, and MEN1 genes; familial medullary thyroid carcinoma, and Hirschsprung's disease, which are associated with mutations in the ret proto-oncogene; familial hypercholesterolemia, which is associated with mutations in the LDL receptor gene; neurofibromatosis and tuberous sclerosis, which are associated with mutations in the NF1 gene, and NF type 2 gene; breast and ovarian cancer, which are associated with mutations in the BRCA1, BRCA2, BRCA3 genes; familial adenomatous polyposis, which is associated with mutations in the APC gene; severe combined immunodeficiency, which is associated with mutations in the adenosine deaminase gene; xeroderma pigmentosum, which is associated with mutations in the XPAC gene; Cockayne's syndrome, which is associated with mutations in the ERCC6 excision repair gene; fragile X, which is associated with mutations in the fmr1 gene; Duchenne's muscular dystrophy, which is associated with mutations in the Duchenne's muscular dystrophy gene; myotonic dystrophy, which is associated with mutations in the myotonic dystrophy protein kinase gene; bulbar muscular dystrophy, which is associated with mutations in the androgen receptor genes; Huntington's disease, which is associated with mutations in the Huntington's gene; Peutz-jegher's syndrome; Lesch-Nyhan syndrome, which is associated with mutations in the HPRT gene; Tay-Sachs disease, which is associated with mutations in the HEXA gene; congenital adrenal hyperplasia, which is associated with mutations in the steroid 21-hydroxylase gene; primary hypertension, which is associated with mutations in the angiotensin gene; hereditary non-polyposis, which is associated with mutations in the HNMLH1 gene; colorectal carcinoma, which is associated with mutations in the 2 mismatch repair genes; colorectal cancer, which is associated with mutations in the APC gene; forms of Alzheimer's disease which have been associated with the apolipoprotein E gene, retinoblastoma, which is associated with mutations in the Rb gene; Li-Fraumeni syndrome, which is associated with mutations in the p53 gene; various malignancies and diseases that are associated with translocations: e.g., in the bcr/abl, bcl-2 gene; chromosomes 11 to 14 and chromosomes 15 to 17 transpositions. The references at the end of the specification which are expressly incorporated herein by reference describe genetic mutations associated with certain diseases which may be tested for in accordance with the invention as well as sequences provided in GENBANK, the contents of which are also expressly incorporated herein by reference.

Double Stranded Experiment

For the purposes of illustration, the two complementary strands of a double-stranded DNA segment are referred to as strand "A" and strand "B". Either strand may be designated "A" or "B". The wild-type "B" strand oligo (ras codon 12) having the oligonucleotide sequence 5'-GCCTACGCCACCAGCTCCAACTAC-3'(SEQ ID NO.3) was coupled to 3.0 micrometers ($\mu$m) latex microspheres (manufactured by Interfacial Dynamics, Portland, Oreg.) by carbodiimide coupling. Double stranded competitor was prepared by combining equal amounts of both the "A" and "B" strands of either the wild-type or mutant version of the oligo, mutant "B" strand having the sequence 5'-GCCTACGCCACAAGCTCCAACTAC-3' (SEQ ID NO.4) (ras codon 12) in 5×SSC buffer. Annealing was accomplished by heating the mixture to 65° C. for five minutes, then cooling slowly to room temperature. Competitive hybridization was accomplished by combining approximately 40 picomoles of the bead-attached oligo (wild-type "B" strand) with the indicated amounts of double stranded competitor in 2.3×SSC buffer at approximately 25° C. Finally, 100 picomoles of the fluorescinated oligo (wild-type "A" strand) was added to the reaction mixture. This mixture was incubated for two hours at room temperature, and then diluted with 300 $\mu$l of saline pH 7.3, and analyzed on the "FACSCAN" (manufactured by Becton-Dickinson Immunocytometry Systems, San Jose, Calif.). The results are shown in Table 20 below and in FIGS. 43a through 43c.

TABLE 20

Double-Stranded Experimental Results Using Wild-Type "B" Oligonucleotide

| Double Stranded Competitor (picomole) | Percent Inhibition (%) | | Fold Competition Wild-Type/Mutant |
|---|---|---|---|
| | Wild-Type | Mutant | |
| 10 | 20 | 9 | 2.2 |
| 100 | 35 | 12 | 2.9 |
| 1000 | 56 | 17 | 3.3 |

These results clearly show that the DNA containing the single point mutation ("Mutant") was a detectably less effective inhibitor of hybridization between the DNA on the beads and the fluorescent oligonucleotide probe at all concentrations of competitor tested.

Single Stranded Experiment

The wild-type "B" strand oligo (ras codon 12) was coupled to 3.0 p1m latex microspheres (manufactured by Interfacial Dynamics) by carbodiimide coupling. Competitive hybridization was accomplished by combining approximately 40 picomoles of the bead-attached oligo with 100 picomoles of the fluorescinated oligo (wild-type "A" strand) in 2.3×SSC buffer. Finally, the indicated amounts of single stranded competitor (either mutant or wild-type) were added to two separate aliquots of the reaction mixture. These aliquots were incubated for two hours at room temperature, and then diluted with 300 μl of saline pH 7.3. and analyzed on the FACSCAN flow cytometer. The result of these experiments are set forth in Table 21 below and in FIGS. 44a 44b.

TABLE 21

Single-Stranded Experimental Results

| Single Stranded Competitor (picomole) | Percent Inhibition (%) | | Fold Competition |
|---|---|---|---|
| | Wild-Type | Mutant | Wild-Type/Mutant |
| 100 "A" Strand | 14 | 6 | 2.4 |
| 1000 "A" Strand | 25 | 11 | 2.3 |

These results clearly show that the DNA containing the single point mutation ("Mutant") was a detectably less effective inhibitor of hybridization between the DNA on the beads and the florescent oligonucleotide probe at all concentrations of competitor tested.

Resequencing Analysis of PCR Products Using Multiplexed Analysis.

This example demonstrates the ability of flow cytometry to perform resequencing analysis of PCR products. As a model system, PCR products were derived from the DQA1 gene, in the region of the gene which determines the major alleles of DQA1. The DQA1 gene represents the DNA coding sequence for the alpha chain of the DQ molecule. DQ is classified as a class II histocompatibility locus and is expressed in allelic form in all humans. Most individuals are heterozygous for DQA, i.e., they express two different DQA alleles. The determination of DQA alleles is used in identity testing for paternity and forensic purposes.

Seventeen alleles of DQA1 have been defined by DNA sequencing; however, eight major alleles account for the large majority of the population. These alleles are determined by fourteen unique DNA sequences contained within four regions of the DQA1 gene; all four regions are contained within a 227 base pair PCR product derived from human genomic DNA.

Flow cytometry was used to determine the presence or absence of all fourteen DNA sequences in a PCR product simultaneously in a single reaction tube, thereby allowing determination of the DQA alleles expressed in a given sample. The system is based on competitive hybridization between the PCR product and complementary oligonucleotide pairs representing each of the fourteen unique DNA sequences. One strand of each oligonucleotide pair is coupled to a unique subset of microspheres and the complementary strand is labeled with a green emitting fluorophore. After coupling, the fourteen unique microsphere subsets were pooled to produce the mixed bead set. After addition of the fourteen fluorescent oligonucleotides and the PCR product to the beadset, the mixture is hybridized and then analyzed by flow cytometry. The ability of the PCR product to inhibit the hybridization of the complementary fluorescent oligonucleotides to their respective microsphere subsets is used to determine the DNA sequences, and thus, the allele(s) present in the PCR product.

Microspheres:

Carboxylate-modified latex (CML) microspheres of 5.5 micron mean diameter were obtained from Bangs Laboratories, Inc. (Carmel, Ind.). The microspheres were differentially dyed with varying concentrations of two fluorescent dyes with orange and red emission spectra to produce fourteen unique microsphere subsets.

Oligonucleotides:

Fourteen oligonucleotide pairs (complementary strands designated "A" and "B") corresponding to allelic sequences within the DQA1 gene (Table 22) were synthesized by Oligos, Etc. (Wilsonville, Oreg.). using standard automated techniques. Each eighteen-base oligonucleotide was substituted at the 5' end with an amino-terminal linker during synthesis.

Oligonucleotide Coupling to Microspheres:

The "B" strand of each oligonucleotide pair was coupled to a unique subset of CML microspheres using carbodiimide chemistry. Briefly, 0.1 μL of a 1 mM solution of oligonucleotide in 0.1 M MES (2-[N-morpholino]ethanesulfonic acid), pH 4.5 was added to 1.0 mL of microspheres (1% solids) in 0.1 M MES, pH 4.5. To this mixture, 0.05 mnL of a 10 mg/mL solution of EDC (1-ethyl-3-[3-dimethylaminopropyl]-carbodiimide hydrochloride) was added and mixed vigorously. The mixture was incubated for 30 minutes at room temperature, followed by another addition of EDC, mixing, and incubation as above. Following the second incubation period, the microspheres were pelleted by centrifugation and resuspended in 0.4 mL of 0.1 M MES, pH 4.5 and stored at 4° C.

Oligonucleotide Labeling:

The "A" strand of each oligonucleotide pair was fluorescently labeled with Bodipy FL-X (6-((4,4-difluoro-5,7-dimethyl-4-bora-3a,4a-diaza-s-indacene-3-propionyl) amino)hexanoic acid, succinimidyl ester) (Molecular Probes, Inc., Eugene, Oreg.). Briefly, a 400 μL solution containing 20 μM oligonucleotide in 0.1 M sodium bicarbonate and 5% DMSO, pH 8.2 was reacted with 30 μL Bodipy FL-X (10 mg/mL in DMSO) for 16–18 hours at room temperature. The mixture was desalted on a PD10 column equilibrated in TE (10 mM TrisHCl, 1 mM ethylenediamine tetraacetic acid (EDTA), pH 8.0) to remove excess unreacted dye and stored at 4° C.

DNA Extraction:

Tissue sample (template) DNA was purified using the QIAmp Blood Kit (Qiagen, Chatsworth, Calif.) for DNA purification. Briefly, $1 \times 10^7$ tissue culture cells or 200 μL whole blood is lysed with Qiagen protease and Buffer AL. The lysate is incubated at 70° C. for 10 minutes followed by addition of 210 μL ethanol. The mixture is applied to a QIAmp spin column and centrifuged at 8,000×g for 1 minute. The filtrate is discarded, 500 μL Buffer AW is added to the column and the centrifugation is repeated; this step is repeated. The filtrates are discarded and the DNA is eluted into a new tube by addition of 200 μL Buffer AE, incubation at room temperature for 1 minute, followed by centrifugation as above.

Polymerase Chain Reaction (PCR:

PCR primers designated DQA AMP-A (5'-ATGGTGTAAA CTTGTACCAGT-3', SEQ ID NO. 5) and DQA AMP-B (5'-TTGGTAGCAG CGGTAGAGTTG-3', SEQ ID NO. 6) (World Health Organization, 1994) were synthesized by Oligos, Etc. (Wilsonville, Oreg.) using standard automated techniques. PCR was performed with reagents (PCR buffer, dNTPs, $MgCl_2$, and TAQ DNA polymerase) from Life Technologies, Inc.(Gaithersburg, Md.). The reaction mixture (50 μL) contained 1 μM of each primer, 200 nM dNTPs, 3 mM MgCl$_2$, 4–10 μg/mL DNA template, and 2.5 units TAQ DNA polymerase in PCR buffer. The PCR reaction was performed on an Idaho Technologies thermal cycler (Idaho Falls, Id.) using and initial step at 94° C. for 45 sec, and 32 cycles of 94° C. for 30 sec, 48° C. for 60 sec, and 72° C. for 60 sec followed by a final hold at 72° C. for 7 minutes. Production of the product was verified by agarose electrophoresis and was quantified by size exclusion chromatography on a Superdex 75 (10/30) column (Pharmacia, Piscataway, N.J.). The PCR product was used without purification.

Competitive Hybridization Analysis:

The hybridization reaction was performed in a total volume of 40 μL, containing approximately 8,000 of each bead subset for a total of approximately 110,000 microspheres, 50 nM of each fluorescent oligonucleotide, and 10–200 nM PCR product, as competitor, in hybridization buffer (3 M trimethyl ammonium chloride, 0.15% sodium dodecyl sulfate, 3 mM EDTA, and 75 mM TrisHCl, pH 8.0). Briefly, the beadset mixture, in hybridization buffer, was equilibrated at 55° C. The mixture of fluorescent oligonucleotides and PCR product was denatured in a boiling water bath for 10 minutes followed by quick-chilling on ice for 2 minutes. The microspheres were added, mixed well, and the entire reaction was allowed to hybridize for 30 minutes at 55° C. Following hybridization, the mixture was diluted to 250 μL using hybridization buffer and analyzed by flow cytometry. Results Microspheres for Multiple Analytes:

FIG. 45 illustrates the classification, using orange and red fluorescence, of the fourteen microsphere subsets used in the DQA1 analysis. Each distinct microsphere subset bears one of the fourteen unique oligonucleotide capture probes on its surface. The level of green fluorescence associated with each subset, after hybridization with the fluorescent oligonucleotide probes, is also determined simultaneously, and measures the reactivity of the fluorescent oligonucleotides (and therefore, the reactivity of the PCR product) with each unique oligonucleotide sequence.

Titration of Fluorescent Oligonucleotide:

To optimize the system for detection of PCR products, fluorescent oligonucleotide was titered in the presence or absence of PCR competitor. FIG. 46 illustrates the hybridization of increasing concentrations of fluorescent oligonucleotide "5503A" to microspheres coupled to oligonucleotide "5503B" in the presence or absence of a 200 nM concentration of double-stranded 0301 PCR product which contains the 5503 sequence. In the absence of competitor, the level of "5503A" which hybridizes to the microspheres, detected as FL1, increases in a linear manner and reaches saturation at approximately 10 nM. In the presence of competitor, the binding curve is shifted to the right indicating inhibition of "5503A" hybridization.

Concentration Dependence of Inhibition and Detection of Point Mutations:

FIG. 47 illustrates the inhibition of fluorescent oligonucleotide hybridization by varying concentrations of complementary and point mutant competitors in the presence of a fixed concentration of fluorescent oligonucleotide. The solid lines show the inhibition of hybridization to bead "3401B" induced by competitors 3401 (u) or 3402 (n). The dashed lines show inhibition of hybridization to bead "3402B" induced by competitors 3401(s) or 3402 (1). Even at the lowest competitor concentration (10 nM), there is approximately a two-fold difference between the reactivity of the identical sequence versus the point mutant.

Specificity of the Multiple Analyte Assay:

The specificity of the reaction of each DNA competitor sequence with the multiplexed microsphere subsets is illustrated in Table 23 and FIG. 48, using double-stranded oligonucleotide competitors. The pattern of reactivity is consistent with the homology of the different oligonucleotides with identical sequences showing maximal reactivity, closely related sequences showing less reactivity, and unrelated sequences showing little or no reactivity.

Allele-Specific Reactivity Patterns:

In order to establish the reactivity patterns of the DQA1 alleles in a model system, simulated alleles were prepared by mixing the oligonucleotides representing the DNA sequences that would be present within a single PCR product for a given allele. FIG. 49 illustrates the typing of four simulated alleles of DQA1. By comparison to the allele reactivity chart shown in Table 24, it can be seen that each of the simulated alleles types correctly.

Typing of Homozygous Penomic DNA:

To verify the ability of flow cytometry to correctly type PCR products prepared from genomic DNA, samples of DNA of known, homozygous DQA1 type were obtained from the UCLA Tissue Typing Laboratory, Los Angeles, Calif. After PCR amplification, these samples were typed using flow cytometry; the results are shown in FIG. 50. By comparison to the allele reactivity chart (Table 24), it can be seen that the system correctly types these samples.

Typing of Heterozypous Genomic DNA:

To determine the ability of multiplexed flow analysis to accurately type heterozygous DQA1 haplotypes, twenty-five samples of known heterozygous DQA1 type were obtained from the UCLA Tissue Typing Laboratory, Los Angeles, Calif. The samples of homozygous DNA used above were added to the panel and all of the samples were coded and typed in a blinded study. The data from this study are presented in Table 25. The last column of Table 25 entitled "Type" indicates whether the haplotype indicated by UCLA and the Luminex analysis agreed. In 34 of 35 samples, the haplotypes reported by both laboratories agreed; sample number 19 was not typed by the UCLA laboratory, but typed clearly as an 0501/0201 heterozygote in the Luminex analysis. Thus, the multiplexed analysis is capable of typing the DQA1 haplotypes with at least 97% accuracy.

These studies have demonstrated that flow cytometry can rapidly and accurately perform resequencing analysis of PCR products. The model system used here required the analysis of fourteen DNA sequences to determine eight different DQA1 alleles. Flow cytometry was able is to perform this analysis in a true simultaneous format, using a single sample of a single PCR product in a single reaction tube. The entire analysis, including setup, hybridization, flow analysis, and data collection and analysis can be accomplished within an hour after PCR amplification of the DNA sample Thus, it is possible to perform tissue typing or other genetic analysis in less than three hours after obtaining a sample of blood, tissue, etcetera, including the time required for extraction of DNA and PCR amplification.

TABLE 22

DQA1 DNA Sequences

| Name | Sequence "A" Strand | Sequence "B" Strand | Allele Specificities |
|---|---|---|---|
| DQA2501 | TGGCCAGTACACCCATGA (SEQ ID NO. 7) | TCATGGGTGTACTGGCCA (SBQ ID NO. 8) | 0101, 0401, 0501 |
| DQA2502 | TGGCCAGTTCACCCATGA (SEQ ID NO. 9) | TCATGGGTGAACTGGCCA (SEQ ID NO. 10) | 0103, 0201, 0601 |
| DQA2503 | TGGGCAGTACAGCCATGA (SEQ ID NO. 11) | TCATGGCTGTACTGCCCA (SEQ ID NO. 12) | 0301 |
| DQA3401 | GAGATGAGGAGTTCTACG (SEQ ID NO. 13) | CGTAGAACTCCTCATCTC (SEQ ID NO. 14) | 0101, 0104 |
| DQA3402 | GAGATGAGCAGTTCTACG (SEQ ID NO. 15) | CGTAGAACTGCTCATCTC (SEQ ID NO. 16) | 0102, 0103, 0501 |
| DQA3403 | GAGACGAGCAGTTCTACG (SEQ ID NO. 17) | CGTAGAACTGCTCGTCTC (SEQ ID NO. 18) | 0401, 0601 |
| DQA3404 | GAGACGAGGAGTTCTATG (SEQ ID NO. 19) | CATAGAACTCCTCGTCTC (SEQ ID NO. 20) | 0201, 0301 |
| DQA4101N | ACCTGGAGAGGAAGGAGA (SEQ ID NO. 21) | TCTCCTTCCTCTCCAGGT (SEQ ID NO. 22) | 0101, 0102, 0201, 0301 |
| DQA4102 | ACCTGGAGAAGAAGGAGA (SEQ ID NO. 23) | TCTCCTTCTTCTCCAGGT (SEQ ID NO. 24) | 0103 |
| DQA4103 | ACCTGGGGAGGAAGGAGA (SEQ ID NO. 25) | TCTCCTTCCTCCCCAGGT (SEQ ID NO. 26) | 0401, 0501, 0601 |
| DQA5501N | TCAGCAAATTTGGAGGTT (SEQ ID NO: 27) | AACCTCCAAATTTGCTGA (SEQ ID NO. 28) | 0101, 0102, 0103 |
| DQA5502N | TCCACAGACTTAGATTTG (SEQ ID NO. 29) | CAAATCTAAGTCTGTGGA (SEQ ID NO. 30) | 0201 |
| DQA5503 | TCCGCAGATTTAGAAGAT (SEQ ID NO. 31) | ATCTTCTAAATCTGCGGA (SEQ ID NO. 32) | 0301 |
| DQA5504 | TCAGACAATTTAGATTTG (SEQ ID NO. 33) | CAAATCTAAATTGTCTGA (SEQ ID NO. 34) | 0401, 0501, 0601 |

TABLE 23

Specificity of Oligonucleotide Inhibition

| Oligo | Bead # 2501 | 2502 | 2503 | 3401 | 3402 | 3403 | 3404 | 4101 | 4102 | 4103 | 5501 | 5502 | 5503 | 5504 |
|---|---|---|---|---|---|---|---|---|---|---|---|---|---|---|
| none | 0% | 0% | 0% | 0% | 0% | 0% | 0% | 0% | 0% | 0% | 0% | 0% | 0% | 0% |
| 2501 | 64% | 10% | 5% | -1% | -6% | 4% | 1% | 4% | 1% | 3% | 5% | -9% | 2% | 3% |
| 2502 | 19% | 77% | -7% | -2% | 0% | 1% | -3% | -3% | -1% | -4% | -4% | -4% | -5% | 4% |
| 2503 | 7% | 1% | 85% | 1% | 2% | 4% | -3% | -2% | 4% | -1% | 1% | -1% | 5% | 6% |
| 3401 | -1% | -1% | -3% | 76% | 1% | 6% | 1% | 3% | 2% | 2% | 5% | -4% | 2% | 5% |
| 3402 | -1% | -8% | -12% | 14% | 83% | 11% | -5% | -5% | -3% | -10% | 0% | -7% | -4% | 1% |
| 3403 | -2% | -3% | -1% | 0% | 7% | 73% | -1% | 2% | 1% | -1% | 5% | -9% | -4% | 2% |
| 3404 | 5% | 5% | 4% | 6% | 2% | 8% | 62% | 10% | 9% | 6% | 10% | 0% | 7% | 9% |
| 4101 | 6% | 4% | 6% | 10% | 5% | 10% | 6% | 79% | 18% | 22% | 31% | 5% | 12% | 12% |
| 4102 | 0% | -1% | -4% | 0% | -3% | 5% | 0% | 8% | 79% | 3% | 7% | -1% | 5% | 4% |
| 4103 | -2% | 11% | 3% | 5% | 6% | 7% | 5% | 4% | 7% | 71% | 0% | 8% | 9% | 6% |
| 5501 | -3% | 3% | 0% | 2% | 5% | 5% | 1% | -1% | 6% | 1% | 79% | 9% | 6% | 4% |
| 5502 | 3% | 5% | 5% | 5% | 7% | 3% | -1% | 1% | 2% | -4% | -7% | 86% | 4% | 1% |
| 5503 | -5% | 0% | -6% | 1% | 2% | 0% | -2% | -8% | 0% | -7% | -9% | 13% | 80% | -5% |
| 5504 | 3% | 8% | 9% | 5% | 6% | 5% | 2% | 2% | 7% | 6% | 4% | 13% | 4% | 93% |

TABLE 24

Allele Reactivity Chart

| Allele | Pattern | Sequence |
|---|---|---|
| 0101 | (1, 1, 1, 1) | 2501 3401 4101 5501 |
| 0102 | (1, 2, 1, 1) | 2501 3402 4101 5501 |
| 0103 | (2, 2, 2, 1) | 2502 3402 4102 5501 |
| 0201 | (2, 4, 1, 2) | 2502 3404 4101 5502 |
| 0301 | (3, 4, 1, 3) | 2503 3404 4101 5503 |
| 0401 | (1, 3, 3, 4) | 2501 3403 4103 5504 |
| 0501 | (1, 2, 3, 4) | 2501 3402 4103 5504 |
| 0601 | (2, 3, 3, 4) | 2502 3403 4103 5504 |

TABLE 25

Blinded typing of Genomic DNA Samples for DQA1

BEAD SUBSET

| | 2501 | 2502 | 2503 | 3401 | 3402 | 3403 | 3404 | 4101 | 4102 | 4103 | 5501 | 5502 | 5503 | 5504 | TYPE |
|---|---|---|---|---|---|---|---|---|---|---|---|---|---|---|---|
| 1 | 4% | 25% | 35% | 7% | 69% | 8% | 58% | 36% | 61% | −1% | 78% | 2% | 75% | −8% | Y |
| 2 | 13% | −5% | −7% | 63% | −4% | −2% | −3% | 37% | 2% | −9% | 77% | 0% | 1% | −11% | Y |
| 3 | 19% | −2% | 40% | 66% | −3% | 0% | 65% | 51% | −2% | −2% | 78% | −2% | 76% | −14% | Y |
| 4 | 22% | 13% | 18% | 33% | 68% | 9% | 1% | −3% | 6% | 33% | −14% | 0% | −11% | 36% | Y |
| 5 | 38% | 1% | −7% | 68% | 78% | 6% | −1% | 40% | −1% | 36% | 76% | −3% | −5% | 48% | Y |
| 6 | −13% | −10% | 11% | −10% | −10% | −7% | 45% | 21% | −4% | −12% | −24% | −9% | 75% | −19% | Y |
| 7 | −7% | 8% | −6% | −11% | −8% | 19% | 27% | 7% | −5% | 16% | −27% | 31% | −6% | 30% | Y |
| 8 | 20% | −5% | −9% | 1% | 65% | 53% | −2% | 37% | −2% | 30% | 76% | −2% | −7% | 43% | Y |
| 9 | 32% | 5% | −1% | 7% | 76% | 5% | 2% | 57% | 0% | −1% | 84% | −3% | −11% | −25% | Y |
| 10 | 32% | 10% | 60% | 4% | 72% | 1% | 71% | 60% | −4% | 7% | 83% | −32% | 76% | −40% | Y |
| 11 | 27% | 7% | 5% | 10% | 70% | 5% | 2% | −14% | −5% | 45% | −21% | −6% | −18% | 44% | Y |
| 12 | 29% | 3% | 57% | 8% | 71% | 6% | 67% | 60% | 0% | 3% | 84% | −4% | 77% | −29% | Y |
| 13 | 25% | 8% | 2% | 66% | −4% | −8% | −8% | 47% | −1% | −4% | 83% | −12% | −22% | −36% | Y |
| 14 | 16% | 8% | 33% | −3% | 0% | 16% | 29% | 24% | 2% | 26% | −25% | −7% | 47% | 17% | Y |
| 15 | 7% | 19% | 8% | −6% | 26% | 0% | 31% | 26% | −5% | 28% | −31% | 36% | −21% | 23% | Y |
| 16 | 32% | 9% | 2% | 18% | 76% | 8% | 5% | −1% | −2% | 48% | −4% | −6% | −17% | 52% | Y |
| 17 | 8% | 0% | 35% | 6% | 53% | 4% | 58% | 45% | 1% | 48% | −13% | −1% | 77% | 41% | Y |
| 18 | 1% | −2% | 55% | 3% | 1% | 1% | 75% | 54% | 4% | 6% | −14% | −3% | 84% | −12% | Y |
| 19 | 12% | 18% | 2% | 5% | 47% | 8% | 54% | 37% | 5% | 46% | −11% | 46% | 1% | 39% | ? |
| 20 | 63% | 15% | 6% | 42% | 87% | 17% | 20% | 64% | 10% | 65% | 87% | 6% | 5% | 60% | Y |
| 21 | 44% | 62% | 8% | 23% | 76% | 13% | 73% | 70% | 11% | 20% | 88% | 64% | 4% | 1% | Y |
| 22 | −6% | 26% | 5% | 4% | −3% | 2% | 55% | 48% | 6% | −1% | −7% | 58% | 1% | −11% | Y |
| 23 | 56% | 67% | 13% | 38% | 87% | 22% | 24% | 12% | 75% | 63% | 89% | 15% | 15% | 63% | Y |
| 24 | 15% | 25% | 5% | 60% | 58% | 7% | 10% | 42% | 61% | −4% | 90% | −2% | −3% | −17% | Y |
| 25 | 47% | 15% | 12% | 75% | 15% | 50% | 17% | 56% | 4% | 55% | 83% | 2% | −5% | 51% | Y |
| 26 | 30% | 8% | 56% | 15% | 71% | 5% | 67% | 65% | 2% | 9% | 85% | −1% | 82% | −18% | Y |
| 27 | 13% | 10% | 10% | 7% | 27% | 21% | 5% | 1% | 3% | 47% | −16% | 5% | −5% | 51% | Y |
| 28 | 23% | 2% | 0% | 17% | 23% | 60% | 14% | −2% | −1% | 58% | −18% | −2% | −3% | 59% | Y |
| 29 | 24% | 6% | 10% | 48% | 46% | 5% | 10% | 56% | 5% | 8% | 86% | 2% | −2% | −16% | Y |
| 30 | 38% | 12% | 11% | 73% | 14% | 48% | 7% | 55% | 6% | 55% | 84% | 1% | −7% | 50% | Y |
| 31 | −1% | −1% | 19% | 0% | 20% | −1% | 26% | 29% | −3% | 31% | −28% | −4% | 70% | 31% | Y |
| 32 | 57% | 16% | 6% | 83% | 81% | 11% | 6% | 59% | 7% | 60% | 86% | 9% | −1% | 53% | Y |
| 33 | −13% | 17% | 24% | 2% | −1% | 29% | 47% | 37% | −6% | 50% | −11% | 0% | 80% | 52% | Y |
| 34 | 33% | 7% | 5% | 19% | 75% | 6% | 13% | 54% | 1% | 2% | 85% | 24% | −3% | −3% | Y |
| 35 | −11% | 19% | 31% | 10% | −14% | 0% | 70% | 46% | −4% | −2% | −57% | 44% | 79% | −8% | Y |

Measuring Enzymes with Bead-Based Assays

Figure 51A:
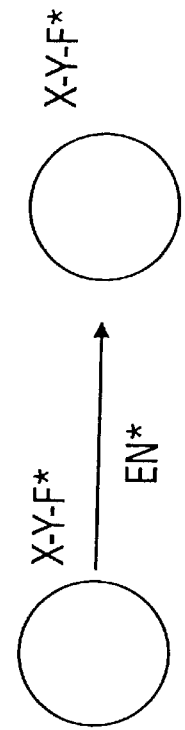
Figure 51B:
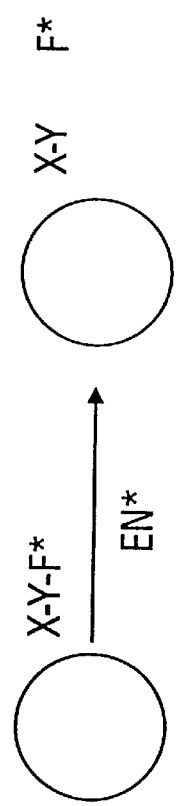
Figure 51C:
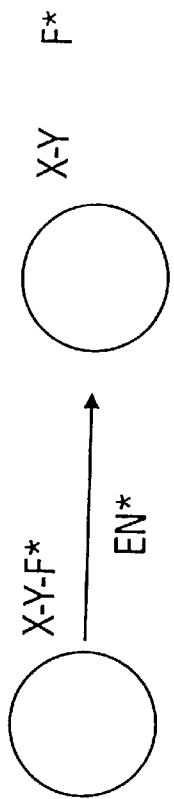
Figure 51D:
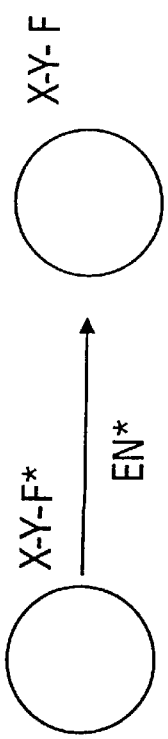
Figure 51F:
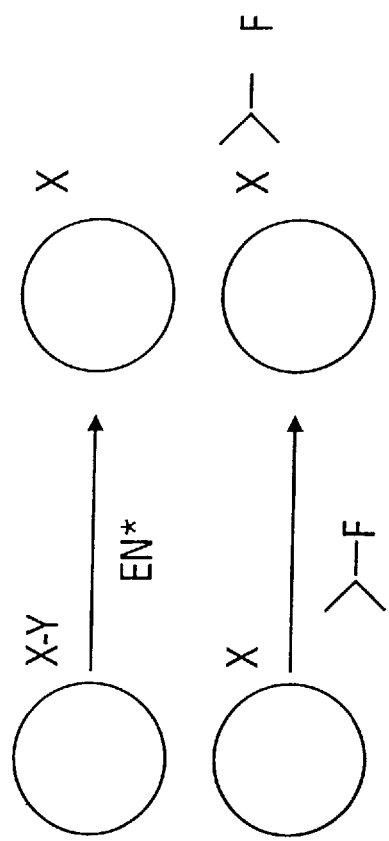

The invention may also be used in several formats for measurement of enzymes, enzyme inhibitors and other analytes. For example, bead subsets can be generated that are modified with selected fluorescent substrates which can be enzymatically cleaved from the bead, resulting in a loss of fluorescence ($F_m$). Enzymes that can be detected and measured using the invention include but are not restricted to, protease, glycosidase, nucleotidase, and oxidoreductase. Any enzyme that results in selected bond cleavage can be measured. A cartoon of the action of enzyme on a bead-bound enzyme is shown in FIG. 51a. An enzyme that acts upon a bead-bound substrate so that the bead-bound substrate becomes fluorescent or loses fluorescence comprises an assay for the level of enzyme affecting such a change. FIGS. 51b and 51c depict these situations. Alteration of the substrate could be an oxidation or reduction, alteration of a chemical bond such a hydrolysis or other alteration of the bead-bound substrate so that the fluorescence of the substrate is altered in intensity or spectrum.

Enzymes that act upon pro-enzymes (convertases) can be measured using a bead-bound substrate providing the reaction mixture contains the pro-enzyme and beads bearing a substrate that can be acted upon by the active form of the enzyme. (Providing the specificity of each activated enzyme is distinct, a multiplexed assay is achievable in which several pro-enzymes can be measured at the same time.) The sample is introduced into a mixture of pro-enzymes under reaction conditions. After a fixed time interval during which the convertase acts upon the pro-enzyme, the beadsets specific for each enzyme generated from each pro-enzyme are, added and the newly generated activities measured in a subsequent time period which is terminated when the beadsets are analyzed by flow cytometry. Such a process for a single pro-enzyme to enzyme conversion is illustrated by the cartoon in FIG. 51d.

Figure 51E:
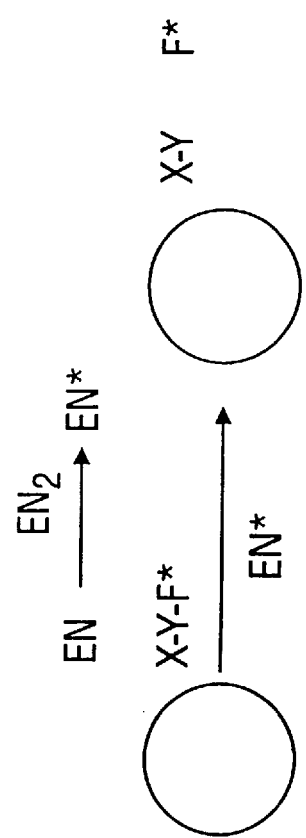

The action of the enzyme can be measured in an indirect but facile manner using a bead bound substrate as depicted in FIG. 51e. The action of the enzyme on the bead-bound substrate results in the formation or revelation of a ligate for a fluorescent ligand present in the reaction mixture. The bead bearing the modified substrate then becomes fluorescent by virtue of binding of the fluorescent ligand to the newly formed ligate. In practice, the enzyme(s) would be added to the beadset under reactive conditions. After a defined time period during which the enzyme acts upon the bead bound substrate, the enzyme action would be stopped and the fluorescent ligands added and after a period for association of ligand with the beadsets, the mixture analyzed by flow cytometry. The fluorescent ligands could be of a single reactivity or multiple ligands employed, the critical specificity is that of the enzyme for the substrate.

The bead-bound substrate may be used to detect the activation of enzyme when the enzyme requires a cofactor for activity. Under this circumstance, the level of the cofactor becomes the limiting component of the reaction mixture and determination of the level of cofactor can be measured. Such a configuration is illustrated in FIG. 51$f$. The reaction mixture contains the bead-bound substrate as well as the apo-enzyme. After introduction of the analyte (enzyme cofactor), the reaction mixture is held under reactive conditions for a fixed period of time followed by analysis of the beads by flow cytometry, the level of cofactor limits the level of enzyme activity. Providing the enzymes present require different cofactors and have action on different substrate-bearing beadsets, several cofactors could be measured in a single assay mixture.

In short, bead-borne substrates can be used as reagent as are soluble substrates for enzymes. However, because each type of bead bearing a unique substrate can be distinguished, a mixture of bead subsets can be used to measure several enzyme activities simultaneously in the same reaction mixture.

Fluids that can be analyzed using these techniques include plasma, serum, tears, mucus, saliva, urine, pleural fluid, spinal fluid and gastric fluid, sweat, semen, vaginal secretions, fluid from ulcers and other surface eruptions, blisters, and abscesses, and extracts of tissues including biopsies of normal, malignant, and suspect tissues. An assay according to this aspect of the invention proceeds as follows:

1. Beads containing reactive surface groups (one of the following: amino, aldehyde, acid chloride, amidine, phenolic hydroxyl, phenyl amine, carboxyl) are obtained that can be discriminated on the basis of, for example, forward angle light scatter, $C_1$, right angle light scatter, $C_2$, and one of several wavelengths of fluorescence $C_3 .. C_n$ which are designated as orange and red fluorescence, for example, and comprise a number of subsets.
2. Subsets thus obtained are derivatized with a peptide (substrate) having a terminal fluorescent green group, for example fluorescein ($F_m$).
3. Unreacted surface groups and hydrophobic surface of the bead are blocked and the subsets are processed by a particle analyzer and sorter (FACSCAN) and a uniform population of particles are separated which have a low coefficient of variance for $F_m$. (e.g., 3%).
4. A fluid to be tested is diluted with an appropriate buffer and added to the beadset mixture to allow enzymes present in the sample to react with (cleave) their corresponding substrate on the surfaces of the beads.
5. After a defined period of time, the reaction is stopped and the entire mixture processed by a flow cytometer and results are determined.

The presence of an enzyme in the clinical sample is indicated by loss of fluorescence resulting from the cleavage of the fluorescent $F_m$ substrate from the bead surface. Because the beads are analyzed in a very small volume (e.g., about 6 picoliters) as they are passed through the flow cytometer's laser beam, interference from free fluorescent molecules (cleaved substrate) will not significantly interfere with the assay. This obviates the requirement of washing of the beads prior to assay and simplifies the procedure significantly.

Time

Time measurement is an important feature of the analysis. The essence of the measurement of an enzyme activity is a change in substrate with time. The activity can be determined by setting a period of time during which the clinical sample is in contact with the beads using standard conditions of pH, ionic composition and temperature. Two alternative processes are available for determination of the bead-bound substrate with time, that is the time expired while the enzyme(s) is (are) acting on each beadset(s).

External Time

In this configuration, as each bead is measured by the flow cytometer, the time at which each measurement was obtained is recorded along with the bead's other measurements. Prior to the beginning of the assay, the baseline measurement is determined. Once the enzyme (clinical sample) is added to the bead mixture, the sample analysis begins. As the beads proceed through the instrument, the time data collected is used to determine the length of time that the bead has been exposed to the clinical sample. The $F_m$ data collected over the period of the assay is used to determine the rate of change of substrate on the beads (kinetics) and thus the rate readily derived for each bead subset in the mixture exposed to the clinical sample.

Internal Time

Time can be determined and at the same time a quality control internally generated by including a "timer" bead subset that bears a substrate which is acted on by an enzyme that does not naturally occur in the clinical sample to be tested. The use of non-pathogenic microbial enzymes and substrates with human samples, for example, would suffice. The corresponding "timer" enzyme is added to the dilution buffer so that a known concentration of the "timer" enzyme is present in the buffer. The degree of action of the "timer" enzyme upon the beads in the "timer" subset can be measured as a function of the loss of fluorescence of the beads in the subset to ensure that proper reaction conditions are achieved. The level of fluorescence of the timer beads can thus be used as an internal standard and an estimation of time.

Determination of Enzyme Inhibitors or Regulators

In addition to direct assay of enzymes, an assay of this type may also be used to detect enzyme inhibitors or regulators. In accordance with this variation, samples being tested for inhibitors are added to the beadset followed by the corresponding enzymes. If inhibitors are present, the measured fluorescent ($F_m$) values will not be decreased to the same extent as a control containing no inhibitors. In accordance with FIG. 52, in a similar manner, inhibitors of enzyme activators or binders of cofactors can be measured.

The present invention provides numerous advantages and overcomes many problems associated with prior art techniques of multiplexed diagnostic and genetic analysis apparatus and methods. It will be appreciated by those of ordinary skill having the benefit of this disclosure that numerous variations from the foregoing illustration will be possible without departing from the inventive concept described herein. Accordingly, it is the claims set forth below, and not merely the foregoing illustration, which are intended to define the exclusive rights claimed in this application program.

REFERENCES

1. Hum. Biol. 64: 167–174(1992) Mutation in Cystic Fibrosis: a Review Spatial Distribution of the DF508. DeBraekeleer,M. and Daigeneault,J.;
2. Science 257: 797–800 (1992) [92358240] The skeletal muscle chloride channel in dominant and recessive human myotonia. M. C. Koch, K. Steinmeyer, C. Lorenz, K.

Ricker, F. Wolf, M. Otto, B. Zoll, Lehmann-Horn, K. H. Grzeschik & T. J. Jentsch;

3. Neuron 12: 281–94 (1994) [94153549] Sodium channel mutations in paramyotonia congenita uncouple inactivation from activation. M. Chahine, A. L. George, M. Zhou, S. Ji, W. Sun, R. L. Barchi & R. Horn. Ann. Neurol. 33: 300–7 (1993) [93270429]; Sodium channel mutations in paramyotonia congenita and hyperkalemic periodic paralysis. L. J. Ptacek, L. Gouw, H. Kwiecinski, P. McManis, J. R. Mendell, R. J. Barohn, A. L. George, R. L. Barchi, M. Robertson & M. F. Leppert;

4. Ann. Neurol. 33: 300–7 (1993) [93270429] Sodium channel mutations in paramyotonia congenita and hyperkalemic periodic paralysis. L. J. Ptacek, L. Gouw, H. Kwiecinski, P. McManis, J. R. Mendell, R. J. Barohn, A. L. George, R. L. Barchi, M. Robertson & M. F. Leppert Cell 67: 1021–7 (1991) [92069747] Identification of a mutation in the gene causing hyperkalemic periodic paralysis. L. J. Ptacek, A. L. George, R. C. Griggs, R. Tawil, R. G. Kallen, R. L. Barchi, M. Robertson & M. F. Leppert;

5. Nature 355: 836–8 (1992) [92168137] Defective anion transport activity of the abnormal band 3 in hereditary ovalocytic red blood cells. A. E. Schofield, D. M. Reardon & M. J. Tanner, 6. J. Clin. Invest 93: 121–30 (1994) [94110314] Duplication of 10 nucleotides in the erythroid band 3 (AE1) gene in a kindred with hereditary spherocytosis and band 3 protein deficiency (band 3PRAGUE). P. Jarolim, H. L. Rubin, S. C. Liu, M. R. Cho, V. Brabec, L. H. Derick, S. J. Yi, S. T. Saad, S. Alper, C. Brugnaraet al.;

7. Acta Physiol. Scand Suppl. 607: 201–7 (1992) [93080072] The Na+/glucose cotransporter (SGLTI). E. M. Wright, E. Turk, K. Hager, L. Lescale-Matys,B. Hirayama, S. Supplisson & D. D. Loo. Nature 350: 354–6 (1991) [91179516]; Glucose/galactose malabsorption caused by a defect in the Na+/glucosecotransporter. E. Turk, B. Zabel, S. Mundlos, J. Dyer & E. M. Wright;

8. Nature 363:458–60(1993)[93275414]Germ-line mutations of the RET proto-oncogene in multiple endocrine neoplasia type 2A. L. M. Mulligan, J. B. Kwok, C. S. Healey, M. J. Elsdon, C. Eng, E. Gardner, D. R. Love, S. E. Mole, J. K. Moore, L. Papi, et al.;

9. Nature 367: 375–6 (1994) [94159102] A mutation in the RET proto-oncogene associated with multiple endocrine neoplasia type 2B and sporadic medullary thyroid carcinoma [see comments] R. M. Hofstra, R. M. Landsvater, I. Ceccherini, R. P. Stulp, T. Stelwagen, Y. Luo, B. Pasini, J. W. Hoppener, H. K. van Amstel, G. Romeo, et al.;

10. Nature 367: 378–80 (1994) [94159104] Mutations of the RET proto-oncogene in Hirschsprung's disease [see comments] P. Edery, S. Lyonnet, L. M. Mulligan, A. Pelet, E. Dow, L. Abel, S. Holder, C. Nihoul-Fekete, B. A. Ponder & A. Munnich; Nature 367: 377–8 (1994) [94159103] Point mutations affecting the tyrosine kinase domain of the RET proto-oncogene in Hirschsprung's disease [see comments] G. Romeo, P. Ronchetto, Y. Luo, V. Barone, M. Seri, I. Ceccherini, B. Pasini, R. Bocciardi, M. Lerone, H. kaariainen, et al.;

11. Hum. Mutat 1: 445–66 (1992) [93250847] Molecular genetics of the LDL receptor gene in familial hypercholesterolemia. H. H. Hobbs, M. S. Brown & J. L. Goldstein; Clin. Chem. 36: 900–3 (1990) [90291682] Use of polymerase chain reaction to detect heterozygous familial hypercholesterolemia. M. Keinanen, J. P. Ojala, E. Helve, K. Aalto-Setala, K. Kontula & P. T. Kovanen;

12. Hum. Genet 93: 351–2 (1994) [94171244] Two CA/GT repeat polymorphisms in intron 27 of the human neurofibromatosis (NF1) gene. C. Lazaro, A. Gaona & X. Estivill; Am J Hum Genet 54: 424-36 (1994) [94160989] Deletions spanning the neurofibromatosis 1 gene: identification and phenotype L. M. Kayes, W. Burke, V. M. Riccardi, R. Bennett, P. Ehrlich, A. Rubenstein & K. Stephens; Cell 75: 1305–15 (1993) [94094325] Identification and characterization of the tuberous sclerosis gene on chromosome 16. The European Chromosome 16 Tuberous Sclerosis Consortium;

13. Hum. Mol. Genet 2:1823–8 (1993) [94108432] Genetic analysis of the BRCA1 region in a large breast/ovarian family: refinement of the minimal region containing BRCA1. D. P. Kelsell, D. M. Black, D. T. Bishop & N. K. Spurr, 14. Hum. Mutat 3: 12–8 (1994) [94163183] Exon eight APC mutations account for a disproportionate number of familial adenomatous polyposis families. D. J. Koorey, G. W. McCaughan, R. J. Trent & N. D. Gallagher, Hum. Mutat 1: 467–73 (1992) [93250848] Screening for germ-line mutations in familial adenomatous polyposis patients 61 new patients and a summary of 150 unrelated patients. H. Nagase, Y. Miyoshi, A. Horii, T. Aoki, G. M. Petersen, B. Vogelstein, E. Maher, M. Ogawa, M. Maruyama, J. Utsunomiya, et al.; Cell 66: 589–600 (1991) [91330306] Identification and characterization of the familial adenomatous polyposis coli gene. J. Groden, A. Thliveris, W. Samowitz, M. Carlson, L. Gelbert, H. Albertsen, G. Joslyn, J. Stevens, L. Spirio, M. Robertsor, et al.;

15. Hum. Mol. Genet 2: 1307–8 (1993) [94004878] A missense mutation in exon 4 of the human adenosine deaminase gene causes severe combined immunodeficiency. U. Atasoy, C. J. Norby-Slycord & M. L. Markert Hum. Mol. Genet 2: 1099–104 (1993) [94004847] The interleukin-2 receptor gamma chain maps to Xq13.1 and is mutated in X-linked severe combined immunodeficiency, SCIDX1 J. M. Puck, S. M. Deschenes, J. C. Pbrter, A. S. Dutra, C. J. Brown, H. F. Willard & P. S. Henthorn; Cell 73: 147–57 (1993) [93214986] Interleukin-2 receptor gamma chain mutation results in X-linked severe combined immunodeficiency in humans. M. Noguchi, H. Yi, H. M. Rosenblatt, A. H. Filipovich, S. Adelstein, W. S. Modi, O. W. McBride & W. J. Leonard; Am. J. Med. Genet 42: 201–7 (1992) [92125333] Five missense mutations at the adenosine deaminase locus (ADA) detected by altered restriction fragments and their frequency in ADA—patients with severe combined immunodeficiency(ADA-SCID). R. Hirschhorn, A. Ellenbogen & S. Tzall;

16. Mutat Res. 273: 193–202 (1992) [92186915] Three nonsense mutations responsible for group A xeroderma pigmentosum. I. Satokata, K. Tanaka, N. Miura, M. Narita, T. Mimaki, Y. Satoh, S. Kondo & Y. Okada; J. Biol. Chem. 266: 19786–9 (1991) [92011785] Identification and characterization of xpac protein, the gene product of the human XPAC (xeroderma pigmentosum group A complementing) gene. N. Miura, I. Miyamoto, H. Asahina, I. Satokata, K. Tanaka & Y. Okada;

17. Nucleic Acids Res. 21: 419–26 (1993) [93181229] Structure and expression of the excision repair gene ERCC6, involved in the human disorder Cockayne's syndrome group B. C. Troelstra, W. Hesen, D. Bootsma & J. H. Hoeijmakers 18. Am. J. Hum. Genet 51: 299–306 (1992) [92351926] A microdeletion of less than 250 kb, including the proximal part of the FMR-1 gene and the fragile-X site, in a male with the clinical phenotype of fragile-X syndrome. D. Wohrle, D. Kotzot, M. C. Hirst, A. Manca, B. Korn, A. Schmidt, G. Barbi, H. D. Rott, A. Poustka, K. E. Davies, et al.;

19. Lancet 341: 273–5 (1993) [93148721] Direct diagnosis of carriers of point mutations in Duchenne muscular dystrophy. S. C. Yau, R. G. Roberts, M. Bobrow & C. G. Mathew.

Hum. Genet 90: 65–70 (1992) [93052247] Molecular genetic analysis of 67 patients with Duchenne/Becker muscular dystrophy. S. Niemann-Seyde, R. Slomski, F. Rininsland, U. Ellermeyer, J. Kwiatkowska & J. Reiss. Hum. Genet 84: 228–32 (1990) [90152651] Rapid detection of deletions in the Duchenne muscular dystrophy gene by PCR amplification of deletion-prone exon sequences. M. Hentemann, J. Reiss, M. Wagner & D. N. Cooper, Nature 322: 73–7 (1986) [86257412] Analysis of deletions in DNA from patients with Becker and Duchenne muscular dystrophy. L. M. Kunkel;

20. Genomics 18: 673–9 (1993) [94140369] Genomic organization and transcriptional units at the myotonic dystrophy locus. D. J. Shaw, M. McCurrach, S. A. Rundle, H. G. Harley, S. R. Crow, R. Sohn, J. P. Thirion, M. G. Hamshere, A. J. Buckler, P. S. Harper, et al. Arch. Neurol. 50: 1173–9 (1993) [94029649] The myotonic dystrophy gene. A. Pizzuti, D. L. Friedman & C. T. Caskey; Hum. Mol. Genet 2: 299–304 (1993) [93271990] Structure and genomic sequence of the myotonic dystrophy (DM kinase) gene. M. S. Mahadevan, C. Amemiya, G. Jansen, L. Sabourin, S. Baird, C. E. Neville, N. Wormskamp, B. Segers, M. Batzer, J. Lamerdin, et al.;

21. Nature 352: 77–9 (1991) [91287825] Androgen receptor gene mutations in X-linked spinal and bulbar muscular atrophy. A. R. La Spada, E. M. Wilson, D. B. Lubahn, A. E. Harding & K. H. Fischbeck; Neurology 42: 2300–2 (1992) [93096171] Strong correlation between the number of CAG repeats in androgen receptor genes and the clinical onset of features of spinal and bulbar muscular atrophy. S. Igarashi, Y. Tanno, 0. Onodera, M. Yamazaki, S. Sato, A. Ishikawa, N. Miyatani, M. Nagashima, Y. Ishikawa, K. Sahashi et al.; Science 256: 784–9 (1992) [92271195] Triplet repeat mutations in human disease. C. T. Caskey, A. Pizzuti, Y. H. Fu, R. G. Fenwick & D. L. Nelson;

22. Hum. Mol. Genet 2: 1713–5 (1993) [94093563] Analysis of the huntingtin gene reveals a trinucleotide-lengthpolymorphism in the region of the gene that contains two CCG-rich stretches and a correlation between decreased age of onset of Huntington's disease and CAG repeat number. D. C. Rubinsztein, D. E. Barton, B. C. Davison & M. A. Ferguson-Smith; Mol. Cell. Probes 7: 235–9 (1993) [93375991] A new polymerase chain reaction (PCR) assay for the trinucleotide repeat that is unstable and expanded on Huntington's disease chromosomes. J. P. Warner, L. H. Barron & D. J. Brock; Cell 72: 971-83 (1993) [93208892] A novel gene containing a trinucleotide repeat that is expanded and unstable on Huntington's disease chromosomes. The Huntington's Disease Collaborative Research Group;

23. J. Clin. Invest 83: 11–3 (1989) [89093407] Identification of a single nucleotide change in the hypoxanthine-guanine phosphoribosyltransferase gene (HPRTYale) responsible for Lesch-Nyhan syndrome. S. Fujimori, B. L. Davidson, W. N. Kelley & T. D. Palella; Proc. Natl. Acad. Sci. U.S.A. 86: 1919–23 (1989) [89184538] Identification of mutations leading to the Lesch-Nyhan syndrome by automated direct DNA sequencing of in vitro amplified cDNA. R. A. Gibbs, P. N. Nguyen, L. J. McBride, S. M. Koepf & C. T. Caskey; Genomics 7: 235–44 (1990) [90269813] Multiplex DNA deletion detection and exon sequencing of the hypoxanthine phosphoribosyltransferase gene in Lesch-Nyhan families. R. A. Gibbs, P. N. Nguyen, A. Edwards, A. B. Civitello & C. T. Caskey;

24. Nature 333: 85–6 (1988) [88202110] Identification of an altered splice site in Ashkenazi Tay-Sachs disease. E. Arpaia, A. Dumbrille-Ross, T. Maler, K. Neote, M. Tropak, C. Troxel, J. L. Stirling, J. S. Pitts, B. Bapat, A. M. Lamhonwah, et al.; J. Biol. Chem. 263: 18587–9 (1988) [89066640] The major defect in Ashkenazi Jews with Tay-Sachs disease is an insertion in the gene for the alpha-chain of beta-hexosaminidase R. Myerowitz & F. C. Costigan; Hum. Mutat 1: 303–9 (1992) [93250824] A mutation common in non-Jewish Tay-Sachs disease: frequency and RNA studies. B. R. Akerman, J. Zielenski, B. L. Triggs-Raine, E. M. Prence, M. R. Natowicz, J. S. Lim-Steele, M. M. Kaback, E. H. Mules, G. H. Thomas, J. T. Clarke, et al.;

25. Clin. EndocrinoL (Oxf) 38: 421–5 (1993) [93306853] Prenatal diagnosis of congenital adrenal hyperplasia by direct detection of mutations in the steroid 21-hydroxylase gene. G. Rumsby, J. W. Honour & C. Rodeck; Proc. Natl. Acad. Sci. U.S.A. 90: 4552–6 (1993) [93281617] Mutations in the CYP11B1 gene causing congenital adrenal hyperplasia and hypertension cluster in exons 6, 7, and 8. K. M. Curnow, L. Slutsker, J. Vitek, T. Cole, P. W. Speiser, M. I. New, P. C. White & L. Pascoe; Hum. Genet 89: 109-10 (1992) [92250001] Prenatal diagnosis of 21-hydroxylase deficiency congenital adrenal hyperplasia using the polymerase chain reaction D. Owerbach, M. B. Draznin, R. J. Carpenter & F. Greenberg;

26. Nucleic Acids Res. 20: 1433 (1992) [92220641] PCR detection of the insertion/deletion polymorphism of the human angiotensin converting enzyme gene (DCP1) (dipeptidyl carboxypeptidase 1). B. Rigat, C. Hubert, P. Corvol & F. Soubrier, Biochem Biophys. Res. Commun. 184: 9–15 (1992) [92231988] Association of a polymorphism of the angiotensin I-converting enzyme gene with essential hypertension. R. Y. Zee, Y. K. Lou, L. R. Griffiths & B. J. Morris;

27. Nature 368: 258–61 (1994) [94195398] Mutation in the DNA mismatch repair gene homologue hMLH1 is associated with hereditary non-polyposis colon cancer. C. E. Bronner, S. M. Baker, P. T. Morrison, G. Warren, L. G. Smith, M. K. Lescoe, M. Kane, C. Earabino, J. Lipford, A. Lindblom, et al.; Oncogene 9: 991–4 (1994) [94151027] DNA alterations in cells from hereditary non-polyposis colorectal cancer patients. C. Wu, Y. Akiyama, K. Imai, S. Miyake, H. Nagasaki, M. Oto, S. Okabe, T. Iwama, K. Mitamura, H. Masumitsq et al.;

28. Science 263: 1625–9 (1994) [94174309] Mutation of a mutL homolog in hereditary colon cancer [see comments] N. Papadopoulos, N. C. Nicolaides, Y. F. Wei, S. M. Ruben, K. C. Carter, C. A. Rosen, W. A. Haseltine, R. D. Fleischmann, C. M. Fraser, M. D. Adams, et al.; Cell 75: 1215–25 (1993) [94084796] Mutations of a mutS homolog in hereditary nonpolyposis colorectal cancer. F. S. Leach, N. C. Nicolaides, N. Papadopoulos, B. Liu, J. Jen, R. Parsons, P. Peltomaki, P. Sistonen, L. A. Aaltonen, M. Nystrom-Lahti;

29. Hum. Mutat 3: 12–8 (1994) [94163183] Exon eight APC mutations account for a disproportionate number of familial adenomatous polyposis families D. J. Koorey, G. W. McCaughan, R. J. Trent & N. D. Gallagher, Hum. Mutat 2: 478–84 (1993) [94154735] Simple, rapid, and accurate determination of deletion mutations by automated DNA sequencing of heteroduplex fragments of the adenomatous polyposis coli (APC) gene generated by PCR amplification. K. Tamura, Y. Yamamoto, Y. Saeki, J. Furuyama & J. Utsunomiya;
30. Biochim Biophys. Acta 1155: 43–61 (1993) [93277907] Molecular characterization of the retinoblastoma susceptibility gene. D. W. Goodrich & W. H. Lee; Br. J. Cancer 68, 958–64 (1993) Mechanisms of oncogenesis in patients with familial retinoblastoma Onadim, Z., Hogg, A. & J. K Cowell;
31. Cancer Res. 54: 1298–304 (1994) [94163623] Prevalence and diversity of constitutional mutations in the p53 gene among 21 Li-Fraumeni families J. M. Birch, A. L. Hartley, K. J. Tricker, J. Prosser, A. Condie, A. M. Kelsey, M. Harris, P. H. Jones, A. Binchy, D. Crowther, et al.;
32. Leukemia 8: 186–9.(1994) [94118546] An optimized multiplex polymerase chain reaction (PCR) for detection of BCR-ABL fusion mRNAs in haematological disorders. N. C. Cross, J. V. Melo, L. Feng & J. M. Goldman; Blood 69: 971–3 (1987) [87129392] bbr-abl RNA in patients with chronic myelogenous leukemia. E. Shtivelman, R. P. Gale, 0. Dreazen, A. Berrebi, R. Zaizov, I. Kubonishi, I. Miyoshi & E. Canaani bcl-2; Diagn. Mol. Pathol. 2: 241–7 (1993) [94163382] Rearrangement of the BCL-2 gene in follicular lymphoma. Detection by PCR in both fresh and fixed tissue samples. J. Liu, R. M. Johnson & S. T. Traweek; Blood 83: 1079–85 (1994) [94154269] Cytometric detection of DNA amplified with fluorescent primers: applications to analysis of clonal bcl-2 and IgH gene rearrangements in malignant lymphomas. R. L. Barker, C. A. Worth & S. C. Peiper, Br. J. Cancer 67: 922–5 (1993) [93264208] Detection of bcl-2/JH rearrangement in follicular and diffuse lymphoma: concordant results of peripheral blood and bone marrow analysis at diagnosis. R. Yuan, P. Dowling, E. Zucca, H. Diggelmann & F. Cavalli;
33. Molecular Cloning: A Laboratory Manual, 2d Ed., Cold Spring Harbor Laboratory Press (1989). J. Sambrook, E. Fritch, & T. Maniatis;
34. Proc. Natl. Acad. Sci. U.S.A. 74: 5463–5467 (1977), DNA Sequencing with Chain Terminating Inhibitors, F. Sanger, S. Niklen & A. R. Coulsen.

SEQUENCE LISTING

```
<160> NUMBER OF SEQ ID NOS: 34

<210> SEQ ID NO 1
<211> LENGTH: 8
<212> TYPE: PRT
<213> ORGANISM: Homo sapiens

<400> SEQUENCE: 1

His Tyr Gly Ser Leu Pro Gln Lys
1               5

<210> SEQ ID NO 2
<211> LENGTH: 6
<212> TYPE: PRT
<213> ORGANISM: Homo sapiens

<400> SEQUENCE: 2

Tyr Gly Ser Leu Pro Gln
1               5

<210> SEQ ID NO 3
<211> LENGTH: 24
<212> TYPE: DNA
<213> ORGANISM: Homo sapiens

<400> SEQUENCE: 3
gcctacgcca ccagctccaa ctac                                            24

<210> SEQ ID NO 4
<211> LENGTH: 24
<212> TYPE: DNA
<213> ORGANISM: Homo sapiens

<400> SEQUENCE: 4
gcctacgcca caagctccaa ctac                                            24

<210> SEQ ID NO 5
<211> LENGTH: 21
<212> TYPE: DNA
<213> ORGANISM: Homo sapiens

<400> SEQUENCE: 5
```

```
atggtgtaaa cttgtaccag t                                              21

<210> SEQ ID NO 6
<211> LENGTH: 21
<212> TYPE: DNA
<213> ORGANISM: Homo sapiens

<400> SEQUENCE: 6
ttggtagcag cggtagagtt g                                              21

<210> SEQ ID NO 7
<211> LENGTH: 18
<212> TYPE: DNA
<213> ORGANISM: Homo sapiens

<400> SEQUENCE: 7
tggccagtac acccatga                                                  18

<210> SEQ ID NO 8
<211> LENGTH: 18
<212> TYPE: DNA
<213> ORGANISM: Homo sapiens

<400> SEQUENCE: 8
tcatgggtgt actggcca                                                  18

<210> SEQ ID NO 9
<211> LENGTH: 18
<212> TYPE: DNA
<213> ORGANISM: Homo sapiens

<400> SEQUENCE: 9
tggccagttc acccatga                                                  18

<210> SEQ ID NO 10
<211> LENGTH: 18
<212> TYPE: DNA
<213> ORGANISM: Homo sapiens

<400> SEQUENCE: 10
tcatgggtga actggcca                                                  18

<210> SEQ ID NO 11
<211> LENGTH: 18
<212> TYPE: DNA
<213> ORGANISM: Homo sapiens

<400> SEQUENCE: 11
tgggcagtac agccatga                                                  18

<210> SEQ ID NO 12
<211> LENGTH: 18
<212> TYPE: DNA
<213> ORGANISM: Homo sapiens

<400> SEQUENCE: 12
tcatggctgt actgccca                                                  18

<210> SEQ ID NO 13
<211> LENGTH: 18
<212> TYPE: DNA
<213> ORGANISM: Homo sapiens
```

-continued

```
<400> SEQUENCE: 13
gagatgagga gttctacg                                                18

<210> SEQ ID NO 14
<211> LENGTH: 18
<212> TYPE: DNA
<213> ORGANISM: Homo sapiens

<400> SEQUENCE: 14
cgtagaactc ctcatctc                                                18

<210> SEQ ID NO 15
<211> LENGTH: 18
<212> TYPE: DNA
<213> ORGANISM: Homo sapiens

<400> SEQUENCE: 15
gagatgagca gttctacg                                                18

<210> SEQ ID NO 16
<211> LENGTH: 18
<212> TYPE: DNA
<213> ORGANISM: Homo sapiens

<400> SEQUENCE: 16
cgtagaactg ctcatctc                                                18

<210> SEQ ID NO 17
<211> LENGTH: 18
<212> TYPE: DNA
<213> ORGANISM: Homo sapiens

<400> SEQUENCE: 17
gagacgagca gttctacg                                                18

<210> SEQ ID NO 18
<211> LENGTH: 18
<212> TYPE: DNA
<213> ORGANISM: Homo sapiens

<400> SEQUENCE: 18
cgtagaactg ctcgtctc                                                18

<210> SEQ ID NO 19
<211> LENGTH: 18
<212> TYPE: DNA
<213> ORGANISM: Homo sapiens

<400> SEQUENCE: 19
gagacgagga gttctatg                                                18

<210> SEQ ID NO 20
<211> LENGTH: 18
<212> TYPE: DNA
<213> ORGANISM: Homo sapiens

<400> SEQUENCE: 20
catagaactc ctcgtctc                                                18

<210> SEQ ID NO 21
<211> LENGTH: 18
<212> TYPE: DNA
<213> ORGANISM: Homo sapiens
```

```
<400> SEQUENCE: 21
acctggagag gaaggaga                                                18

<210> SEQ ID NO 22
<211> LENGTH: 18
<212> TYPE: DNA
<213> ORGANISM: Homo sapiens

<400> SEQUENCE: 22
tctccttcct ctccaggt                                                18

<210> SEQ ID NO 23
<211> LENGTH: 18
<212> TYPE: DNA
<213> ORGANISM: Homo sapiens

<400> SEQUENCE: 23
acctggagaa gaaggaga                                                18

<210> SEQ ID NO 24
<211> LENGTH: 18
<212> TYPE: DNA
<213> ORGANISM: Homo sapiens

<400> SEQUENCE: 24
tctccttctt ctccaggt                                                18

<210> SEQ ID NO 25
<211> LENGTH: 18
<212> TYPE: DNA
<213> ORGANISM: Homo sapiens

<400> SEQUENCE: 25
acctggggag gaaggaga                                                18

<210> SEQ ID NO 26
<211> LENGTH: 18
<212> TYPE: DNA
<213> ORGANISM: Homo sapiens

<400> SEQUENCE: 26
tctccttcct ccccaggt                                                18

<210> SEQ ID NO 27
<211> LENGTH: 18
<212> TYPE: DNA
<213> ORGANISM: Homo sapiens

<400> SEQUENCE: 27
tcagcaaatt tggaggtt                                                18

<210> SEQ ID NO 28
<211> LENGTH: 18
<212> TYPE: DNA
<213> ORGANISM: Homo sapiens

<400> SEQUENCE: 28
aacctccaaa tttgctga                                                18

<210> SEQ ID NO 29
<211> LENGTH: 18
<212> TYPE: DNA
```

-continued

```
<213> ORGANISM: Homo sapiens

<400> SEQUENCE: 29
tccacagact tagatttg                                                 18

<210> SEQ ID NO 30
<211> LENGTH: 18
<212> TYPE: DNA
<213> ORGANISM: Homo sapiens

<400> SEQUENCE: 30
caaatctaag tctgtgga                                                 18

<210> SEQ ID NO 31
<211> LENGTH: 18
<212> TYPE: DNA
<213> ORGANISM: Homo sapiens

<400> SEQUENCE: 31
tccgcagatt tagaagat                                                 18

<210> SEQ ID NO 32
<211> LENGTH: 18
<212> TYPE: DNA
<213> ORGANISM: Homo sapiens

<400> SEQUENCE: 32
atcttctaaa tctgcgga                                                 18

<210> SEQ ID NO 33
<211> LENGTH: 18
<212> TYPE: DNA
<213> ORGANISM: Homo sapiens

<400> SEQUENCE: 33
tcagacaatt tagatttg                                                 18

<210> SEQ ID NO 34
<211> LENGTH: 18
<212> TYPE: DNA
<213> ORGANISM: Homo sapiens

<400> SEQUENCE: 34
caaatctaaa ttgtctga                                                 18
```

- 139 -

MICROFICHE APPENDIX A

- 140 -

```
VERSION 2.00
Begin Form Form1
    BackColor       =   &H00FFFF80&
    BorderStyle     =   3  'Fixed Double
    Caption         =   "Digital Diagnostics, Inc."
    ClientHeight    =   6912
    ClientLeft      =   840
    ClientTop       =   1452
    ClientWidth     =   9480
    FillColor       =   &H00FFFFFF&
    FillStyle       =   4  'Upward Diagonal
    ForeColor       =   &H00808080&
    Height          =   7332
    Left            =   792
    LinkTopic       =   "Form1"
    MaxButton       =   0  'False
    MinButton       =   0  'False
    ScaleHeight     =   6912
    ScaleWidth      =   9480
    Top             =   1080
    Width           =   9576
    Begin Data Dataint
        Caption         =   "Dataint"
        Connect         =   ""
        DatabaseName    =   "C:\ACCESS\ORBIT.MDB"
        Exclusive       =   0  'False
        Height          =   252
        Left            =   8160
        Options         =   0
        ReadOnly        =   0  'False
        RecordSource    =   "interpret"
        Top             =   0
        Visible         =   0  'False
        Width           =   912
    End
    Begin Data Datatst
        Caption         =   "Datatst"
        Connect         =   ""
        DatabaseName    =   "C:\ACCESS\ORBIT.MDB"
        Exclusive       =   0  'False
        Height          =   252
        Left            =   8160
        Options         =   0
        ReadOnly        =   0  'False
        RecordSource    =   "testdef"
        Top             =   0
        Visible         =   0  'False
        Width           =   912
    End
    Begin Data Datahld
        Caption         =   "Datahld"
        Connect         =   ""
        DatabaseName    =   "C:\ACCESS\ORBIT.MDB"
        Exclusive       =   0  'False
        Height          =   252
        Left            =   8160
        Options         =   0
        ReadOnly        =   0  'False
        RecordSource    =   "class_tab"
        Top             =   0
        Visible         =   0  'False
```

```
        Width           =       912         -141-
    End
    Begin PictureBox WWPic
        BackColor       =       &H00C0C0C0&
        BorderStyle     =       0  'None
        Height          =       495
        Index           =       1
        Left            =       9000
        Picture         =       (Icon)
        ScaleHeight     =       492
        ScaleWidth      =       372
        TabIndex        =       38
        Top             =       2400
        Width           =       375
    End
    Begin PictureBox PRPic
        BackColor       =       &H00C0C0C0&
        BorderStyle     =       0  'None
        Height          =       495
        Index           =       1
        Left            =       9000
        Picture         =       (Icon)
        ScaleHeight     =       492
        ScaleWidth      =       372
        TabIndex        =       37
        Top             =       3000
        Width           =       375
    End
    Begin PictureBox PRPic
        BackColor       =       &H00C0C0C0&
        BorderStyle     =       0  'None
        Height          =       495
        Index           =       0
        Left            =       9000
        Picture         =       (Icon)
        ScaleHeight     =       492
        ScaleWidth      =       372
        TabIndex        =       36
        Top             =       3000
        Visible         =       0  'False
        Width           =       375
    End
    Begin PictureBox WWPic
        BackColor       =       &H00C0C0C0&
        BorderStyle     =       0  'None
        Height          =       495
        Index           =       0
        Left            =       9000
        Picture         =       (Icon)
        ScaleHeight     =       492
        ScaleWidth      =       372
        TabIndex        =       35
        Top             =       2400
        Visible         =       0  'False
        Width           =       375
    End
    Begin PictureBox SFPic
        BackColor       =       &H00C0C0C0&
        BorderStyle     =       0  'None
        Height          =       495
        Index           =       1
```

- 142 -

```
      Left            =     9000
      Picture         =     (Icon)
      ScaleHeight     =     492
      ScaleWidth      =     372
      TabIndex        =     34
      Top             =     1800
      Width           =     375
   End
   Begin PictureBox SFPic
      BackColor       =     &H00C0C0C0&
      BorderStyle     =     0  'None
      Height          =     495
      Index           =     0
      Left            =     9000
      Picture         =     (Icon)
      ScaleHeight     =     492
      ScaleWidth      =     372
      TabIndex        =     33
      Top             =     1800
      Visible         =     0  'False
      Width           =     375
   End
   Begin PictureBox FCPic
      BackColor       =     &H00C0C0C0&
      BorderStyle     =     0  'None
      Height          =     495
      Index           =     2
      Left            =     9000
      Picture         =     (Icon)
      ScaleHeight     =     492
      ScaleWidth      =     372
      TabIndex        =     32
      Top             =     1200
      Width           =     375
   End
   Begin Timer Timer1
      Interval        =     2000
      Left            =     9120
      Top             =     0
   End
   Begin PictureBox Picture1
      BackColor       =     &H00FFFF80&
      BorderStyle     =     0  'None
      Height          =     495
      Left            =     960
      Picture         =     (Icon)
      ScaleHeight     =     492
      ScaleWidth      =     492
      TabIndex        =     31
      Top             =     120
      Width           =     495
   End
   Begin Data Data2
      Caption         =     "Data2"
      Connect         =     ""
      DatabaseName    =     "C:\ACCESS\orbit.MDB"
      Exclusive       =     0     'False
      Height          =     270
      Left            =     8160
      Options         =     0
      ReadOnly        =     0     'False
```

```
         RecordSource    =    "assay"    -143-
         Top             =    0
         Visible         =    0     'False
         Width           =    1455
      End
      Begin ComboBox CubeSel
         Height          =    300
         Left            =    120
         Style           =    2     'Dropdown List
         TabIndex        =    30

Top             =    960
         Width           =    1815
      End
      Begin Data Data1
         Caption         =    "Data1"
         Connect         =    ""
         DatabaseName    =    "C:\ACCESS\orbit.MDB"
         Exclusive       =    0     'False
         Height          =    270
         Left            =    8355
         Options         =    0
         ReadOnly        =    0     'False
         RecordSource    =    "cubes"
         Top             =    0
         Visible         =    0     'False
         Width           =    1140
      End
      Begin SSCommand ResPrint
         Caption         =    "Print"
         Font3D          =    0     'None
         Height          =    495
         Left            =    7920
         Picture         =    (none)
         TabIndex        =    22
         Top             =    6120
         Width           =    1455
      End
      Begin SSCommand ResSave
         Caption         =    "Save"
         Font3D          =    0     'None
         Height          =    495
         Left            =    7920
         Picture         =    (none)
         TabIndex        =    21
         Top             =    5520
         Width           =    1455
      End
      Begin SSCommand ResClear
         Caption         =    "Clear"
         Font3D          =    0     'None
         Height          =    495
         Left            =    7920
         Picture         =    (none)
         TabIndex        =    20
         Top             =    4920
         Width           =    1455
      End
      Begin Grid Grid1
         FixedCols       =    0
         Height          =    2295
```

```
      Left            =   2640        -144-
      Rows            =   64
      ScrollBars      =   2    'Vertical
      TabIndex        =   19
      Top             =   4440
      Width           =   5175
   End
   Begin GRAPH Graph1

AsciiSymbol     =   "0"

GraphCaption    =   "Classification"

GraphTitle      =   "Classification"
      GraphType       =   9    'Scatter
      GridStyle       =   3    'Horizontal and Vertical
      Height          =   2295

Left            =   120

NumPoints       =   20
      NumSets         =   16

TabIndex        =   18
      Top             =   4440
      Width           =   2415

End
   Begin SSPanel Panel3D2
      Alignment       =   0    'Left Justify - TOP
      BackColor       =   &H00C0C0C0&
      BevelInner      =   1    'Inset
      Caption         =   "Operator Insturctions"
      Font3D          =   0    'None
      Height          =   615
      Left            =   120
      TabIndex        =   15
      Top             =   3720
      Width           =   9375
      Begin TextBox OpInst
         Height       =   375
         Left         =   2040
         MultiLine    =   -1   'True
         TabIndex     =   16
         Top          =   120
         Width        =   5655
      End
```

```
        Begin SSCommand OpInstOK    -145-
            Caption        =    "OK"
            Font3D         =    0    'None
            Height         =    375
            Left           =    8040
            Picture        =    (none)
            TabIndex       =    17
            Top            =    120
            Width          =    855
        End
    End
    Begin TextBox SIBox
        Height        =    1815
        Left          =    120
        MultiLine     =    -1    'True
        TabIndex      =    14
        Top           =    1680
        Width         =    3735
    End
    Begin SSPanel Panel3D1
        Alignment     =    0    'Left Justify - TOP
        BackColor     =    &H00C0C0C0&
        Caption       =    "Cytometer Status"
        Font3D        =    0    'None
        Height        =    2535
        Left          =    7680
        TabIndex      =    12
        Top           =    960
        Width         =    1815
        Begin PictureBox FCPic
            BackColor     =    &H00C0C0C0&
            BorderStyle   =    0    'None
            Height        =    495
            Index         =    1
            Left          =    1320
            Picture       =    (Icon)
            ScaleHeight   =    492
            ScaleWidth    =    372
            TabIndex      =    25
            Top           =    240
            Visible       =    0    'False
            Width         =    375
        End
        Begin PictureBox FCPic
            BackColor     =    &H00C0C0C0&
            BorderStyle   =    0    'None
            Height        =    495
            Index         =    0
            Left          =    1320
            Picture       =    (Icon)
            ScaleHeight   =    492
            ScaleWidth    =    372
            TabIndex      =    24
            Top           =    240
            Visible       =    0    'False
            Width         =    375
        End
        Begin Label Label10
            Alignment     =    1    'Right Justify
            BackStyle     =    0    'Transparent
            Caption       =    "Pressure"
```

```
                Height          =    255        - 146 -
                Left            =    120
                TabIndex        =    29
                Top             =    2160
                Width           =    1095
            End
            Begin Label Label9
                Alignment       =    1     'Right Justify
                BackStyle       =    0     'Transparent
                Caption         =    "Waste Water"
                Height          =    255
                Left            =    0
                TabIndex        =    28
                Top             =    1560
                Width           =    1215
            End
            Begin Label Label8
                Alignment       =    1     'Right Justify
                BackStyle       =    0     'Transparent
                Caption         =    "Sheath Fluid"
                Height          =    255
                Left            =    120
                TabIndex        =    27
                Top             =    960
                Width           =    1095
            End
            Begin Label Label7
                Alignment       =    1     'Right Justify
                BackStyle       =    0     'Transparent
                Caption         =    "Flow Control"
                Height          =    255
                Left            =    120
                TabIndex        =    26
                Top             =    360
                Width           =    1095
            End
        End
        Begin SSFrame TstCtl
            Caption         =    "Test Control"
            Font3D          =    0     'None
            Height          =    2535
            Left            =    3960
            TabIndex        =    4
            Top             =    960
            Width           =    1935
            Begin SSCommand TCHalt
                Caption         =    "Counts"
                Enabled         =    0     'False
                Font3D          =    0     'None
                Height          =    495
                Left            =    240
                Picture         =    (none)
                TabIndex        =    7
                Top             =    1680
                Width           =    1455
            End
            Begin SSCommand TCStart
                Caption         =    "Start Test"
                Enabled         =    0     'False
                Font3D          =    0     'None
                Height          =    495
```

```
            Left            =    240      -147-
            Picture         =    (none)
            TabIndex        =    6
            Top             =    1080
            Width           =    1455
         End
         Begin SSCommand TCInit
            Caption         =    "Initialize"
            Enabled         =    0    'False
            Font3D          =    0    'None
            Height          =    495
            Left            =    240
            Picture         =    (none)
            TabIndex        =    5
            Top             =    480
            Width           =    1455
         End
      End
      Begin SSFrame MacCtl
         Caption            =    "Machine Control"
         Font3D             =    0    'None
         Height             =    2535
         Left               =    5880
         TabIndex           =    3
         Top                =    960
         Width              =    1815
         Begin SSCommand MCEnd
            Caption         =    "Exit"
            Font3D          =    0    'None
            Height          =    495
            Left            =    240
            Picture         =    (none)
            TabIndex        =    10
            Top             =    1680
            Width           =    1335
         End
         Begin SSCommand MCAdjust
            Caption         =    "Manual Adjust"
            Font3D          =    0    'None
            Height          =    495
            Left            =    240
            Picture         =    (none)
            TabIndex        =    9
            Top             =    1080
            Width           =    1335
         End
         Begin SSCommand MCCalib
            Caption         =    "Calibrate"
            Font3D          =    0    'None
            Height          =    495
            Left            =    240
            Picture         =    (none)
            TabIndex        =    8
            Top             =    480
            Width           =    1335
         End
      End
      Begin ComboBox AssaySel
         Height             =    300
         Left               =    2040
         Style              =    2    'Dropdown List
```

```
        TabIndex         =    2         - 148 -
        Top              =    960
        Width            =    1815
     End
     Begin Label Label6
        Alignment        =    2    'Center
        BackStyle        =    0    'Transparent
        BorderStyle      =    1    'Fixed Single
        Caption          =    "Results"
        FontBold         =    -1   'True
        FontItalic       =    -1   'True
        FontName         =    "MS Sans Serif"
        FontSize         =    12
        FontStrikethru   =    0    'False
        FontUnderline    =    0    'False
        ForeColor        =    &H00000080&
        Height           =    375
        Left             =    7920
        TabIndex         =    23
        Top              =    4440
        Width            =    1455
     End
     Begin Label Label4
        BackStyle        =    0    'Transparent
        Caption          =    "Sample Identification"
        Height           =    255
        Left             =    120
        TabIndex         =    13
        Top              =    1440
        Width            =    2535
     End
     Begin Line Line1
        X1               =    0
        X2               =    9480
        Y1               =    3600
        Y2               =    3600
     End
     Begin Label Label2
        BackStyle        =    0    'Transparent
        Caption          =    "Specific Assay"
        Height           =    255
        Left             =    2040
        TabIndex         =    0
        Top              =    720
        Width            =    1575
     End
     Begin Label Label1
        BackStyle        =    0    'Transparent
        Caption          =    "Assay Cube"
        Height           =    255
        Left             =    120
        TabIndex         =    1
        Top              =    720
        Width            =    1575
     End
     Begin Label Label3
        Alignment        =    2    'Center
        BackStyle        =    0    'Transparent
        Caption          =    "Orbit Diagnostic Operating System"
        FontBold         =    -1   'True
```

- 149 -

```
        FontItalic      =   0       'False
        FontName        =   "MS Sans Serif"
        FontSize        =   18
        FontStrikethru  =   0       'False
        FontUnderline   =   0       'False
        ForeColor       =   &H00808000&
        Height          =   495
        Left            =   120
        TabIndex        =   11
        Top             =   120
        Width           =   9255
    End
End
```

```
VERSION 2.00                           - 150 -
Begin Form Form2
    BorderStyle       =   3   'Fixed Double
    Caption           =   "Manual Adjust"
    ClientHeight      =   6612
    ClientLeft        =   1212
    ClientTop         =   1128
    ClientWidth       =   5508
    Height            =   7032
    Left              =   1164
    LinkTopic         =   "Form2"
    MaxButton         =   0   'False
    MinButton         =   0   'False
    ScaleHeight       =   6612
    ScaleWidth        =   5508
    Top               =   756
    Width             =   5604
    Begin SSFrame Frame3D5
        Caption       =   "DDM Select"
        Font3D        =   3   'Inset w/light shading
        ForeColor     =   &H00000000&
        Height        =   735
        Left          =   2760
        TabIndex      =   63
        Top           =   5880
        Width         =   1455
        Begin OptionButton Option1
            BackColor     =   &H000000FF&
            Caption       =   "Option1"
            Height        =   255
            Index         =   2
            Left          =   1080
            TabIndex      =   66
            Top           =   360
            Width         =   255
        End
        Begin OptionButton Option1
            BackColor     =   &H000080FF&
            Caption       =   "Option1"
            Height        =   255
            Index         =   1
            Left          =   600
            TabIndex      =   65
            Top           =   360
            Width         =   255
        End
        Begin OptionButton Option1
            BackColor     =   &H0000FF00&
            Caption       =   "Option1"
            Height        =   255
            Index         =   0
            Left          =   120
            TabIndex      =   64
            Top           =   360
            Value         =   -1  'True
            Width         =   255
        End
        Begin Shape Shape3
            BackColor     =   &H000000FF&
            BackStyle     =   1   'Opaque
            Height        =   495
```

- 151 -

```
        Left            =   960
        Top             =   240
        Width           =   495
     End
     Begin Shape Shape2
        BackColor       =   &H000080FF&
        BackStyle       =   1  'Opaque
        Height          =   495
        Left            =   480
        Top             =   240
        Width           =   495
     End
     Begin Shape Shape1
        BackColor       =   &H0000FF00&
        BackStyle       =   1  'Opaque
        Height          =   495
        Left            =   0
        Top             =   240
        Width           =   495
     End
  End
  Begin SSPanel Panel3D3
     Alignment       =   0  'Left Justify - TOP
     BackColor       =   &H00C0C0C0&
     BevelInner      =   1  'Inset
     BorderWidth     =   4
     Font3D          =   0  'None
     Height          =   1095
     Left            =   4200
     TabIndex        =   56
     Top             =   2880
     Width           =   1335
     Begin PictureBox Picture1
        BackColor       =   &H00FFFF80&
        BorderStyle     =   0  'None
        Height          =   855
        Left            =   120
        Picture         =   (Icon)
        ScaleHeight     =   852
        ScaleWidth      =   1092
        TabIndex        =   57
        Top             =   120
        Width           =   1095
        Begin Data facset
           Caption         =   "Data1"
           Connect         =   ""
           DatabaseName    =   "C:\ACCESS\orbit.MDB"
           Exclusive       =   0     'False
           Height          =   270
           Left            =   0
           Options         =   0
           ReadOnly        =   0     'False
           RecordSource    =   "facs_settings"
           Top             =   600
           Visible         =   0     'False
           Width           =   1140
        End
        Begin Label Label11
           BackStyle       =   0  'Transparent
           Caption         =   "ORBIT"
           ForeColor       =   &H00808000&
```

```
                    Height          =   255  -152-
                    Left            =   360
                    TabIndex        =   58
                    Top             =   480
                    Width           =   735
                End
            End
        End
        Begin SSPanel Panel3D2
            Alignment       =   0   'Left Justify - TOP
            BackColor       =   &H00C0C0C0&
            BevelInner      =   1   'Inset
            BorderWidth     =   4
            Font3D          =   0   'None
            Height          =   2655
            Left            =   4200
            TabIndex        =   54
            Top             =   3960
            Width           =   1335
            Begin SSCommand Command3D5
                Caption         =   "Done"
                Font3D          =   0   'None
                Height          =   495
                Left            =   120
                Picture         =   (none)
                TabIndex        =   62
                Top             =   1920
                Width           =   1095
            End
            Begin SSCommand Command3D4
                Caption         =   "Save"
                Font3D          =   0   'None
                Height          =   495
                Left            =   120
                Picture         =   (none)
                TabIndex        =   61
                Top             =   1320
                Width           =   1095
            End
            Begin SSCommand Command3D3
                Caption         =   "Reset"
                Font3D          =   0   'None
                Height          =   495
                Left            =   120
                Picture         =   (none)
                TabIndex        =   60
                Top             =   720
                Width           =   1095
            End
            Begin SSCommand Command3D2
                Caption         =   "Set"
                Font3D          =   0   'None
                Height          =   495
                Left            =   120
                Picture         =   (none)
                TabIndex        =   59
                Top             =   120
                Width           =   1095
            End
            Begin SSCommand Command3D1
                Caption         =   "exit"
```

```
            Font3D        =   0    'None
            Height        =   375
            Left          =   240
            Picture       =   (none)
            TabIndex      =   55
            Top           =   2880
            Width         =   735
        End
    End
    Begin SSPanel Panel3D1
        Alignment         =   0    'Left Justify - TOP
        BackColor         =   &H00C0C0C0&
        BevelInner        =   1    'Inset
        BorderWidth       =   4
        Caption           =   "Status"
        Font3D            =   0    'None
        Height            =   2895
        Left              =   4200
        TabIndex          =   53
        Top               =   0
        Width             =   1335
        Begin Label Stat
            Alignment     =   2    'Center
            BackStyle     =   0    'Transparent
            Caption       =   "Label15"
            Height        =   255
            Index         =   3
            Left          =   120
            TabIndex      =   74
            Top           =   2520
            Width         =   1095
        End
        Begin Label Label15
            Alignment     =   2    'Center
            BackStyle     =   0    'Transparent
            Caption       =   "DDM"
            Height        =   255
            Left          =   120
            TabIndex      =   73
            Top           =   2280
            Width         =   1095
        End
        Begin Label Stat
            Alignment     =   2    'Center
            BackStyle     =   0    'Transparent
            Caption       =   "Label15"
            Height        =   255
            Index         =   2
            Left          =   120
            TabIndex      =   72
            Top           =   1920
            Width         =   1095
        End
        Begin Label Stat
            Alignment     =   2    'Center
            BackStyle     =   0    'Transparent
            Caption       =   "Label15"
            Height        =   255
            Index         =   1
            Left          =   120
            TabIndex      =   71
```

```
         Top             =    1320
         Width           =    1095
      End
      Begin Label Stat
         Alignment       =    2  'Center
         BackStyle       =    0  'Transparent
         Caption         =    "Label15"
         Height          =    255
         Index           =    0
         Left            =    120
         TabIndex        =    70
         Top             =    720
         Width           =    1095
      End
      Begin Label Label14
         Alignment       =    2  'Center
         BackStyle       =    0  'Transparent
         Caption         =    "Samp. Volts"
         Height          =    255
         Left            =    120
         TabIndex        =    69
         Top             =    1680
         Width           =    1095
      End
      Begin Label Label13
         Alignment       =    2  'Center
         BackStyle       =    0  'Transparent
         Caption         =    "Laser Amps"
         Height          =    255
         Left            =    120
         TabIndex        =    68
         Top             =    1080
         Width           =    1095
      End
      Begin Label Label12
         Alignment       =    2  'Center
         BackStyle       =    0  'Transparent
         Caption         =    "Laser Volts"
         Height          =    255
         Left            =    120
         TabIndex        =    67
         Top             =    480
         Width           =    1095
      End
   End
End
Begin SSFrame Frame3D4
   Caption         =    "DDM Amp"
   Font3D          =    3  'Inset w/light shading
   ForeColor       =    &H00000000&
   Height          =    975
   Left            =    0
   TabIndex        =    46
   Top             =    5640
   Width           =    2775
   Begin HScrollBar ddmscroll
      Height          =    255
      Index           =    0
      LargeChange     =    10
      Left            =    720
      Max             =    999
      TabIndex        =    51
```

```
         Top             =   240      - 155 -
         Width           =   1335
      End
      Begin TextBox ddmtxt
         Height          =   285
         Index           =   0
         Left            =   2160
         TabIndex        =   50
         Text            =   "Text1"
         Top             =   240
         Width           =   495
      End
      Begin HScrollBar ddmscroll
         Height          =   255
         Index           =   1
         LargeChange     =   10
         Left            =   720
         Max             =   999
         TabIndex        =   48
         Top             =   600
         Width           =   1335
      End
      Begin TextBox ddmtxt
         Height          =   285
         Index           =   1
         Left            =   2160
         TabIndex        =   47
         Text            =   "Text1"
         Top             =   600
         Width           =   495
      End
      Begin Label Label10
         BackStyle       =   0  'Transparent
         Caption         =   "FLA"
         Height          =   255
         Index           =   5
         Left            =   120
         TabIndex        =   52
         Top             =   240
         Width           =   615
      End
      Begin Label Label10
         BackStyle       =   0  'Transparent
         Caption         =   "FLW"
         Height          =   255
         Index           =   4
         Left            =   120
         TabIndex        =   49
         Top             =   600
         Width           =   615
      End
   End
   Begin SSFrame Frame3D3
      Caption            =   "Trigger Level"
      Font3D             =   3  'Inset w/light shading
      ForeColor          =   &H00000000&
      Height             =   2055
      Left               =   2760
      TabIndex           =   38
      Top                =   3840
      Width              =   1455
```

```
                              - 156 -
Begin VScrollBar VScroll1
    Height          =    1575
    LargeChange     =    10
    Left            =    960
    Max             =    999
    TabIndex        =    41
    Top             =    360
    Width           =    255
End
Begin SSOption trigger
    Caption         =    "FL3"
    Font3D          =    0  'None
    Height          =    255
    Index           =    4
    Left            =    120
    TabIndex        =    45
    Top             =    1680
    Width           =    615
End
Begin SSOption trigger
    Caption         =    "FL2"
    Font3D          =    0  'None
    Height          =    255
    Index           =    3
    Left            =    120
    TabIndex        =    44
    Top             =    1440
    Width           =    615
End
Begin SSOption trigger
    Caption         =    "FL1"
    Font3D          =    0  'None
    Height          =    255
    Index           =    2
    Left            =    120
    TabIndex        =    43
    Top             =    1200
    Width           =    615
End
Begin SSOption trigger
    Caption         =    "SSC"
    Font3D          =    0  'None
    Height          =    255
    Index           =    1
    Left            =    120
    TabIndex        =    42
    Top             =    960
    Width           =    615
End
Begin TextBox trigval
    Height          =    285
    Left            =    120
    TabIndex        =    40
    Text            =    "Text2"
    Top             =    360
    Width           =    615
End
Begin SSOption trigger
    Caption         =    "FSC"
    Font3D          =    0  'None
    Height          =    255
```

```
              Index         =    0
              Left          =    120
              TabIndex      =    39
              Top           =    720
              Width         =    615
          End
      End
      Begin SSFrame Frame3D2
          Caption        =    "Compensation"
          Font3D         =    3  'Inset w/light shading
          ForeColor      =    &H00000000&
          Height         =    1815
          Left           =    0
          TabIndex       =    25
          Top            =    3840
          Width          =    2775
          Begin TextBox Text1
              Height        =    285
              Index         =    3
              Left          =    2160
              TabIndex      =    33
              Text          =    "Text1"
              Top           =    1440
              Width         =    495
          End
          Begin TextBox Text1
              Height        =    285
              Index         =    2
              Left          =    2160
              TabIndex      =    32
              Text          =    "Text1"
              Top           =    1080
              Width         =    495
          End
          Begin TextBox Text1
              Height        =    285
              Index         =    1
              Left          =    2160
              TabIndex      =    31
              Text          =    "Text1"
              Top           =    720
              Width         =    495
          End
          Begin TextBox Text1
              Height        =    285
              Index         =    0
              Left          =    2160
              TabIndex      =    30
              Text          =    "Text1"
              Top           =    360
              Width         =    495
          End
          Begin HScrollBar HScroll1
              Height        =    255
              Index         =    3
              LargeChange   =    10
              Left          =    720
              Max           =    999
              TabIndex      =    29
              Top           =    1440
              Width         =    1335
```

```
                                                 - 158 -
    End
    Begin HScrollBar HScroll1
        Height          =    255
        Index           =    2
        LargeChange     =    10
        Left            =    720
        Max             =    999
        TabIndex        =    28
        Top             =    1080
        Width           =    1335
    End
    Begin HScrollBar HScroll1
        Height          =    255
        Index           =    1
        LargeChange     =    10
        Left            =    720
        Max             =    999
        TabIndex        =    27
        Top             =    720
        Width           =    1335
    End
    Begin HScrollBar HScroll1
        Height          =    255
        Index           =    0
        LargeChange     =    10
        Left            =    720
        Max             =    999
        TabIndex        =    26
        Top             =    360
        Width           =    1335
    End
    Begin Label Label10
        BackStyle       =    0   'Transparent
        Caption         =    "FL3-2"
        Height          =    255
        Index           =    3
        Left            =    120
        TabIndex        =    37
        Top             =    1440
        Width           =    615
    End
    Begin Label Label10
        BackStyle       =    0   'Transparent
        Caption         =    "FL2-3"
        Height          =    255
        Index           =    2
        Left            =    120
        TabIndex        =    36
        Top             =    1080
        Width           =    615
    End
    Begin Label Label10
        BackStyle       =    0   'Transparent
        Caption         =    "FL2-1"
        Height          =    255
        Index           =    1
        Left            =    120
        TabIndex        =    35
        Top             =    720
        Width           =    615
    End
```

```
                        - 159 -
    Begin Label Label10
        BackStyle       =   0   'Transparent
        Caption         =   "FL1-2"
        Height          =   255
        Index           =   0
        Left            =   120
        TabIndex        =   34
        Top             =   360
        Width           =   615
    End
End
Begin SSFrame modefr
    Caption         =   "Mode"
    Font3D          =   3   'Inset w/light shading
    ForeColor       =   &H00000000&
    Height          =   975
    Left            =   0
    TabIndex        =   14
    Top             =   2880
    Width           =   4215
    Begin SSRibbon fl3mod
        AutoSize        =   0   'None
        BackColor       =   &H00C0C0C0&
        GroupAllowAllUp =   0   'False
        GroupNumber     =   5
        Height          =   240
        Index           =   1
        Left            =   2760
        PictureDisabled =   (none)
        PictureDn       =   (none)
        PictureDnChange =   1   'Dither 'PictureUp' Bitmap
        PictureUp       =   (none)
        Top             =   600
        Value           =   -1  'True
        Width           =   495
    End
    Begin SSRibbon fl3mod
        AutoSize        =   0   'None
        BackColor       =   &H00C0C0C0&
        GroupAllowAllUp =   0   'False
        GroupNumber     =   5
        Height          =   240
        Index           =   0
        Left            =   2760
        PictureDisabled =   (none)
        PictureDn       =   (none)
        PictureDnChange =   1   'Dither 'PictureUp' Bitmap
        PictureUp       =   (none)
        Top             =   360
        Width           =   495
    End
    Begin SSRibbon fl2mod
        AutoSize        =   0   'None
        BackColor       =   &H00C0C0C0&
        GroupAllowAllUp =   0   'False
        GroupNumber     =   4
        Height          =   240
        Index           =   1
        Left            =   2280
        PictureDisabled =   (none)
        PictureDn       =   (none)
```

```
        PictureDnChange =      1   'Dither 'PictureUp' Bitmap
        PictureUp       =      (none)
        Top             =      600
        Value           =      -1  'True
        Width           =      495
    End
    Begin SSRibbon fl2mod
        AutoSize        =      0   'None
        BackColor       =      &H00C0C0C0&
        GroupAllowAllUp =      0   'False
        GroupNumber     =      4
        Height          =      240
        Index           =      0
        Left            =      2280
        PictureDisabled =      (none)
        PictureDn       =      (none)
        PictureDnChange =      1   'Dither 'PictureUp' Bitmap
        PictureUp       =      (none)
        Top             =      360
        Width           =      495
    End
    Begin SSRibbon fl1mod
        AutoSize        =      0   'None
        BackColor       =      &H00C0C0C0&
        GroupAllowAllUp =      0   'False
        GroupNumber     =      3
        Height          =      240
        Index           =      1
        Left            =      1800
        PictureDisabled =      (none)
        PictureDn       =      (none)
        PictureDnChange =      1   'Dither 'PictureUp' Bitmap
        PictureUp       =      (none)
        Top             =      600
        Value           =      -1  'True
        Width           =      495
    End
    Begin SSRibbon fl1mod
        AutoSize        =      0   'None
        BackColor       =      &H00C0C0C0&
        GroupAllowAllUp =      0   'False
        GroupNumber     =      3
        Height          =      240
        Index           =      0
        Left            =      1800
        PictureDisabled =      (none)
        PictureDn       =      (none)
        PictureDnChange =      1   'Dither 'PictureUp' Bitmap
        PictureUp       =      (none)
        Top             =      360
        Width           =      495
    End
    Begin SSRibbon sscmod
        AutoSize        =      0   'None
        BackColor       =      &H00C0C0C0&
        GroupAllowAllUp =      0   'False
        GroupNumber     =      2
        Height          =      240
        Index           =      1
        Left            =      1320
        PictureDisabled =      (none)
```

```
        PictureDn         =    (none)
        PictureDnChange   =    1    'Dither 'PictureUp' Bitmap
        PictureUp         =    (none)
        Top               =    600
        Value             =    -1   'True
        Width             =    495
    End
    Begin SSRibbon sscmod
        AutoSize          =    0    'None
        BackColor         =    &H00C0C0C0&
        GroupAllowAllUp   =    0    'False
        GroupNumber       =    2
        Height            =    240
        Index             =    0
        Left              =    1320
        PictureDisabled   =    (none)
        PictureDn         =    (none)
        PictureDnChange   =    1    'Dither 'PictureUp' Bitmap
        PictureUp         =    (none)
        Top               =    360
        Width             =    495
    End
    Begin SSRibbon fscmod
        AutoSize          =    0    'None
        BackColor         =    &H00C0C0C0&
        GroupAllowAllUp   =    0    'False
        Height            =    240
        Index             =    1
        Left              =    840
        PictureDisabled   =    (none)
        PictureDn         =    (none)
        PictureDnChange   =    1    'Dither 'PictureUp' Bitmap
        PictureUp         =    (none)
        Top               =    600
        Value             =    -1   'True
        Width             =    495
    End
    Begin SSRibbon fscmod
        AutoSize          =    0    'None
        BackColor         =    &H00C0C0C0&
        GroupAllowAllUp   =    0    'False
        Height            =    240
        Index             =    0
        Left              =    840
        PictureDisabled   =    (none)
        PictureDn         =    (none)
        PictureDnChange   =    1    'Dither 'PictureUp' Bitmap
        PictureUp         =    (none)
        Top               =    360
        Width             =    495
    End
    Begin Label Label9
        Alignment         =    2    'Center
        BackStyle         =    0    'Transparent
        Caption           =    "F13"
        Height            =    255
        Left              =    2760
        TabIndex          =    15
        Top               =    120
        Width             =    495
    End
```

```
Begin Label Label8                         - 162 -
    Alignment        =    2    'Center
    BackStyle        =    0    'Transparent
    Caption          =    "FL2"
    ForeColor        =    &H00000000&
    Height           =    255
    Left             =    2280
    TabIndex         =    16
    Top              =    120
    Width            =    495
End
Begin Label Label7
    Alignment        =    2    'Center
    BackStyle        =    0    'Transparent
    Caption          =    "FL1"
    ForeColor        =    &H00000000&
    Height           =    255
    Left             =    1800
    TabIndex         =    17
    Top              =    120
    Width            =    495
End
Begin Label Label6
    Alignment        =    2    'Center
    BackStyle        =    0    'Transparent
    Caption          =    "SSC"
    Height           =    255
    Left             =    1320
    TabIndex         =    20
    Top              =    120
    Width            =    495
End
Begin Label Label4
    Alignment        =    2    'Center
    BackColor        =    &H00000000&
    BackStyle        =    0    'Transparent
    Caption          =    "FSC"
    ForeColor        =    &H00000000&
    Height           =    255
    Left             =    840
    TabIndex         =    21
    Top              =    120
    Width            =    495
End
Begin Label Label5
    BackStyle        =    0    'Transparent
    Caption          =    "Log"
    Height           =    255
    Left             =    120
    TabIndex         =    24
    Top              =    360
    Width            =    615
End
Begin Label Linear
    BackStyle        =    0    'Transparent
    Caption          =    "Linear"
    Height           =    255
    Left             =    120
    TabIndex         =    23
    Top              =    600
    Width            =    855
```

```
            End
End
Begin SSFrame Frame3D1
    Caption         =   "Amplifier"
    Font3D          =   3   'Inset w/light shading
    ForeColor       =   &H00000000&
    Height          =   1455
    Left            =   0
    TabIndex        =   8
    Top             =   1440
    Width           =   4215
    Begin SpinButton Spina
        BackColor       =   &H000000FF&
        Delay           =   100
        ForeColor       =   &H00C0C0C0&
        Height          =   495
        Index           =   4
        Left            =   3360
        LightColor      =   &H000000C0&
        ShadeColor      =   &H00000080&
        ShadowBackColor =   &H000000FF&
        ShadowForeColor =   &H000000FF&
        SpinBackColor   =   &H000000FF&
        SpinForeColor   =   &H00404040&
        TdThickness     =   2
        Top             =   720
        Width           =   495
    End
    Begin SpinButton Spina
        BackColor       =   &H000080FF&
        Delay           =   100
        ForeColor       =   &H00C0C0C0&
        Height          =   495
        Index           =   3
        Left            =   2640
        LightColor      =   &H000080FF&
        ShadeColor      =   &H00404080&
        ShadowBackColor =   &H000080FF&
        ShadowForeColor =   &H000080FF&
        SpinBackColor   =   &H000080FF&
        SpinForeColor   =   &H00404040&
        TdThickness     =   2
        Top             =   720
        Width           =   495
    End
    Begin SpinButton Spina
        BackColor       =   &H0000FF00&
        Delay           =   100
        ForeColor       =   &H00C0C0C0&
        Height          =   495
        Index           =   2
        Left            =   1920
        LightColor      =   &H0000C000&
        ShadeColor      =   &H00008000&
        ShadowBackColor =   &H0000FF00&
        ShadowForeColor =   &H0000FF00&
        SpinBackColor   =   &H0000FF00&
        SpinForeColor   =   &H00404040&
        TdThickness     =   2
        Top             =   720
        Width           =   495
```

- 164 -

```
End
Begin SpinButton Spina
    BackColor       =   &H00FFFF00&
    Delay           =   100
    Height          =   495
    Index           =   1
    Left            =   1080
    SpinBackColor   =   &H00FFFF00&
    TdThickness     =   1
    Top             =   720
    Width           =   495
End
Begin SpinButton Spina
    BackColor       =   &H0080FF80&
    ForeColor       =   &H00FFFF00&
    Height          =   495
    Index           =   0
    Left            =   360
    LightColor      =   &H00FFFF80&
    ShadeColor      =   &H00FFFF80&
    ShadowForeColor =   &H0080FF80&
    SpinBackColor   =   &H0080FF80&
    SpinForeColor   =   &H80000008&
    TdThickness     =   1
    Top             =   720
    Width           =   495
End
Begin TextBox amp
    Height          =   285
    Index           =   4
    Left            =   3360
    TabIndex        =   13
    Text            =   "Text1"
    Top             =   360
    Width           =   495
End
Begin TextBox amp
    Height          =   285
    Index           =   3
    Left            =   2640
    TabIndex        =   12
    Text            =   "Text1"
    Top             =   360
    Width           =   495
End
Begin TextBox amp
    Height          =   285
    Index           =   2
    Left            =   1920
    TabIndex        =   11
    Text            =   "Text1"
    Top             =   360
    Width           =   495
End
Begin TextBox amp
    Height          =   285
    Index           =   1
    Left            =   1080
    TabIndex        =   10
    Text            =   "Text1"
    Top             =   360
```

```
            Width           =    495      - 165 -
        End
        Begin TextBox amp
            Height          =    285
            Index           =    0
            Left            =    360
            TabIndex        =    9
            Text            =    "Text1"
            Top             =    360
            Width           =    495
        End
        Begin Label Label3
            Alignment       =    2  'Center
            BackStyle       =    0  'Transparent
            Caption         =    "SSC"
            Height          =    255
            Left            =    1080
            TabIndex        =    22
            Top             =    1200
            Width           =    495
        End
        Begin Label Label1
            Alignment       =    2  'Center
            BackStyle       =    0  'Transparent
            Caption         =    "FSC"
            Height          =    255
            Index           =    4
            Left            =    360
            TabIndex        =    19
            Top             =    1200
            Width           =    495
        End
        Begin Label Label1
            Alignment       =    2  'Center
            BackStyle       =    0  'Transparent
            Caption         =    "FSC"
            Height          =    15
            Index           =    3
            Left            =    0
            TabIndex        =    18
            Top             =    240
            Width           =    495
        End
    End
End
Begin TextBox txtNumber
    Height          =    285
    Index           =    4
    Left            =    3360
    TabIndex        =    5
    Text            =    "Text1"
    Top             =    360
    Width           =    495
End
Begin TextBox txtNumber
    Height          =    285
    Index           =    3
    Left            =    2640
    TabIndex        =    4
    Text            =    "Text1"
    Top             =    360
    Width           =    495
```

```
End
Begin TextBox txtNumber
   Height         =   285
   Index          =   2
   Left           =   1920
   TabIndex       =   3
   Text           =   "Text1"
   Top            =   360
   Width          =   495
End
Begin TextBox txtNumber
   Height         =   285
   Index          =   1
   Left           =   1080
   TabIndex       =   2
   Text           =   "Text1"
   Top            =   360
   Width          =   495
End
Begin SpinButton Spin1
   BackColor         =   &H0000FF00&
   Delay             =   100
   ForeColor         =   &H00C0C0C0&
   Height            =   495
   Index             =   2
   Left              =   1920
   LightColor        =   &H0000C000&
   ShadeColor        =   &H00008000&
   ShadowBackColor   =   &H0000FF00&
   ShadowForeColor   =   &H0000FF00&
   SpinBackColor     =   &H0000FF00&
   SpinForeColor     =   &H00404040&
   TdThickness       =   2
   Top               =   720
   Width             =   495
End
Begin SpinButton Spin1
   BackColor         =   &H00FFFF00&
   Delay             =   100
   Height            =   495
   Index             =   1
   Left              =   1080
   SpinBackColor     =   &H00FFFF00&
   TdThickness       =   1
   Top               =   720
   Width             =   495
End
Begin SSFrame PMT
   Caption        =   "Photo Multiplier"
   Font           =   3   'Inset w/light shading
   Height         =   1455
   Index          =   0
   Left           =   0
   TabIndex       =   0
   Top            =   0
   Width          =   4215
   Begin SpinButton Spin1
      BackColor      =   &H000000FF&
      Delay          =   100
      ForeColor      =   &H00C0C0C0&
      Height         =   495
```

```
              Index            =    4           -167-
              Left             =    3360
              LightColor       =    &H000000C0&
              ShadeColor       =    &H00000080&
              ShadowBackColor  =    &H000000FF&
              ShadowForeColor  =    &H000000FF&
              SpinBackColor    =    &H000000FF&
              SpinForeColor    =    &H00404040&
              TdThickness      =    2
              Top              =    720
              Width            =    495
           End
           Begin SpinButton Spin1
              BackColor        =    &H000080FF&
              Delay            =    100
              ForeColor        =    &H00C0C0C0&
              Height           =    495
              Index            =    3
              Left             =    2640
              LightColor       =    &H000080FF&
              ShadeColor       =    &H00404080&
              ShadowBackColor  =    &H000080FF&
              ShadowForeColor  =    &H000080FF&
              SpinBackColor    =    &H000080FF&
              SpinForeColor    =    &H00404040&
              TdThickness      =    2
              Top              =    720
              Width            =    495
           End
           Begin TextBox txtNumber
              Height           =    285
              Index            =    0
              Left             =    360
              TabIndex         =    1
              Text             =    "Text1"
              Top              =    360
              Width            =    495
           End
           Begin SpinButton Spin1
              BackColor        =    &H0080FF80&
              ForeColor        =    &H00FFFF00&
              Height           =    495
              Index            =    0
              Left             =    360
              LightColor       =    &H00FFFF80&
              ShadeColor       =    &H00FFFF80&
              ShadowForeColor  =    &H0080FF80&
              SpinBackColor    =    &H0080FF80&
              SpinForeColor    =    &H80000008&
              TdThickness      =    1
              Top              =    720
              Width            =    495
           End
           Begin Label Label2
              Alignment        =    2  'Center
              BackStyle        =    0  'Transparent
              Caption          =    "SSC"
              Height           =    255
              Left             =    1080
              TabIndex         =    7
              Top              =    1200
```

```
            Width           =   495        - 168 -
        End
        Begin Label Label1
            Alignment       =   2  'Center
            BackStyle       =   0  'Transparent
            Caption         =   "FSC"
            Height          =   255
            Index           =   0
            Left            =   360
            TabIndex        =   6
            Top             =   1200
            Width           =   495
        End
    End
    Begin Line Line2
        X1              =   2160
        X2              =   3360
        Y1              =   3120
        Y2              =   3600
    End
    Begin Line Line1
        X1              =   2160
        X2              =   3360
        Y1              =   3120
        Y2              =   3600
    End
End
```

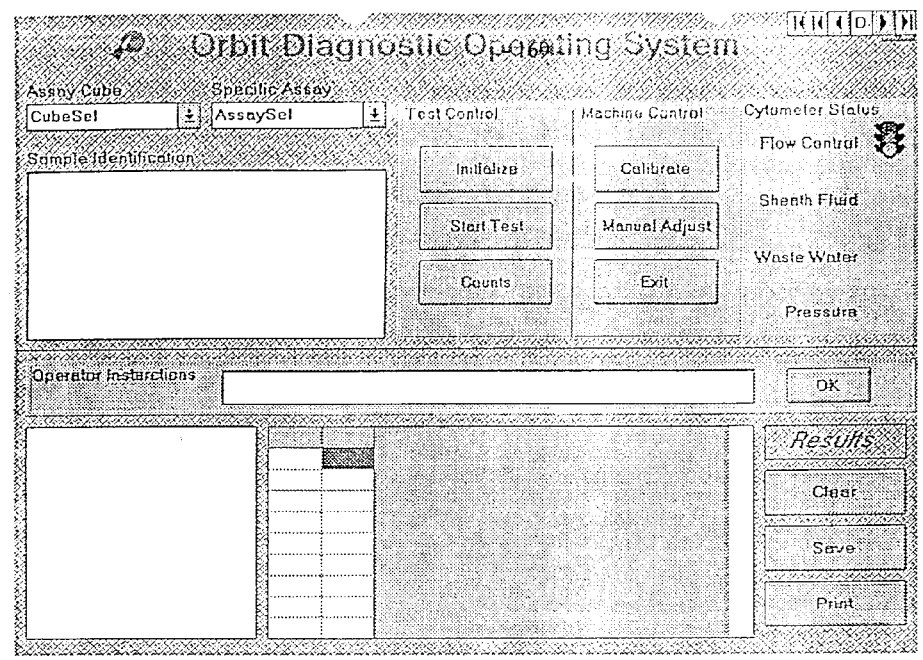

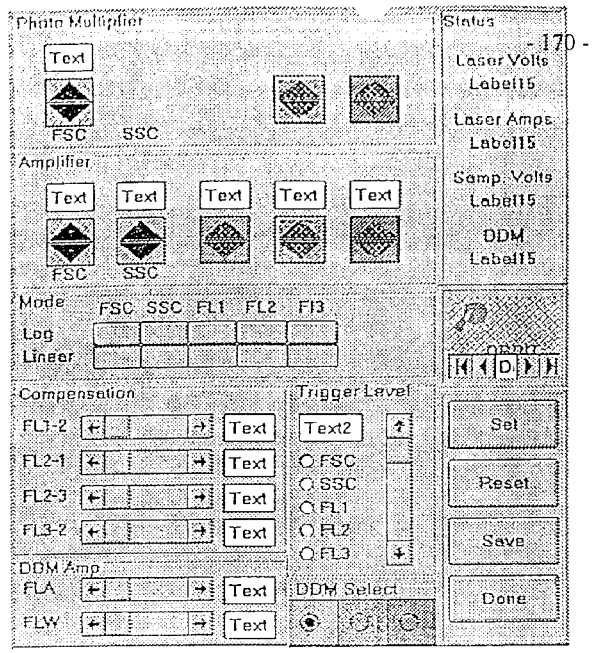

- 171 -

```
Option Explicit

Function vbgenproc ()

End Function

Sub AssaySel_Click ()
Dim y As Integer
Dim x As Integer

'find assay record selected data2.Refresh
Do While Not (AssaySel.Text = data2.Recordset("assay_name"))
    data2.Recordset.MoveNext
Loop 'get number of events required by this assay events = data2.Recordset("event_count")

'clear the testdef table;  it holds the name of each token (biomolocule
' assayed) and the base green and over under values For x = 0 To 1023
For y = 0 To 1
testdef(y, x) = 0
Next y
Next x datatst.Refresh 'now load the new values for this assay Do While Not datatst.Recordset.EOF
    If AssaySel.Text = datatst.Recordset("assay") Then
    x = datatst.Recordset(2)   'token value
    tkname(x) = datatst.Recordset("token_name")
    For y = 0 To 1
    testdef(y, x) = datatst.Recordset(y + 4) 'load over under green and bas
en
    Next y End If
    datatst.Recordset.MoveNext Loop If x = 0 Then MsgBox "There are no Measurement Parameters defined for this
", 48, "Assay Select"
lasttst = x End Sub Sub CubeSel_Click ()
Dim y As Integer
Dim x As Integer
data2.Refresh
AssaySel.Clear
Do While Not data2.Recordset.EOF
```

- 172 -

```
        If CubeSel.Text = data2.Recordset("... _name") Then AssaySel.AddItem d
ecordset("assay_name")
        data2.Recordset.MoveNext Loop y = ReadPanel(tbuf(0))

loadpbuf
For x = 13 To 42
If pbuf(x) <> tbuf(x) Then y = SendPanel(x, pbuf(x))
If y > 30 Then MsgBox "Flow Cytometer is not responding", 48, "Set Flow Cy
r"
Next x
datahld.Refresh
x = 0

Do While Not datahld.Recordset.EOF
    If CubeSel.Text = datahld.Recordset("cube_name") Then
    For y = 0 To 7
    hldtab(y, x) = datahld.Recordset(y + 3)
    Next y
    x = x + 1
    End If
    datahld.Recordset.MoveNext Loop
If x = 0 Then MsgBox "There are no Classification Parameters defined for t
be", 48, "Cube Select"
lastnode = x End Sub Sub Form_Load ()
Dim x As Integer
'x = InitBrd()
data1.Refresh Do While Not data1.Recordset.EOF
    CubeSel.AddItem data1.Recordset("cube_name")
    data1.Recordset.MoveNext
Loop state = 0
grid1.ColWidth(0) = 2400
grid1.ColWidth(1) = 2600
For x = 1 To 63
grid1.RowHeight(x) = 500
Next x
grid1.Row = 0
grid1.Col = 0
grid1.Text = "Biomolecule Assayed"
grid1.Col = 1
grid1.Text = "Result of Assay"
End Sub Sub MCAdjust_Click ()
If form1!CubeSel.Text <> "" Then Form2.Show End Sub
```

- 173 -

```
Sub MCCalib_Click ()
OpInst.Text = "Load Calibration Beads into FACS"

End Sub

Sub MCEnd_Click ()
End

End Sub

Sub OpInstOK_Click ()
state = state + 1
Select Case state
Case 0

Case 1
OpInst.Text = "Calibration Complete, Select Cube and Assay"
Case Else
OpInst.Text = ""
TCInit.Enabled = True
End Select End Sub Sub ResClear_Click ()
Dim x
For x = 1 To 12
grid1.Row = x
grid1.Col = 0
grid1.Text = ""
grid1.Col = 1
grid1.Text = ""
Next x
grid1.Row = 0
TCStart.Enabled = False End Sub Sub TCHalt_Click ()

' during development, the halt button displays the results of classificatic
' by token, **** token 0 is the reject class Dim x As Integer
Dim y As Integer
Dim z As Integer
Dim measure As Integer x = DoTest(lbuf(0, 0), hldtab(0, 0), testdef(0, 0), results(0, 0), events,
ode, lasttst)

For y = 0 To 1023
If results(2, y) <> 0 Then
            grid1.Row = grid1.Row + 1
            grid1.Col = 0
            grid1.Text = "bead " & y
            grid1.Col = 1
            grid1.Text = results(2, y)
End If
```

```
Next y

End Sub

Sub TCInit_Click ()
Dim x As Integer
Dim y As Integer
'x = InitBrd()
If AssaySel.Text = "" Then
OpInst.Text = "You must select a Cube and Assay first!"
Else
For x = 0 To 1023
For y = 0 To 3
results(y, x) = 0
Next y
Next x OpInst.Text = "Initialization Complete"
TCStart.Enabled = True
TCHalt.Enabled = True
End If End Sub Sub TCStart_Click ()
Dim x As Integer
Dim y As Integer
Dim z As Integer
Dim measure As Integer x = DoTest(lbuf(0, 0), hldtab(0, 0), testdef(0, 0), results(0, 0), events,
ode, lasttst)

dataint.Refresh
Do While Not dataint.Recordset.EOF
    If AssaySel.Text = dataint.Recordset("assay") Then
        For x = 0 To 4
        resline(x) = dataint.Recordset(x + 2) 'move to temp area
        Next x z = resline(0)    'token value
        'test***************************** results(2, z) = results(2, z) + 1
        results(0, z) = results(0, z) + 1

If resline(2) = 0 Then
            measure = results(3, z) / results(2, z) 'sum green over total (
        Else measure = results(1, z) / results(0, z)'over count divided by
        End If If ((measure >= resline(3)) And (measure <= resline(4))) Then
            grid1.Row = grid1.Row + 1
            grid1.Col = 0
            grid1.Text = tkname(z)
            grid1.Col = 1
            grid1.Text = dataint.Recordset("interpretation")
        End If
```

- 175 -

```
    End If
        dataint.Recordset.MoveNext
Loop graph1.RandomData = 1
graph1.Refresh
state = 0
'AssaySel.Clear
OpInst.Text = "Test Complete"

End Sub

Sub Timer1_Timer ()
Dim x, y, z  As Integer
y = ReadPanel(tbuf(0))

x = tbuf(38)
    ' set Waste Water indicator
    y = x And 1
    z = 1
    If y = 1 Then z = 0
    WWPic(z).Visible = False
    WWPic(y).Visible = True ' set Sheath Fluid
    y = (x And 2) / 2
    z = 1
    If y = 1 Then z = 0
    SFPic(z).Visible = False
    SFPic(y).Visible = True 'set pressure
    y = (x And &H80) / &H80
    z = 1
    If y = 1 Then z = 0
    PRPic(z).Visible = False
    PRPic(y).Visible = True 'set flow
    y = x And &H70   'mask bits
    Select Case y
    Case &H10
        FCPic(0).Visible = True
        FCPic(1).Visible = False
        FCPic(2).Visible = False
    Case &H20
        FCPic(0).Visible = False
        FCPic(1).Visible = False
        FCPic(2).Visible = True
    Case &H40
        FCPic(0).Visible = False
        FCPic(1).Visible = True
        FCPic(2).Visible = False
    Case 0
        FCPic(0).Visible = False
        FCPic(1).Visible = False
```

```
        FCPic(2).Visible = True
End Select

End Sub
```

- 177 -

```
Option Explicit
Dim photo(5)   As Integer
Dim ampnum(5) As Integer

Dim mode(5) As Integer
Dim thresh(5) As Integer
Dim fcomp(5) As Integer
Dim trigsav As Integer Sub Check3D1_Click (Value As Integer)
pbuf(39) = Value End Sub Sub Check3D2_Click (Value As Integer)
pbuf(40) = 2 * (Value + 1)

End Sub

Sub setpvals ()
' this sets the manual adjust screen to reflect
' the current values in pbuf Dim x As Integer
For x = 0 To 4
txtNumber(x) = pbuf(x + 13)
amp(x) = pbuf(x + 18)
Next x fscmod(pbuf(23)).Value = True
sscmod(pbuf(24)).Value = True
fl1mod(pbuf(25)).Value = True
fl2mod(pbuf(26)).Value = True
fl3mod(pbuf(27)).Value = True For x = 29 To 33
If pbuf(x) <> 0 Then
trigval = pbuf(x)
trigger(x - 29).Value = True
End If
Next x For x = 0 To 3
text1(x) = pbuf(x + 34)
Next x ddmtxt(0) = pbuf(41)
ddmtxt(1) = pbuf(42)

If pbuf(40) <> 0 Then option1(pbuf(40) - 2).Value = True stat(0).Caption = Format$(pbuf(10) * .05, "###.00")
stat(1).Caption = Format$(pbuf(11) * .02, "###.00")
stat(2).Caption = Format$(pbuf(12) / 100, "###.00")

If pbuf(39) = 1 Then
stat(3).Caption = "Enabled"
Else stat(3).Caption = "Disabled"
End If
```

- 178 -

```
End Sub

Sub amp_Change (Index As Integer)
If Val(amp(Index).Text) > 999 Then amp(Index).Text = "999"
pbuf(Index + 18) = Val(amp(Index).Text)
amp(Index).Text = Format(pbuf(Index + 18))

End Sub

Sub Command3D1_Click ()
form2.Hide
End Sub

Sub Command3D2_Click ()
Dim x As Integer
Dim y As Integer
Dim z As Integer
y = ReadPanel(tbuf(0))
For x = 13 To 42
If pbuf(x) <> tbuf(x) Then y = SendPanel(x, pbuf(x))
Next x
End Sub Sub Command3D3_Click ()
Dim y As Integer
Dim x As Integer
loadpbuf
setpvals
For x = 13 To 42
y = SendPanel(x, pbuf(x))
If y > 30 Then MsgBox "Flow Cytometer is not responding", 48, "Set Flow Cyt
r"
Next x End Sub Sub Command3D4_Click ()
savepbuf
End Sub Sub Command3D5_Click ()
form2.Hide End Sub Sub ddmscroll_Change (Index As Integer)
pbuf(Index + 41) = ddmscroll(Index).Value
ddmtxt(Index) = Format(ddmscroll(Index))

End Sub

Sub ddmtxt_Change (Index As Integer)
If Val(ddmtxt(Index)) > 999 Then ddmtxt(Index) = "999"
ddmscroll(Index).Value = Val(ddmtxt(Index))
pbuf(Index + 41) = ddmscroll(Index).Value End Sub
```

- 179 -

```
Sub f11mod_Click (Index As Integer, Value As Integer)
pbuf(25) = Index
If Index = 0 Then
    spina(2).Enabled = False
    amp(2).Enabled = False
Else
    spina(2).Enabled = True
    amp(2).Enabled = True
End If End Sub Sub f12mod_Click (Index As Integer, Value As Integer)
pbuf(26) = Index
If Index = 0 Then
    spina(3).Enabled = False
    amp(3).Enabled = False
Else
    spina(3).Enabled = True
    amp(3).Enabled = True
End If End Sub Sub f13mod_Click (Index As Integer, Value As Integer)
pbuf(27) = Index
If Index = 0 Then
    spina(4).Enabled = False
    amp(4).Enabled = False
Else
    spina(4).Enabled = True
    amp(4).Enabled = True
End If End Sub Sub Form_Load ()
Dim x As Integer
Dim y As Integer
loadpbuf
setpvals
form2.Caption = form1!CubeSel.Text & " Cube Manual Adjust"

End Sub

Sub fscmod_Click (Index As Integer, Value As Integer)
pbuf(23) = Index
If Index = 0 Then
    spina(0).Enabled = False
    amp(0).Enabled = False
Else
    spina(0).Enabled = True
    amp(0).Enabled = True
End If End Sub Sub HScroll1_Change (Index As Integer)
```

```
pbuf(Index + 34) = HScroll1(Index).Value
text1(Index) = Format(HScroll1(Index))
End Sub Sub Option1_Click (Index As Integer)
pbuf(40) = Index + 2
pbuf(39) = 1
End Sub Sub Spin1_SpinDown (Index As Integer)
Dim min
pbuf(Index + 13) = pbuf(Index + 13) - 1
If Index = 0 Then min = 0 Else min = 150
If pbuf(Index + 13) < min Then pbuf(Index + 13) = min
txtNumber(Index).Text = Format(pbuf(Index + 13))
End Sub Sub Spin1_SpinUp (Index As Integer)
Dim max
pbuf(Index + 13) = pbuf(Index + 13) + 1
If Index = 0 Then max = 4 Else max = 999
If pbuf(Index + 13) > max Then pbuf(Index + 13) = max
txtNumber(Index).Text = Format(pbuf(Index + 13))

End Sub

Sub Spina_SpinDown (Index As Integer)
Dim min
pbuf(Index + 18) = pbuf(Index + 18) - 1
min = 100
If pbuf(Index + 18) < min Then pbuf(Index + 18) = min
amp(Index).Text = Format(pbuf(Index + 18))

End Sub

Sub Spina_SpinUp (Index As Integer)
Dim max
pbuf(Index + 18) = pbuf(Index + 18) + 1
max = 999
If pbuf(Index + 18) > max Then pbuf(Index + 18) = max
amp(Index).Text = Format(pbuf(Index + 18))

End Sub

Sub sscmod_Click (Index As Integer, Value As Integer)
pbuf(24) = Index
If Index = 0 Then
    spina(1).Enabled = False
    amp(1).Enabled = False
Else
    spina(1).Enabled = True
    amp(1).Enabled = True
End If End Sub Sub Text1_Change (Index As Integer)
If Val(text1(Index)) > 999 Then text1(Index) = "999"
HScroll1(Index).Value = Val(text1(Index))
pbuf(Index + 34) = HScroll1(Index).Value
```

- 181 -

```
End Sub

Sub trigger_Click (Index As Integer, Value As Integer)
Dim x
For x = 29 To 33
pbuf(x) = 0
Next x
pbuf(Index + 29) = Val(trigval.Text)
trigsav = Index
pbuf(28) = 128 + Index
End Sub Sub trigval_Change ()
If Val(trigval.Text) > 999 Then trigval.Text = "999"
VScroll1.Value = Val(trigval.Text)
pbuf(trigsav + 29) = VScroll1.Value End Sub Sub VScroll1_Change ()
trigval.Text = Format(VScroll1.Value)
pbuf(trigsav + 29) = VScroll1.Value End Sub
```

```
Option Explicit
Global pbuf(64) As Integer
Global tbuf(64) As Integer

Global lbuf(8, 32) As Integer
Global hldtab(7, 1023) As Integer
Global results(3, 1023) As Long
Global testdef(1, 1023) As Integer
Global resline(5) As Integer
Global tkname(1024) As String
Global state As Integer
Global lastnode As Integer
Global lasttst As Integer
Global events As Long Declare Function DoTest Lib "c:\msvc\bin\orbit.dll" (lbuf As Integer, hldta
Integer, testdef As Integer, results As Long, ByVal events&, ByVal lastnode
Val lasttst%) As Integer
Declare Function InitBrd Lib "c:\msvc\bin\orbit.dll" () As Integer
Declare Function SendPanel Lib "c:\msvc\bin\orbit.dll" (ByVal parm%, ByVal
l%) As Integer
Declare Function ReadPanel Lib "c:\msvc\bin\orbit.dll" (pbuf As Integer) As
ger
Declare Function ReadList Lib "c:\msvc\bin\orbit.dll" (lbuf As Integer) As
er Sub loadpbuf ()
' for a selected cube, the data base values are loaded into pbuf Dim x As Integer
form2!facset.Refresh
Do While form2!facset.Recordset.EOF = False
If form1!CubeSel.Text = form2!facset.Recordset(0) Then Exit Do
form2!facset.Recordset.MoveNext
Loop For x = 0 To 42
pbuf(x) = form2!facset.Recordset(x + 1)
Next x End Sub Sub savepbuf ()
' This saves the current values in pbuf to the data base Dim x As Integer
form2!facset.Refresh
Do While form2!facset.Recordset.EOF = False
If form1!CubeSel.Text = form2!facset.Recordset(0) Then Exit Do
form2!facset.Recordset.MoveNext
Loop
form2!facset.Recordset.Edit
For x = 0 To 42
form2!facset.Recordset(x + 1) = pbuf(x)
Next x
form2!facset.Recordset.Update
End Sub
```

- 183 -

```
Option Explicit
```

- 184 -

```
///////////////////////////////////////////////////////
//
// MDXDLL.DLL source.
//
/////////////////////////////////////////////////////// include <windows.h>
include "mdxdll.h"

int WINAPI _export InitBrd(void)
{
__asm
        {
        mov     dx,brdctrl
        mov     ax,20h
        out     dx,ax
        mov     dx,brdctrl
        in      ax,dx
        or      ax,outfifoclr   ;set both fifos to clear
        or      ax,infifoclr
        out     dx,ax mov     dx,inpxfer
        mov     ax,0    ;set xfer count to 0
        out     dx,ax mov     dx,prtctrl
        mov     ax,0
        or      ax,ctl0 ;set control lines to idle
        or      ax,ctl1
        out     dx,ax mov     dx,prtctrl
        in      ax,dx
        mov     bx,preset       ;reset facs
        not     bx
        and     ax,bx
        out     dx,ax or      ax,preset       ;toggle
        out     dx,ax mov     dx,brdsts
        in      ax,dx mov     dx,inpxfer
        mov     ax,0
        out     dx,ax
        mov     dx,prtctrl
        mov     ax,6    ;assert ctl0 &1
        out     dx,ax // asm code here }
//SendPanel(ddmena,1);
return(0);
} int WINAPI _export SendPanel(int parm, int PanVal)
```

- 185 -

```
{
int i = 0;

__asm
    {
        mov     dx,brdctrl
        in      ax,dx
        mov     bx,inen
        not     bx
        and     ax,bx
        or      ax,outen
        out     dx,ax mov     dx,prtctrl
        in      ax,dx
        mov     bx,ctl0
        not     bx
        and     ax,bx
        out     dx,ax mov     dx,brdctrl
        in      ax,dx
        or      ax,outfifoclr
        out     dx,ax
        mov     bx,outfifoclr
        not     bx
        and     ax,bx
        out     dx,ax mov     dx,bdata
        mov     ax,1
        out     dx,ax mov     bx,parm     ;get code
        shl     bx,10
        mov     ax,PanVal   ;get panel value
        and     ax,3ffh
        or      ax,bx
        out     dx,ax       ;send it out mov     dx,dlyctrl
        mov     ax,0160h
        out     dx,ax mov     dx,brdctrl
        in      ax,dx
        or      ax,hshken
        out     dx,ax
        mov     cx,4000 wsend:  mov     dx,brdsts
        in      ax,dx
        mov     bx,ax
        and     bx,1        ;1=empty fifo
        loope   wsend
        and     ax,40h      ;bit 6 = 1 = xfer pending
        jnz     wsend
        mov     dx,prtctrl
        in      ax,dx
        or      ax,ctl0
        out     dx,ax
```

- 186 -

```
        mov     dx,brdctrl
        in      ax,dx
        mov     bx,outen
        or      bx,hshken
        not     bx
        and     ax,bx
        out     dx,ax mov     dx,dlyctrl
        mov     ax,0101h
        out     dx,ax
        // asm code here }
return(i);

} int WINAPI _export ReadPanel(int __far *pbuf)
{
int far* pbufptr = pbuf;

__asm
        {
        mov     dx,brdctrl
        in      ax,dx
        or      ax,outfifoclr   ;set both fifos to clear
        or      ax,infifoclr
        out     dx,ax mov     dx,inpxfer
        mov     ax,0     ;set xfer count to 0
        out     dx,ax mov     dx,prtctrl
        mov     ax,0
        or      ax,ctl0  ;set control lines to idle
        or      ax,ctl1
        out     dx,ax mov     dx,prtctrl
        in      ax,dx
        or      ax,preset       ;toggle
        out     dx,ax lowlp:  mov     dx,prtsts
        in      ax,dx
        mov     bx,ax
        and     ax,sts1  ;has sts1 gone low yet?
        jz      waithigh        ;yes, wait for it to go back high
        jmp     lowlp    ;*************** waithigh:

mov     dx,brdctrl      ;no, panel coming so set up read
        in      ax,dx
        and     al,0eeh  ;handsk off out off
        or      ax,8     ;clr in fifo
        out     dx,ax
```

```
            and     al,0f7h   ;fifo clr off      - 187 -
            out     dx,ax mov     dx,inpxfer      ;set up xfer count
            mov     ax,43
            out     dx,ax mov     dx,prtctrl
            in      ax,dx
            mov     bx,ctl0
            not     bx
            and     ax,bx
            out     dx,ax     ;set ctl0 to request panel data mov     dx,dlyctrl
            mov     ax,101h
            out     dx,ax mov     dx,brdctrl
            in      ax,dx
            or      ax,hshken       ;initiate handshake
            out     dx,ax waitdata:
            mov     dx,brdsts
            mov     bx,xferincom
            or      bx,xferpend
            in      ax,dx
            and     ax,bx     ;wait until xfer not pending
            jnz     waitdata        ;or incomplete mov     dx,prtctrl  ;done
            in      ax,dx
            or      ax,ctl0 ;stop
            out     dx,ax
            mov     dx,brdctrl
            in      ax,dx
            and     al,0ebh ;turn off handshake and input enable
            out     dx,ax
            push    di
            push    es
            mov     cx,43
            les     di,pbufptr
            mov     dx, bdata
readlp:
            in      ax,dx     ;read data from fifo
            mov     bx,ax
            and     ax,3ffh
            and     bx,0fc00h
            shr     bx,9      ;right 10 * 2
            mov     word ptr es:[di+bx],ax
            loop    readlp
            pop             es
            pop             di }
return(0);
} int WINAPI _export DoTest(int __far *lbuf, int __far *hldtab,
                    int __far *testdef, long __far *results,
                    long events, int lastnode, int lasttst)
```

- 188 -

```
{
int far* lbufptr = lbuf;
int far* hldptr = hldtab;
int far* testptr = testdef;
long far* resptr = results;

int x,y,z,bdi,goodcnt,token = 0;

while (events > 0)
        {
            goodcnt = ReadList(lbufptr);
            if (goodcnt > 0)
                {
                    for (bdi = 0; bdi < goodcnt; bdi++)
                        {
                        x = y = 0;
                        // orange correction goes here for lbufptr[bdi][f12]
                        // x is the current node in the hld table
                        token = -1;
                        while (token < 0)
                                {
                                z = lbufptr[bdi * 8 + (hldptr[x * 8])];
                                // z is the value of the parameter under test
                                if ((z >= hldptr[x * 8 + 2]) && (z <= hldptr[x * 8 + 3])) // val && high val
                                        {
                                        if (hldptr[x * 8 + 4] == 0) token = hldptr[x * 8 + // 0 means done, get token true
                                        else x = hldptr[x * 8 + 4]; // get node true
                                        }
                                else
                                        {
                                        if (hldptr[x * 8 + 5] == 0) token = hldptr[x * 8 + // get token false
                                        else x = hldptr[x * 8 + 5]; // get node false
                                        }
                                }
                        events--;
                        z = lbufptr[bdi * 8 + 2]; // z is FL1
                        if (z < testptr[token * 2 + 1]) resptr[token * 4]++; //inc count
                        if (z > testptr[token * 2 + 1]) resptr[token * 4 + 1]++; // ver count
                        resptr[token * 4 + 2]++;   // inc total count
                        resptr[token * 4 + 3] += z;  //sum FL1
                        }
                }

}

__asm
        {
          nop
        }
return(0);
} int WINAPI _export ReadList(int __far *lbuf)
```

- 189 -

```
{
int far* lbufptr = lbuf;
int i = 0;

__asm
    {
    ;****************************************************************
    ;                   read list mode
    ;**************************************************************** mov     dx,brdctrl
            in      ax,dx
            or      ax,outfifoclr   ;set both fifos to clear
            or      ax,infifoclr
            out     dx,ax mov     dx,inpxfer
            mov     ax,0            ;set xfer count to 0
            out     dx,ax mov     dx,prtctrl
            mov     ax,0
            or      ax,ctl0         ;set control lines to idle
            or      ax,ctl1
            out     dx,ax mov     dx,prtctrl
            in      ax,dx
            or      ax,preset       ;toggle
            out     dx,ax lowlp1:     mov     dx,prtsts
            in      ax,dx
            mov     bx,ax
            and     ax,sts0         ;has sts0 gone low yet?
            jz      waithigh1       ;yes, wait for it to go back high
            jmp     lowlp1  ;  ******** waithigh1:

mov     dx,brdctrl      ;no, list mode coming so set up read
            in      ax,dx
            and     al,0eeh         ;handsk off out off
            or      ax,8            ;clr in fifo
            out     dx,ax and     al,0f7h         ;fifo clr off
            out     dx,ax push    es
            push    di
            push    ds
            push    si
            les     di,lbufptr mov     dx,inpxfer      ;set up xfer count
            mov     ax,120          ;7 vals + chk sum * 15 events
            out     dx,ax mov     dx,prtctrl
            in      ax,dx
```

```
                mov     bx,ctl1                     - 190 -
                not     bx
                and     ax,bx
                out     dx,ax       ;set ctl1 to request list data mov     dx,dlyctrl
                mov     ax,101h
                out     dx,ax mov     dx,brdctrl
                in      ax,dx
                or      ax,hshken       ;initiate handshake
                out     dx,ax waitdata1:
                mov     dx,brdsts
                mov     bx,xferincom
                or      bx,xferpend
                in      ax,dx
                and     ax,bx       ;wait until xfer not pending
                jnz     waitdata1       ;or incomplete
                mov     dx,bdata
                mov     cx,120   ;number of words to read
chunk:  in      ax,dx
                stosw
                loop    chunk
                mov     dx,prtctrl   ;done
                in      ax,dx
                or      ax,ctl1 ;stop
                out     dx,ax
                mov     dx,brdctrl
                in      ax,dx
                and     al,0ebh ;turn off handshake and input enable
                out     dx,ax les     di,lbufptr
                lds     si,lbufptr
                mov     cx,15    ;up to 15 good events could be present ;check alignment mov     dx,0     ;count of good records test    word ptr [si],0e000h
                jz      alnok
                dec     cx       ;only 14 max possible now
                push    cx
                mov     cx,7     ;seven other possible alignments
alnlp:  lodsw
                test    ax,0e000h
                jz      nowalnok        ;now have alignment
                loop    alnlp
                pop     cx
                jmp     badbuff
nowalnok:
                sub     si,2    ;repoint to good align
                pop     cx      ;restore loop count
alnok:  push    cx
                mov     cx,7
                mov     bx,0
sumchk: lodsw
```

```
                add     bx,                      - 191 -
                loop    sumchk
                lodsw
                cmp     bx,ax    ;is check sum good
                jne     nocopy
                sub     si,16    ;repoint to start of rec
                mov     cx,8
        clncpy: lodsw
                and     ax,3ffh  ;knock off parm number
                stosw
                loop    clncpy
                inc     dx       ;count good records
        nocopy: pop     cx
                loop    alnok
        badbuff:
                mov     i,dx pop     si
                pop     ds
                pop     di
                pop     es }
return(i);
}

////////////////////////////////////////////////////////////
//
//   DLL Initialization and exit.
//
int WINAPI LibMain(HANDLE hInst, WORD wDataSeg,
                   WORD cbHeapSize, LPSTR lpszCmdLine)
{
    hModInst = hInst;
    if (cbHeapSize != 0)
        UnlockData(0);
    return 1;
} int _export WINAPI WEP(int nParam)
{
    return 1;
}
```

```
#define    GlobalFreePtr(lp)        \
                (GlobalUnlockPtr(lp), (BOOL)GlobalFree(GlobalPtrHandle(lp)))

////////////////////////////////////////////////////////////
```

```
//////////////////////////////////////////////////////
//
//  Include file for MDXDLL.DLL
//
////////////////////////////////////////////////////// ifdef __cplusplus
extern "C" {
#endif

//////////////////////////////////////////////////////
//
// Define DEBUG macros.
//
#if defined(_DEBUG) && !defined(_AFX)

char _sz_ASSERT[255];

#define ASSERT(a)   if(!(a)) { wsprintf(_sz_ASSERT, \
    "assertion failed in file %s at line %d\r\n",   \
    (LPSTR)(__FILE__),__LINE__); OutputDebugString(_sz_ASSERT); }
#define TRACE(a)    OutputDebugString(a"\r\n")
#define TRACE1(a,b)    { wsprintf(_sz_ASSERT,a"\r\n",(int)(b)); \
    OutputDebugString(_sz_ASSERT); }
#define TRACE2(a,b,c)  { wsprintf(_sz_ASSERT,a"\r\n",(int)(b),(int)(c)); \
    OutputDebugString(_sz_ASSERT); } endif if !defined(_DEBUG) && !defined(_AFX)

define ASSERT(a)
#define TRACE(a)
#define TRACE1(a,b)
#define TRACE2(a,b,c)

#endif

//////////////////////////////////////////////////////
//
// From Windowsx.h
//
#define     GlobalPtrHandle(lp)         \
            ((HGLOBAL)LOWORD(GlobalHandle(SELECTOROF(lp))))

#define     GlobalLockPtr(lp)           \
            ((BOOL)SELECTOROF(GlobalLock(GlobalPtrHandle(lp))))
#define     GlobalUnlockPtr(lp)         \
            GlobalUnlock(GlobalPtrHandle(lp))

#define     GlobalAllocPtr(flags, cb)   \
            (GlobalLock(GlobalAlloc((flags), (cb))))
#define     GlobalReAllocPtr(lp, cbNew, flags) \
            (GlobalUnlockPtr(lp), GlobalLock(GlobalReAlloc(GlobalPtrHandle(lp) , (cbNew
lags))))
#define     GlobalFreePtr(lp)           \
            (GlobalUnlockPtr(lp), (BOOL)GlobalFree(GlobalPtrHandle(lp)))

//////////////////////////////////////////////////////
```

- 193 -

```
//
// Global variables.
//

HINSTANCE hModInst;      // module handle.

// Cytomation board definitions define base     0x240
define bdata    base + 0
#define brdctrl  base + 2
#define brdsts   base + 4
#define prtctrl  base + 6
#define prtsts   base + 8
#define dlyctrl  base + 0x0a
define inpxfer  base + 0x0c //facs codes define ddmena   39

//board control define outen       1
define outfifoclr  2
#define inen        4
#define infifoclr   8
#define hshken      0x10

//board status define outfifoe    1
define outfifoh    2
#define outfifof    4
#define infifoe     8
#define infifoh     0x10
#define infifof     0x20
#define xferpend    0x40
#define xferincom   0x80

//port control define preset   1
define ctl0     2
#define ctl1     4

//port status define eir      1
define psts     2
#define sts0     4
#define sts1     8

/////////////////////////////////////////////////////////
//
// Exported Functions.
//

/////////////////////////////////////////////////////////
```

```
//
// Local Functions.
// int WINAPI _export SendPanel(int parm, int PanVal);
int WINAPI _export ReadPanel(int pbuf[]);
int WINAPI _export ReadList(int lbuf[]);
int WINAPI _export InitBrd (void);
int WINAPI _export DoTest(int lbuf[], int hldtab[],
                          int testdef[], long results[],
                          long events, int lastnode, int lasttst);

#ifdef __cplusplus
}
#endif
```

- 195 -

```
;---------------------------------------------------------------
;
; Module Definition file for MDXDLL.DLL
;
;---------------------------------------------------------------
LIBRARY    MDXDLL DESCRIPTION  'MDXDLL Library'

EXETYPE    WINDOWS

CODE       PRELOAD MOVABLE
DATA       PRELOAD MOVABLE

HEAPSIZE   1024

EXPORTS
    WEP                @1 RESIDENTNAME
    InitBrd            @2
    SendPanel          @3
    ReadPanel          @4
    ReadList           @5
    DoTest             @6
```

What is claimed is:

1. A computer readable medium storing an assay database for processing a pooled population of subsets of particles during flow analysis, said assay database comprising: (a) a discriminant function table encoding a decision tree for classifying in real time each particle according to its subset based at least in part on at least one classification parameter including at least one respective fluorescence emission intensity, and (b) an assay definition table encoding a decision tree for defining an assay by identifying a respective subset and as least one baseline assay measurement value for interpreting an assay result.

2. The computer readable medium according to claim 1, wherein said discriminant function table includes, for each subset, at least one of high and low classification parameter values.

3. A machine readable assay database, stored in a storage device, for the processing of flow-cytometric measurement data comprising:
   (a) an assay definition table, said assay definition table encoding (1) one or more measurement subset token identifiers, (2) for each subset token identifier, one or more baseline measurement parameter values, and (3) for each subset token identifier, an interpretation test-type token;
   (b) a discriminant function table, said discriminant function table encoding a real-time classification decision tree based on one or more classification measurement parameters, said one or more classification measurement parameters encoded in said flow-cytometric measurement data;
   (c) an interpretation table, said interpretation table encoding textual assay outcome-description information; and
   (d) a results table, said results table capable of encoding statistical accumulation of real-time flow-cytometric measurement data.

4. The computer readable medium according to claim 1, wherein said assay database further includes an interpretation table including at least one textual message for each assay result based on the at least one baseline assay measurement value.

5. The computer readable medium according to claim 1, wherein said assay database further includes a results table encoding, for each subset, at least one of a total number of particles classified per subset, a running sum of collected assay measurement values, a total number of particles having collected assay measurement values less than the at least one baseline assay measurement value, and a total number of particles having collected assay measurement values at least as great as the at least one baseline assay measurement value.

6. A computer readable medium storing an assay database for processing a pooled population of subsets of particles during flow analysis, said assay database comprising: (a) a discriminant function table encoding a decision tree for classifying in one step each particle according to its subset based at least in part on at least one classification parameter including at least one respective fluorescence emission intensity, and (b) an assay definition table encoding a decision tree for defining an assay by identifying a respective subset and as least one baseline assay measurement value for interpreting an assay result.

7. A computer readable medium storing an assay database for processing a pooled population of subsets of particles during flow analysis, said assay database comprising: (a) a discriminant function table encoding a decision tree for classifying each particle according to its subset based at least in part on at least one classification parameter, and (b) an assay definition table encoding a decision tree for defining an assay based at least in part on at least one baseline measurement parameter value.

8. The computer readable medium of claim 7 in which said classification parameter includes at least one fluorescence emission intensity.

9. The computer readable medium of claim 7 in which said at least one classification parameter includes at least two fluorescence emission intensities.

10. The computer readable medium of claim 7 in which said baseline measurement arameter value is used for interpreting an assay result.

11. The computer readable medium of claim 7 in which said assay definition table further encodes at least one measurement subset token identifiers.

12. The computer readable medium of claim 7 in which said assay database further comprises an interpretation table.

13. The computer readable medium of claim 7 in which said assay database further comprises a results table.

* * * * *